United States Patent
Liu et al.

(10) Patent No.: US 10,960,167 B2
(45) Date of Patent: Mar. 30, 2021

(54) ZONE HEATING FOR RESPIRATORY CIRCUITS

(71) Applicant: Fisher & Paykel Healthcare Limited, Auckland (NZ)

(72) Inventors: Po-Yen Liu, Auckland (NZ); Peter Alan Seekup, Auckland (NZ); Anthony James Newland, Auckland (NZ); Malcolm David Smith, Auckland (NZ); Ping Si, Auckland (NZ); Helgard Oosthuysen, Auckland (NZ); Matthew Robert Wilson, Auckland (NZ); Ian Lee Wai Kwan, Auckland (NZ); Sinaa Alnashi, Auckland (NZ); Paul James Tonkin, Auckland (NZ); Kiel Anthony McCool, Auckland (NZ); David Robert Kemps, Auckland (NZ); Yayi Lin, Auckland (NZ); Callum McDonald Ross, Auckland (NZ); David John Sims, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 356 days.

(21) Appl. No.: 15/758,714

(22) PCT Filed: Sep. 9, 2016

(86) PCT No.: PCT/NZ2016/050144
§ 371 (c)(1),
(2) Date: Mar. 8, 2018

(87) PCT Pub. No.: WO2017/043981
PCT Pub. Date: Mar. 16, 2017

(65) Prior Publication Data
US 2018/0280651 A1    Oct. 4, 2018

Related U.S. Application Data

(60) Provisional application No. 62/216,232, filed on Sep. 9, 2015, provisional application No. 62/380,195, filed on Aug. 26, 2016.

(51) Int. Cl.
*A61M 16/16* (2006.01)
*A61M 16/10* (2006.01)
(Continued)

(52) U.S. Cl.
CPC ...... *A61M 16/1095* (2014.02); *A61M 16/024* (2017.08); *A61M 16/026* (2017.08);
(Continued)

(58) Field of Classification Search
CPC .............. A61F 2007/0061; A61F 7/12; A61M 16/0003; A61M 16/0051; A61M 16/0066;
(Continued)

(56) References Cited

U.S. PATENT DOCUMENTS

| 485,127 A | 10/1892 | Lynch |
| 2,073,335 A | 3/1937 | Connell |

(Continued)

FOREIGN PATENT DOCUMENTS

| AU | 1448473 | 9/1976 |
| AU | 2003278649 A1 | 6/2004 |

(Continued)

OTHER PUBLICATIONS

US 10,426,912 B2, 10/2019, Buswell et al. (withdrawn)
(Continued)

*Primary Examiner* — Annette Dixon
(74) *Attorney, Agent, or Firm* — Knobbe, Martens, Olson & Bear, LLP

(57) ABSTRACT

Some embodiments provide for an inspiratory limb for a breathing circuit that includes a first segment that comprises
(Continued)

a first heater wire circuit and a second segment that comprises a second heater wire circuit. The inspiratory limb can include an intermediate connector that includes a connection circuit that electrically couples the first heater wire circuit to the second heater wire circuit. The inspiratory limb can be configured to operate in two modes wherein, in a first mode, electrical power passes through the first electrical connection to provide power to the first heater wire circuit without providing power to the second heater wire circuit, and in a second mode, electrical power pass through the first electrical connection to provide power to both the first heater wire circuit and the second heater wire circuit.

20 Claims, 55 Drawing Sheets

(51) Int. Cl.
    *A61M 16/08*    (2006.01)
    *H05B 1/02*    (2006.01)
    *H05B 3/58*    (2006.01)
    *A61M 16/00*    (2006.01)
    *A61M 16/01*    (2006.01)

(52) U.S. Cl.
    CPC .... *A61M 16/0816* (2013.01); *A61M 16/0875* (2013.01); *A61M 16/0891* (2014.02); *A61M 16/16* (2013.01); *A61M 16/161* (2014.02); *H05B 1/025* (2013.01); *H05B 3/58* (2013.01); *A61M 16/01* (2013.01); *A61M 2016/0033* (2013.01); *A61M 2016/0039* (2013.01); *A61M 2016/1025* (2013.01); *A61M 2202/0208* (2013.01); *A61M 2205/18* (2013.01); *A61M 2205/3368* (2013.01); *A61M 2205/3653* (2013.01); *A61M 2205/50* (2013.01); *H05B 2203/012* (2013.01); *H05B 2203/022* (2013.01)

(58) Field of Classification Search
    CPC ............ A61M 16/0069; A61M 16/024; A61M 16/026; A61M 16/06; A61M 16/0633; A61M 16/0666; A61M 16/0816; A61M 16/0833; A61M 16/0841; A61M 16/0875; A61M 16/107; A61M 16/1075; A61M 16/108; A61M 16/1085; A61M 16/109; A61M 16/1095; A61M 16/12; A61M 16/142; A61M 16/16; A61M 16/161; A61M 16/162; A61M 16/164; A61M 2016/0027; A61M 2016/0039; A61M 2202/0208; A61M 2205/14; A61M 2205/3368; A61M 2205/3375; A61M 2205/3569; A61M 2205/3584; A61M 2205/3592; A61M 2205/3633; A61M 2205/3653; A61M 2205/50; A61M 2205/502; A61M 2205/52; A61M 2205/6018; A61M 2205/6054; A61M 2205/8212; A61M 2205/8262; A61M 2206/14; A61M 2230/04; G05D 23/1931; G05D 23/22; H02J 1/14; Y10S 261/65

See application file for complete search history.

(56) References Cited

U.S. PATENT DOCUMENTS

| | | |
|---|---|---|
| 2,516,864 A | 8/1950 | Gilmore et al. |
| 2,788,936 A | 4/1957 | Kemnitz |
| 2,874,722 A | 2/1959 | Hamblin |
| 3,117,596 A | 1/1964 | Khan |
| 3,163,707 A | 12/1964 | Darling |
| 3,283,580 A | 11/1966 | Jacob et al. |
| 3,394,954 A | 7/1968 | Sarns |
| 3,495,628 A | 2/1970 | Boender |
| 3,582,968 A | 6/1971 | Buiting |
| 3,584,193 A | 6/1971 | Badertscher |
| 3,638,926 A | 2/1972 | Melville et al. |
| 3,695,267 A | 10/1972 | Hirtz et al. |
| 3,766,914 A | 10/1973 | Jacobs |
| 3,914,349 A | 10/1975 | Stipanuk |
| 3,926,223 A | 12/1975 | Petzetakis |
| 3,963,856 A | 6/1976 | Carlson et al. |
| 3,990,727 A | 11/1976 | Gallagher |
| 4,013,122 A | 3/1977 | Long |
| 4,013,742 A | 3/1977 | Lang |
| 4,033,808 A | 7/1977 | Petzetakis |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,110,419 A | 8/1978 | Miller |
| 4,111,197 A | 9/1978 | Warncke et al. |
| 4,160,466 A | 7/1979 | Jousson |
| 4,172,105 A | 10/1979 | Miller et al. |
| 4,301,200 A | 11/1981 | Langenfeld |
| 4,333,451 A | 6/1982 | Paluch |
| 4,428,403 A | 1/1984 | Lee et al. |
| 4,430,994 A | 2/1984 | Clawson et al. |
| 4,487,232 A | 12/1984 | Kanao |
| 4,490,575 A | 12/1984 | Kutnyak |
| 4,500,480 A | 2/1985 | Cambio, Jr. |
| 4,529,867 A | 7/1985 | Velnosky et al. |
| 4,531,551 A | 7/1985 | Eichelberger et al. |
| 4,553,023 A | 11/1985 | Jameson et al. |
| 4,574,188 A | 3/1986 | Midgley et al. |
| 4,597,917 A | 7/1986 | Lunsford |
| 4,621,632 A | 11/1986 | Bartels et al. |
| 4,640,804 A | 2/1987 | Mizoguchi |
| 4,676,237 A | 6/1987 | Wood et al. |
| 4,684,786 A | 8/1987 | Mann et al. |
| 4,686,354 A | 8/1987 | Makin |
| 4,695,955 A | 9/1987 | Faisandier |
| 4,708,831 A * | 11/1987 | Elsworth ........... A61M 16/0051 261/130 |
| 4,710,887 A | 12/1987 | Ho |
| 4,722,334 A | 2/1988 | Blackmer et al. |
| 4,753,758 A | 6/1988 | Miller |
| 4,773,448 A | 9/1988 | Francis |
| 4,780,247 A | 10/1988 | Yasuda |
| 4,829,781 A | 5/1989 | Hitzler |
| 4,829,997 A | 5/1989 | Douwens et al. |
| 4,829,998 A | 5/1989 | Jackson |
| 4,844,512 A | 7/1989 | Gahwiler |
| 4,861,523 A | 8/1989 | Beran |
| 4,903,736 A | 2/1990 | Baston et al. |
| 4,911,157 A | 3/1990 | Miller |
| 4,911,357 A | 3/1990 | Kitamura |
| 4,921,642 A | 5/1990 | LaTorraca |
| 4,941,469 A | 7/1990 | Adahan |
| 4,967,744 A | 11/1990 | Chua |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,127,442 A | 7/1992 | Blomqvist |
| 5,148,801 A | 9/1992 | Douwens et al. |
| 5,164,652 A | 11/1992 | Johnson et al. |
| 5,213,376 A | 5/1993 | Szabo |
| 5,224,923 A | 7/1993 | Moffett et al. |
| 5,230,331 A | 7/1993 | Rusz et al. |
| 5,231,979 A | 8/1993 | Rose et al. |
| 5,336,156 A | 8/1994 | Miller et al. |
| 5,346,128 A | 9/1994 | Wacker |
| 5,347,211 A | 9/1994 | Jakubowski |
| 5,367,604 A | 11/1994 | Murray |
| 5,388,443 A | 2/1995 | Manaka |
| 5,392,770 A | 2/1995 | Clawson et al. |
| 5,404,729 A | 4/1995 | Matsuoka et al. |
| 5,405,269 A | 4/1995 | Stupecky |

(56) References Cited

U.S. PATENT DOCUMENTS

| | | | |
|---|---|---|---|
| 5,428,752 A | 6/1995 | Goren et al. | |
| 5,449,234 A | 9/1995 | Gipp et al. | |
| 5,454,061 A | 9/1995 | Carlson | |
| 5,482,031 A | 1/1996 | Lambert | |
| 5,516,466 A | 5/1996 | Schlesch et al. | |
| 5,529,060 A | 6/1996 | Salmon et al. | |
| 5,537,996 A | 7/1996 | McPhee | |
| 5,551,731 A | 9/1996 | Gray et al. | |
| 5,558,084 A | 9/1996 | Daniell et al. | |
| 5,564,415 A | 10/1996 | Dobson et al. | |
| 5,588,423 A | 12/1996 | Smith | |
| 5,591,292 A | 1/1997 | Blomqvist | |
| 5,600,752 A | 2/1997 | Lopatinsky | |
| 5,630,806 A | 5/1997 | Inagaki | |
| 5,637,168 A | 6/1997 | Carlson | |
| 5,640,951 A | 6/1997 | Huddart et al. | |
| 5,673,687 A | 10/1997 | Dobson et al. | |
| 5,759,149 A | 6/1998 | Goldberg et al. | |
| 5,769,071 A | 6/1998 | Turnbull | |
| 5,778,872 A | 7/1998 | Fukunaga et al. | |
| 5,848,223 A | 12/1998 | Carlson | |
| 5,906,201 A | 5/1999 | Nilson | |
| 5,943,473 A | 8/1999 | Levine | |
| 5,988,164 A | 11/1999 | Paluch | |
| 5,991,507 A | 11/1999 | Bencsits | |
| 6,010,118 A | 1/2000 | Milewicz | |
| 6,024,694 A | 2/2000 | Goldberg et al. | |
| 6,038,457 A | 3/2000 | Barkat | |
| 6,050,260 A | 4/2000 | Daniell et al. | |
| 6,078,730 A | 6/2000 | Huddart et al. | |
| 6,095,505 A * | 8/2000 | Miller | A61M 16/1075 128/203.27 |
| 6,105,649 A | 8/2000 | Levingston et al. | |
| 6,109,782 A | 8/2000 | Fukura et al. | |
| 6,125,847 A | 10/2000 | Lin | |
| 6,138,674 A | 10/2000 | Gull et al. | |
| 6,142,974 A | 11/2000 | Kistner et al. | |
| 6,158,431 A | 12/2000 | Poole | |
| 6,167,883 B1 | 1/2001 | Beran et al. | |
| 6,189,870 B1 | 2/2001 | Withall | |
| 6,190,480 B1 | 2/2001 | Carlson | |
| 6,219,490 B1 | 4/2001 | Gibertoni et al. | |
| 6,272,933 B1 | 8/2001 | Gradon et al. | |
| 6,311,958 B1 | 11/2001 | Stanek | |
| 6,347,646 B2 | 2/2002 | Fukui et al. | |
| 6,349,722 B1 | 2/2002 | Gradon et al. | |
| 6,367,472 B1 | 4/2002 | Koch | |
| 6,367,510 B1 | 4/2002 | Carlson | |
| 6,374,864 B1 | 4/2002 | Philip | |
| 6,384,755 B1 | 5/2002 | Hayden | |
| 6,394,084 B1 | 5/2002 | Nitta | |
| 6,394,145 B1 | 5/2002 | Bailly | |
| 6,397,841 B1 | 6/2002 | Kenyon et al. | |
| 6,397,846 B1 | 6/2002 | Skog et al. | |
| 6,398,197 B1 | 6/2002 | Dickinson et al. | |
| 6,463,925 B2 | 10/2002 | Nuckols et al. | |
| 6,474,335 B1 | 11/2002 | Lammers | |
| 6,537,405 B1 | 3/2003 | Henderson et al. | |
| 6,540,734 B1 | 4/2003 | Chiu et al. | |
| 6,543,412 B2 | 4/2003 | Amou et al. | |
| 6,564,011 B1 | 5/2003 | Janoff et al. | |
| 6,584,972 B2 | 7/2003 | McPhee | |
| 6,594,366 B1 | 7/2003 | Adams | |
| 6,668,828 B1 | 12/2003 | Figley et al. | |
| 6,691,707 B1 | 2/2004 | Gunaratnam et al. | |
| 6,694,974 B1 | 2/2004 | George-Gradon et al. | |
| 6,718,974 B1 | 4/2004 | Moberg | |
| 6,827,109 B2 | 12/2004 | Mccaughtry | |
| 6,918,389 B2 | 7/2005 | Seakins et al. | |
| 6,932,119 B2 | 8/2005 | Carlson | |
| 6,953,354 B2 | 10/2005 | Edirisuriya et al. | |
| 7,086,422 B2 | 8/2006 | Kressierer/Huber et al. | |
| 7,096,864 B1 | 8/2006 | Mayer et al. | |
| 7,120,354 B2 | 10/2006 | Mackie et al. | |
| 7,156,127 B2 | 1/2007 | Moulton et al. | |
| 7,157,035 B2 | 1/2007 | Edirisuriya et al. | |
| 7,291,240 B2 | 11/2007 | Smith et al. | |
| 7,468,116 B2 | 12/2008 | Smith et al. | |
| 7,559,324 B2 | 7/2009 | Smith et al. | |
| 7,588,029 B2 | 9/2009 | Smith et al. | |
| 7,588,186 B2 | 9/2009 | Steffen et al. | |
| 7,637,288 B2 | 12/2009 | Huber et al. | |
| 7,647,926 B2 | 1/2010 | Gerder et al. | |
| 7,766,050 B2 | 8/2010 | Patel | |
| 7,814,907 B2 | 10/2010 | Bremner et al. | |
| 7,965,930 B2 | 6/2011 | Carlson et al. | |
| 7,983,542 B2 * | 7/2011 | McGhin | G05D 23/1931 392/485 |
| 7,997,267 B2 | 8/2011 | Ging et al. | |
| 8,091,547 B2 | 1/2012 | Thudor et al. | |
| 8,122,882 B2 | 2/2012 | Mcghin et al. | |
| 8,186,345 B2 | 5/2012 | Payton et al. | |
| 8,235,041 B2 | 8/2012 | Seakins et al. | |
| 8,333,194 B2 | 12/2012 | Lewis et al. | |
| 8,333,199 B2 | 12/2012 | Landis et al. | |
| 8,360,059 B2 | 1/2013 | Koulechov et al. | |
| 8,453,641 B2 | 6/2013 | Payton et al. | |
| 8,459,259 B2 | 6/2013 | Klasek et al. | |
| 8,469,025 B2 | 6/2013 | Mayer et al. | |
| 8,522,782 B2 | 9/2013 | Lewis et al. | |
| 8,563,863 B2 | 10/2013 | Carlson | |
| 8,563,864 B2 | 10/2013 | Carlson | |
| 8,631,789 B2 | 1/2014 | Virr et al. | |
| 8,709,187 B2 | 4/2014 | Smith et al. | |
| 8,733,349 B2 | 5/2014 | Bath et al. | |
| 8,844,522 B2 * | 9/2014 | Huby | A61M 16/0003 128/203.14 |
| 9,119,933 B2 | 9/2015 | Bedford et al. | |
| 9,440,040 B2 | 9/2016 | Klasek et al. | |
| 9,517,321 B2 | 12/2016 | Buechi et al. | |
| 9,555,210 B2 | 1/2017 | Seakins et al. | |
| 9,572,949 B2 | 2/2017 | Vos et al. | |
| 9,855,398 B2 * | 1/2018 | Klasek | A61M 16/0875 |
| 10,080,866 B2 | 9/2018 | Stoks et al. | |
| 10,589,050 B2 | 3/2020 | Buswell et al. | |
| 2001/0017134 A1 | 8/2001 | Bahr | |
| 2001/0050080 A1 | 12/2001 | Seakins et al. | |
| 2002/0038392 A1 | 3/2002 | De La Huerga | |
| 2002/0120236 A1 | 8/2002 | Diaz et al. | |
| 2002/0124847 A1 | 9/2002 | Smith et al. | |
| 2002/0173717 A1 | 11/2002 | Rohling et al. | |
| 2002/0186966 A1 | 12/2002 | Zimmer et al. | |
| 2003/0059213 A1 | 3/2003 | Mackie et al. | |
| 2003/0183294 A1 | 10/2003 | Carlson | |
| 2003/0236015 A1 | 12/2003 | Edirisuriya et al. | |
| 2004/0074493 A1 | 4/2004 | Seakins et al. | |
| 2004/0074495 A1 | 4/2004 | Wickham et al. | |
| 2004/0079371 A1 | 4/2004 | Gray | |
| 2004/0099268 A1 | 5/2004 | Smith et al. | |
| 2004/0101026 A1 | 5/2004 | Nitta et al. | |
| 2004/0149284 A1 | 8/2004 | Smith et al. | |
| 2004/0182392 A1 | 9/2004 | Gerder et al. | |
| 2004/0244858 A1 | 12/2004 | Jeong | |
| 2005/0059957 A1 | 6/2005 | Byerly et al. | |
| 2005/0152733 A1 | 7/2005 | Marchan | |
| 2006/0165829 A1 | 7/2006 | Smith et al. | |
| 2006/0283447 A1 | 12/2006 | Dhuper et al. | |
| 2007/0047733 A1 | 3/2007 | Bremer et al. | |
| 2007/0051368 A1 | 3/2007 | Seakins et al. | |
| 2007/0079982 A1 | 4/2007 | Laurent et al. | |
| 2007/0107737 A1 | 5/2007 | Landis et al. | |
| 2007/0277828 A1 | 12/2007 | Ho et al. | |
| 2008/0078259 A1 | 4/2008 | Duff | |
| 2008/0105257 A1 | 5/2008 | Klasek et al. | |
| 2008/0173305 A1 | 7/2008 | Frater | |
| 2008/0202512 A1 | 8/2008 | Kressierer/Huber et al. | |
| 2008/0251073 A1 | 10/2008 | Jassell et al. | |
| 2008/0264413 A1 | 10/2008 | Doherty et al. | |
| 2009/0078259 A1 | 3/2009 | Kooij et al. | |
| 2009/0078440 A1 | 3/2009 | Carlson et al. | |
| 2009/0110379 A1 | 4/2009 | McGhin et al. | |
| 2009/0126817 A1 | 5/2009 | Gray | |
| 2009/0149696 A1 | 6/2009 | Chilton, III | |
| 2009/0320840 A1 | 12/2009 | Klasek et al. | |

(56) References Cited

U.S. PATENT DOCUMENTS

| | | |
|---|---|---|
| 2010/0083965 A1 | 4/2010 | Virr et al. |
| 2010/0116272 A1 | 5/2010 | Row et al. |
| 2010/0224276 A1 | 9/2010 | Forrester et al. |
| 2011/0023874 A1 | 2/2011 | Bath et al. |
| 2011/0046494 A1 | 2/2011 | Balji et al. |
| 2011/0155132 A1 | 6/2011 | Virr et al. |
| 2011/0168287 A1 | 7/2011 | Carlson |
| 2012/0125333 A1 | 5/2012 | Bedford et al. |
| 2012/0255758 A1 | 10/2012 | Lee |
| 2013/0104888 A1 | 5/2013 | Landis et al. |
| 2013/0104901 A1 | 5/2013 | Landis et al. |
| 2013/0174839 A1 | 7/2013 | Ging et al. |
| 2013/0239966 A1 | 9/2013 | Klasek et al. |
| 2013/0255677 A1 | 10/2013 | Varga |
| 2013/0280055 A1 | 10/2013 | Daly et al. |
| 2013/0340752 A1 | 12/2013 | Landis et al. |
| 2014/0037276 A1 | 2/2014 | Carlson |
| 2014/0130802 A1 | 5/2014 | Virr et al. |
| 2014/0202460 A1 | 7/2014 | Bath et al. |
| 2014/0216459 A1 | 8/2014 | Vos et al. |
| 2014/0236083 A1 | 8/2014 | Sims |
| 2014/0246021 A1 | 9/2014 | Buechi et al. |
| 2014/0311487 A1 | 10/2014 | Buechi et al. |
| 2014/0318536 A1 | 10/2014 | Landis et al. |
| 2014/0366876 A1 | 12/2014 | Huby et al. |
| 2015/0090260 A1 | 4/2015 | Seakins et al. |
| 2015/0306333 A1 | 10/2015 | Amadio et al. |
| 2016/0256657 A1 | 9/2016 | Klasek et al. |
| 2016/0271356 A1 | 9/2016 | Robertson et al. |
| 2016/0354573 A1 | 12/2016 | Buswell et al. |
| 2017/0095637 A1 | 4/2017 | Seakins |
| 2017/0100556 A1 | 4/2017 | Munkelt et al. |
| 2018/0214657 A1 | 8/2018 | Forrester |
| 2018/0214659 A1 | 8/2018 | Forrester |
| 2018/0280651 A1 | 10/2018 | Liu et al. |
| 2019/0076620 A1 | 3/2019 | Stoks et al. |
| 2020/0016361 A1 | 1/2020 | Buswell et al. |

FOREIGN PATENT DOCUMENTS

| | | |
|---|---|---|
| AU | 2007317198 A1 | 5/2008 |
| CA | 2674249 C | 4/2014 |
| CN | 2243015 Y | 12/1996 |
| CN | 1549910 | 11/2004 |
| CN | 101018582 A | 8/2007 |
| CN | 101541367 A | 9/2007 |
| CN | 201672170 U | 12/2010 |
| DE | 36 29 353 | 1/1988 |
| DE | 4020522 A1 | 1/1992 |
| DE | 40 34 611 | 5/1992 |
| DE | 4102223 A1 | 7/1992 |
| DE | 9200567 U1 | 7/1992 |
| DE | 33 11 811 | 10/1994 |
| DE | 94 09 231.1 | 12/1994 |
| DE | 19647548 A1 | 5/1998 |
| DE | 19958296 C1 | 9/2001 |
| DE | 20202906 U1 | 5/2002 |
| DE | 10312881 B3 | 5/2004 |
| DE | 20 2004 006 484 U1 | 9/2005 |
| DE | 202005008156 U1 | 11/2006 |
| DE | 202006007397 U1 | 9/2007 |
| DE | 202006007397 U1 | 10/2007 |
| DE | 102006056781 A1 | 6/2008 |
| DE | 102007003454 | 7/2008 |
| DE | 102007003454 A1 | 7/2008 |
| DE | 102007003455 A1 | 8/2008 |
| DE | 202007018764 U1 | 6/2009 |
| DE | 102011055439 A1 | 5/2013 |
| EP | 0111248 A2 | 6/1984 |
| EP | 0201985 | 11/1986 |
| EP | 0232864 A2 | 8/1987 |
| EP | 0 258 928 | 9/1988 |
| EP | 0342802 | 11/1989 |
| EP | 0 481 459 | 4/1992 |
| EP | 0 556 561 | 8/1993 |
| EP | 616 166 | 9/1994 |
| EP | 0621050 A2 | 10/1994 |
| EP | 0 672 430 | 9/1995 |
| EP | 0 885 623 | 12/1998 |
| EP | 0956068 | 11/1999 |
| EP | 1078645 | 2/2001 |
| EP | 1127583 | 8/2001 |
| EP | 1 138 341 | 10/2001 |
| EP | 1145678 | 10/2001 |
| EP | 1147004 B1 | 2/2003 |
| EP | 1352670 A1 | 10/2003 |
| EP | 1380276 A1 | 1/2004 |
| EP | 1396277 A2 | 3/2004 |
| EP | 1535722 A2 | 6/2005 |
| EP | 1579984 A2 | 9/2005 |
| EP | 2075026 A1 | 7/2009 |
| EP | 2079505 | 7/2009 |
| EP | 2269680 A1 | 1/2011 |
| EP | 2133611 B1 | 9/2011 |
| EP | 2269680 | 9/2012 |
| EP | 2514478 | 7/2013 |
| EP | 2689174 | 1/2014 |
| EP | 2337604 | 3/2014 |
| EP | 2747816 B1 | 1/2018 |
| GB | 1 167 551 | 10/1969 |
| GB | 2056611 | 3/1981 |
| GB | 2173274 A | 10/1986 |
| GB | 2 277 689 | 11/1994 |
| JP | S56-109189 U | 8/1981 |
| JP | S59-113392 | 6/1984 |
| JP | 05-317428 | 12/1993 |
| JP | 08-061731 | 3/1996 |
| JP | H08-109984 A | 4/1996 |
| JP | H09-234247 | 9/1997 |
| JP | H09-276408 | 10/1997 |
| JP | H11-33119 A | 2/1999 |
| JP | H11-286058 | 10/1999 |
| JP | 2001-129091 | 5/2001 |
| JP | 2001-511507 A | 8/2001 |
| JP | 2003-139276 A | 5/2003 |
| JP | 2004-148817 | 5/2004 |
| JP | 4422293 B2 | 2/2010 |
| NZ | 579384 | 5/2011 |
| NZ | 587113 | 12/2011 |
| NZ | 589766 | 5/2012 |
| NZ | 575837 | 7/2012 |
| NZ | 583968 | 10/2012 |
| NZ | 597827 | 6/2013 |
| NZ | 590924 | 8/2013 |
| NZ | 600986 | 8/2013 |
| NZ | 597179 | 9/2013 |
| NZ | 605324 | 6/2014 |
| NZ | 605326 | 7/2014 |
| NZ | 607629 | 7/2014 |
| NZ | 610299 | 11/2014 |
| NZ | 701541 | 5/2015 |
| NZ | 625795 | 6/2015 |
| NZ | 620739 | 8/2015 |
| NZ | 625605 | 4/2016 |
| NZ | 710351 | 1/2017 |
| NZ | 631008 | 7/2017 |
| SU | 379270 | 4/1973 |
| WO | WO 92/21163 A1 | 11/1992 |
| WO | WO 1996/020748 A1 | 7/1996 |
| WO | WO 97/18001 | 5/1997 |
| WO | WO 97/18001 A1 | 5/1997 |
| WO | WO 98/26826 | 6/1998 |
| WO | WO 01/10489 | 2/2001 |
| WO | WO 02/32486 | 4/2002 |
| WO | WO 2003/022342 A1 | 3/2003 |
| WO | WO 2003/026721 A2 | 4/2003 |
| WO | WO 2004/024429 A1 | 3/2004 |
| WO | WO 2004/039444 A1 | 5/2004 |
| WO | WO 2004/105847 | 12/2004 |
| WO | WO 2004/105848 A1 | 12/2004 |
| WO | WO 2005/021076 A2 | 3/2005 |
| WO | WO 2006/092001 A1 | 9/2006 |
| WO | WO 2006/095151 | 9/2006 |
| WO | WO 2007/051230 A1 | 5/2007 |

(56) References Cited

FOREIGN PATENT DOCUMENTS

| | | |
|---|---|---|
| WO | WO 2008/055307 A1 | 5/2008 |
| WO | WO 2008/055308 A1 | 5/2008 |
| WO | WO 2008/060046 A1 | 5/2008 |
| WO | WO 2008/060295 | 5/2008 |
| WO | WO 2008/076230 | 6/2008 |
| WO | WO 2009/015410 | 2/2009 |
| WO | WO 2009/015410 A1 | 2/2009 |
| WO | WO 2009/022004 A2 | 2/2009 |
| WO | WO 2010/084183 A2 | 7/2010 |
| WO | WO 2011/051837 | 5/2011 |
| WO | WO 2011/051837 A1 | 5/2011 |
| WO | WO 2011/051870 A1 | 5/2011 |
| WO | WO 2011/136665 A1 | 11/2011 |
| WO | WO 2011/162622 A1 | 12/2011 |
| WO | WO 2012/053910 A1 | 4/2012 |
| WO | WO 2012/164407 A1 | 12/2012 |
| WO | WO 2013/026901 A1 | 2/2013 |
| WO | WO 2013/045575 | 4/2013 |
| WO | WO 2013/072119 A1 | 5/2013 |
| WO | WO 2013/127474 | 9/2013 |
| WO | WO 2013/137753 A1 | 9/2013 |
| WO | WO 2013/147623 A1 | 10/2013 |
| WO | WO 2013/165263 A1 | 11/2013 |
| WO | WO 2014/025266 | 2/2014 |
| WO | WO 2014/077706 | 5/2014 |
| WO | WO 2014/077706 A1 | 5/2014 |
| WO | WO 2014/088430 A1 | 6/2014 |
| WO | WO 2014/205513 | 12/2014 |
| WO | WO 2015/038013 | 3/2015 |
| WO | WO 2015/038013 A1 | 3/2015 |
| WO | WO 2015/142192 | 9/2015 |
| WO | WO 2017/043981 A1 | 3/2017 |
| WO | WO 2018/116187 | 6/2018 |

OTHER PUBLICATIONS

International Search Report in corresponding International Patent Application No. PCT/NZ2016/050144, dated Dec. 22, 2016, in 8 pages.
MR810 Respiratory Humidifier Technical Manual, Revision C.
Fisher & Paykel Healthcare, Annual Report 2003.
Fisher & Paykel Healthcare, FY04 Full Year Overview & Update, May 24, 2004.
Fisher & Paykel Healthcare, Full Year Analyst Briefing, Jun. 5, 2002.
MR850 Respiratory Humidifier Instruction Sheet, Rev. G, Feb. 2004.

* cited by examiner

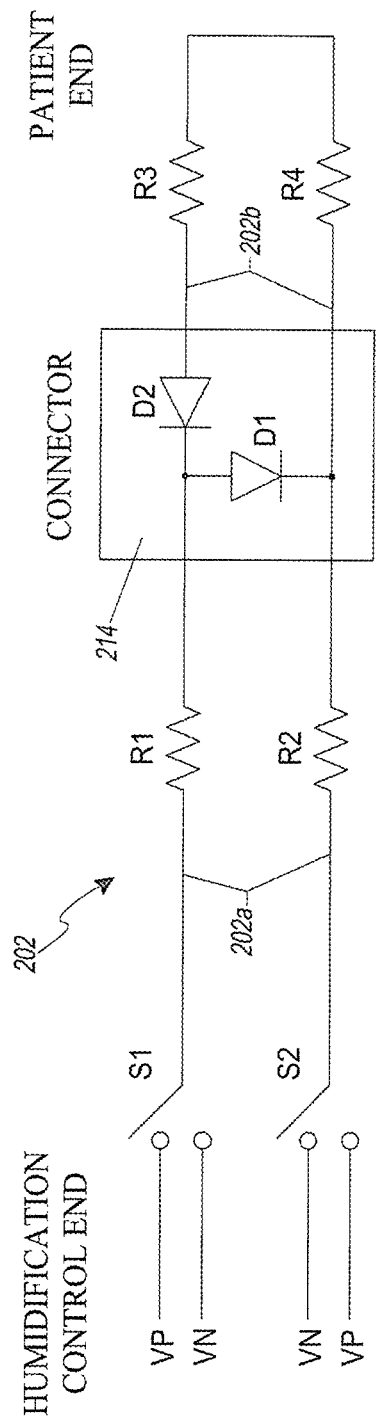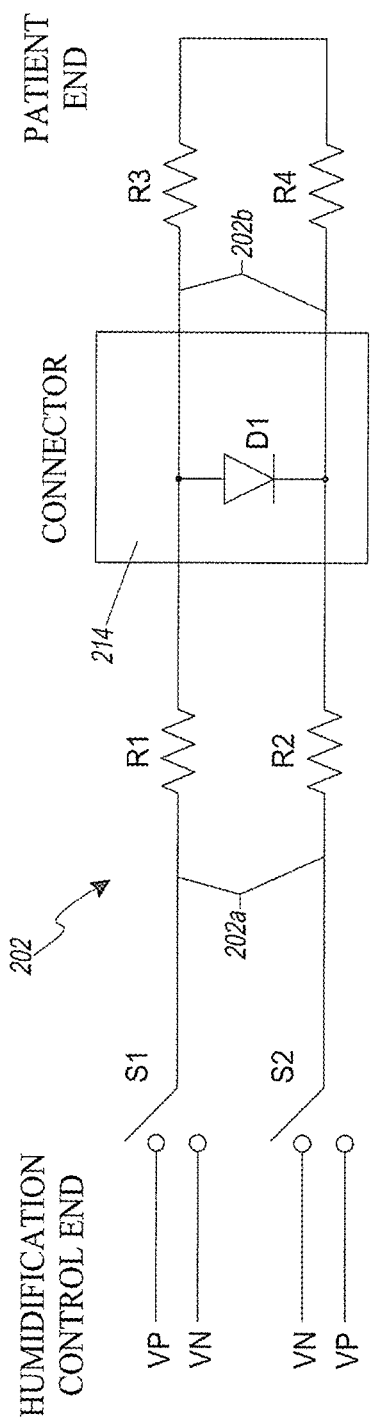
FIG. 3A
FIG. 3B

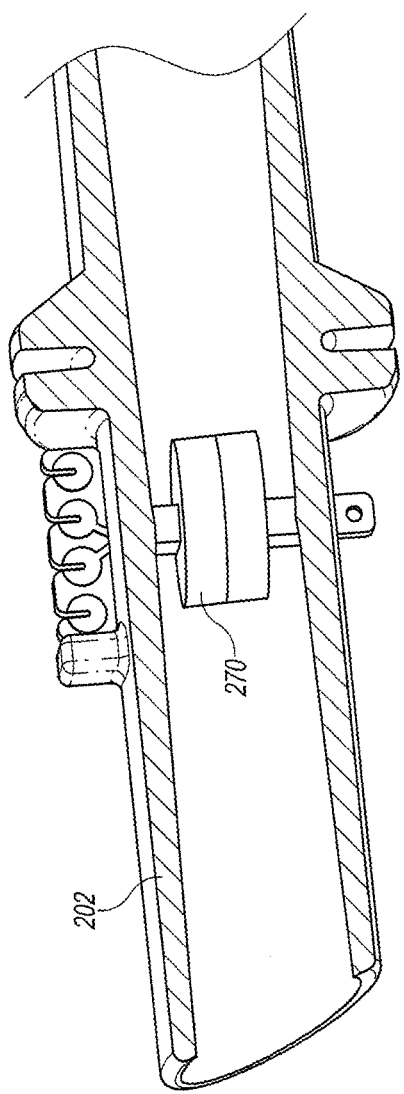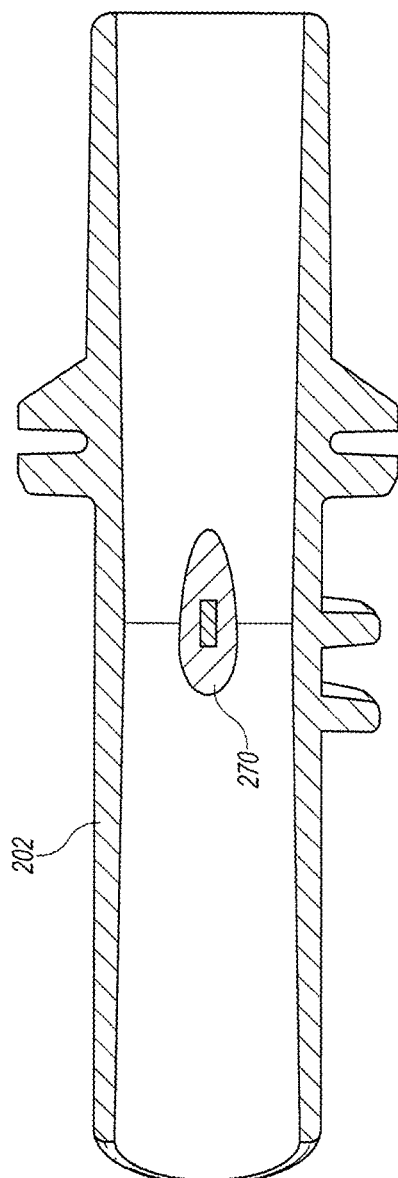

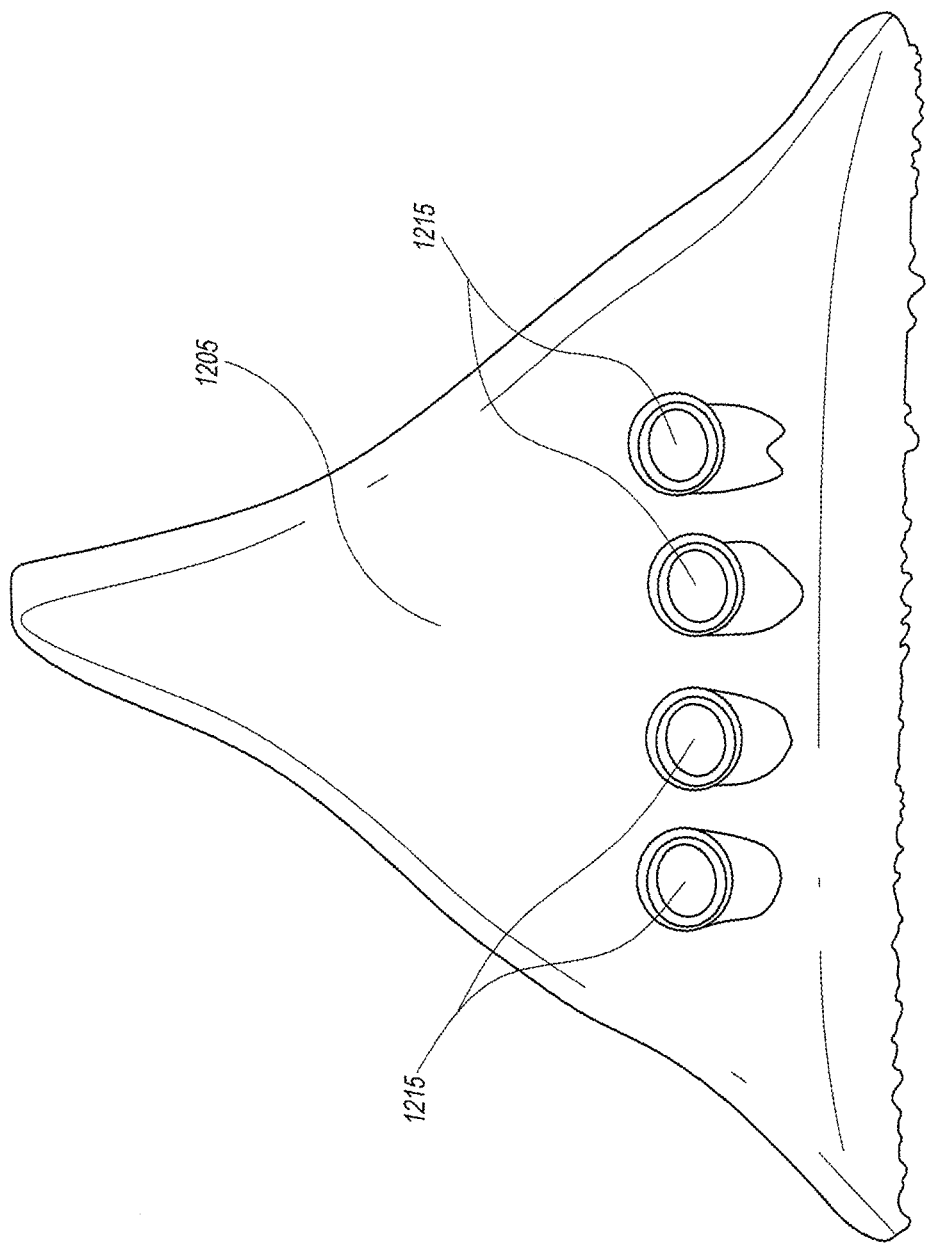

ZONE HEATING FOR RESPIRATORY CIRCUITS

INCORPORATION BY REFERENCE

Any and all applications for which a foreign or domestic priority claim is identified in the Application Data Sheet as filed with the present application are hereby incorporated by reference under 37 CFR 1.57.

FIELD OF THE DISCLOSURE

The present disclosure generally relates to humidification systems for providing humidified gases to users, and more particularly to heating gases in respiratory circuits used with humidification systems.

BACKGROUND

Many gas humidification systems deliver heated and humidified gases for various medical procedures, including respiratory treatment, laparoscopy, and the like. These systems can be configured to control temperature, humidity and flow rates using feedback from sensors. To maintain desirable properties upon delivery to a user, a breathing circuit can have heaters associated with gas conduits where the heaters provide heat to the gas as it flows to and/or from the user. The conduit heaters can be controlled to provide heat to the gas so that the gas arrives to the user having desirable properties such as temperature and/or humidity. A humidification system can include a temperature sensor to provide feedback to a humidification controller which can adjust and/or modify power delivered to the conduit heaters to achieve a target temperature at a location along an associated conduit.

SUMMARY

The systems, methods and devices described herein have innovative aspects, no single one of which is indispensable or solely responsible for their desirable attributes. Without limiting the scope of the claims, some of the advantageous features will now be summarized.

Some embodiments provide for an inspiratory limb for a breathing circuit. The inspiratory limb described herein is particularly useful in situations where heated and humidified gases must pass through two distinct environments. This can be a problem, for example, in infant incubators where the temperature is significantly higher than the surrounding environment or where a portion of the conduit delivering the gases to the patient is under a blanket. The embodiments disclosed herein, however, can be used in any environment where heated and/or humidified gas is delivered to a patient and are not limited to uses where the inspiratory limb passes through two distinct environments.

The inspiratory limb can include a first segment of the inspiratory limb that comprises a first structure forming a conduit, the conduit configured to transport a humidified gas, and wherein the first segment of the inspiratory limb includes a first heater wire circuit. The inspiratory limb can include a second segment of the inspiratory limb that comprises a second structure forming a conduit configured to transport the humidified gas, wherein the second structure is configured to mechanically couple to the first structure of the first segment to form an extended conduit for the humidified gas and wherein the second segment of the inspiratory limb includes a second heater wire circuit. The inspiratory limb can include an intermediate connector that includes a connection circuit that electrically couples the first heater wire circuit to the second heater wire circuit, wherein the intermediate connector can be coupled to a patient end of the first segment of the inspiratory limb and a chamber end of the second segment of the inspiratory limb to form a single conduit for the humidified gases. The intermediate connector can be covered by a portion of the first segment of the inspiratory limb, a portion of the second segment of the inspiratory limb, or a portion of both the first and second segments of the inspiratory limb such that the intermediate connector is internal to the inspiratory limb.

The inspiratory limb can be configured to operate in two heating modes. In a first heating mode, electrical power passes through the intermediate connector to provide power to the first heater wire circuit without providing power to the second heater wire circuit. In a second heating mode, electrical power passes through the intermediate connector to provide power to both the first heater wire circuit and the second heater wire circuit. For example, the intermediate connector can include electrical components configured to direct electrical power along different paths based at least in part on a direction of current flow and/or a polarity of voltage. The intermediate connector can include conductive tracks which can provide a short (e.g., a direct electrical connection with no intervening electrical components) between one or more wires in the first heater wire circuit and one or more wires in the second heater wire circuit. The intermediate connector can include conductive tracks which electrically couple one or more wires in the first heater wire circuit to one or more wires in the second heater wire circuit, where the conductive tracks include electrical components such as, for example and without limitation, diodes, transistors, capacitors, resistors, logic gates, integrated circuits, or the like. In certain embodiments, the intermediate connector includes a diode electrically coupled to both the first heater wire circuit and the second heater wire circuit. In certain embodiments, the inspiratory limb can further comprise a first sensor circuit having a first sensor positioned at the intermediate connector. In certain embodiments, the inspiratory limb further comprises a second sensor circuit having a second sensor positioned at a patient-end connector, the patient-end connector being positioned at a patient end of the second segment of the inspiratory limb. The inspiratory limb can be configured to operate in two sensing modes. In a first sensing mode, signals from the first sensor are received without receiving signals from the second sensor. In a second sensing mode, signals from the second sensor are received without receiving signals from the first sensor. In some embodiments, sensing includes receiving signals from both the first and second sensors in parallel. In such embodiments, an algorithm can determine a parameter measured by the first sensor based at least in part on the signals received in parallel from both the first and second sensors. In certain embodiments, the intermediate connector includes a diode electrically coupled to both the first sensor circuit and the second sensor circuit. The patient-end connector can be configured to provide electrical connections for the second sensor circuit. Similarly, the patient-end connector can be configured to provide electrical connections for the second heater wire circuit. The sensors can be temperature sensors, humidity sensors, flow sensors, or the like. The first and second sensors can be sensors configured to measure one or more parameters, such as temperature, humidity, flow rate, oxygen percentage, or the like. In some embodiments, the first and second sensors are configured to measure at least one like parameter (e.g., temperature, humidity, flow rate, etc.). In some embodiments, more than two sensors can be included and can be positioned at the intermediate connector and/or the patient-end connector.

Some embodiments provide for a respiratory humidification system with an inspiratory limb and a controller. The inspiratory limb can include a first segment having a first heater wire circuit, a second segment having a second heater wire circuit, an intermediate connector having a connector circuit configured to electrically couple the first heater wire circuit to the second heater wire circuit, a first sensor positioned at a patient end of the first segment, and a second sensor positioned at a patient end of the second segment. The controller can be adapted to selectively switch between a first mode and a second mode wherein in the first mode the controller provides electrical power to the first heater wire circuit through the connector circuit and in a second mode the controller provides electrical power to the first and second heater wire circuits. In certain embodiments, the respiratory humidification system switches between modes based at least in part on input from one or both sensors. In certain embodiments, the switching is done based at least in part on parameters including one or more of temperature, flow, humidity, power, or any combination of these. The parameters can be derived or obtained directly from the first sensor, the second sensor, or a combination of both sensors. In certain embodiments, the first and second modes are defined by a direction of current flow or a polarity of voltage provided by a power source. In some embodiments, the respiratory humidification system can include more than two sensors which provide input used to control heating of the inspiratory limb.

Some embodiments provide for a dual limb circuit that can include an inspiratory limb. Such an inspiratory limb can include a first segment having a first heater wire circuit, a second segment of the inspiratory limb having a second heater wire circuit, an intermediate connector having a connector circuit configured to electrically couple the first heater wire circuit to the second heater wire circuit, a first sensor positioned at a patient end of the first segment, and a second sensor positioned at a patient end of the second segment. The dual limb circuit can also include an expiratory limb with an expiratory heater wire circuit. The dual limb system can further include an interface connected to the inspiratory limb and the expiratory limb. The dual limb system can further include a controller adapted to selectively switch between a first mode and a second mode wherein in the first mode the controller provides electrical power to the first heater wire circuit through the connector circuit and in a second mode the controller provides electrical power to the first and second heater wire circuits. In certain embodiments, heating of the expiratory limb is performed using the expiratory heater wire circuit independent of the heating of the inspiratory limb using the first and second heater wire circuits. In certain embodiments, the expiratory limb is powered in parallel with the first heater wire circuit in the first segment of the inspiratory limb and/or in parallel with the first and second heater wire circuits. In certain embodiments, the expiratory limb can be designed to be powered in only the first mode, only the second mode, or in both the first mode and in the second mode. In certain embodiments, the interface is connected via a wye-piece. Any suitable patient interface can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows.

In some embodiments, a segmented inspiratory limb is provided, wherein the structure of the segments comprise an elongate tube. The elongate tubes can include a first elongate member comprising a hollow body spirally wound to form at least in part a conduit having a longitudinal axis, a lumen extending along the longitudinal axis, and a hollow wall surrounding the lumen. The elongate tubes can include a second elongate member spirally wound and joined between adjacent turns of the first elongate member, the second elongate member forming at least a portion of the lumen of the elongate tube. In certain implementations, the first elongate member forms in longitudinal cross-section a plurality of bubbles with a flattened surface at the lumen. In certain implementations, adjacent bubbles are separated by a gap above the second elongate member. In certain implementations, adjacent bubbles are not directly connected to each other. In certain implementations, the plurality of bubbles has perforations.

Some embodiments provide for a respiratory humidification system with two control circuits. The respiratory humidification system can include an inspiratory limb including a first segment with a first heater wire, a second segment with a second heater wire. The respiratory humidification system can also include a sensor positioned at a patient end of the second segment for measuring a patient end parameter. The first and second heater wires are electrically coupled, the first heater wire forming a first heater circuit and the first and second wire forming a second heater circuit. The respiratory humidification system can include a hardware controller configured to receive an output of the sensor. The hardware controller can be further configured to provide electrical power to the first heater circuit when a difference between the output of the sensor and a patient end parameter set point is below a predetermined threshold and to provide electrical power to the second heater circuit when the difference between the output of the sensor and the patient end parameter set point is at or above the predetermined threshold. When the hardware controller provides electrical power to the first heater circuit, the hardware controller can be configured to provide a maximum power to the first heater circuit. In some embodiments, the respiratory humidification system can further include an intermediate connector having a connector circuit configured to electrically connect the first and second heater wires. In some embodiments, the patient end parameter can be temperature. In some embodiments, the first and second heater wires can be exposed to different ambient environments. In some embodiments, the first and second heater wires can be exposed to different ambient temperatures. In some embodiments, power supplied to the first and/or the second heater circuits can be determined by a PID control scheme.

Some embodiments provide for a respiratory humidification system with two control circuits. The respiratory humidification system can include an inspiratory limb including a first segment with a first heater wire, a second segment with a second heater wire, and a temperature sensor positioned at a patient end of the second segment for measuring a patient end parameter. The first and second heater wires can be electrically coupled, the first heater wire forming a first heater circuit and the first and second wire forming a second heater circuit, the first and second heater wires configured to heat respiratory gases passing through the inspiratory limb. The respiratory humidification system can include a flow sensor in a flow path of the system and configured to measure a flow rate of the respiratory gases. The respiratory humidification system can include a hardware processor in electrical communication with the first and second heater wires and the temperature and flow sensors. The hardware processor can be configured to execute software instructions which can cause the processor to control the first and second heater circuits. When a difference between an output of the sensor and a patient end parameter set point is below a predetermined error threshold, the processor can be configured to heat the respiratory gases using the first heater circuit until a maximum temperature is reached in the first heater wire. When the difference between the output of the sensor and the patient end parameter set point is at or above the predetermined error threshold, the processor can be configured to heat the respiratory gases using the second heater circuit. The maximum power provided to the first heater circuit can be a first maximum value or a second maximum value based on the flow rate, the first maximum value being higher than the second maximum value.

In some embodiments, the maximum power can be the first maximum value when the measured flow rate is higher than a flow rate threshold, and a second maximum value when the measured flow rate is below the flow rate threshold. In some embodiments, the flow rate threshold can be between about 2.4 lpm and about 5 lpm. In some embodiments, the flow rate threshold can be about 3.5 lpm. In some embodiments, the flow rate threshold can be about 3 lpm.

In other embodiments, when the first maximum power is being provided to the first heater circuit and the measured flow rate decreases to a high flow to low flow threshold, the maximum power provided to the first heater circuit can switch to the second maximum power. When the second maximum power is being provided to the first heater circuit and the flow rate increases to a low flow to high flow threshold, the maximum power provided to the first heater circuit can switch to the first maximum power, the high flow to low flow threshold being lower than the low flow to high flow threshold. In some embodiments, the high flow to low flow threshold can be between about 2.4 lpm and about 5 lpm. In some embodiments, the low flow to high flow threshold is about 6.5 lpm.

In some embodiments with the flow sensor, a portion of the first segment of the inspiratory limb that is adjacent to the second segment can be exposed to the same ambient environment as the second segment. In some embodiments, the portion of the first segment and the second segment can be inside an incubator and a remaining portion of the first segment can outside the incubator.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIGS. 3A and 3B illustrate example circuit diagrams including an active rectified power source for providing power to heater wires in a segmented inspiratory limb of a breathing circuit, wherein the circuit is configured to power heater wires in a first segment of the inspiratory limb in a first mode and to power heater wires in both segments in a second mode.

FIGS. 15B-15E illustrate example embodiments of patient-end connectors.

FIG. 18G illustrates another example second elongate member.

DETAILED DESCRIPTION

Figure 1:
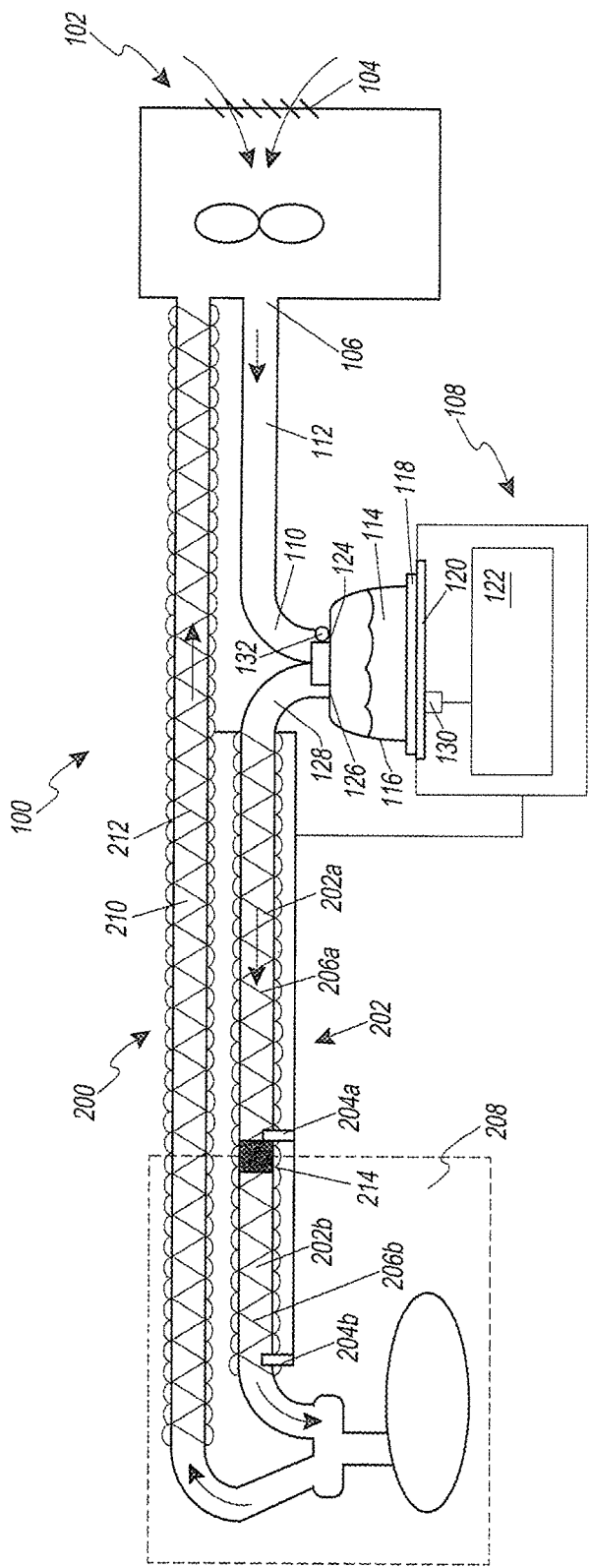
FIG. 1 illustrates an example respiratory humidification system for delivering humidified gas to a user, the respiratory humidification system having a breathing circuit that includes a segmented inspiratory limb with sensors in each segment.

Certain embodiments and examples of segmented inspiratory limbs, multiple-zone heating, and heating of inspiratory and/or expiratory limbs are described herein. Those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described herein.

Described herein are systems and methods for providing heat to a segmented inspiratory limb or providing heat to inspiratory and/or expiratory limbs in a breathing circuit of a respiratory humidification system. It will be understood that although much of the description herein is in the context of segmented inspiratory and/or expiratory limbs in breathing circuits, one or more features of the present disclosure can also be implemented in other scenarios where it is desirable to provide differential heating in segmented gas delivery conduits or independent heating of separate gas delivery conduits such as in respiratory, surgical, or other applications.

The disclosure references heater wires, heating elements, and/or heaters in the context of providing heat to a conduit. Heater wire, for example, is a broad term and is to be given its ordinary and customary meaning to a person of ordinary skill in the art (that is, it is not to be limited to a special or customized meaning) and includes, without limitation, heater strips and/or conductive elements that produce heat when electrical power is provided. Examples of such heating elements include wires made of a conductive metal (e.g., copper), conductive polymers, conductive inks printed on a surface of a conduit, conductive materials used to create a track on a conduit, and the like. Furthermore, the disclosure references conduits, limbs, and medical tubes in the context of gas delivery. Tube, for example, is a broad term and is to be given its ordinary and customary meaning to a person of ordinary skill in the art and includes, without limitation, passageways having a variety of cross-sections such as cylindrical and non-cylindrical passageways. Certain embodiments may incorporate a composite tube, which may generally be defined as a tube comprising two or more portions, or, specifically, in some embodiments, two or more components, as described in greater detail below. The segmented limbs comprising the disclosed medical tubes can also be used in breathing circuits such as a continuous, variable, or bi-level positive airway pressure (PAP) system or other form of respiratory therapy. The terms conduit and limb should be construed in a manner that is similar to tube.

When a heated, humidified breathing tube is used for an incubator or a temperature controlled environment (or any region where there is a temperature change, such as around radiant warmers used for burn victims, or under a blanket used by a patient), the breathing tube may pass through at least two distinct zones: a lower temperature zone (such as the one outside the incubator) and a higher temperature zone (such as the one inside the incubator). If the tube is heated by a single heater along its full length, one of the zones will tend to be at an undesirable, unsuitable, or non-optimal temperature, depending on which zone is sensed (e.g., which zone contains a temperature sensor). If the heater is controlled to a sensor inside the incubator (such as to a patient-end temperature sensor), the section outside the incubator will tend to be too cool, which can lead to condensation. Conversely, if the heater is controlled to a sensor outside the incubator, the section inside the incubator will tend to be too hot, which can lead to overheated gas being provided to the patient. Accordingly, the present disclosure describes systems and methods that provide for control over heat in a segmented breathing tube wherein each segment has an associated sensor providing feedback to a control module. Although several embodiments are described herein with respect to two zones, such a system could also be extended to apply to uses with additional zones, segments, or regions. For example, in an embodiment comprising three temperature zones, segments of the breathing tube may be heated based at least in part on three different temperature sensors in the zones. Furthermore, the embodiments disclosed herein can control the heat delivered to a breathing tube based at least in part on a parameter at the patient end, bypassing or ignoring one or more of the sensors at intermediate points along the tube. Moreover, the embodiments disclosed herein can control the heat delivered to a breathing tube using parameters provided by sensors including, for example and without limitation, temperature sensors, humidity sensors, flow sensors, oxygen sensors, and the like.

A control module can monitor and control the heating temperatures in multiple zones or sections. The control module can be configured to provide heat to a first section of the breathing tube in a first mode and to the entire breathing tube in a second mode using embodiments of connector assemblies described herein. The embodiments described herein can be used without flying leads, exposed connectors, and/or patient-end electrical connections. Flying leads as used herein include electrical connections that extend externally of the breathing tubes, internally through the breathing tubes, and incorporated, molded, or otherwise formed or included as part of the breathing tubes. The control module can be located within the humidifier or externally to it. In some embodiments, the control module is located within the humidifier to control the heater wires associated with a first segment of an inspiratory limb, a second segment of an inspiratory limb, and an expiratory limb as well as read parameters from sensors associated with the first and second segments of the inspiratory limb and/or the expiratory limb. In some embodiments, the control module is configured to independently control heater wires associated with an inspiratory limb and heater wires associated with an expiratory limb.

The control module can also adaptively change the temperature for the segments. For example, the control module can monitor temperature sensors associated with one or more segments. The monitoring can be continuous, based on intervals, or other schemes such as interrupt or event-based monitoring. For example, the monitoring of temperature sensors can be based on reading values from an analog to digital converter, determining a voltage or current, sensing a logic condition, reading thermostatic devices, measuring thermistor values, measuring resistance temperature detectors, measuring the voltage of a thermocouple, or other methods for sensing temperature, including, but not limited to the use of semiconductor junction sensor, infrared or thermal radiation sensors, thermometers, indicators, or the like. In some embodiments, the temperature sensors are thermistors.

In some embodiments, the ratio of the power delivered to the first segment of the inspiratory limb and the second segment of the inspiratory limb can change during use based at least in part on feedback from sensors associated with each segment. For example, the ratio of power can be changed in a manner such that each segment is heated to a temperature to reduce or eliminate condensation. As a further example, the ratio of power can be changed so that overheated gas is not provided to the patient. In some embodiments, the ratio of power can be continuously changed based on feedback from sensors (e.g., temperature sensors, humidity sensors, oxygen sensors, flow sensors, etc.). The ratio of power can be changed in different ways. For example, the ratio of power can be changed by altering the amplitude of a power signal (including, without limitation, the voltage and/or current), the duration of the power signal, the duty cycle of the power signal, or other suitable changes to the power signal. In an embodiment, the ratio of power is changed by altering the magnitude of the current provided. Similarly, in some embodiments, the ratio of power delivered to the inspiratory limb and the expiratory limb can change during use based at least in part on feedback from sensors associated with each limb.

Some embodiments provide for an inspiratory limb comprising heater wires that are not within the gas path, but are contained within a material that separates them from the gas path and that also insulates them from an external environment. In some embodiments, the circuitry used to provide power to heater wires in the segments and to read the sensors is internal to the inspiratory limb such that it is not exposed to the external environment. In some embodiments, the heater wire is molded into the inspiratory or expiratory tube such that the ends of the heater wires in complementary segments of the tube contact an intermediate connector such that the heater wires electrically couple to the intermediate connector, wherein the intermediate connector can be configured to provide circuitry for heater wire control and/or sensor readings. In some embodiments, a duty cycle of a power source applied to a heater wire can be modulated, modified and/or varied to alter an amount of heat delivered to a gas as it flows along the associated segment or limb.

Some embodiments described herein provide for a respiratory humidification system that is configured to deliver warm, humidified gas to a patient or other user. The gas is passed through a liquid chamber which is filled with a liquid (e.g., water) that is heated using a heater plate. The liquid evaporates in the chamber and combines with the gas which flows over it, thereby heating and/or humidifying the gas. The humidified gas can be directed to an inspiratory limb having one or more heater wires associated therewith. The heater wires can be selectively powered to provide a defined, desired, appropriate, or selected amount of heat to the humidified gas. In some embodiments, the respiratory humidification system can be used in conjunction with an incubator or radiant warmer or a temperature controlled environment. The temperature controlled environment may be a substantially sealed environment where the temperature within the environment is strictly controlled within pre-defined temperature limits. A temperature controlled environment as referred to defines a sealed enclosure that includes a strict temperature control. The inspiratory limb can be segmented such that a first segment is outside the incubator and a second segment is inside the incubator. Furthermore, a first set of heater wires can be associated with the first segment and a second set of heater wires can be associated with the second segment. The humidification system can be configured to provide power to the first set of heater wires in a first mode and to the first set and second set of heater wires in a second mode. In some embodiments, the humidification system can be configured to provide power to the first set of heater wires in a first mode and to the second set of heater wires in a second mode. In some embodiments the first section or first set of heater wires is heated and both the first and second sets of heater wires are only heated if there is a sudden change in the temperature controlled environment or incubator such as due to draft, or a fan or a blanket being placed over the sensor of the tube within the incubator. The inspiratory limb can include sensors at the end of each segment to provide feedback to the humidification system for use in selecting a power to deliver to the sets of heater wires in the segments. In some embodiments a sensor may be located only at the end of the entire tube, and the sensor may be located within the temperature controlled environment or incubator or radiant warmer. In some embodiments, the humidification system can include an expiratory limb having associated heater wires which are also selectively controlled by the humidification system. In the present disclosure, the segmented limb is described with reference to an inspiratory limb. However, the described features can be applied to an expiratory limb as well.

Respiratory Humidification Systems

FIG. 1 illustrates an example respiratory humidification system 100 for delivering humidified gas to a user, the respiratory humidification system 100 having a breathing circuit 200 that includes a segmented inspiratory limb 202 with first and second sensors 204a, 204b in each segment. The segmented inspiratory limb 202 can be used in conjunction with an incubator 208, as illustrated, or with another system where there are different temperatures along different segments of the inspiratory limb 202, such as in conjunction with a radiant warmer or a temperature controlled environment. The segmented inspiratory limb 202 can be used to provide different levels of heat to different, first and second, segments of the inspiratory limb 202a, 202b to reduce or prevent condensation and/or to control a temperature of gas delivered to a user.

The illustrated respiratory humidification system 100 comprises a pressurized gas source 102. In some implementations, the pressurized gas source 102 comprises a fan, blower, or the like. In some implementations, the pressurized gas source 102 comprises a ventilator or other positive pressure generating device. In some implementations the gases source can be a pressurized gases reservoir and the gases can be supplied by an outlet such as a wall gases source in a hospital. The pressurized gas source 102 comprises an inlet 104 and an outlet 106.

The pressurized gas source 102 provides a flow of fluid (e.g., oxygen, anesthetic gases, air, air and oxygen mixture, a gases mixture or the like) to a humidification unit 108. The fluid flow passes from the outlet 106 of the pressurized gas source 102 to an inlet 110 of the humidification unit 108. In the illustrated configuration the humidification unit 108 is separate from the gases source 102 and is removably connectable to the gases source 102. In the illustrated configuration, the humidification unit 108 is shown separate of the pressurized gas source 102 with the inlet 110 of the humidification unit 108 connected to the outlet 106 of the pressurized gas source 102 with a conduit 112. In some implementations, the pressurized gas source 102 and the humidification unit 108 can be integrated into a single housing.

While other types of humidification units can be used with certain features, aspects, and advantages described in the present disclosure, the illustrated humidification unit 108 is a pass-over humidifier that comprises a humidification chamber 114 and an inlet 110 to the humidification chamber 114. In some implementations, the humidification chamber 114 comprises a body 116 having a base 118 attached thereto. A compartment can be defined within the body 116 that is adapted to hold a volume of liquid that can be heated by heat conducted or provided through the base 118. In some implementations, the base 118 is adapted to contact a heater plate 120. The heater plate 120 can be controlled through a controller 122 or other suitable component such that the heat transferred into the liquid can be varied and controlled.

The controller 122 of the humidification unit 108 can control operation of various components of the respiratory humidification system 100. While the illustrated system is illustrated as using a single controller 122, multiple controllers can be used in other configurations. The multiple controllers can communicate or can provide separate functions and, therefore, the controllers need not communicate. In some implementations, the controller 122 may comprise a microprocessor, a processor, or logic circuitry with associated memory or storage that contains software code for a computer program. In such implementations, the controller 122 can control operation of the respiratory humidification system 100 in accordance with instructions, such as contained within the computer program, and also in response to internal or external inputs. The controller 122, or at least one of the multiple controllers, can be located with the breathing circuit, either attached to the breathing circuit or integrated as part of the breathing circuit.

The body 116 of the humidification chamber 114 comprises a port 124 that defines the inlet 110, and a port 126 that defines an outlet 128 of the humidification chamber 114. As liquid contained within the humidification chamber 114 is heated, liquid vapor is mixed with gases introduced into the humidification chamber 114 through the inlet port 124. The mixture of gases and vapor exits the humidification chamber 114 through the outlet port 126.

The respiratory humidification system 100 includes a breathing circuit 200 comprising the inspiratory limb 202 connected to the outlet 128 that defines the outlet port 126 of the humidification unit 108. The inspiratory limb 202 conveys toward a user the mixture of gases and water vapor that exits the humidification chamber 114. The inspiratory limb 202 can include inspiratory heater wires 206 positioned along the inspiratory limb 202, wherein the inspiratory heater wires 206 is configured to reduce condensation along the inspiratory limb 202, to control a temperature of gas arriving at the user, to maintain humidity of the gas, or any combination of these. The inspiratory heater wires 206 can raise or maintain the temperature of the gases and water vapor mixture being conveyed by the inspiratory limb 202. In some implementations, the inspiratory heater wires 206 can be a wire that defines a resistance heater. By increasing or maintaining the temperature of the gases and water vapor mixture leaving the humidification chamber 114, the water vapor is less likely to condensate out of the mixture.

The respiratory humidification system 100 can be used in conjunction with an incubator 208. The incubator 208 can be configured to maintain a desired environment for a user within the incubator 208, such as a selected, defined, or desired temperature. Within the incubator 208, therefore, an interior ambient temperature may be different than a temperature outside the incubator 208. Thus, the incubator 208 causes, defines, creates, or maintains different temperature zones along the inspiratory limb 202, where the interior temperature is typically hotter than the exterior temperature. Having at least two different temperature zones along the inspiratory limb 202 can create problems during delivery of gas to a user such as condensation along the inspiratory limb 202, delivering a gas that has a temperature that is too high, or both.

The respiratory humidification system 100 can include an expiratory limb 210 with associated heating element 212. In some embodiments, the expiratory limb 210 and the inspiratory limb 202 can be connected using a suitable fitting (e.g., a wye-piece). In some embodiments, the respiratory humidification system 100 can be used in conjunction with a radiant warmer, under a blanket, or in other systems or situations that create two or more temperature zones. The systems and methods described herein can be used with such systems and are not limited to implementations incorporating incubators.

The inspiratory limb 202 can be divided into first and second segments 202a and 202b where a first segment 202a can be a portion of the inspiratory limb 202 that is outside the incubator 208 and a second segment 202b (e.g., an incubator extension), can be a portion of the inspiratory limb 202 that is inside the incubator 208. The first and second segments 202a, 202b can be different lengths or the same length. In some embodiments, the second segment 202b can be shorter than the first segment 202a, and, in certain implementations, the second segment 202b can be about half as long as the first segment 202a. The first segment 202a, for example, can have a length that is at least about 0.5 m and/or less than or equal to about 2 m, at least about 0.7 m and/or less than or equal to about 1.8 m, at least about 0.9 m and/or less than or equal to about 1.5 m, or at least about 1 m and/or less than or equal to about 1.2 m. The second segment 202b, for example, can have a length that is at least about 0.2 m and/or less than or equal to about 1.5 m, at least about 0.3 m and/or less than or equal to about 1 m, at least about 0.4 m and/or less than or equal to about 0.8 m, or at least about 0.5 m and/or less than or equal to about 0.7 m.

The first and second segments of the inspiratory limb 202a, 202b can be coupled to one another to form a single conduit for gas delivery. In some embodiments, the first segment 202a can include one or more first heater wires 206a and one or more first sensors 204a and can be used without the second segment 202b. The controller 122 can be configured to control the first heater wires 206a and read the first sensor 204a without the second segment 202b being coupled to the first segment 202a. Furthermore, when the second segment 202b is coupled to the first segment 202a, the controller 122 can be configured to control the first and second heater wires 206a, 206b and read the first and second sensors 204a, 204b in their respective segments. In some embodiments, the controller 122 can be configured to control the respective first and second heater wires 206a, 206b and to read the respective first and second sensors 204a, 204b when the second segment 202b is attached; and to control the first heater wires 206a and to read the first sensor 204a when the second segment 202b is not attached, without modification to the controller 122 or humidification unit 108. Thus, the same controller 122 and/or humidification unit 108 can be used whether the inspiratory limb 202 includes both the first and second segments 202a, 202b, or only the first segment 202a. In some embodiments, the controller 122 can be further configured to control heater wires 212 in the expiratory limb 210 without modification to the controller 122 or humidification unit 108. Accordingly, the respiratory humidification system 100 can function with or without the second segment 202b attached and/or with or without the expiratory limb 210 attached. It is to be understood that without the second segment 202b, the first segment 202a of the inspiratory limb 202 can function as a stand-alone inspiratory limb, such as when a patient interface is attached to the end of the first segment to provide gases to a patient. In some configurations the controller 122 can control either both the first and second segments 202a, 202b or control simply the first segment 202a or simply the second segment 202b.

In one configuration the controller 122 is configured to control the first and second segments 202a, 202b or just the first segment 202a, based only on readings from sensor 204b. In this configuration the inspiratory limb 202 may include only one sensor 204b located at the end of the second segment, with no first sensor 204a.

In some embodiments, the first and second segments 202a, 202b are permanently joined together to form a single conduit for gas delivery. As used here, permanently joined can mean that the first and second segments 202a, 202b are joined together in a manner that makes it difficult to separate the segments, such as through the use of adhesives, friction fits, overmolding, mechanical connectors, and the like. In some embodiments, the first and second segments 202a, 202b are configured to be releasably coupled. For example, the first segment 202a can be used for gas delivery without the second segment 202b, or the first and second segments 202a, 202b can be coupled together to form a single conduit for gas delivery. In some embodiments, the first and second segments 202a, 202b can be configured such that they can be coupled together in only one configuration. For example, the first segment 202a can have a defined chamber end (e.g., an end closest to the chamber 114 or humidification unit 108 along a direction of the flow of the humidified gas to the patient) and a defined patient end (e.g., an end closest to the patient along a direction of the flow of the humidified gas to the patient) wherein the chamber end is configured to couple to components at the chamber 114 and/or humidification unit 108. The second segment 202b can have a defined chamber end and a defined patient end wherein the chamber end is configured to only couple to the patient end of the first segment 202a. The chamber end of the first segment 202a can be configured to not couple with either end of the second segment 202b. Similarly, the patient end of the first segment 202a can be configured to not couple with the patient end of the second segment 202b. Similarly, the patient end of the second segment 202b can be configured to not couple with either end of the first segment 202a. Accordingly, the first and second segments 202a, 202b can be configured to be coupled in only one way to form a single conduit for gas delivery. In some embodiments, the first and second segments 202a, 202b can be configured to be coupled in a variety of configurations. For example, the first and second segments 202a, 202b can be configured to not include a defined patient end and/or a defined chamber end. As another example, the first and second segments 202a, 202b can be configured such that the patient end and/or the chamber end of the first segment 202a can couple to either the chamber end or the patient end of the second segment 202b. Similarly, the first and second segments 202a, 202b can be configured such that the chamber end and/or the patient end of the second segment 202b can couple to either the chamber end or the patient end of the second segment 202b.

The respiratory humidification system 100 can include an intermediate connector 214 that can be configured to electrically couple elements of the first and second segments 202a, 202b of the inspiratory limb 202. The intermediate connector 214 can be configured to electrically couple the first heater wires 206a in the first segment 202a to the second heater wires 206b in the second segment 202b to enable control of the heater wires 206a, 206b using the controller 122. The intermediate connector 214 can be configured to electrically couple the second sensor 204b in the second segment 202b to the first sensor 204a in the first segment to enable the controller 122 to acquire their respective outputs. The intermediate connector 214 can include electrical components that enable selective control of the heater wires 206a, 206b and/or selective reading of the first and second sensors 204a, 204b. For example, the intermediate connector 214 can include electrical components that direct power through the first heater wires 206a in a first mode and through the first and second heater wires 206a, 206b in a second mode. The electrical components included on the intermediate connector 214 can include, for example and without limitation, resistors, diodes, transistors, relays, rectifiers, switches, capacitors, inductors, integrated circuits, microcontrollers, microprocessors, RFID chips, wireless communication sensors, and the like. In some embodiments, the intermediate connector 214 can be configured to be internal to the inspiratory limb 202 such that it is substantially shielded from external elements (e.g., less than 1% of the water, particulates, contaminates, etc. from an environment external to the inspiratory limb 202 contacts the intermediate connector 214). In some embodiments, some of the electrical components on the intermediate connector 214 can be configured to be physically isolated from the humidified gas within the inspiratory limb 202 to reduce or prevent damage that may result from exposure to humidity. In some embodiments, the intermediate connector 214 can include relatively inexpensive passive electrical components to reduce cost and/or increase reliability.

The inspiratory limb 202 can include first and second sensors 204a, 204b in respective first and second segments of the inspiratory limb 202a, 202b. The first sensor 204a can be positioned near an end of the first segment 202a, close to the incubator 208 so that the parameter derived from the first sensor 204a corresponds to a parameter of the humidified gas entering the second segment 202b. The second sensor 204b can be positioned near an end of the second segment 202b so that the parameter derived from the second sensor 204b corresponds to a parameter of the humidified gas delivered to the patient or user. The output of the sensors 204a, 204b can be sent to the controller 122 as feedback for use in controlling power delivered to the first and second heater wires 206a, 206b of the first and second segments 202a, 202b of the inspiratory limb. In some embodiments, one or both of the sensors 204a, 204b can be temperature sensors, humidity sensors, oxygen sensors, flow sensors, or the like. A temperature sensor can be any suitable type of temperature sensor including, for example and without limitation, a thermistor, thermocouple, digital temperature sensor, transistor, and the like. The parameters provided by or derived from the sensors can include, for example and without limitation, temperature, humidity, oxygen content, flow rate, or any combination of these or the like.

The controller 122 can be configured to control the heater wires 206a and 206b, to receive feedback from the first and second sensors 204a and 204b, to provide logic to control power to the heater wires 206a and 206b, to adjust control of the heater wires 206a and 206b in response to readings from the first and second sensors 204a and 204b, to detect a presence of a second segment 202b of the inspiratory limb 202, to derive parameters from the readings from the sensors 204a and 204b, and the like. In some embodiments, the controller 122 includes a power source configured to deliver electrical power to the heater wires. The power source can be a source of alternating current or direct current. In some embodiments, the controller 122 can receive input from a heater plate sensor 130. The heater plate sensor 130 can provide the controller 122 with information regarding a temperature and/or power usage of the heater plate 120. In some embodiments, the controller 122 can receive input from a flow sensor 132. Any suitable flow sensor 132 can be used and the flow sensor 132 can be positioned between ambient air and the humidification chamber 114 or between the pressurized gas source 102 and the humidification chamber 114. In the illustrated system, the flow sensor 132 is positioned on the inlet port 124 of the humidification chamber 114.

Segmented Inspiratory Limbs

Figure 2:
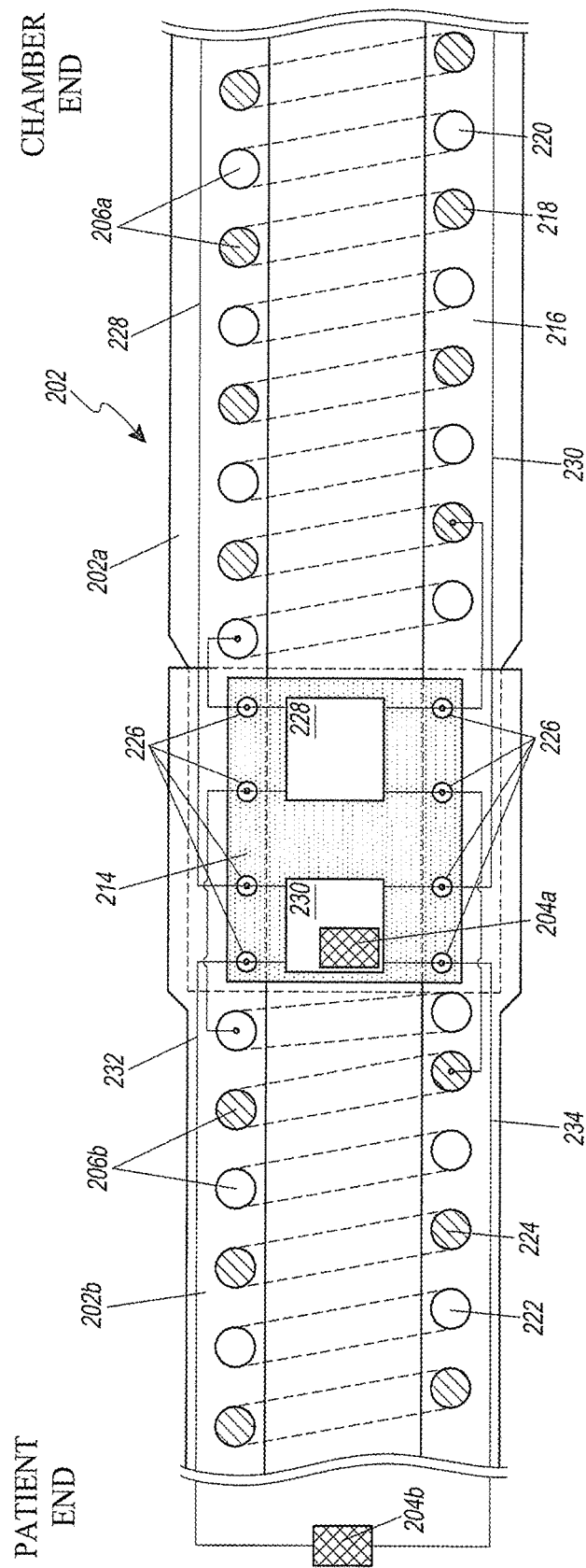
FIG. 2 illustrates a segmented inspiratory limb for use with a humidification system, the segmented inspiratory limb having an intermediate connector configured to couple heater wires and sensors in the two segments.

FIG. 2 illustrates a portion of a segmented inspiratory limb 202 for use with a respiratory humidification system 100, the segmented inspiratory limb 202 comprising a first segment 202a and a second segment 202b and having an intermediate connector 214 configured to couple first heater wires 206a to second heater wires 206b and a first sensor 204a to a second sensor 204b in the respective first and second segments 202a and 202b. Coupling the two segments 202a and 202b can comprise mechanically coupling the segments to form a single conduit through which humidified gases can be delivered to a user wherein mechanically coupling the segments 202a and 202b can result in electrically coupling the respective heater wires 206a, 206b and the respective sensors 204a, 204b through the intermediate connector 214.

The segmented inspiratory limb 202 can comprise a structure 216 forming a lumen through which humidified gases can pass. The structure 216 can include paths formed within walls of the structure 216 configured to house the heater wires 206a or 206b such that the heater wires 206a or 206b are shielded from the humidified gases travelling through the lumen and/or are covered by an external surface of the structure 216 so that they are not exposed. For example, the structure 216 can be a spiral bubble tube wherein the heater wire paths are coils molded into the tube. The structure 216 can comprise any type of suitable material and can include insulating material and/or flexible material. In some embodiments, the structure 216 and the intermediate connector 214 can be configured such that, when the first and second segments 202a and 202b are mechanically coupled, the heater wires 206a and 206b wrap over the intermediate connector 214 in such a way as to be electrically coupled to the intermediate connector 214. In some embodiments, the first segment 202a and/or the intermediate connector 214 can exclude any flying leads for connecting to the second segment 202b, thereby facilitating connection of the second segment 202b to the first segment 202a.

The structure 216 at complementary ends of the first and second segments 202a and 202b can be configured to house the intermediate connector 214. Thus, the intermediate connector 214 can be internal to the inspiratory limb 202. In some embodiments, the complementary ends of the first and second segments 202a and 202b can be configured to shield the intermediate connector 214 from humidified gases travelling through the inspiratory limb 202. In some embodiments, the intermediate connector 214 is both internal to the inspiratory limb 202 and shielded from humidified gases in the conduit, thereby reducing or eliminating exposure of electrical connections on the intermediate connector 214. In an exemplary configuration the intermediate connector or at least the portion of the intermediate connector 214 that is internal to the lumen is overmoulded with silicone or plastics material to form a protective layer or coating.

In some embodiments, the first heater wires 206a can comprise two wires 218 and 220 and the second heater wires 206b can comprise two wires 222 and 224. The two wires 218 and 220 in the first segment 202a can be electrically coupled to one another through electrical components 228 wherein the electrical coupling creates an electrical path through the wire 218, at least a portion of the electrical components 228, and the wire 220. Similarly, the two wires 222 and 224 in the second segment 202b can be electrically coupled to one another through electrical components 228 and/or electrically shorted together at an end of the second segment 202b opposite the intermediate connector 214, such as through a patient-end connector (not shown) as described in greater detail herein with reference to FIGS. 3A, 3B, 8A, 8B, 9, and 13. By coupling the wires 222 and 224 of the second segment 202b at the intermediate connector 214, electrical connections at the patient end of the inspiratory limb 202 are reduced or eliminated which can reduce cost, system complexity, and/or risk to the patient.

The intermediate connector 214 can be configured to allow a single controller to control power to the heater wires 206a, 206b, wherein the controller can be the humidifier controller 122 as described herein with reference to FIG. 1. In some embodiments, the humidifier controller 122 controls the heater wires without any additional control functionality located on the intermediate connector 214. For example, the intermediate connector 214 can include passive components without any logic circuitry wherein the passive components direct power to heater wires 206a and/or 206b as selected by the controller 122. This can allow the intermediate connector 214 to be designed using relatively inexpensive components and can reduce the complexity of the design.

In some embodiments, heating of the two segments 202a and 202b can be accomplished using a maximum of four wires in each segment 202a, 202b. For example, in the first segment 202a the four wires can include a first heater wire 218, a second heater wire 220, a signal sensor wire 228, and a return sensor wire 230. In the second segment 202b the four wires can include a first heater wire 222, a second heater wire 224, a signal sensor wire 232, and a return sensor wire 234. By coupling the second heater wires 222, 224 to the first heater wires 218, 220 at connection points 226, and by coupling the second sensor wires 232, 234 to the first sensor wires 228, 230 at connection points 226, a controller can be configured to provide power independently to the first heater wires 206a and the second heater wires 206b and to read sensor data independently from the sensors 204a and 204b without including more than four wires in either segment 202a or 202b. In some embodiments, control of the heater wires 206a and 206b and reading of the sensors 204a and 204b can be accomplished using less than four wires in each segment (e.g., using 3 wires or using 2 wires) or using more than four wires in each segment (e.g., using 5 wires, using 6 wires, using 7 wires, using 8 wires, or using more than 8 wires).

The intermediate connector 214 can include electrical components 228 configured to allow a controller 122 to selectively control heater wires 206a, 206b. The controller 122 can be configured to control heating of the inspiratory limb 202 using two modes wherein a first control mode comprises providing power to the heater wires 206a in the first segment, and a second control mode comprises providing power to the heater wires 206a and 206b in the first and second segments 202a and 202b. Thus, the controller 122 can be configured to independently control heater wire sections. This ability allows for the controller 122 to control heating of the inspiratory limb 202 when the second segment 202b is not present by solely controlling the heating of the inspiratory limb according to the first control mode, thereby allowing for the respiratory humidification system 100 to be used in a variety of circumstances without modifying the controller 122 or humidification unit 108. In some embodiments, the control modes can include a mode where power is delivered only to the heater wires 206b in the second segment 202b. In some embodiments, the controller 122 includes an electrical power source that provides electrical current. The first and second control modes can be based at least in part on the voltage supplied by the power source wherein a positive voltage or positive current can trigger the first control mode and a negative voltage or a negative current can trigger the second control mode. In some embodiments, the power source provides rectified AC or DC power to the heater wires 206a, 206b and a change in the rectification or polarity triggers a change in the control mode. By switching control modes, control of heating in the breathing circuit 200 can be accomplished with any power supply that can switch the polarity of the output signal. In some embodiments, the amount of power provided to the heater wires 206a, 206b can be adjusted by adjusting a duty cycle of power applied to the heater wires 206a, 206b. For example, pulse-width modulation (PWM) can be used to power the heater wires 206a, 206b and the duty cycle of the PWM signal can be adjusted to control the power delivered. In another example, the amount of power provided to the heater wires 206a, 206b can be adjusted by controlling the amplitude of the power signal.

The intermediate connector 214 can include electrical components 230 configured to allow a controller 122 to selectively read sensors 204a, 204b. Selective reading can be accomplished through the use of a source of electrical current wherein applying a positive current across the wires 228 to 230 can result in the controller 122 measuring a signal from the first sensor 204a and applying a negative current across the wires 228 and 230 can result in the controller 122 measuring a signal from the second sensor 204b or from both the first and second sensors 204a, 204b, as described herein with reference to FIGS. 6A, 6B, and 7. The controller 122 can use the readings from the sensors 204a, 204b to adjust power to the heater wires 206a, 206b, using, for example pulse-width modulation. The first sensor 204a can be positioned near the connection or intersection of the first and second segments 202a and 202b to provide to the controller 122 a parameter of gases entering the second segment 202b, which can correspond to entering an incubator or other such region having a different ambient temperature. The second sensor 204b can be positioned at a patient end of the second segment 202b to provide to the controller 122 a parameter of gases delivered to the patient or a parameter of gases prior to the final piece before the patient, such as a wye-piece. The controller 122 can use these readings to adjust power to the heater wires 206a, 206b to maintain the temperature of the gas at the patient end of the inspiratory limb 202 at a targeted or suitable temperature. The targeted or suitable temperature can vary depending at least in part on the application and environment it is being used in, and can be about 37° C., about 40° C., at least about 37° C. and/or less than or equal to about 38° C., at least about 36.5° C. and/or less than or equal to about 38.5° C., at least about 36° C. and/or less than or equal to about 39° C., at least about 35° C. and/or less than or equal to about 40° C., at least about 37° C. and/or less than or equal to about 41° C., or at least about 39.5° C. and/or less than or equal to about 40.5° C. In some embodiments, the second sensor 204b can be positioned inside the incubator but not attached to the breathing circuit. By measuring parameters inside the incubator, the temperature of the second segment 202b can be calculated, for example.

The controller 122 can independently control the amount of power delivered in the first and second control modes, as described herein. Based at least in part on feedback from the sensors 204a and/or 204b, the controller 122 can independently adjust power delivered in the first and second control modes, thereby resulting in varying heater power ratios between the first and second segments 202a and 202b.

In some embodiments, the first sensor 204a is positioned within the flow of gas within the inspiratory limb 202. In some embodiments, the intermediate connector 214 or the first segment 202a can include a mechanical component that decreases turbulence in the flow of the gas across the first sensor 204a which can increase accuracy in the readings of the sensor 204a. For example, the mechanical connector can have an aerodynamic cross section, examples of which are described for patient-end connectors with reference to FIGS. 15B-15E. In some embodiments, the mechanical component (e.g., a cross-member feature within the inspiratory conduit) that decreases turbulence also secures the sensor 204a within the flow of the gases. In some embodiments, the intermediate connector 214 and the mechanical component are configured to thermally isolate the sensor 204a from the electrical components on the intermediate connector 214, which may be advantageous where the sensor 204a is a temperature sensor, for example.

In some embodiments, the intermediate connector 214 includes additional connection points in addition to the connection points 226 illustrated in FIG. 2. The additional connection points can be used to incorporate further functionality into the breathing circuit such as, for example, incorporating a memory device (PROM) or (EPROM), a microcontroller, additional circuits, and the like.

Intermediate Connector Circuits

FIG. 3A illustrates a circuit diagram of an example intermediate connector 214 including an active rectified power source for providing power to heater wires in a segmented inspiratory limb of a breathing circuit, wherein the circuit is configured to power heater wires R1 and R2 in a first segment of the inspiratory limb in a first mode and to power heater wires R1, R2, R3, and R4 in both segments in a second mode. By providing diodes D1 and D2 on the intermediate connector 214 and switches S1 and S2, power can be alternatively applied through heater wires R1 and R2, where the resistors represent the heater wires, or through heater wires R1, R2, R3, and R4.

The power source is represented in the figure using VP and VN which correspond to terminals of a power supply. In an embodiment, the voltage supply is an alternating current (AC) power supply. Alternatively, the power source can be a direct current (DC) power supply. Although described in this embodiment as diodes, D1 and D2 can include any of a plurality of different types of flow control devices such as, for example and without limitation, rectifiers, transistors, relays, switches, triacs, mosfets, thyristors (SCR), thermostats, and the like.

The switches S1 and S2 switch between the VP and VN terminals of the power source. In an embodiment, switches S1 and S2 are switched every half-cycle of an AC power cycle so that approximately equal current is drawn from the power source during every half cycle. The circuit illustrated in FIG. 3A can be used to control the heaters R1, R2, R3, and R4 in two control modes, wherein a first control mode corresponds to providing power only to R1 and R2, and a second control mode corresponds to providing power to R1, R2, R3 and R4. To provide power only to the heaters R1 and R2 in the first segment 202a (corresponding to the first control mode), switch S1 connects to VP and switch S2 connects to VN during a positive cycle from the power source, and switch S1 connects to VN and switch S2 connects to VP during a negative cycle from the power source. In the first control mode, current flows through R1, R2, and D1 while D2 prevents current from flowing through R3 and R4. To provide power to the heaters R1, R2, R3, and R4 in the first and second segments 202a, 202b (corresponding to the second control mode), switch S1 connects to VN and switch S2 connects to VP during a positive cycle from the power source, and switch S1 connects to VP and switch S2 connects to VN during a negative cycle from the power source. In the second control mode, current flows through R1, R2, R3, R4 and D2 while D1 prevents current from shorting across the wires to bypass heaters R3 and R4. Switching of switches S1 and S2 can be accomplished through hardware or software that adds logic to the system, as described herein with reference to FIG. 5. In some embodiments, switching of switches S1 and S2 is performed at the zero crossing of an AC power cycle. In some embodiments, the falling and rising edges of zero crossing circuitry are not delayed by the same amount and the circuit is not active near the zero crossing. Thus, the switching of switches S1 and S2 can be performed with or without zero-crossing switching detection and/or logic.

The diodes D1 and D2 can dissipate power in the circuit, and therefore generate heat. In some embodiments, Schottky diodes can be used where it is desirable to reduce power dissipation in relatively high-temperature environments. Schottky diodes can be operated near a maximum junction temperature to reduce or minimize power dissipation, which may be desirable in certain implementations of the respiratory humidification system described herein. In some embodiments, the heat generated by the diode can influence temperature readings of the sensor 204a. To reduce this influence, the diodes can be thermally connected to an airflow path of the circuit. To reduce this influence and to dissipate the heat generated by the diodes, a heat sink or pad can be included on the intermediate connector 214 that is thermally coupled to the ambient environment. To reduce this influence, and the influence of other components on the intermediate connector 214, the sensor 204a (e.g., a thermistor or other temperature sensor) can be thermally insulated from the components and physically located relatively far from the other components, as described with reference to FIGS. 14A-B, and 15.

FIG. 3B illustrates another circuit diagram of an example intermediate connector 214 including an active rectified power source for providing power to the heater wires in a segmented inspiratory limb of a breathing circuit, wherein the circuit is configured to power the heater wires R1 and R2 in a first segment of the inspiratory limb in a first mode and to power the heater wires R1, R2, R3, and R4 in both segments in a second mode. As shown in FIG. 3B, only diode D1 may be provided and the path of power through the heater wires R1 and R2 or through the heater wires R1 through R4 can still be controlled, as previously described with respect to FIG. 3A. The diode D2 that was shown in the circuit of FIG. 3A is eliminated. The circuit shown in FIG. 3B, having only one diode D1, can result in less heat generated by the circuit, reduced parts costs, and a smaller circuit board. The remaining portions of the circuit shown in FIG. 3B operate in a manner that is similar to the description of FIG. 3A. In embodiments without D2, as illustrated in FIG. 3B, most of the current flows through R1, R2 and D1 with only residual current flowing through R3 and R4. The residual current through R3 and R4 can be negligible such that it does not affect the performance of the humidification system.

In addition to the AC operation described with respect to FIGS. 3A and 3B, similar circuits can be operated with a DC supply. Switches S1 and S2 can be switched based at least in part on, for example, time, an output current of the supply, feedback from sensors, or other control inputs. In such an embodiment, the circuits illustrated in FIG. 3A or 3B also can be used to control the heaters R1, R2, R3, and R4 in two control modes, wherein a first control mode corresponds to providing power only to R1 and R2, and a second control mode corresponds to providing power to R1 through R4. To provide power only to the heaters R1 and R2 in the first segment 202a (corresponding to the first control mode), switch S1 connects to VP and switch S2 connects to VN. In the first control mode, current flows through R1, R2, and D1. D2 prevents current from flowing through R3 and R4 in the circuit shown in FIG. 3A. However, D2 is an optional component as shown in FIG. 3B. To provide power to the heaters R1, R2, R3, and R4 in the first and second segments 202a, 202b (corresponding to the second control mode), switch S1 connects to VN and switch S2 connects to VP. In the second control mode, current flows through R1, R2, R3, R4, while D1 prevents current from shorting across the wires to bypass heaters R3 and R4. As previously described, switching can be accomplished through hardware or software that adds logic to the system, as described herein with reference to FIG. 5.

Control of Inspiratory and Expiratory Limb Heaters

FIG. 1 also illustrates an example respiratory humidification system 100 having an inspiratory limb 202 and an expiratory limb 210, wherein the humidification system 100 is configured to control heater wires 206, 212 in both limbs. In some embodiments, the expiratory heater wires 212 in the expiratory limb 210 can be electrically coupled to the inspiratory heater wires 206 outside the humidification unit 108 and controller 122 so that control of the expiratory heater wires 212 can be implemented without affecting other control modes and without additional switching transistors. Similarly, the expiratory heater wires 212 can be electrically coupled to the inspiratory heater wires 206 within the humidification unit 108. Connection of the expiratory heater wires 212 to the inspiratory heater wires 206 can be done in the humidification unit 108, on the intermediate connector 214, in a sensor cartridge at the humidification unit 108, or the like. Thus, the controller 122 can control the expiratory heater wires 212 with no additional electrical connections at the patient end, the presence of which may increase risk, system complexity, and cost. Examples of electrical coupling of the expiratory heater wires 212 and the inspiratory heater wires 206 inside the humidification unit 108 are shown in FIGS. 4A-4D, 8A, and 8B.

Figure 4A:
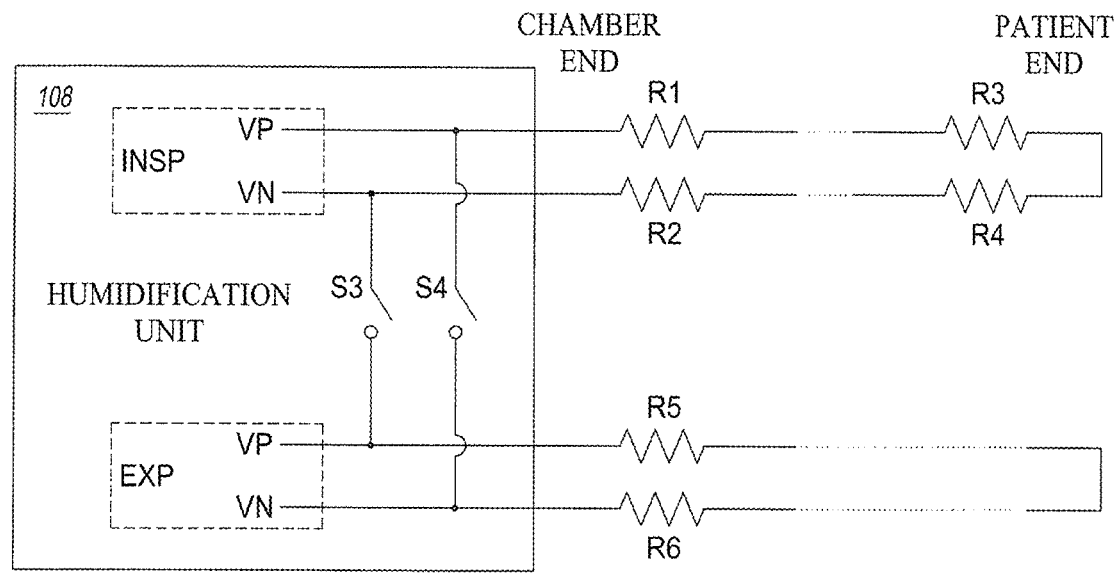
FIGS. 4A-4D illustrate example humidification systems having an inspiratory limb and an expiratory limb, wherein the humidification systems are configured to control heater wires in both limbs.

With reference to FIG. 4A, the humidification unit 108 can incorporate switches or relays S3 and S4 to select between independent and dependent control of the inspiratory heater wires and the expiratory heater wires. In some embodiments, the switches or relays are activated when a tube (e.g., an inspiratory limb or an expiratory limb) with an appropriate identification is connected to the humidification unit 108, such as through an identification resistor detected and/or measured by the humidification unit 108. For example, when the switches are not activated (e.g., both switches S3, S4 are open), the heater wires in the inspiratory limb and/or the heater wires in the expiratory limb can be individually and/or independently controlled.

When an appropriate tube is connected or the system otherwise determines it is appropriate, the switches S3 and S4 can be closed to simultaneously control the inspiratory limb and the expiratory limb. The humidification unit 108 can include an inspiratory power source INSP and an expiratory power source EXP, wherein the system can implement switching in each power source as described herein with reference to FIGS. 3A and 3B. For example, with reference to FIG. 3A, the inspiratory power source can have switches S1 and S2 configured to selectively direct positive and negative cycles to the heaters R1 through R4. Similarly, with reference to FIG. 4A, the expiratory power source EXP can include switches configured to selectively direct power to the expiratory limb having heaters R5 and R6. In some embodiments, when the switches S3 and S4 are closed, both switches in expiratory power source EXP can be opened such that power is provided to the inspiratory heater wires and the expiratory heater wires by the inspiratory power source INSP. In some embodiments, the humidification unit 108 does not include an expiratory power source EXP. In such embodiments, the inspiratory power source INSP is used to provide power to the inspiratory heater wires when the switches S3 and S4 are open and to provide power to both the inspiratory and expiratory heater wires when the switches S3 and S4 are closed. Thus, the inspiratory heater wires 206 can be controlled in the same way as before, but now the system can use the switches S3, S4 to simultaneously control power to the expiratory heater wires 212 and the inspiratory heater wires 206 using a unified electrical circuit and/or control system. By way of example, the humidification unit 108 can operate in two modes relative to the inspiratory limb 202 (e.g., the first mode being where the humidification unit 108 provides power to the heaters R1 and R2 and the second mode being where it provides power to the heaters R1 to R4) while selectively controlling power to the heaters R5 and R6 in the expiratory limb such that the humidification unit 108 can provide no power to the heaters R5 and R6, or provide power to the heaters R5 and R6 while operating in the first mode, in the second mode, or in both modes. As previously described, a connection between the inspiratory limb 202 and expiratory limb 210 can be made internal or external to the humidification unit 108. In an embodiment, the connection is made in a sensor cartridge, the intermediate connector 214, or in another location.

In some embodiments, an expiratory circuit configured to connect the expiratory heater wires 212 to the controller 122 can be implemented at the intermediate connector 214 shown on FIG. 1. The expiratory circuit can be connected in one or more of several ways. For example, the expiratory circuit can be connected in parallel with the heater wires 206*a* in the first segment 202*a* or with the heater wires 206*b* in the second segment 202*b*. In some embodiments, the intermediate connector 214 can include an internal fly or flying lead making the expiratory circuit available on the intermediate connector 214. In some embodiments, the intermediate connector 214 can be connected to an added third channel to so that there are no fly leads between the inspiratory and expiratory circuits. A heater wire driver control circuit can be added to the controller 122 to accommodate such embodiments.

Figure 4B:
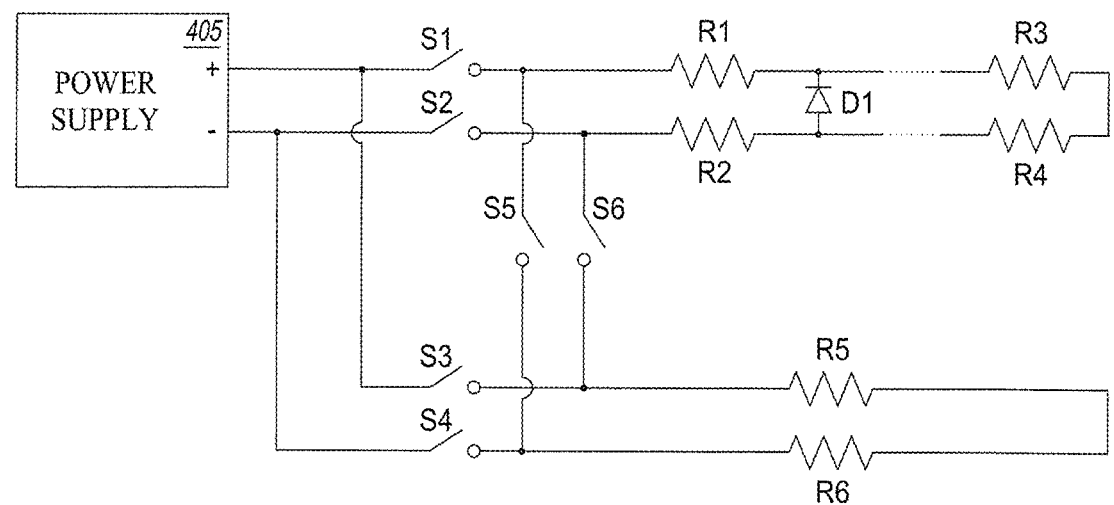

FIG. 4B illustrates an example embodiment of a humidification system incorporating a power supply 405 to provide power to both the inspiratory heater wires R1 to R4 and the expiratory heater wires R5 and R6 through a combination of switches or relays S1 to S6 and diode D1. In the illustrated embodiment, the humidification system is configured to provide power to the expiratory heater wires when only the inspiratory heater wires R1, R2 in the first segment of the inspiratory limb are receiving power (e.g., in a first operation mode) or when the inspiratory heater wires R1 to R4 in both segments are receiving power (e.g., in a second operation mode). The power supply 405 can be any suitable power supply including, for example, a power supply which provides alternating current in a sine wave, sawtooth, square wave, or other form. In some embodiments, the power supply 405 is a transformer which provides an alternating current signal with a voltage of at least about 22 VAC, at least about 5 VAC or less than or equal to about 30 VAC, at least about 10 VAC or less than or equal to about 25 VAC, at least about 12 VAC or less than or equal to about 22 VAC.

With continued reference to FIG. 4B, the humidification system can be configured to provide power to the expiratory heater wires R5, R6 in the first operation mode while the power supply 405 is providing power in a negative cycle. To do so, switches S1, S2, S5, S6 close and switches S3, S4 open. The current flows from the negative terminal of the power supply 405 through switch S2 and branches to provide power to the heater wires in both the inspiratory limb and the expiratory limb. In the inspiratory limb, the current flows to inspiratory heater wire R2, then through diode D1 to inspiratory heater wire R1, and then returns to the positive terminal on the power supply 405 through switch S1. In the expiratory limb, the current flows through switch S6 to expiratory heater wire R5, then to expiratory heater wire R6, and then returns to the positive terminal on the power supply 405 through switches S5 and S1.

Similarly, with continued reference to FIG. 4B, the humidification system can be configured to provide power to the expiratory heater wires R5, R6 in the first operation mode while the power supply 405 is providing power in a positive cycle. To do so, switches S3, S4, S5, S6 close and switches S1, S2 open. The current flows from the positive terminal of the power supply 405 through switch S3 and branches to provide power to the heater wires in both the inspiratory limb and the expiratory limb. In the inspiratory limb, the current flows through switch S6 to inspiratory heater wire R2, then through diode D1 to inspiratory heater wire R1, and then returns to the negative terminal on the power supply 405 through switches S5 and S4. In the expiratory limb, the current flows to expiratory heater wire R5, then to expiratory heater wire R6, and then returns to the negative terminal on the power supply 405 through switch S4.

With continued reference to FIG. 4B, the humidification system can be configured to provide power to the expiratory heater wires R5, R6 in the second operation mode while the power supply 405 is providing power in a positive cycle. To do so, switches S1, S2, S5, S6 close and switches S3, S4 open. The current flows from the positive terminal of the power supply 405 through switch S1 and branches to provide power to the heater wires in both the inspiratory limb and the expiratory limb. In the inspiratory limb, the current flows to inspiratory heater wire R1, then bypasses diode D1 to flow to inspiratory heater wire R3, then to inspiratory heater wire R4, then to inspiratory heater wire R2, and then returns to the negative terminal on the power supply 405 through switch S2. In the expiratory limb, the current flows through switch S5 to expiratory heater wire R6, then to expiratory heater wire R5, and then returns to the negative terminal on the power supply 405 through switches S6 and S2.

Similarly, with continued reference to FIG. 4B, the humidification system can be configured to provide power to the expiratory heater wires R5, R6 in the second operation mode while the power supply 405 is providing power in a negative cycle. To do so, switches S3, S4, S5, S6 close and switches S1, S2 open. The current flows from the negative terminal of the power supply 405 through switch S4 and branches to provide power to the heater wires in both the inspiratory limb and the expiratory limb. In the inspiratory limb, the current flows through switch S5 to inspiratory heater wire R1, then bypasses diode D1 to flow to inspiratory heater wire R3, then to inspiratory heater wire R4, then to inspiratory heater wire R2, and then returns to the positive terminal on the power supply 405 through switches S6 and S3. In the expiratory limb, the current flows to expiratory heater wire R6, then to expiratory heater wire R5, and then returns to the positive terminal on the power supply 405 through switch S3.

Figure 4C:
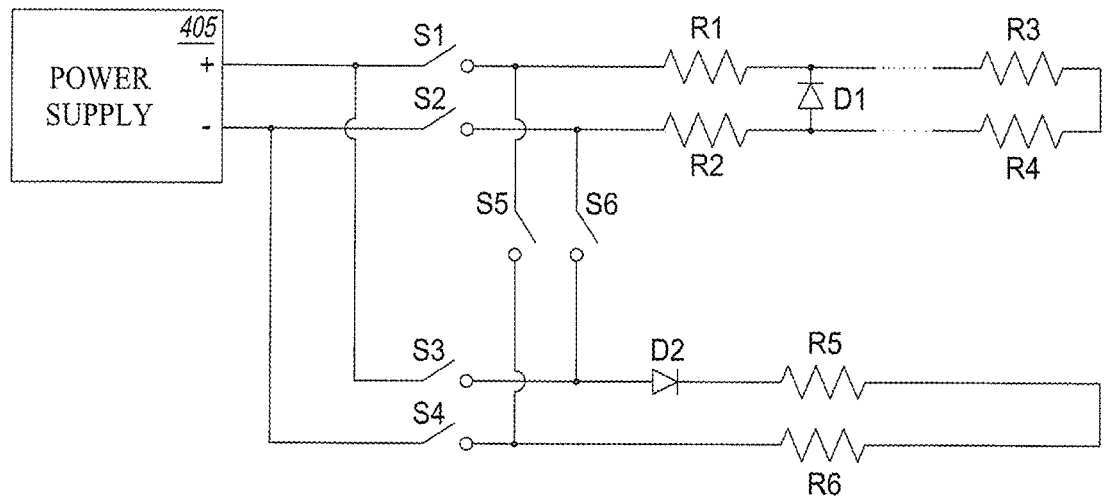

FIG. 4C illustrates an example embodiment of a humidification system incorporating a power supply 405 to provide power to both the inspiratory heater wires R1 to R4 and the expiratory heater wires R5 and R6 through a combination of switches or relays S1 to S6 and diodes D1, D2. In the illustrated embodiment, the humidification system is configured to provide power to the expiratory heater wires only when the inspiratory heater wires R1, R2 in the first segment of the inspiratory limb are receiving power (e.g., only in the first operation mode).

With continued reference to FIG. 4C, the humidification system can be configured to provide power to the expiratory heater wires R5, R6 in the first operation mode while the power supply 405 is providing power in a negative cycle. To do so, switches S1, S2, S5, S6 close and switches S3, S4 open. The current flows from the negative terminal of the power supply 405 through switch S2 and branches to provide power to the heater wires in both the inspiratory limb and the expiratory limb. In the inspiratory limb, the current flows to inspiratory heater wire R2, then through diode D1 to inspiratory heater wire R1, and then returns to the positive terminal on the power supply 405 through switch S1. In the expiratory limb, the current flows through switch S6 and through diode D2 to expiratory heater wire R5, then to expiratory heater wire R6 and then returns to the positive terminal on the power supply 405 through switches S5 and S1.

Similarly, with continued reference to FIG. 4C, the humidification system can be configured to provide power to the expiratory heater wires R5, R6 in the first operation mode while the power supply 405 is providing power in a positive cycle. To do so, switches S3, S4, S5, S6 close and switches S1, S2 open. The current flows from the positive terminal of the power supply 405 through switch S3 and branches to provide power to the heater wires in both the inspiratory limb and the expiratory limb. In the inspiratory limb, the current flows through switch S6 to inspiratory heater wire R2, then through diode D1 to inspiratory heater wire R1, and then returns to the negative terminal on the power supply 405 through switches S5 and S4. In the expiratory limb, the current flows through diode D2 to expiratory heater wire R5, then to expiratory heater wire R6, and then returns to the negative terminal on the power supply 405 through switch S4.

With continued reference to FIG. 4C, the humidification system can be configured to provide power only to the inspiratory heater wires R1 to R4 (and not to provide power to the expiratory heater wires R5, R6) in the second operation mode while the power supply 405 is providing power in a positive cycle. To do so, switches S1, S2, S5, S6 close and switches S3, S4 open. The current flows from the positive terminal of the power supply 405 through switch S1 to inspiratory heater wire R1, the current then bypasses diode D1 and flows to inspiratory heater wire R3, to inspiratory heater wire R4, to inspiratory heater wire R2 and back to the negative terminal on the power supply 405 through switch S2. The current does not flow through the expiratory heater wires because of diode D2 which blocks the flow of current through that circuit on a positive cycle with the switches configured as described.

Similarly, with continued reference to FIG. 4C, the humidification system can be configured to provide power only to the inspiratory heater wires R1 to R4 (and not to provide power to the expiratory heater wires R5, R6) in the second operation mode while the power supply 405 is providing power in a negative cycle. To do so, switches S3, S4, S5, S6 close and switches S1, S2 open. The current flows from the positive terminal of the power supply 405 through switches S4 and S5 to inspiratory heater wire R1, the current then bypasses diode D1 and flows to inspiratory heater wire R3, to inspiratory heater wire R4, to inspiratory heater wire R2 and back to the negative terminal on the power supply 405 through switches S6 and S3. The current does not flow through the expiratory heater wires because of diode D2 which blocks the flow of current through that circuit on a negative cycle with the switches configured as described.

Figure 4D:
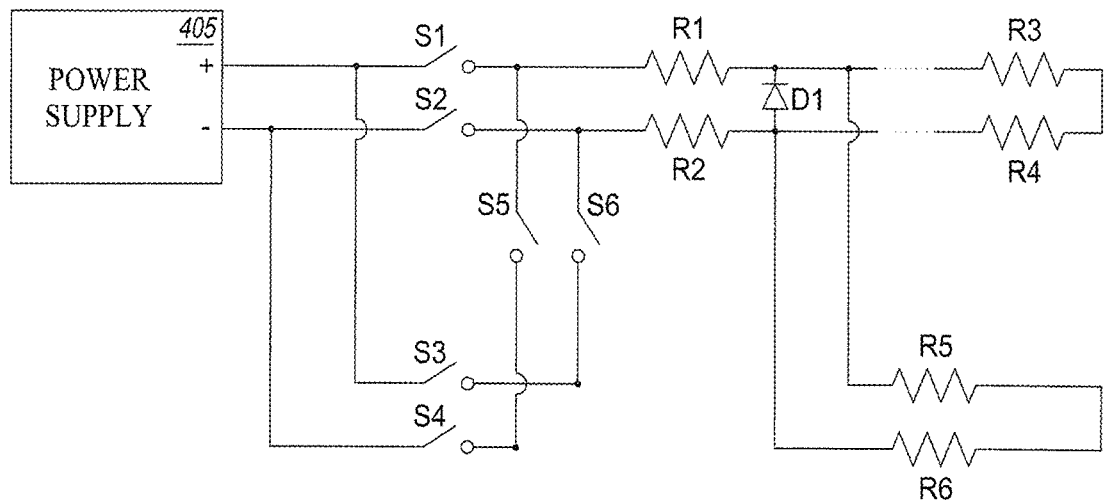

FIG. 4D illustrates an example embodiment of a humidification system incorporating a power supply 405 to provide power to both the inspiratory heater wires R1 to R4 and the expiratory heater wires R5 and R6 through a combination of switches or relays S1 to S6 and diode D1 with the expiratory heater wires R5, R6 being electrically coupled to the inspiratory heater wires R1 to R4 on a patient side of the heater wires in the first segment of the inspiratory limb, which can occur an intermediate connector, such as any of the intermediate connectors described herein. As described with reference to FIG. 4D, the expiratory heater wires R5, R6 are coupled to the inspiratory heater wires R1 to R4 at the intermediate connector, but any suitable location after the inspiratory heater wires in the first segment can be used for coupling the heater wires in the inspiratory and expiratory limb. In the illustrated embodiment, the humidification system is configured to provide power to the expiratory heater wires only when the inspiratory heater wires R1 to R4 in both segments of the inspiratory limb are receiving power (e.g., only in the second operation mode).

With continued reference to FIG. 4D, the humidification system can be configured to provide power to the inspiratory heater wires R1 to R4 and to the expiratory heater wires R5, R6 in the second operation mode while the power supply 405 is providing power in a positive cycle. To do so, switches S1, S2, S5, S6 close and switches S3, S4 open. The current flows from the positive terminal of the power supply 405 through switch S1 to inspiratory heater wire R1, then bypasses diode D1 and branches to provide power to the heater wires in both the second segment of the inspiratory limb and the expiratory limb. In the second segment of the inspiratory limb, the current flows to inspiratory heater wire R3, then to inspiratory heater wire R4, returning to the intermediate connector. In the expiratory limb, current flows to R5 and then to R6, returning back to the intermediate connector. The current then flows through inspiratory heater wire R2 and then returns to the negative terminal on the power supply 405 through switch S2.

Similarly, with continued reference to FIG. 4D, the humidification system can be configured to provide power to the expiratory heater wires R5, R6 in the second operation mode while the power supply 405 is providing power in a negative cycle. To do so, switches S3, S4, S5, S6 close and switches S1, S2 open. The current flows from the negative terminal of the power supply 405 through switches S4 and S5 to inspiratory heater wire R1, then bypasses diode D1 and branches to provide power to the heater wires in both the second segment of the inspiratory limb and the expiratory limb. In the second segment of the inspiratory limb, the current flows to inspiratory heater wire R3, then to inspiratory heater wire R4, returning to the intermediate connector. In the expiratory limb, current flows to R5 and then to R6, returning back to the intermediate connector. The current then flows through inspiratory heater wire R2 and then returns to the positive terminal on the power supply 405 through switches S6 and S3.

With continued reference to FIG. 4D, the humidification system can be configured to provide power only to the inspiratory heater wires R1 and R2 in the first segment of the inspiratory limb (and not to provide power to the expiratory heater wires R5, R6) in the first operation mode while the power supply 405 is providing power in a negative cycle. To do so, switches S1, S2, S5, S6 close and switches S3, S4 open. The current flows from the negative terminal of the power supply 405 through switch S2 to inspiratory heater wire R2, the current then flows through diode D1 to inspiratory heater wire R1, and then returns to the positive terminal on the power supply 405 through switch S1.

Similarly, with continued reference to FIG. 4D, the humidification system can be configured to provide power only to the inspiratory heater wires R1 and R2 in the first segment of the inspiratory limb (and not to provide power to the expiratory heater wires R5, R6) in the first operation mode while the power supply 405 is providing power in a positive cycle. To do so, switches S3, S4, S5, S6 close and switches S, S2 open. The current flows from the positive terminal of the power supply 405 through switches S3 and S6 to inspiratory heater wire R2, the current then flows through diode D1 to inspiratory heater wire R1, and returns back to the negative terminal on the power supply 405 through switches S5 and S4.

Other circuit designs and configurations are possible for controlling inspiratory heaters, segmented inspiratory heaters, and/or expiratory heaters. Control of electrical power to the various heaters can be controlled by a controller or control module, such as the controller 122 described with reference to FIG. 1. The control module can be configured to coordinate opening and closing of switches to selectively control electrical power to one or more heaters. For example, switches can open and close to control the amount of power delivered to a heater. In certain implementations, a power source provides an alternating electrical current and the switches can be controlled to modulate the amount of electrical power to one or more heaters using, for example, pulse width modulation techniques. As another example, the control module can coordinate operation of switches to control to which heaters or heater segments electrical power is delivered. In some embodiments, each zone or heater wire to be heated may include a dedicated power source. This may enable removal of the diodes configured to regulate current flow in the heater wire circuits. In some embodiments, control algorithms can use flow information to directly control a fixed duty cycle of the first heater segment. In some embodiments, control algorithms can use ambient temperature readings or measurements to directly control the fixed duty cycle of the first heater segment to a tailored value.

In some embodiments, a temperature measurement at a midpoint, or between the patient end and the chamber end, may be used by control modules. For example, a control module can utilize such a midpoint temperature measurement to adapt the duty cycle of the first heater segment to maintain a targeted midpoint temperature. The duty cycle of the first heater segment can be adapted to maintain a targeted temperature differential with respect to the chamber output dew point (humidity) which is related to the chamber output temperature. The duty cycle of the first heater segment can be continuously adapted to maintain a targeted temperature differential with respect to the patient-end measured temperature. The chamber output temperature may be advantageously decreased by a calculated targeted level based at least in part on the duty cycle of the combined first and second heater segments (defined by the patient-end temperature) if the duty cycle remains at 100% for a tailored period of time and the patient-end temperature is less than the targeted set point by a tailored amount whilst the flow has been determined to be non-zero.

In some embodiments, at least a single measurement point in the system for temperature feedback control can be implemented, and this can be positioned at the system output. Such a configuration may be sufficient for achieving a targeted gas condition. In certain implementations, a dual zone system may not comprise a temperature sensor if prior knowledge of the heat transfer characteristics of each zone is established for known environmental operating conditions. In such a system, separate power levels may be established for each zone such that a targeted gas output condition may be obtained from an accurate measurement of the mass flow through the system and knowledge of the gas condition entering the gas delivery system.

Figure 21A:
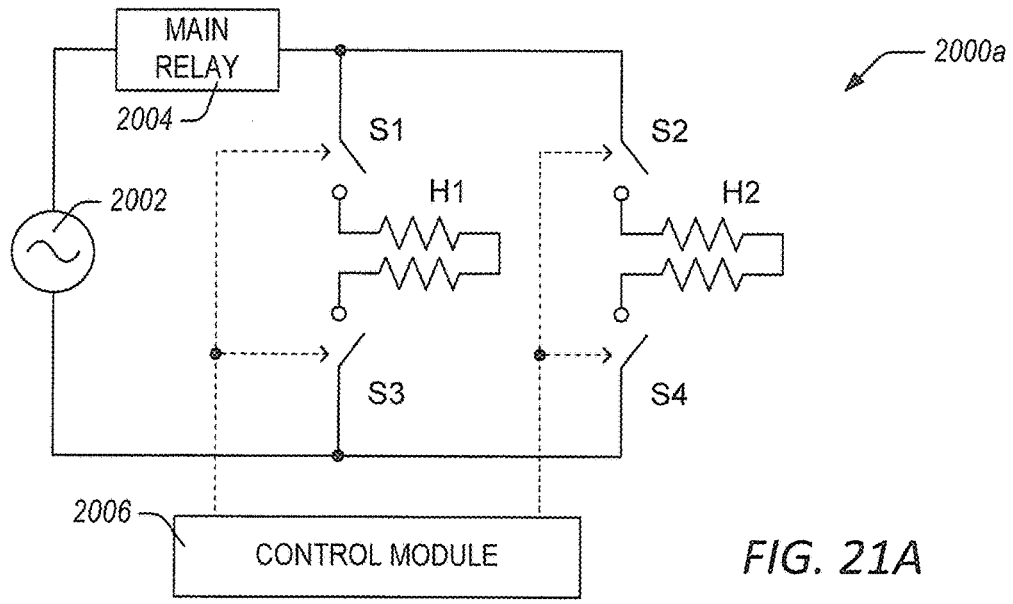
FIG. 21A illustrates an example circuit diagram configured to independently control two heaters.

FIG. 21A illustrates an example circuit diagram 2000a configured to independently control two heaters H1, H2 (e.g., inspiratory heater, expiratory heater, segmented heaters, etc.). As used herein, independent control can mean that the delivery of electrical power to one of the two heaters does not determine whether electrical power is delivered to the other heater. For example, switches S1 and S3 can be closed and switches S2 and S4 can be open to deliver power to just heater H1, switches S1 and S3 can be open and switches S2 and S4 can be closed to deliver power to just heater H2, or switches S1 to S4 can be closed to deliver power to both heaters H1, H2.

The circuit 2000a can include a power source 2002 configured to provide electrical power. The power source 2002 can be a source of alternating current or direct current. The power source 2002 can be an electrical voltage source or an electrical current source. The circuit 2000a can include a main relay 2004 configured to control delivery of electrical power to the components of the circuit 2000a. The main relay 2004 can be opened (e.g., be put into a state that does not allow electrical current to flow) when a fault condition is detected by the system or when the system decides to cut off electrical power to the heaters and/or other electrical components of the breathing circuit.

In some embodiments, the system can be configured to detect when there is a likely short between a low power circuit and a high power circuit (e.g., a short circuit between heater and sensor wires). There may be a short circuit when the high power circuit and the low power circuit receive electrical power from a common source and/or receive electrical power from a common circuit. In certain implementations, the high power circuit and the low power circuit receive electrical power from a transformer that rectifies electrical power (e.g., from an AC electrical source), decreases (or increases) the output electrical voltage for the high power circuit (e.g., using voltage dividers), and decreases the output electrical voltage for the low power circuit (e.g., using voltage dividers). For example, the high power circuit can be configured to provide about 22 V and the low power circuit can be configured to provide about 3.3 V. Other voltages are also possible. For example, the high power circuit can provide a voltage of at least about 50 V, at least about 30 V and/or less than about 50 V, at least about 20 V and/or less than about 30 V, or at least about 10 V and/or less than about 25 V. As another example, the low power circuit can provide a voltage of at least about 5 V, at least about 3 V and/or less than about 5 V, at least about 2 V and/or less than about 3.5 V, or at least about 1.5 V and/or less than about 2 V. The actual voltage on the low power circuit can depend on the temperature(s) measured by the one or more temperature sensors coupled to the low power circuit. For example, in a low power circuit providing about 3.3 V, a thermistor measuring a temperature of about 50° C. can output a voltage of about 0 V and a thermistor measuring a temperature of about 20° C. can output a voltage of about 1.2 V.

The system can include a first comparator referenced to the output of a series of dividers electrically coupled to a transformer output configured to provide the voltage for the low power circuit. The first comparator can provide an out of range signal when the voltage exceeds an expected voltage (e.g., the voltage that the comparator is configured to detect). For example, where the expected range is between 0 and 1.2 V or 1.5 V, the comparator can be configured to provide a signal indicating a possible short circuit when the voltage exceeds 1.2 V or 1.5 V. The system can include a second comparator referenced to ground and configured to provide a signal indicating a possible short circuit when the voltage is negative. The system can be configured to provide a signal indicating a potential short circuit immediately (e.g., in real time or in near real time) upon detecting the voltage outside the expected range. In some implementations, the system can include logic configured to ignore the short circuit signal, to trigger a warning, and/or to turn off or decrease power to the high power circuit and/or the low power circuit. If the system receives an out of range signal it can open the main relay 2004 to cut off electrical power to the electrical components (e.g., heater wires, sensors, etc.). A short circuit may occur where there is a leak of voltage from the high power circuit to the low power circuit which can increase the voltage on the low power circuit outside the expected range. Similarly, if a negatively-biased electrical voltage to be supplied to the high power circuit leaks to the low power circuit, the voltage on the low power circuit may become negative.

The circuit 2000a can include switches S1 to S4 to control electrical power to the heaters H1, H2. As used herein, the term switches can be used to indicate electrical switches and/or any other combination of electrical and/or electromechanical components configured to control the flow of electrical current. For example, switches can comprise MOSFETs, diodes, transistors, or a combination of these or the like. The heaters H1, H2 can be any of the heaters described herein.

The circuit 2000a can include a control module 2006 configured to control the switches S1 to S4. The control module 2006 can be configured to provide signals to the switches to indicate a desired state of the receiving switch. For example, the control module can send a signal (e.g., a voltage over a threshold voltage) to switches S1 and S3 or switches S2 and S4 to control them to close. The control module 2006 can be configured to control switches S1 and S3 using one signal and switches S2 and S4 using another signal. In this way, pairs of switches (e.g., switches S1, S3 and/or switches S2, S4) can synchronize their operation (e.g., open and close at or near the same time). The circuit 2000a is configured to independently control heaters H1, H2 by independently controlling the opening and closing of the pair of switches S, S3 and the pair of switches S2, S4.

Figure 21B:
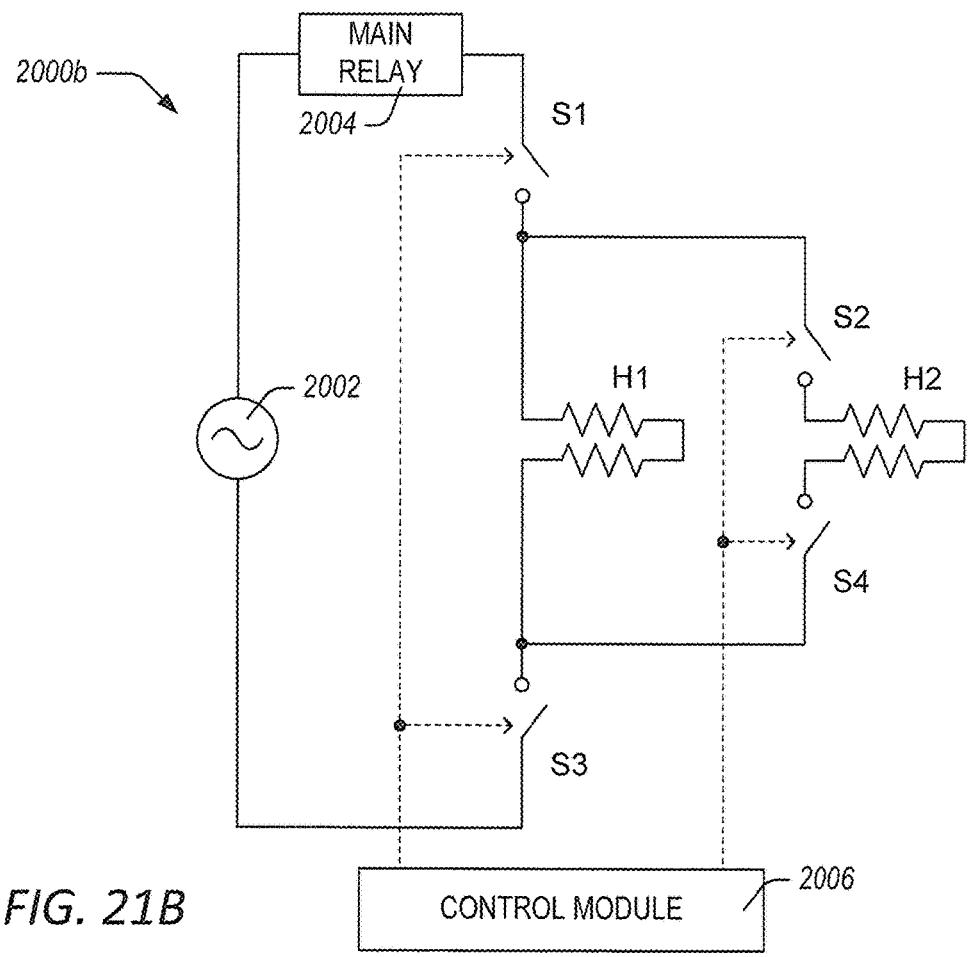
FIG. 21B illustrates an example circuit diagram configured to provide gated control of two heaters.

FIG. 21B illustrates an example circuit diagram 2000b configured to provide gated control of heaters H1, H2. The circuit 2000b is similar to the circuit 2000a except that the flow of electrical power to the lines controlled by switches S2 and S4 is controlled by the switches S1 and S3, respectively. In this way, the control module 2006 can provide gated control of heaters H1, H2. As used herein, gated control can mean that the flow of electrical power to heater H1 is controlled by switches S1 and S3, whereas the flow of electrical power to heater H2 is controlled at a first level by switches S1 and S3 and at a second level by switches S2 and S4. For example, electrical power may flow to heater H2 when switches S1 and S3 are closed depending on the state of switches S2 and S4. However, if switches S1 and S3 are open, the state of switches S2 and S4 is not relevant as electrical power will not flow to heater H2. In this way, the hardware can control operation of the heaters H1, H2. This results in gated control of heater H2 as the control module 2006 can control power to heater H2 using switches S1 and S3 (e.g., providing a gate for electrical power for heater H2). This can be beneficial where hardware control of the heaters H1, H2 is desirable to provide an additional control mechanism in addition to software control of the heaters. For example, control software on a humidification apparatus may request that heater H2 be powered on but that request can be overridden by the hardware configuration.

Figure 21C:
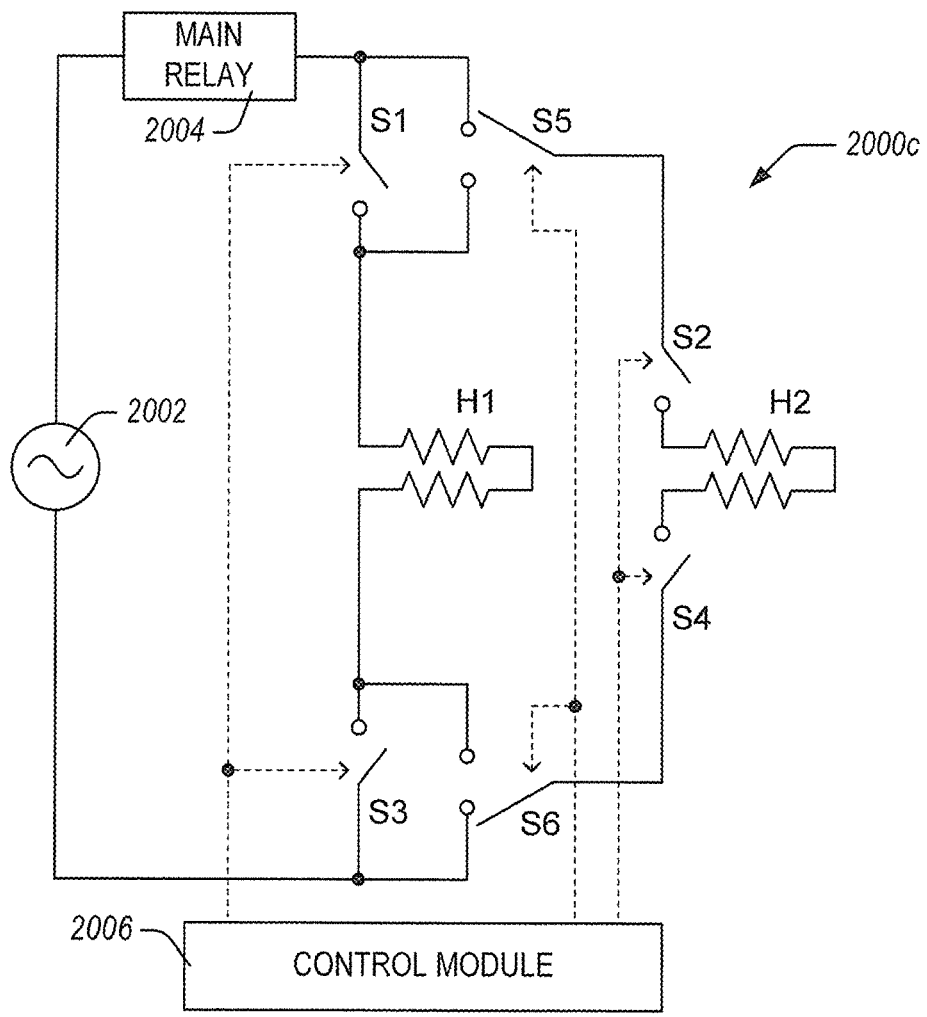
FIG. 21C illustrates an example circuit diagram configured to switch between independent control and gated control of two heaters.

FIG. 21C illustrates an example circuit diagram 2000c configured to switch between independent control and gated control of heaters H1, H2. The control module 2006 can control switches S5, S6 to selectively put the circuit 2000c into an independent control configuration, similar to the circuit 2000a described herein with reference to FIG. 21A, or a gated control configuration, similar to the circuit 2000b described herein with reference to FIG. 21B. The circuit 200c provides the benefits of both the circuits 2000a, 2000b and to select the desired, appropriate, and/or suitable configuration with the control module 2006.

Figure 22A:
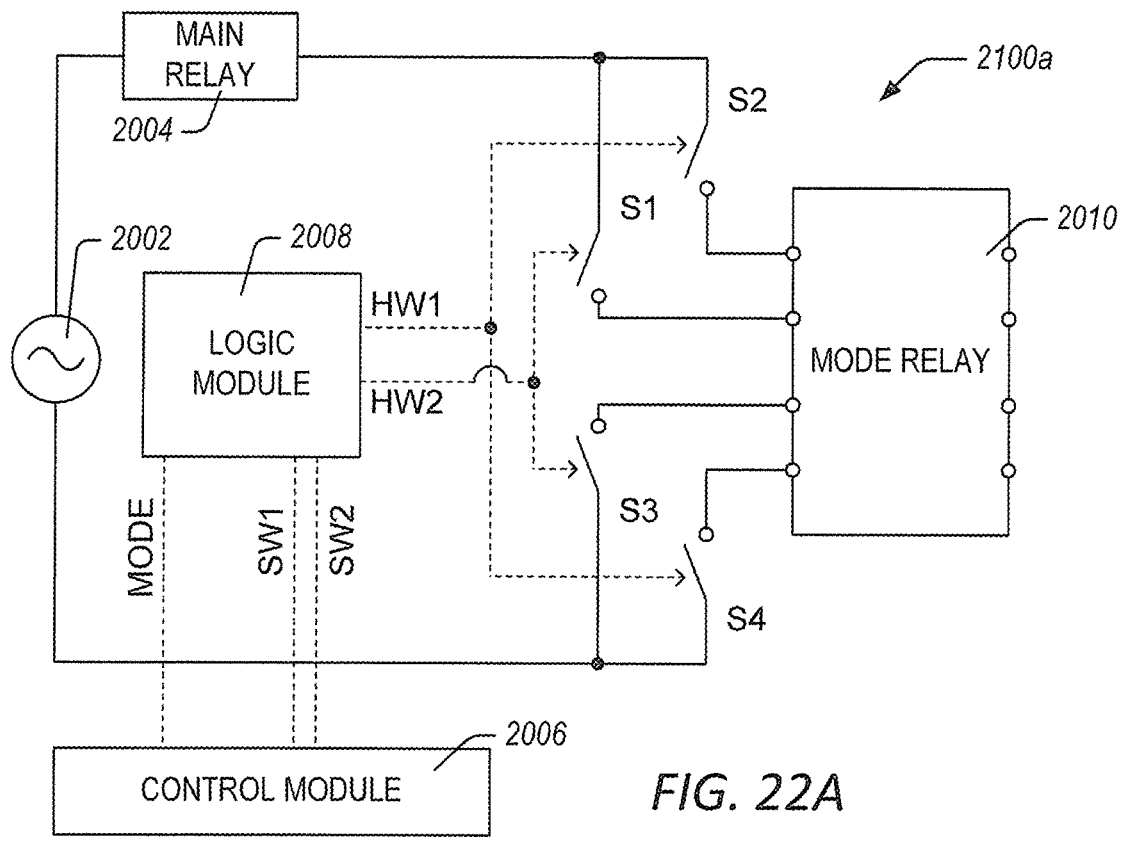
FIG. 22A illustrates an example circuit diagram including a logic module and a mode relay configured to enable control of two heaters or a segmented heater.

FIG. 22A illustrates an example circuit diagram 2100a including a logic module 2008 and a mode relay 2010 configured to enable control of two heaters (e.g., an inspiratory and an expiratory heater) or a segmented heater (e.g., heaters in a segmented inspiratory conduit). The circuit diagram 2100a includes a power source 2002, a main relay 2004, and a control module 2006 similar to the circuit diagrams 2000a, 2000b, and 2000c described herein with reference to FIGS. 21A-21C. The switches S1 to S4 are configured in a manner similar to circuit diagram 2000a. However, the logic module 2008 interfaces with the control module 2006 to control switches S1 to S4. Furthermore, the mode relay 2010 provides dynamic configurations for different heater configurations.

The logic module 2008 receives control signals SW1, SW2 from the control module 2006 and processes these signals based at least in part on a mode signal MODE from the control module 2006. The mode signal MODE can indicate an intended, selected, or desired mode for the circuit 2100a. For example, the mode signal MODE can be used to indicate to the logic module 2008 that the operation of the circuit 2100a should be for independent control of heaters or for a segmented heater. Based on the control signals SW1, SW2 and the mode signal MODE, the logic module 2008 outputs switch signals HW1, HW2 to respectively control pairs of switches S, S3 and S2, S4.

Figure 22B:
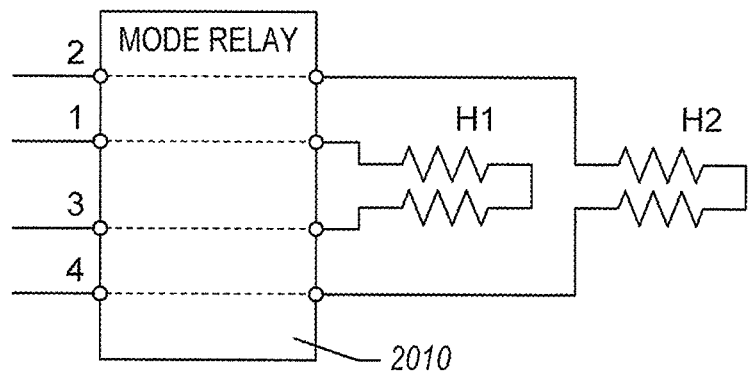
FIG. 22B illustrates a block diagram of the mode relay configured to control two heaters.

In certain implementations, the mode signal MODE can be used to indicate an independent heater control mode to the logic module 2008. In this case, the logic module 2008 can be configured to pass the control signals SW1, SW2 to the output switch signals HW1, HW2 with little or no modification. In this way, the control module 2006 can independently control two heaters. In some embodiments, the mode relay 2010 receives an indication of the operation mode similar to the indication provided by the mode signal MODE. In response to the received indication, the mode relay 2010 can provide electrical connections for lines 1-4 (corresponding to the lines controlled by switches S1-S4). For example, as illustrated in FIG. 22B, the mode relay 2010 can provide an electrical pass-through for lines 1-4 to enable independent control of heaters H1, H2, similar to the operation of circuit 2000a described herein with reference to FIG. 21A.

Figure 22C:
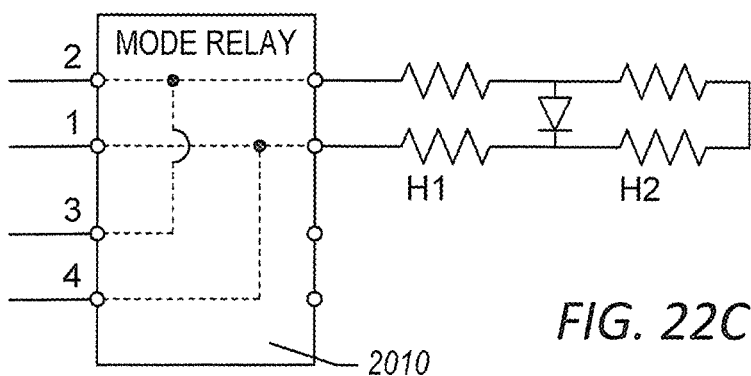
FIG. 22C illustrates a block diagram of the mode relay configured to control a segmented heater.

In certain implementations, the mode signal MODE can be used to indicate a segmented heater control mode to the logic module 2008. In this case, the logic module 2008 can be configured to output switch control signals HW1, HW2 to selectively control switches S1 to S4 to provide rectified electrical signals to a segmented heater. In this way, the control module 2006 can control a segmented heater as described elsewhere herein. In some embodiments, the mode relay 2010 receives an indication of the operation mode similar to the indication provided by the mode signal MODE. In response to the received indication, the mode relay 2010 can provide electrical connections for lines 1-4 (corresponding to the lines controlled by switches S1-S4). For example, as illustrated in FIG. 22C, the mode relay 2010 can electrically couple lines 1 and 4 and electrically couple lines 2 and 3 to enable control of a segmented heater comprising heater segments H1 and H2, similar to the operation of other circuits configured to control segmented heaters described herein. In this mode, the mode relay 2010 provides the ability to turn on heater segment H1 or both heater segments H1 and H2 based at least in part on a configuration of switches S1 to S4 and a polarity of electrical voltage/current.

For example, in segmented heater mode, the control module 2006 can use control signal SW1 to indicate a desire or request to provide power to both heater segments H1, H2. In response, the logic module 2008 can provide switch control signal HW1 controlling switches S1 and S3 to close during a positive polarity signal from the power source 2002 and switch control signal HW2 controlling switches S2 and S4 to close during a negative polarity signal from the power source 2002. Similarly, the control module 2006 can use control signal SW2 to indicate a desire or request to provide power to just heater segment H1. In response, the logic module 2008 can provide switch control signal HW2 controlling switches S2 and S4 to close during a positive polarity signal from the power source 2002 and switch control signal HW1 controlling switches S1 and S3 to close during a negative polarity signal from the power source 2002. In this way, the logic module 2008 enables rectification of voltage/current to the segmented heaters H1, H2.

The logic module 2008 enables a safety latch that may be implemented when operating in the segmented heater control. The logic module 2008 can be configured to set both switch control signals HW1, HW2 to control switches S1 to S4 to open if both control signals SW1, SW2 indicate a request to operate in their requested mode. This can be used to reduce or prevent malfunctioning associated with providing power to the segmented heaters. For example, the power source 2002 can be used to provide alternating current, or positively and negatively biased electrical voltages in turn. These currents and/or biased voltages can be controlled by switches S1 to S4. Closing all the switches S1 to S4 may cause both directions of current or both positively and negatively biased voltages to be provided to the heater circuit 2100a at the same time which may damage the system. The logic module 2008 can include a latch that opens the main relay 2004 when the control module 2006 (e.g., through a software or hardware malfunction) activates incompatible heater drivers (e.g., when both sets of switches S1, S3 and S2, S4 are activated or closed).

Figure 23:
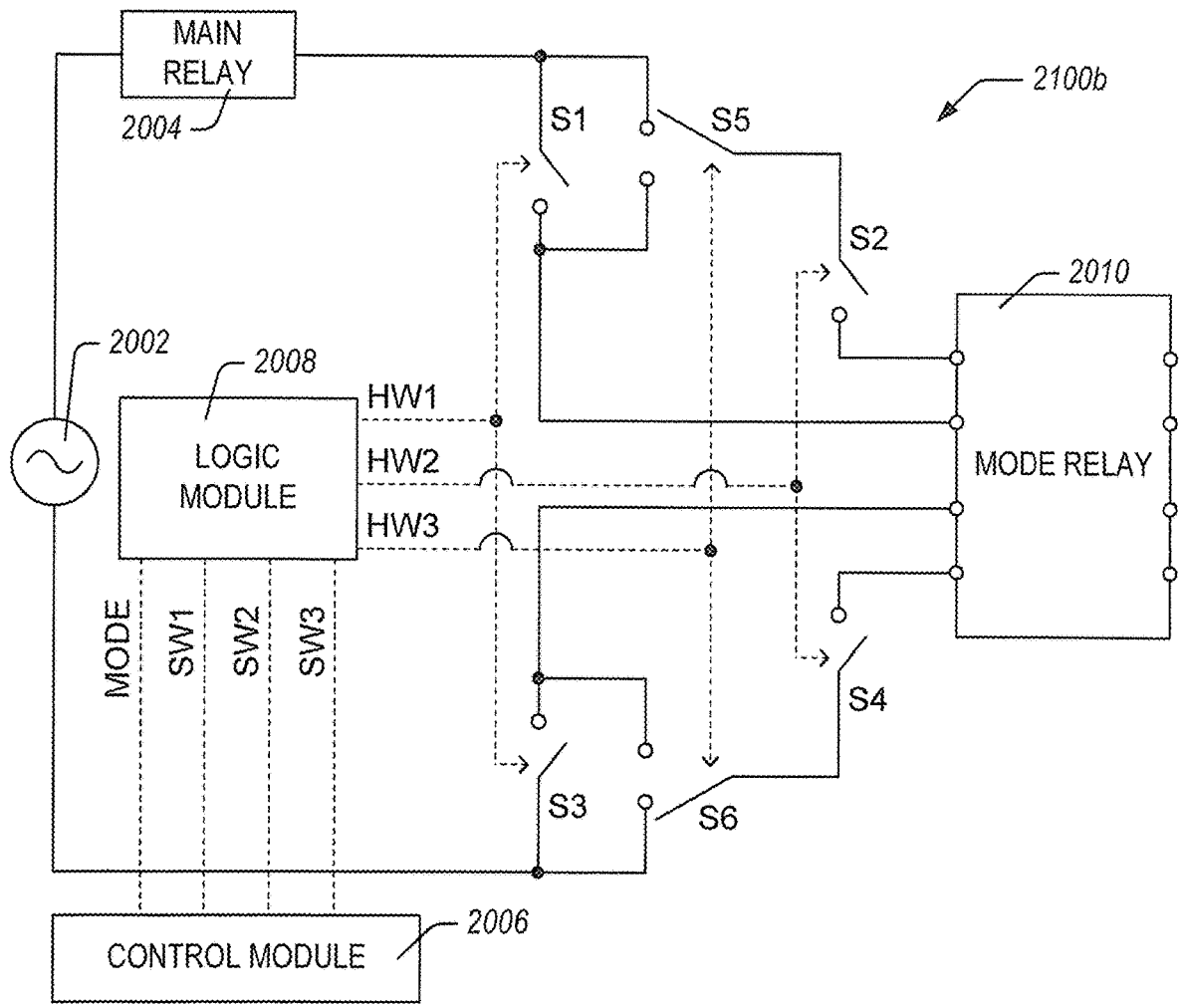
FIG. 23 illustrates an example circuit diagram configured to switch between independent control of two heaters or gated control of two heaters and to provide the functionality described with respect to the example circuit diagram illustrated in FIG. 22A.

FIG. 23 illustrates an example circuit diagram 2100b configured to switch between independent control (e.g., the circuit diagram 2000a described herein with reference to FIG. 21A) or gated control (e.g., the circuit diagram 2000b described herein with reference to FIG. 21B) of two heaters and to provide the functionality described with respect to the example circuit diagram 2100a illustrated in FIG. 22A. The circuit diagram 2100b provides the switching functionality of circuit diagram 2000c, described herein with reference to FIG. 21C, along with the functionality provided by circuit diagram 2100a, described herein with reference to FIG. 22A. To enable this functionality, the control module 2006 can provide an additional control signal SW3 that the logic module 2008 can use to provide switch control signal HW3 to operate switches S5 and S6. The switches S5 and S6 can be configured so that switches S1 and S2 are in parallel and switches S3 and S4 are in parallel when operating in independent heater control mode and when operating in segmented heater control mode. The switches S5 and S6 can be configured so that switches S1 and S2 are in series and switches S3 and S4 are in series when operating in gated heater control mode. The logic module 2008 can perform additional checks to verify that the control signal SW3 is appropriate based at least in part on the mode signal MODE, where the mode signal can be configured to provide an indication of a selection, request, or desire to operate in independent heater control mode, gated heater control mode, or segmented heater control mode.

Figure 24A:
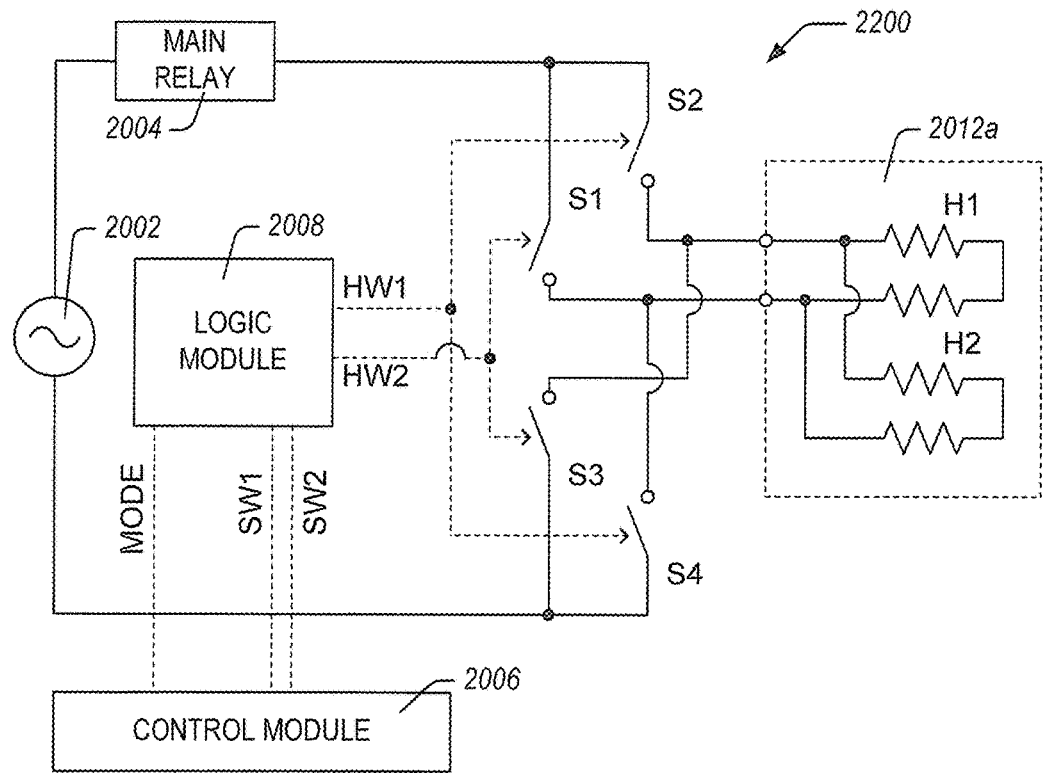
FIG. 24A illustrates an example circuit diagram configured to control two heaters in parallel.

FIG. 24A illustrates an example circuit diagram 2200 configured to control two heaters H1, H2 in parallel. The circuit 2200 can be configured to couple to a heater module 2012a, the heater module 2012a including the heaters H1, H2. The circuit 2200 can be configured to provide electrical connections for the heater module 2012a, the electrical connections similar to those provided by the mode relay 2010 when it is configured in the manner described herein with reference to FIG. 22C. The circuit 2200 can otherwise be configured to the circuit 2100a, described herein with reference to FIG. 22A.

Figure 24B:
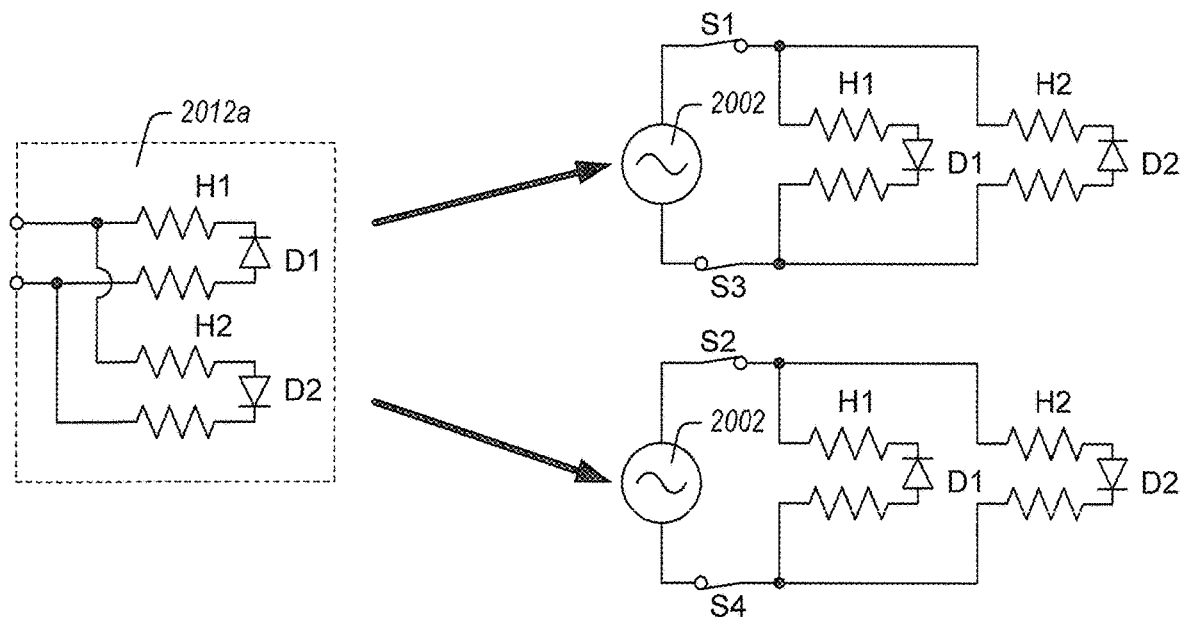
FIG. 24B illustrates an example configuration of the heater module illustrated in FIG. 24A wherein the heaters both include a diode to control the flow of electrical current.

With reference to FIG. 24A, the circuit 2200 can be configured to power the heaters H1, H2 in the heater module 2012a in parallel. In some embodiments, the heater module 2012a can include one or more diodes to direct or limit the flow of electrical current to one or more of the heaters in the heater module 2012a. For example, FIG. 24B illustrates an example configuration of the heater module 2012a wherein the heaters H1, H2 both include a diode to control the flow of electrical current. The diodes D1, D2 can be used to control when electrical power flows through the associated heater H1, H2 to provide additional control capabilities.

FIG. 24B also illustrates simplified circuit diagrams demonstrating the functionality of the circuit 2200 with the heater module 2012a configured to include diodes D1, D2. When switches S1 and S3 are closed (and switches S2 and S4 are open), positive current provided by the power source 2002 flows through heater H1 but not heater H2 and negative current provided by the power source 2002 flows through heater H2 but not heater H1. Similarly, when switches S2 and S4 are closed (and switches S1 and S3 are open), positive current provided by the power source 2002 flows through heater H2 but not heater H1 and negative current provided by the power source 2002 flows through heater H1 but not heater H2. In this way, the control module can coordinate the opening and closing of pairs of switches S1, S3 and S2, S4 with the polarity of the electrical voltage or current provided by the power source 2002 to selectively energize heaters H1, H2. In some implementations, the diodes D1, D2 can be configured to have different biases so that electrical current flows through heaters H1, H2 opposite to that described above. In certain implementations, either one of diodes D1 or D2 can be removed so that electrical current is restricted in one of heaters H1, H2 but not the other.

Figure 24C:
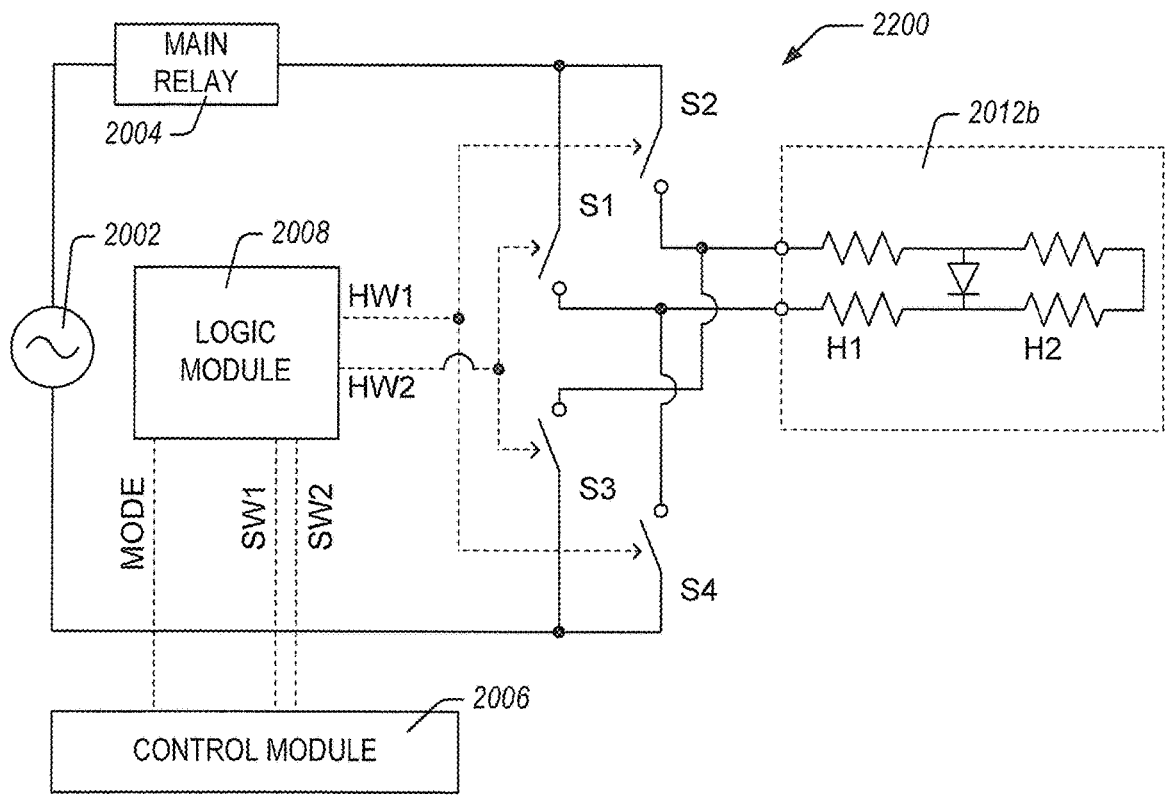
FIG. 24C illustrates the example circuit diagram illustrated in FIG. 24A configured to control a segmented heater through the use of a heater module.
Figure 24D:
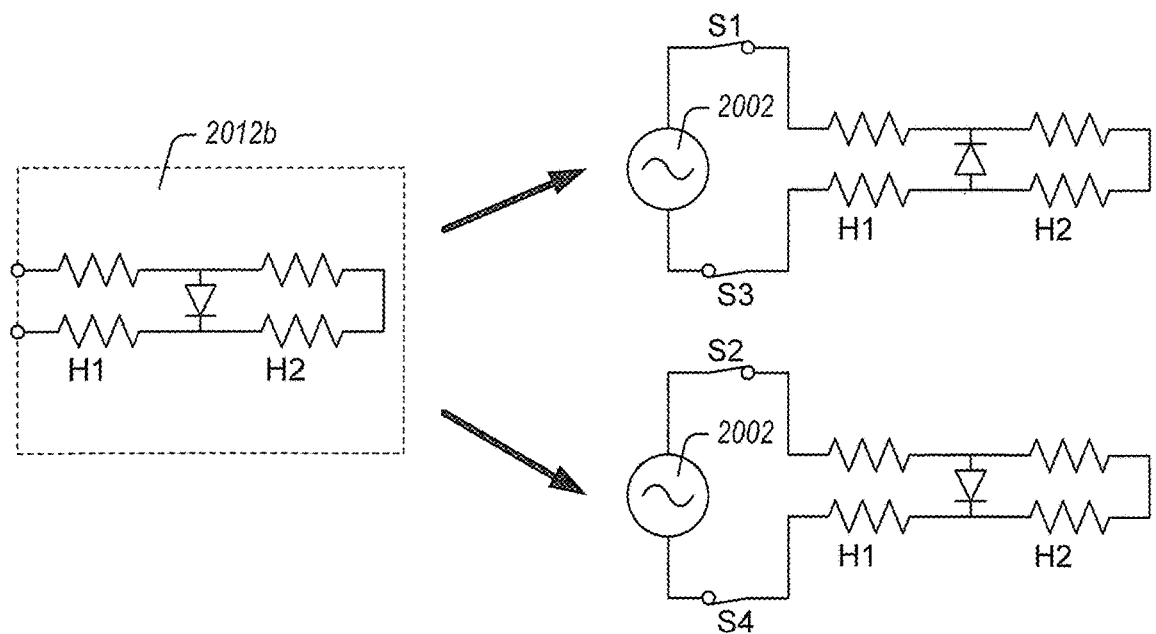
FIG. 24D illustrates an example configuration of the heater module illustrated in FIG. 24C.

FIG. 24C illustrates the example circuit diagram 2200 configured to control a segmented heater through the use of a heater module 2012b. In this configuration, the circuit 2200 with the heater module 2012b operates in a similar fashion as circuit 2100a when the mode relay 2010 in the circuit 2100a is configured to electrically couple lines 1 and 4 and electrically couple lines 2 and 3 to enable control of a segmented heater comprising heater segments H1 and H2, as described herein with reference to FIG. 22C. FIG. 24D illustrates an example configuration of the heater module 2012b as well as simplified circuit diagrams of the circuit 2200 to demonstrate the functionality of the circuit when the switches are in various configurations. As described elsewhere herein, both heater segments H1, H2 can be powered when a positive current is provided by the power source 2002 and switches S1, S3 are closed or when a negative current is provided by the power source 2002 and switches S2, S4 are closed. Heater segment H1 can be powered when a negative current is provided by the power source 2002 and switches S1, S3 are closed or when a positive current is provided by the power source 2002 and switches S2, S4 are closed.

The circuit diagram 2200 can advantageously allow for connectivity with different heater modules to allow a single circuit design to operate different heater configurations. This can also simplify control systems design, software design, and increase interoperability of components for different breathing apparatuses.

Figure 25A:
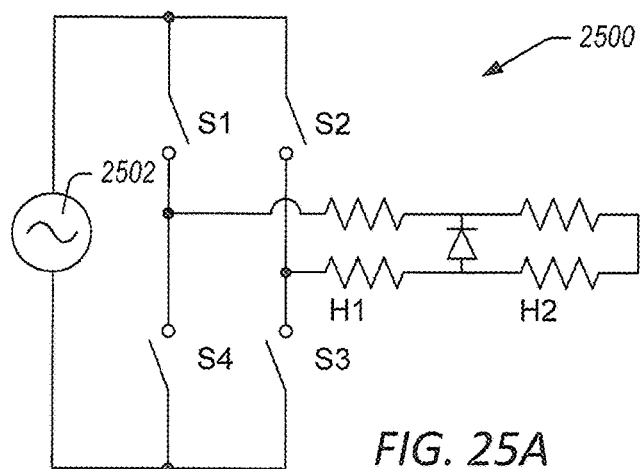
FIGS. 25A-25C illustrate another example circuit diagram configured to control two heaters in parallel using an active rectifier circuit.
Figure 25B:
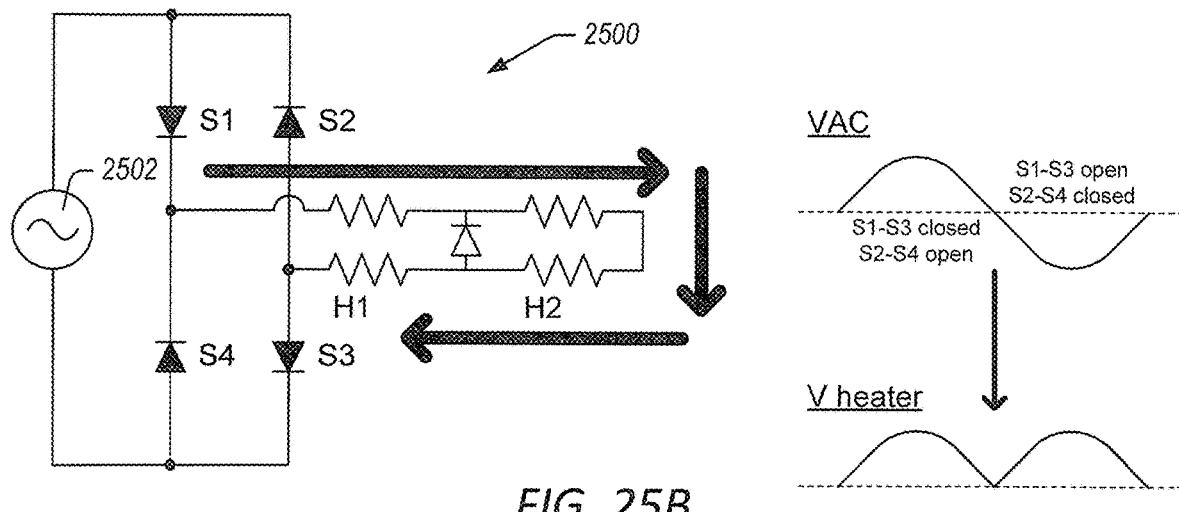
Figure 25C:
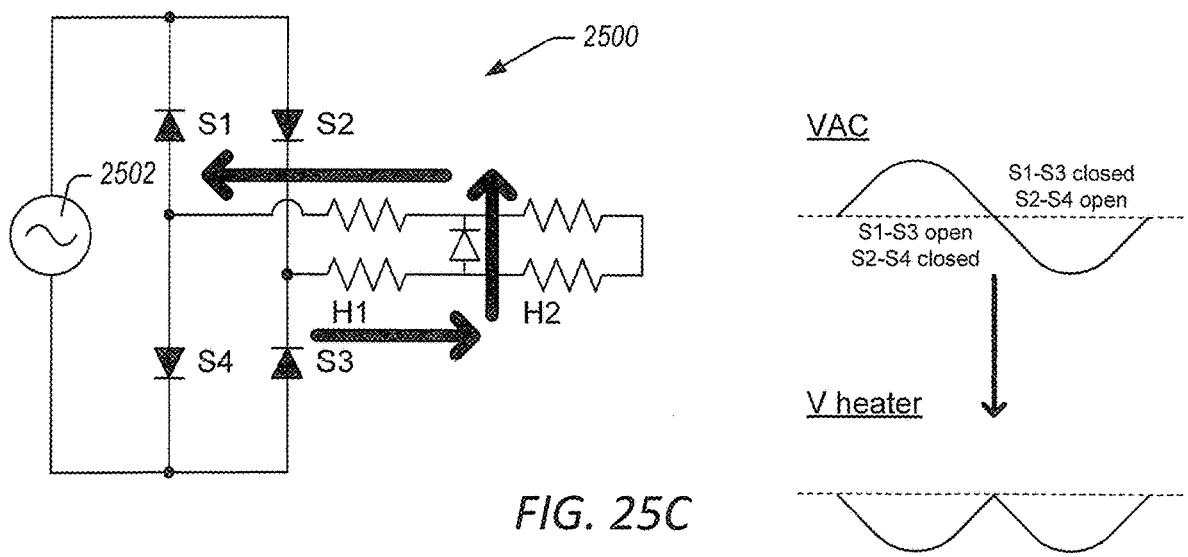

FIGS. 25A-25C illustrate an example circuit diagram 2500 for controlling a segmented heater through the use of an active rectifier circuit using back-to-back MOSFETs to quickly and finely control the direction of current from an A/C power source 2502. To facilitate the description of how the example circuit 2500 controls the segmented heater, FIGS. 25B and 25C illustrate the switches S1-S4 as diodes to make it easier to understand the resulting flow of current in the circuit for particular control modes and for particular configurations of open and closed switches, as described below. However, it is to be understood that the switches S1-S4 are electrical switches, such as MOSFETs, as illustrated in FIG. 25A.

The active rectifier circuit 2500 can act to provide current to a targeted heater segment H1 and/or H2 by selectively switching MOSFETs S, S2, S3, and S4. For example, FIG. 25B illustrates the circuit configuration to provide power to heater segments H1 and H2. The MOSFETs S1 and S3 can be closed (e.g., switched on) and the MOSFETs S2 and S4 can be opened (e.g., switched off) when a positive current is provided by the power source 2502 and the MOSFETs S1 and S3 can be opened (e.g., switched off) and the MOSFETs S2 and S4 can be closed (e.g., switched on) when a negative current is provided by the power source 2502. FIG. 25C illustrates the circuit configuration to provide power to heater segment H1. The MOSFETs S1 and S3 can be opened (e.g., switched off) and the MOSFETs S2 and S4 can be closed (e.g., switched on) when a positive current is provided by the power source 2502 and the MOSFETs S1 and S3 can be closed (e.g., switched on) and the MOSFETs S2 and S4 can be opened (e.g., switched off) when a negative current is provided by the power source 2502.

In some embodiments, an expiratory heater is electrically coupled to the first heater segment H1. In such embodiments, the expiratory heater receives power when the first heater segment H1 receives power.

The circuit diagram 2500 advantageously allows a segmented heater to be controlled using a single power source and a patient-end temperature sensor (e.g., a thermistor). For example, the circuit diagram 2500 can be implemented in a system that does not include a temperature sensor on an intermediate connector connecting the first heater segment H1 to the second heater segment H2. The circuit diagram 2500 can be implemented using a control system that is configured to alter the switching of the MOSFET pairs to heat either the first heater segment H1 (e.g., an inner loop HW1 of an inspiratory limb) or the first and second heater segments H1, H2 (e.g., an outer loop HW2 of an inspiratory limb comprising the inspiratory limb and an extension limb), which will be described in greater details below. HW2 can comprise both H1 and H2 i.e. the entire heating circuit along the entire tube.

Detecting a Connected Extension of an Inspiratory Limb

Figure 5:
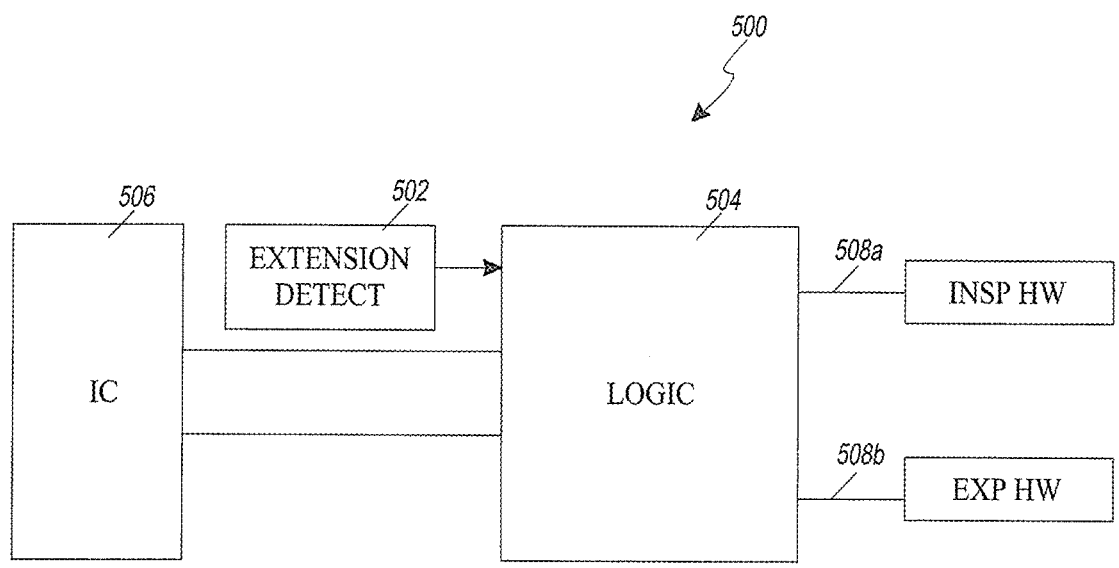
FIG. 5 illustrates a block diagram of an example system configured to detect a presence of an extension of an inspiratory limb and to provide power to heater wires in the inspiratory limb, the extension of the inspiratory limb, and an expiratory limb.

FIG. 5 illustrates a block diagram of an example system 500 configured to detect a presence of an extension of an inspiratory limb using extension detect module 502 and to provide power to heater wires in the inspiratory limb (e.g., a first segment of the inspiratory limb), the extension of the inspiratory limb (e.g., a second segment of the inspiratory limb), and/or an expiratory limb. The logic module 504, which can comprise hardware, software, or some combination of both, can be configured to provide the logic that enables the switching described for the different control modes, as described with reference to, for example, FIGS. 3A, 3B, 4, 8A, and 8B. The logic module 504 can receive signals from an integrated circuit 506 that is part of the respiratory humidification system 100. In some embodiments, the logic module 504 is software embedded wholly or partially within the integrated circuit 506 which converts signals from the integrated circuit 506. The combination of the logic module 504 and the integrated circuit 506 can be configured to detect a zero-level crossing, or where voltage or current transitions from positive to negative or vice versa, and to change states of switches according to a control mode. The logic module 504 can output PWM signals 508a, 508b according to a desired, selected, or defined power output where the PWM signal is delivered to the inspiratory heater wires (INSP HW), the expiratory heater wires (EXP HW), or both.

In some embodiments, the system 500 can include an extension detect module 502 configured to detect whether the second segment 202b is connected to the breathing circuit 200. The extension detect module 502 can produce an "enable signal" if the second segment 202b is connected. The logic module 504 can receive the "enable signal" and adjust switching accordingly. In some embodiments, the "enable signal" indicates to the logic module 504 that the system 500 will not control the inspiratory and expiratory circuits independently and simultaneously.

In some embodiments, the extension detect module 502 can be configured to detect the presence of the second segment 202b by switching on both the inspiratory and expiratory circuits and detecting whether a hardware overcurrent event is detected. If the overcurrent event is not detected when either are switched on individually but it is detected with they are both switched on together, the extension detect module 502 can produce an "enable signal" indicating that the second segment 202b is connected. In some embodiments, the extension detect module 502 can detect the presence of the second segment 202b by detecting a resistance of an identification resistor or of heater wires in each section using current measurements. Based at least in part on the current measurements of the various sections, the extension detect module 502 can produce an "enable signal" if current measurements for different cycles differ where different control modes are being implemented as described above with reference to FIGS. 3A, 3B, 4, 8A, and 8B.

Sensor Circuits

Figure 6A:
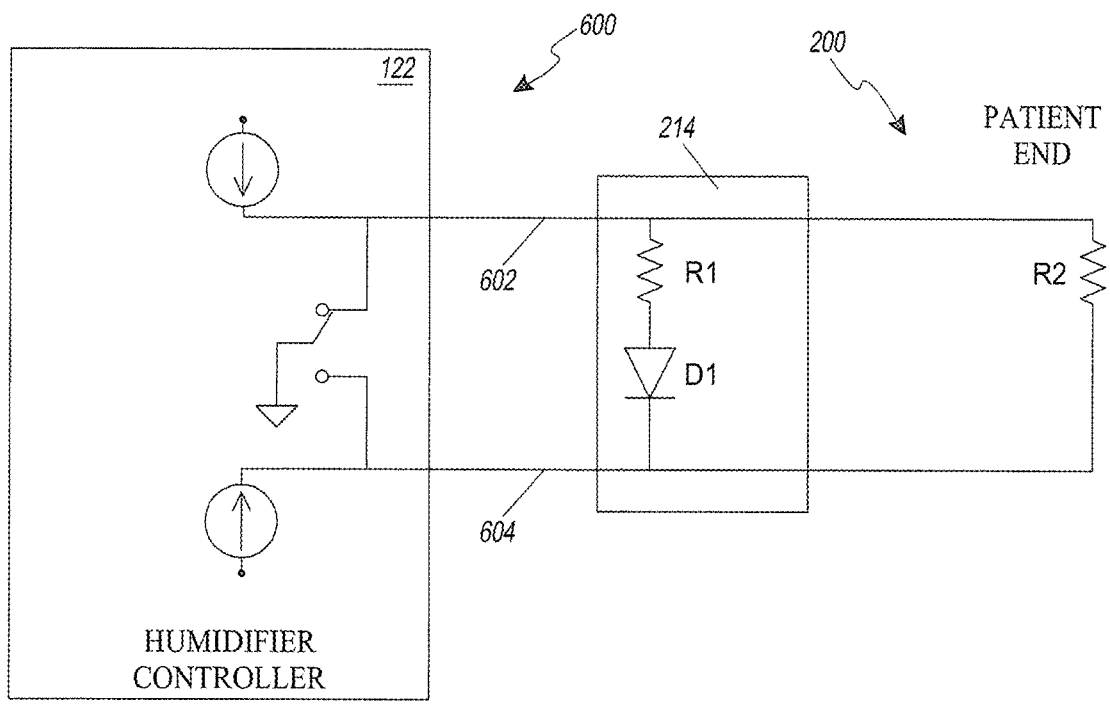
FIGS. 6A and 6B illustrate example circuit diagrams in a humidification system, wherein the circuits are configured to read data from two sensors.
Figure 6B:
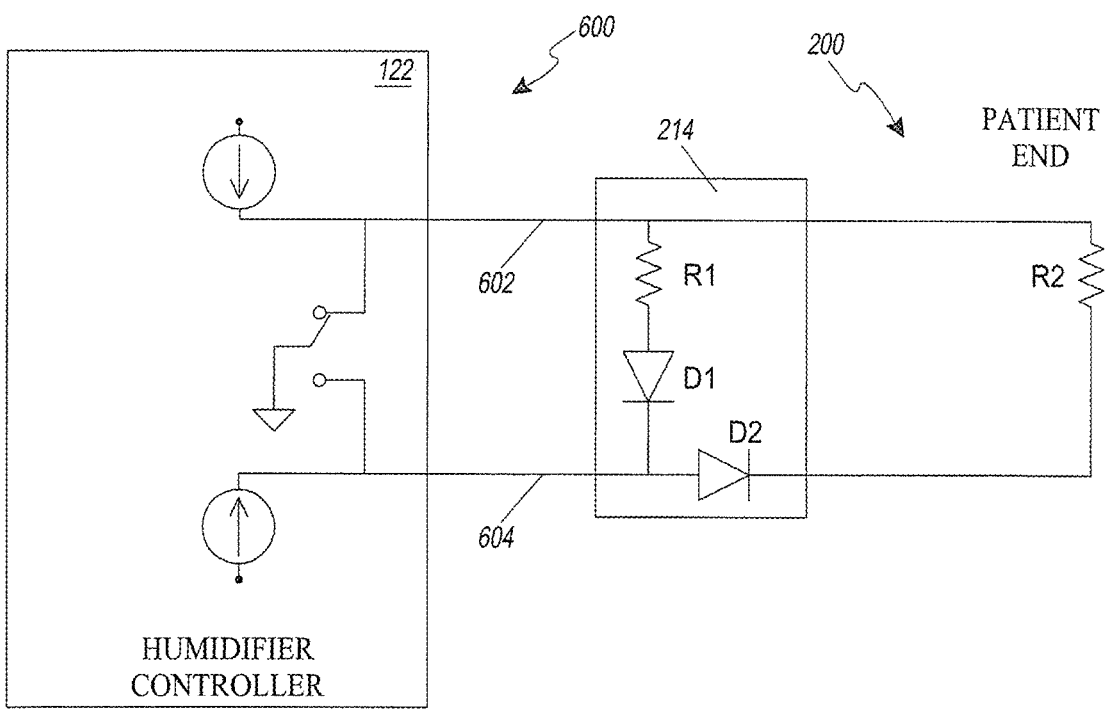

FIGS. 6A and 6B illustrate example circuit diagrams in a respiratory humidification system 100, wherein the circuit 600 is configured to read data from two sensors R1 and R2. With reference to FIGS. 6A and 6B, the sensors R1 and R2 are represented using resistors, but any suitable type of sensor can be used such as, for example and without limitation, temperature sensors, humidity sensors, flow sensors, oxygen sensors, and the like. In some embodiments, the sensors can be temperature sensors such as thermistors. In such embodiments, the sensors R1 and R2 respectively represent a first thermistor at the intermediate connector 214 and a second thermistor at a patient end of the breathing circuit 200 (e.g., on a patient-end connector). The two thermistors R1 and R2 can be measured using two wires in the breathing circuit 200 using the circuit 600 in conjunction with a current or voltage source and switches in the humidifier controller 122. While the description with reference to FIGS. 6A and 6B involves thermistors, it is applicable to other suitable sensors which affect voltages and/or currents provided to circuits with which they are associated.

To selectively read the sensors R1 and R2, current is supplied in either polarity through lines 602 and 604. To measure the patient-end sensor R2, the humidifier controller 122 sets the switch to connect the top current supply to ground. Current then flows from the bottom current supply through R2 and to ground through the switch. Current is blocked from going through R1 by diode D1. The humidifier controller 122 can be configured to measure the voltage drop from the bottom current supply to ground, and to derive the resistance of sensor R2 based at least in part on the supplied current and measured voltage. To measure the sensor R1 positioned at the intermediate connector 214, the humidifier controller 122 can read the patient-end sensor R2 and record the result. The humidifier controller 122 can then set the switch to connect the bottom current supply to ground. Current then flows from the top current supply through R1 and R2 to ground through the switch. The humidifier controller 122 can be configured to measure the voltage drop from the top current supply to ground, and to derive the resistance of sensor R1 based at least in part on the supplied current, the measured voltage, and the recorded result from measuring the resistance of R2. In some embodiments, a voltage drop across D1 is accounted for in the derivation of the resistance of R1. In the embodiment illustrated in FIG. 6A, by placing D1 near R1, the temperature of the diode D1 can be calculated which can be used in the calculation of the voltage drop across D1. One potential advantage of the configuration illustrated in FIG. 6A is that the measurements of the sensor R2 at the patient end may be more accurate because the measurements are made without passing through a diode, as illustrated in the embodiment of FIG. 6B, which can introduce uncertainties or errors.

In some embodiments, as illustrated in FIG. 6B, an additional diode D2 can be added to the intermediate connector 214. In such embodiments, the humidifier controller 122 can be configured to measure sensors R1 and R2 in a fashion similar to the embodiment illustrated in FIG. 6A and described above. A difference is that when measuring sensor R1, current flows through R1 and D1 and not through R2 because the diode D2 blocks current flow through R2. In this way, the measurement of sensor R1 can be substantially isolated or separated from the measurement of sensor R2. Similar to the derivation of the resistance of sensor R1, the voltage drop across the diode D2 can be accounted for in deriving the resistance of sensor R2. By placing D1 and D2 near R1, the temperature of the diodes can be calculated which can be used in the calculation of the voltage drops across D1 and D2, respectively.

In certain embodiments, the measurement of sensors R1, R2 is performed in software running in a controller connected to the circuits of FIG. 6A or 6B. The direction and amount of current supplied to the circuit can be controlled by such software. An accurate measurement of the resistance of sensors R1, R2 can be obtained by measuring the voltages using, for example, an analog to digital converter. To minimize or eliminate the effects of variances caused by the diodes D1 and/or D2, the software can supply two different currents (I1 and I2) in the same direction. This will result in two different voltage readings (V1 and V2) corresponding to the two different currents (I1 and I2). Using these two voltages and currents, the software can solve for the voltage drop of the diodes D1, D2 and resistances for sensors R1, R2. For sensor R1, for example, the voltage drop can be solved with the following equation: $Vdrop=((V1*I2-V2*I1)/((V1-V2)/R2+I2-I1))$. The resistance of sensor R1 can be calculated using the following equation: $R1=(V2-Vdrop)/(I2-V2/R2)$. In an embodiment, the calculated Vdrop has a constant error from a measured Vdrop that is corrected in software. In an embodiment, the Vdrop is increased by approximately 15% as an error compensation.

In some embodiments, the sensors R1 and R2 (e.g., thermistors) can be removed. In such embodiments, more accurate sensors can be included in the system. This may allow a symmetrical intermediate connector to be used (e.g., a mechanically and electrically independent connector). For example, the intermediate connector can be physically connected in two ways and still operate to mechanically couple segments of an inspiratory limb and to electrically direct power to the targeted segments of a segmented heater. In some of the embodiments described herein, if the connector is plugged in backward, the diodes and other electrical components may be configured such that the control algorithms provide power to an undesired portion of a segmented heater.

Figure 7:
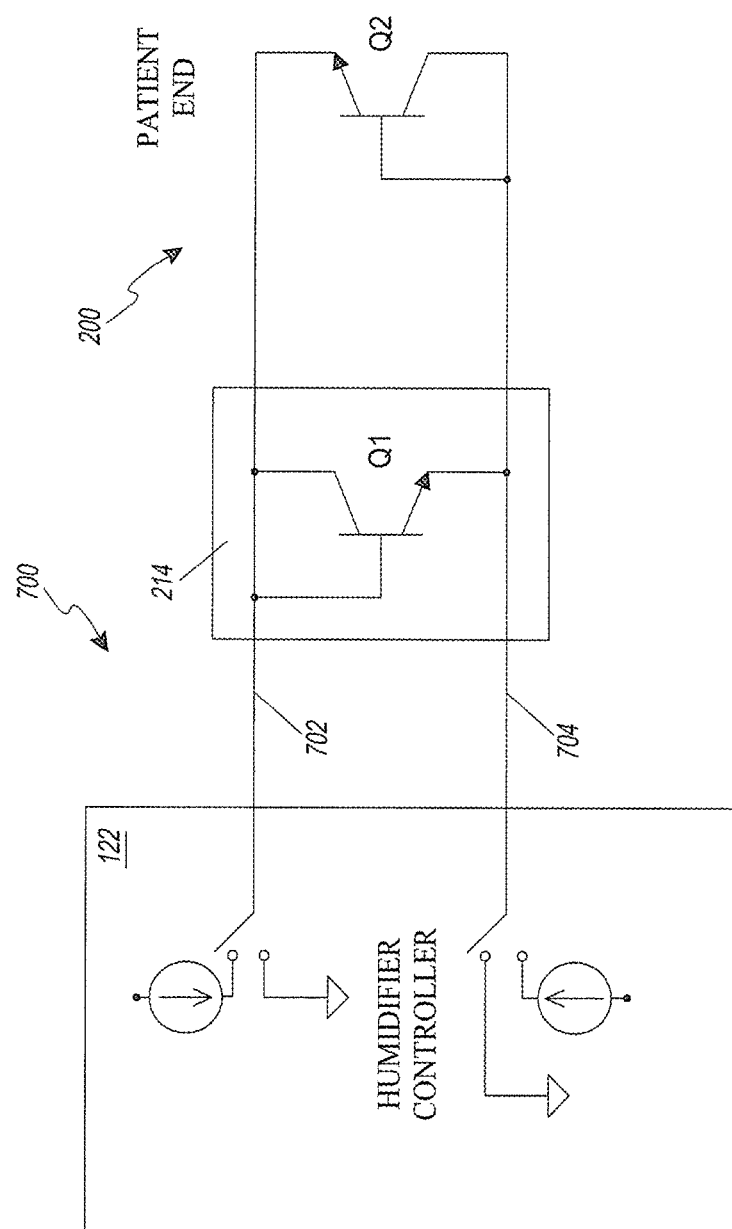
FIG. 7 illustrates an example circuit diagram in a humidification system, wherein the circuit is configured to read temperature data using two transistors.

FIG. 7 illustrates an example circuit diagram in the respiratory humidification system 100, wherein the circuit 700 is configured to read temperature data using two transistors Q1 and Q2 acting as temperature sensors. The temperature measurement can be based at least in part on a temperature effect of the pn-junction of the base and emitter terminals of the transistors. The switching of the current in the humidifier controller 122 can be the same as for the circuit described with reference to FIGS. 6A and 6B or it can be an alternate configuration, as shown. For example, the illustrated switching configuration uses two switches with two power sources and two grounds to selectively provide electrical power to the wires. In a first configuration, the top switch electrically connects a top power source to wire 702 and the bottom switch electrically connects the ground to wire 704. In a second configuration, the top switch electrically connects the ground to wire 702 and the bottom switch electrically connects the bottom power source to wire 704. By using transistors Q1 and Q2 as temperature sensors, the diodes can be removed as the transistors provide the functionality of the temperature sensors and the diodes.

Breathing Circuit Hardware Configurations

Figure 8A:
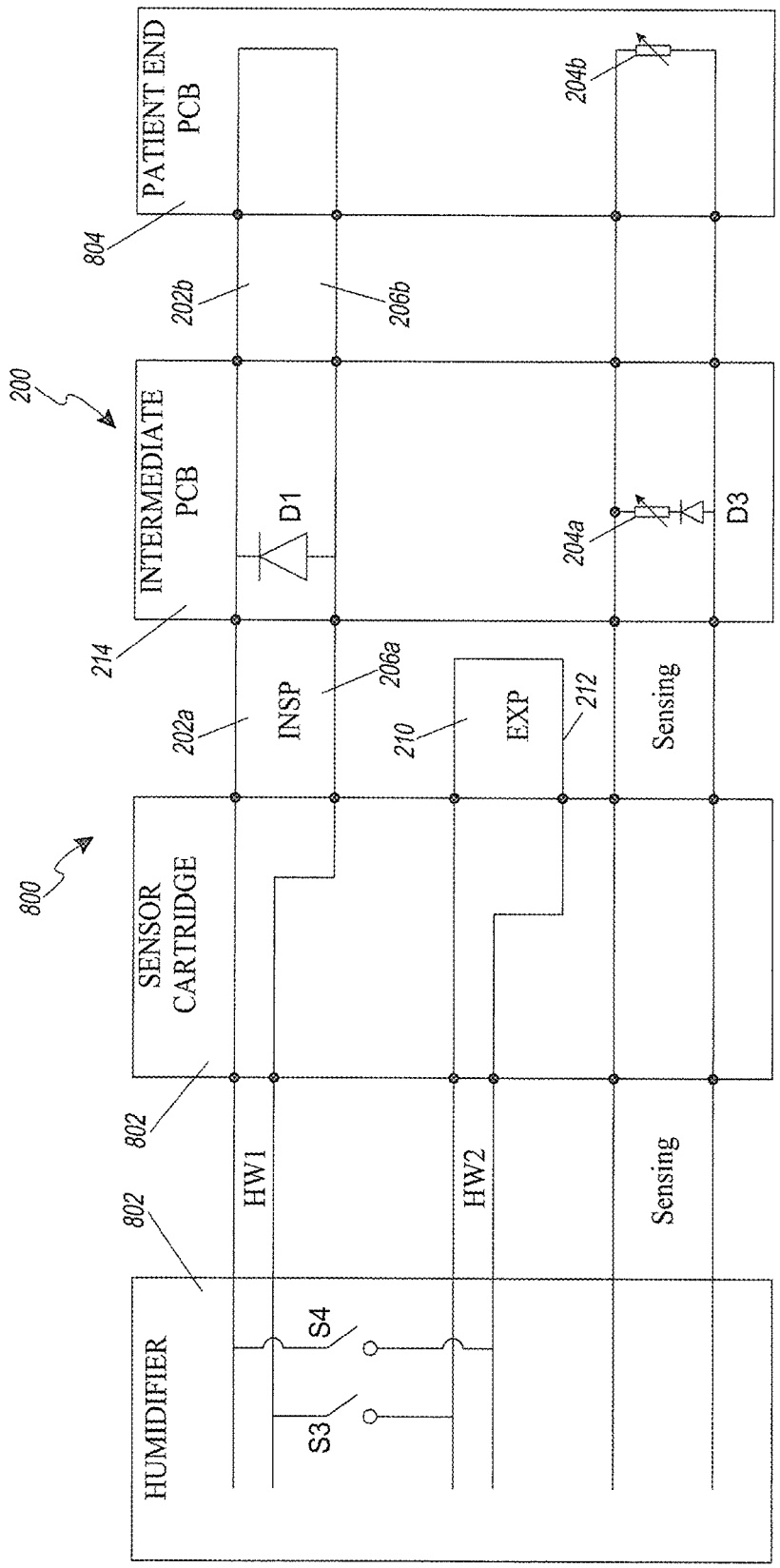
FIGS. 8A and 8B illustrate example diagrams of hardware configurations for a breathing circuit with an inspiratory limb and an expiratory limb, the inspiratory limb having a first and a second segment.

FIG. 8A illustrates an example diagram of a hardware configuration 800 for a breathing circuit 200 having a first segment 202a of an inspiratory limb, a second segment 202b of the inspiratory limb, and an expiratory limb 210. The hardware configuration 800 can include a humidification unit 108 configured to couple the wiring of the heater wires HW1 and HW2 through switches or relays S3 and S4, and the wiring for sensors 204a, 204b. In some embodiments, the sensor cartridge 802 can be configured to couple the wiring of the heater wires HW1, HW2 and the wiring for sensors 204a, 204b. The switches S3, S4 can be used to selectively control power to the heater wires HW2 of the expiratory limb 210, as described with reference to FIG. 4A with similar functionality described with reference to FIGS. 4B-4D. In some embodiments, the switches S3 and S4 both default to an open position, and are closed when an appropriate tube is connected to the humidification unit 108 (e.g., an inspiratory limb or expiratory limb with an appropriate identification resistor). In this way, the hardware configuration 800 can be used to provide power to heater wires HW1 and/or to heater wires HW2. Independent of whether the heater wires HW2 are receiving electrical power, the heater wires HW1 can be controlled in two modes. In a first mode, the first heater wires 206a receive electrical power while the second heater wires 206b do not. In a second mode, the first and second heater wires 206a, 206b receive electrical power. In the illustrated embodiment, heater wires HW2 are able to be powered when the heater wires HW1 are being controlled in either of the first or second modes. It is to be understood that the heater wires HW2 of the expiratory limb can be selectively controlled while the heater wires HW1 of the inspiratory limb remain in a single mode. For example, when the heater wires HW1 of the inspiratory limb are being controlled in a first mode (or a second mode), the heater wires HW2 of the expiratory limb can alternately receive or not receive power based at least in part on the operation of switches S3 and S4 without any change in control mode of the heater wires HW1. Similarly, the heater wires HW2 of the expiratory limb can remain receiving power while the heater wires HW1 of the inspiratory limb are changed between the first and second modes.

The hardware configuration 800 can include an intermediate printed circuit board (PCB) 214 that includes two diodes, with one diode being a power diode D1 and another diode being a signal diode D3. The intermediate PCB 214 can include heat pads to dissipate heat generated by the diodes D1, D3 to reduce the effects on the sensor 204a. The hardware configuration 800 can include a patient-end PCB 804 having two heater wires and a sensor 204b, wherein the heater wires 206b are directly electrically coupled. In the first mode of operation, electrical power can be provided to HW1 such that current flows through heater wires 206a and through diode D1 while substantially no current flows through heater wires 206b (e.g., less than 1% of the current through heater wires 206a flows through heater wires 206b). In the second mode of operation, electrical power can be provided to HW1 such that current flows through heater wires 206a and 206b. The first and second modes of operation can be controlled at least in part by the direction of the current flow through the heater wires HW1.

Figure 8B:
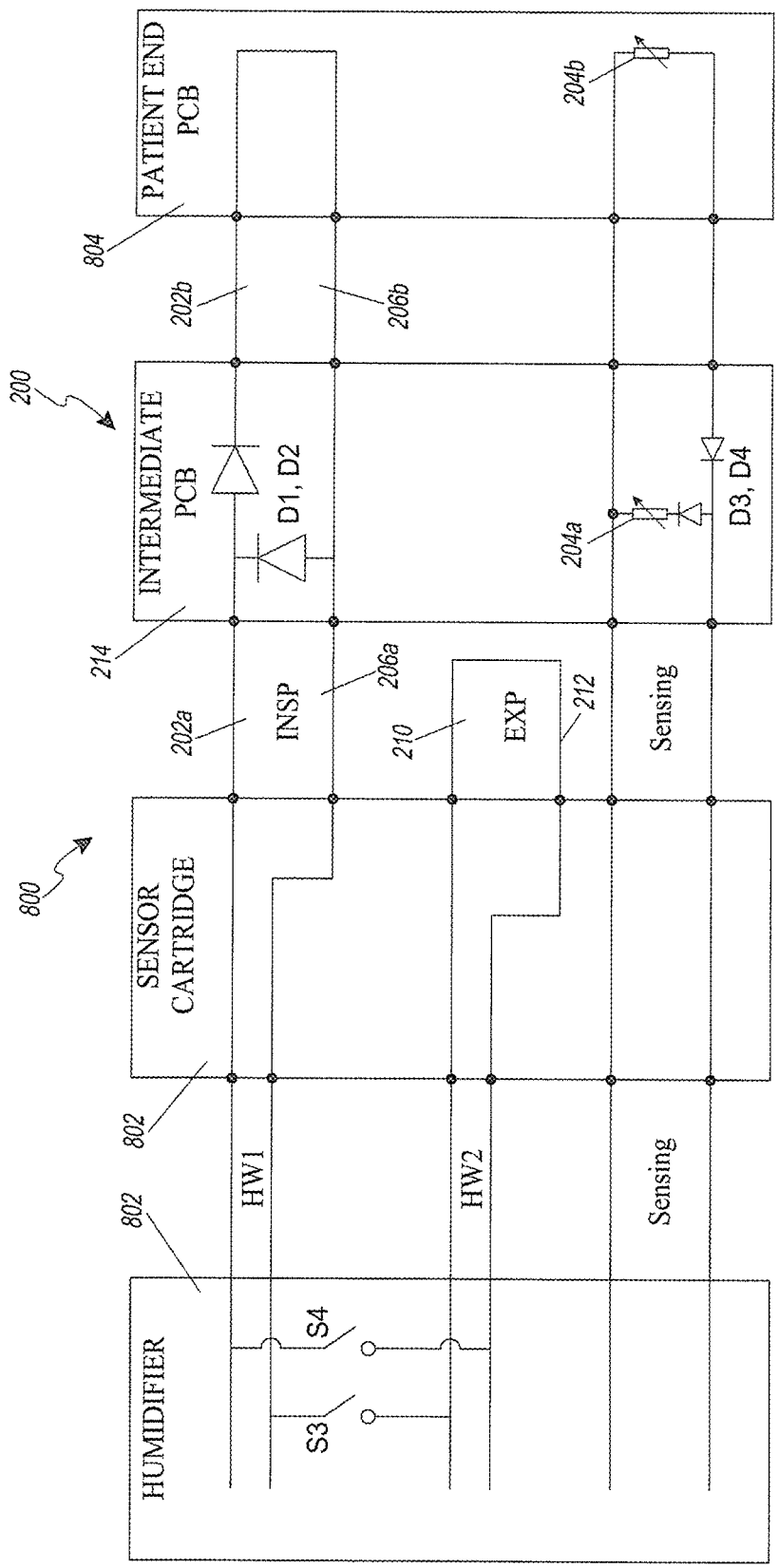

In certain embodiments, diodes D2 and D4 can be added to hardware configuration 800, as shown in FIG. 8B. In such an embodiment, the software for the sensing circuit can be altered to account for increased heat. In some embodiments, the signal diodes D3, D4 are positioned close to one another so they experience the same or similar ambient conditions to reduce differential effects caused by differing ambient temperatures. The circuit 200 otherwise operates in a manner similar to the circuit shown in FIG. 8A.

In some embodiments, comparing FIG. 8A to FIG. 8B, removing diode D4 improves patient-end sensing reliability. For example, diodes can fail in an open position. If diode D4 fails open, reading the patient-end temperature may not be possible. In the circuit shown in FIG. 8A, if diode D3 fails, the patient-end sensor 204b can still be read. The removal of diode D2 can have similar advantages.

In some embodiments, the sensor cartridge 802 can be located within the humidification system 100 or external to the system.

Example Segmented Inspiratory Limb with a Connector Having a Microcontroller

Figure 9:
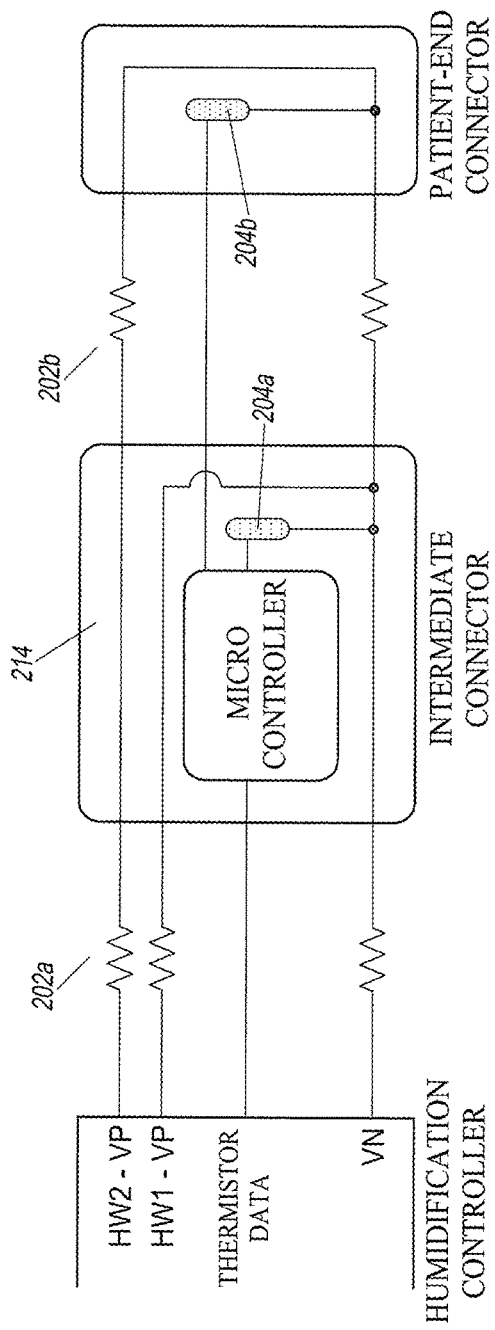
FIG. 9 illustrates an example embodiment of a humidification system that utilizes a microcontroller in an intermediate connector to measure data for controlling heating and to read sensor values in an inspiratory limb.

FIG. 9 illustrates an example embodiment of a respiratory humidification system 100 that utilizes a microcontroller in an intermediate connector 214 to measure data for controlling heating and to read sensor values in an inspiratory limb 202. In some embodiments, one or more microcontrollers can be incorporated in a sensor cartridge, in the humidifier, in the intermediate connector 214, or in any combination of these. The microcontroller provides similar functionality as described herein when incorporated on the sensor cartridge, for example. The illustrated example embodiment uses one heater wire as a common reference, the wire connected to VN, and connects the two heater wires HW1, HW2 and the sensor wires to the common reference. The example embodiment also converts both sensors' 204a, 204b readings into a digital signal in the intermediate connector 214 to send to the humidifier controller 122. This can reduce or eliminate isolation issues by referencing the sensors 204a, 204b to a common reference point and by sending a digital parameter reading which can be passed through an optocoupler on the controller 122 which will isolate the signal, as described herein with reference to FIG. 12. Using this example embodiment can allow for two independent channels of control to heat just the first segment 202a or the first and second segments 202a, 202b of the inspiratory limb to provide a desired, selected, or defined heating control.

Figure 10:
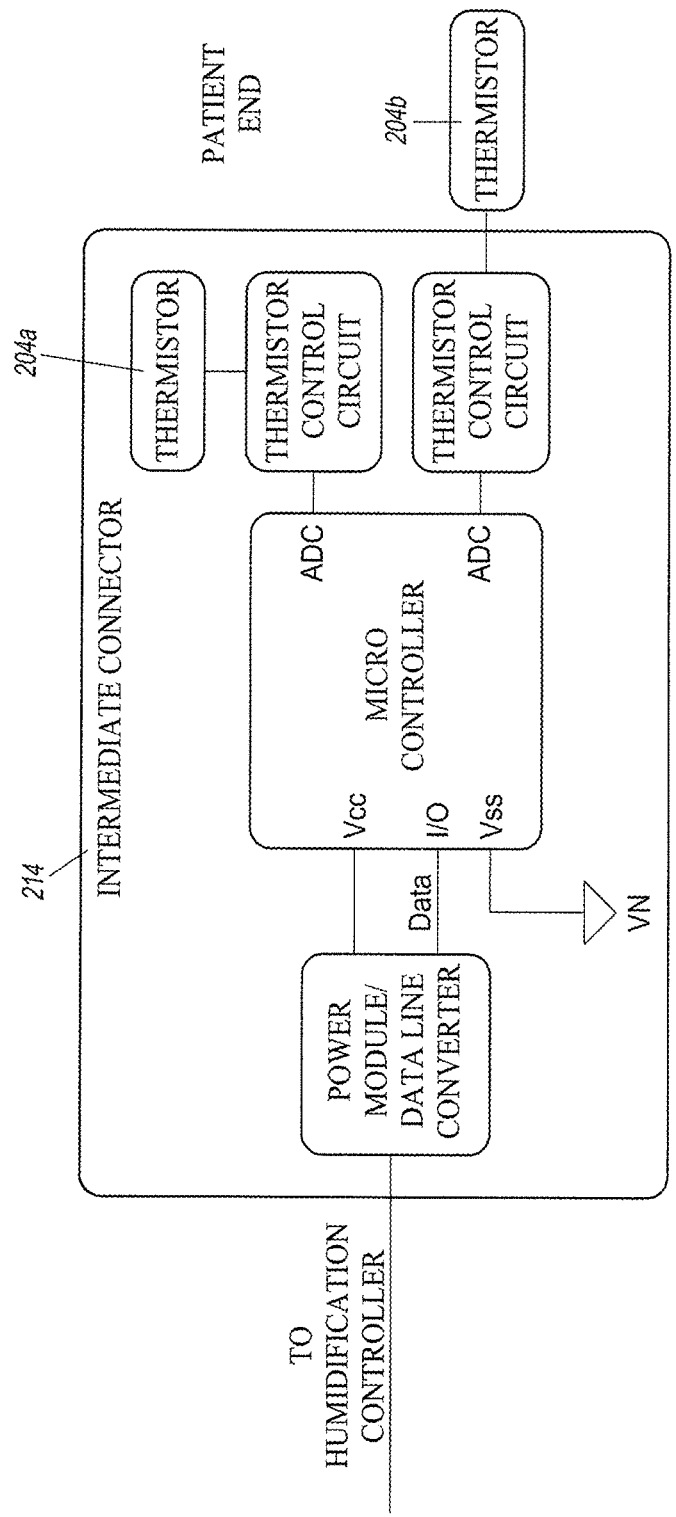
FIG. 10 illustrates a block diagram of an example intermediate connector for an inspiratory limb, wherein the intermediate connector uses a microcontroller.
Figure 11:
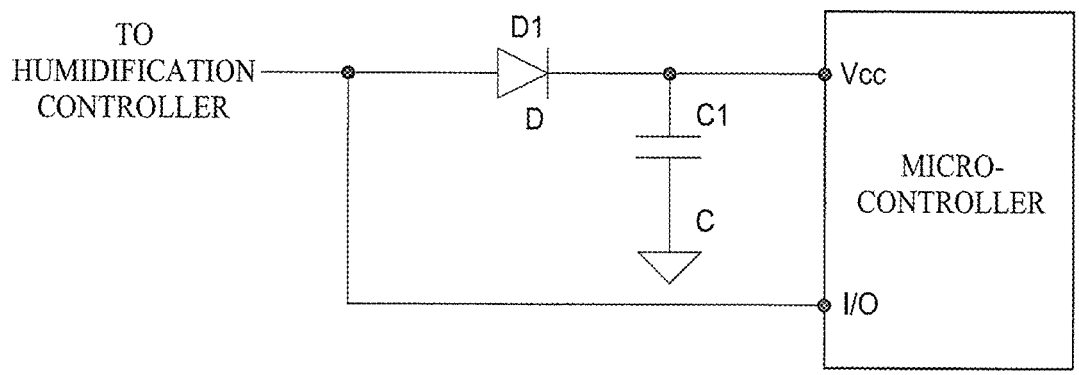
FIG. 11 illustrates a circuit diagram for an example power module and data line converter included in the intermediate connector illustrated in FIG. 10.

FIG. 10 illustrates a block diagram of an intermediate connector 214 for an inspiratory limb 202, wherein the intermediate connector 214 uses a microcontroller. The microcontroller can be used to measure an analog signal from the sensors 204a and 204b and convert the analog signal into a digital signal using analog-to-digital converters (ADCs). The converted digital signal can be sent to the humidifier controller 122 on a single data line. The data line can be used to allow communication between the microcontroller and the humidifier controller 122 to provide temperature data. The data line can be used to provide power to the microcontroller by pulling the data line high on the humidifier controller 122 when data is not being sent. The power module and data line converter can include a capacitor and a diode so that the capacitor is charged when the data line is high. The charged capacitor can be used to power the microcontroller when the data line is being used for communication. The circuit diagram for an example power module and data line converter is illustrated in FIG. 11.

Temperature sensing using this configuration can be accomplished using a current source or a voltage source on the intermediate connector 214 to drive the thermistors so they can be read by the microcontroller. This can be done using, for example, transistors or an op-amp. Data line communication can be accomplished using a time-slot based approach where each logic level can be sent and read in a predefined time slot. In this way, one wire can be used to allow two-way communication between the humidifier controller 122 and the microcontroller.

Figure 12:
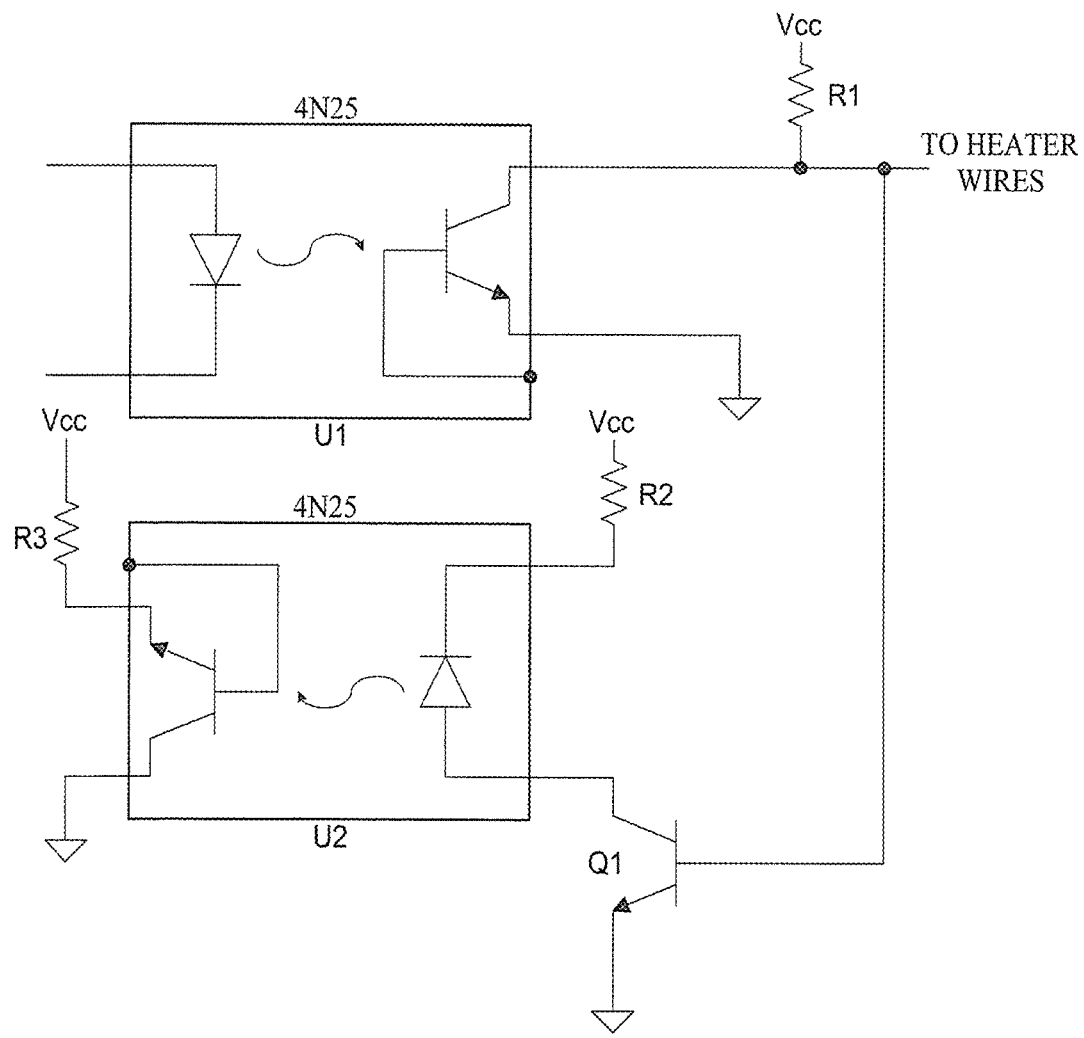
FIG. 12 illustrates a circuit diagram of an example dual optocoupler circuit used in conjunction with the intermediate connector illustrated in FIG. 10 to provide two-way data communication between a control side and an AC side on a power board.

The humidifier controller 122 can include a DC power supply that is referenced to VN. A capacitor can be included which can be charged when the heater wires are on and can provide power to the microcontroller while the heater wires are turned off. The humidifier controller 122 can include a dual optocoupler circuit 1200, as illustrated in FIG. 12. The dual optocoupler circuit can be used to isolate signals and for two-way data communication between the controller 122 and a power supply.

In some embodiments, calibration data can be stored on the microcontroller which can be read when a breathing circuit is connected. In some embodiments, part identification numbers or serial numbers can be stored to determine an origin of a connected circuit.

Segmented Inspiratory Limbs with Digital Temperature Sensors

Figure 13:
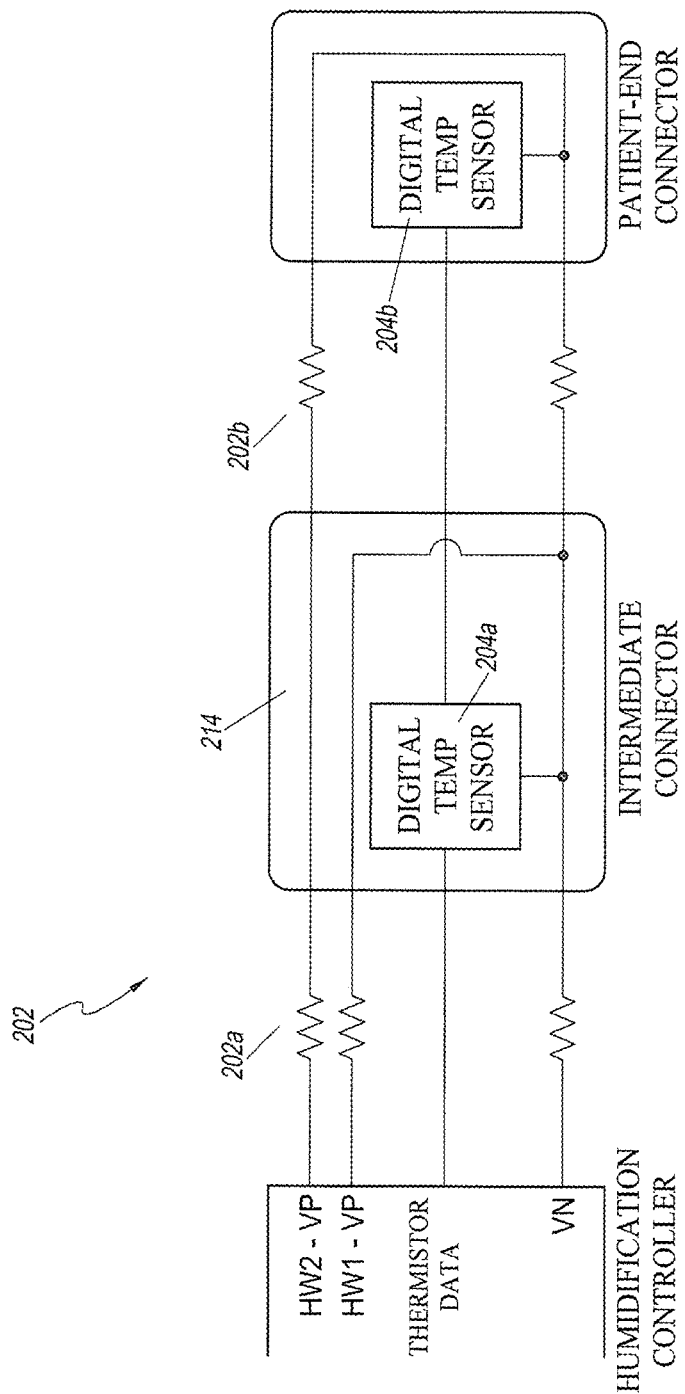
FIG. 13 illustrates a circuit diagram of an example humidification system incorporating digital temperature sensors for use with a breathing circuit having an inspiratory limb with at least two segments.

FIG. 13 illustrates a circuit diagram of an example respiratory humidification system 100 incorporating sensors 204a, 204b for use with a breathing circuit 200 having an first segment 202a and an intermediate connector 214 coupling a second segment 202b to form the inspiratory limb 202. The sensors 204a, 204b can utilize a single line for communication and power, simplifying circuit design and reducing an amount of wires used in the system 100, similar to the design described with reference to FIG. 9. The design illustrated in FIG. 13, can implement the temperature sensors and data communication as a single chip rather than a combination of circuit elements which may be desirable.

Intermediate Connector Board

Figure 14B:
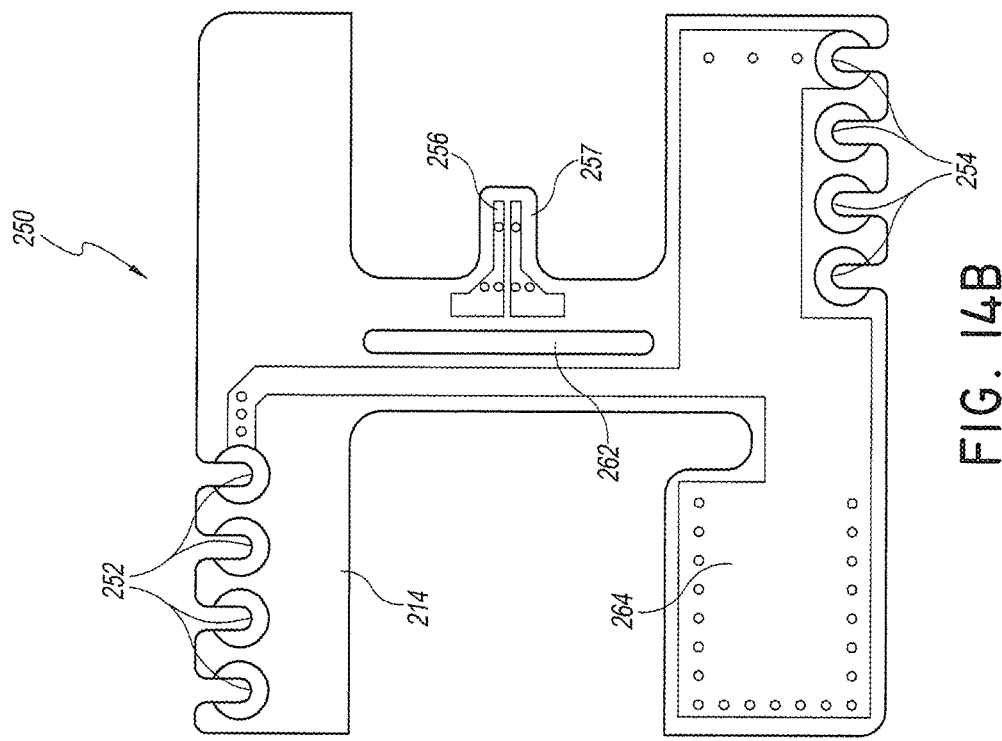
FIGS. 14A and 14B illustrate an example printed circuit board ("PCB") of an intermediate connector.
Figure 14A:
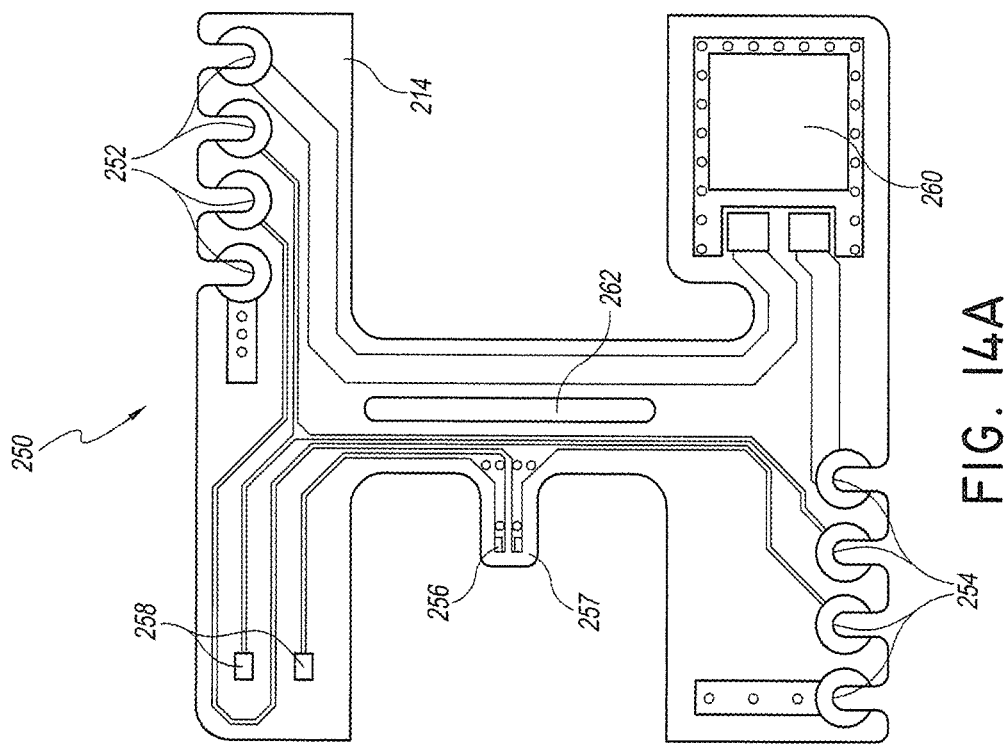

FIGS. 14A and 14B illustrate an example intermediate PCB 250 of the intermediate connector 214, the respective figures illustrating two sides of the intermediate PCB 250. The intermediate PCB 250 includes connection pads 252, 254 for the heater wires and sensor connections. The connection pads 252, 254 are configured to be on opposite sides of the intermediate PCB 250 to facilitate connections with heater wires wound spirally around an inspiratory limb.

The intermediate PCB 250 includes sensor connection pads 256 for the sensor, such as a thermistor or other temperature measurement component, or humidity sensor, or a flow sensor, or the like. The sensor can be coupled to a diode (e.g., diode D3 described with reference to FIG. 8B) through signal connection pads 258 on the intermediate PCB 250. As illustrated, the intermediate PCB 250 includes a gap 262 configured to thermally insulate the sensor from the other electrical components and tracks. In some embodiments, the gap 262 can be filled with an insulating material to further thermally isolate the sensor connected to sensor connection pads 256. In addition, the intermediate PCB 250 can be configured to position the sensor apart from the other active and/or passive electrical components, such as with the protruding feature 257.

The intermediate PCB 250 includes power connection pad 260 for a diode electrically coupled to the heater wires through electrical tracks on the intermediate PCB 250. The diode can be the diode D1 described with reference to FIG. 3B, 6B, or 8B. The power connection pad 260 can be electrically and thermally coupled to heat sink 264 to aid in dissipating heat, to reduce or minimize effects on the accuracy of the parameter reading of the sensor coupled to the sensor connection pads 256.

Figure 14D:
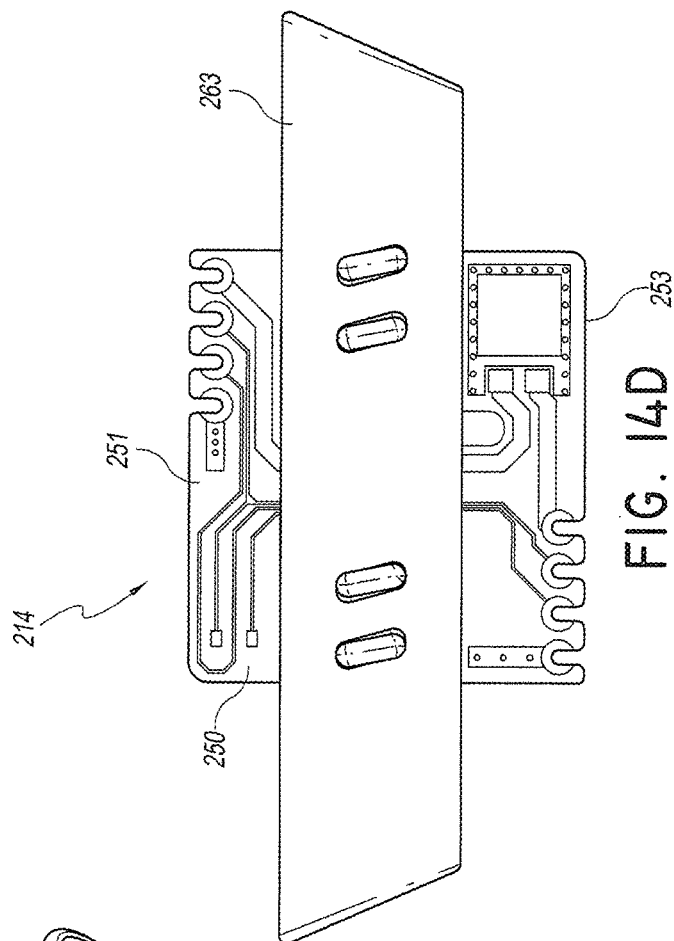
FIGS. 14C and 14D illustrate example embodiments of intermediate connectors.
Figure 14C:
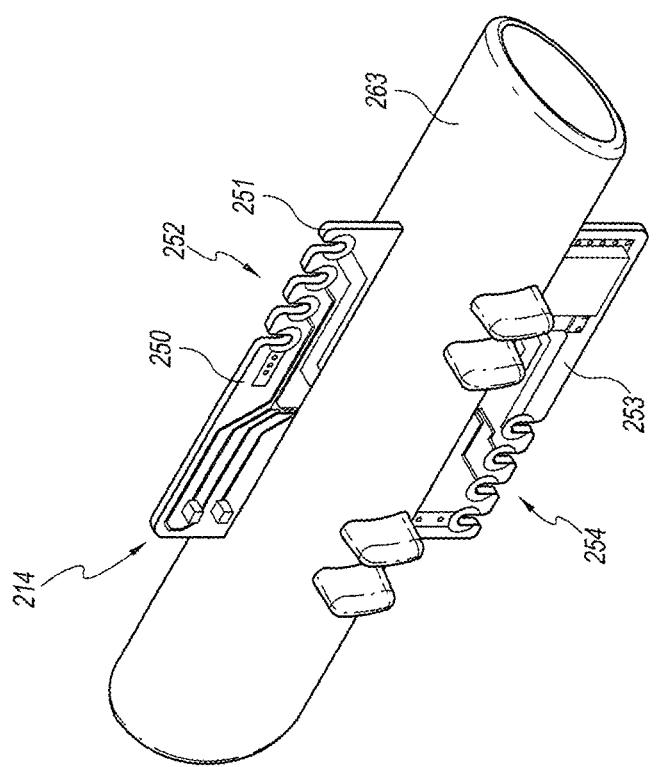

FIGS. 14C and 14D illustrate example embodiments of intermediate connectors 214 comprising an intermediate PCB 250 and an intermediate connection element 263. The intermediate connection element 263 can be configured to direct a portion of the humidified gas flowing through an inspiratory limb through a conduit formed by the intermediate connection element 263. A sensor on the intermediate PCB 250 can then provide a signal corresponding to a parameter of the gas flowing through the intermediate connection element 263, the parameter being representative of at least one property (e.g., temperature, humidity, flow rate, oxygen percentage, etc.) of the humidified gas at that point in the inspiratory limb. In some embodiments, the intermediate connection element 263 is configured to provide mechanical support for the intermediate PCB 250, to position it within the inspiratory limb. In some embodiments, the intermediate connection element 263 is configured to provide mechanical support for joining two segments of an inspiratory limb together at or near the intermediate connector 214.

The intermediate connector 214 includes first connection pads 252 on a first side of the intermediate PCB 250 and second connection pads 254 on a second side of the intermediate PCB 250, the second side being on an opposite side of the intermediate PCB 250. The first and second connection pads 252, 254 can be configured to provide electrical contacts for heater wires in respective first and second segments of a segmented inspiratory limb, as described herein. In some embodiments, heater wires in a segment of an inspiratory limb are spirally wound. The intermediate PCB 250 is configured to electrically couple spirally-wound heater wires and/or signal wires (e.g., temperature sensor wires) in a first segment to spirally-wound heater wires and/or signal wires in a second segment.

In some embodiments, the intermediate PCB 250 includes a first portion extending across a lumen formed by the intermediate connection element 263 along a diameter or chord line, such that a portion of the intermediate PCB 250 generally bisects at least part of the flow path of the gas. The first portion of the intermediate PCB 250 can be overmolded by an overmolding composition. The intermediate PCB 250 can include a second portion 251 adjacent the first portion projecting outward from an exterior of the intermediate connection element 263 in a direction away from the lumen. The second portion 251 of the intermediate PCB 250 includes one or more connection pads 252 configured to receive one or more wires from a first segment of the inspiratory limb. The intermediate PCB 250 can include a third portion 253 adjacent the first portion projecting outward from the exterior of the intermediate connection element 263 in a direction away from the lumen and in a direction opposite the second portion 251. The third portion 253 can include one or more connection pads 254 on the intermediate PCB 250 configured to receive one or more wires from a second segment of the inspiratory limb. The intermediate PCB 250 can include one or more conductive tracks configured to electrically couple the one or more connection pads 252 of the second portion 251 to the one or more connection pads 254 of the third portion 253 and configured to provide an electrical connection between the wires in the first segment and the wires in the second segment of the inspiratory limb.

In some embodiments, the intermediate PCB 250 can limit the number of contact pads for wires to four. In such an embodiment, the wires could overlap and maintain continuity of the tube. It may be beneficial in such an embodiment to maintain the orientation and/or order of the wires.

Figure 34:
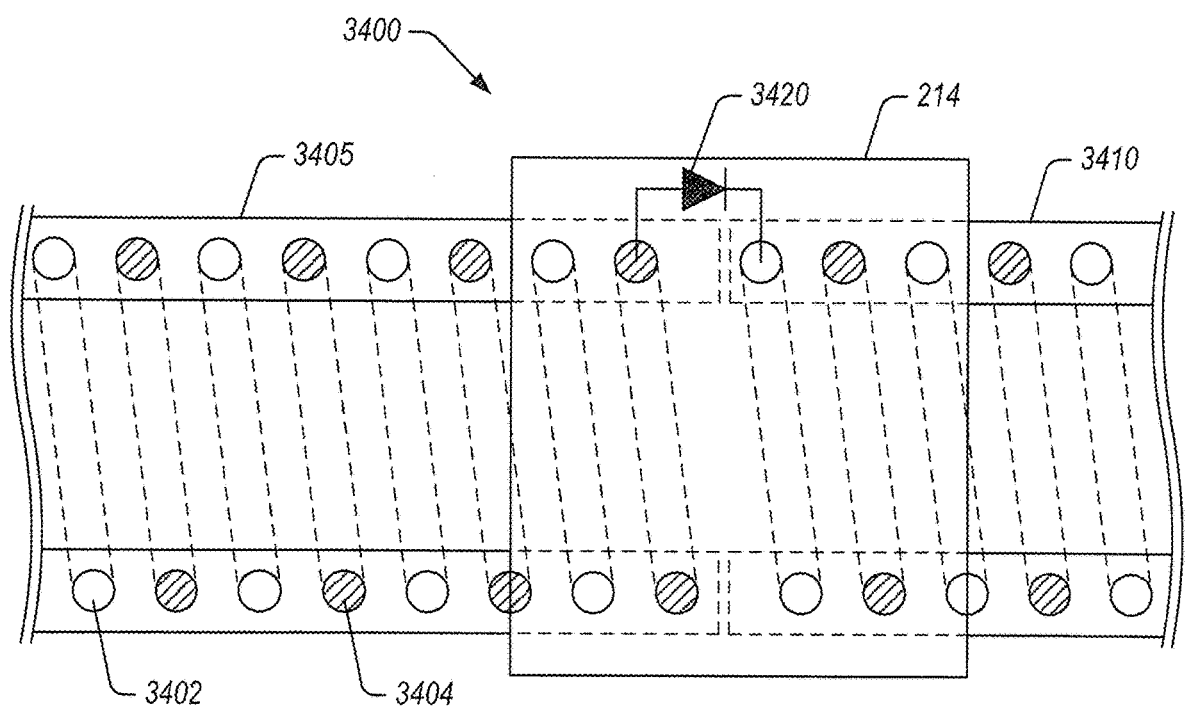
FIG. 34 illustrates an example embodiment of an inspiratory limb and extension limb with heater wires directly coupled together with a diode.

FIG. 34 illustrates an example embodiment of an inspiratory limb 3405 and extension limb 3410 with heater wires 3402, 3404 directly coupled together with a diode 3420. In some embodiments, the intermediate connector 214 can be configured to include a diode to directly connect the wires 3402, 3404. For example, the wires 3402, 3404 could be laser ablated so that they are exposed. The diode 3420 can be configured to contact the wires across the heater wires 3402, 3404 where there is no sensor and no intermediate PCB, as described herein. In such a configuration, the inspiratory limb and extension limb can be advantageously configured such that there is no unheated section. Similarly, this configuration can reduce or eliminate condensate, dendrite growth, heater wire or sensing wire electrical shorts, printed circuit boards in the intermediate connector, breaking of the circuit, and/or resistance to flow.

Patient-End Connector Board

Figure 15A:
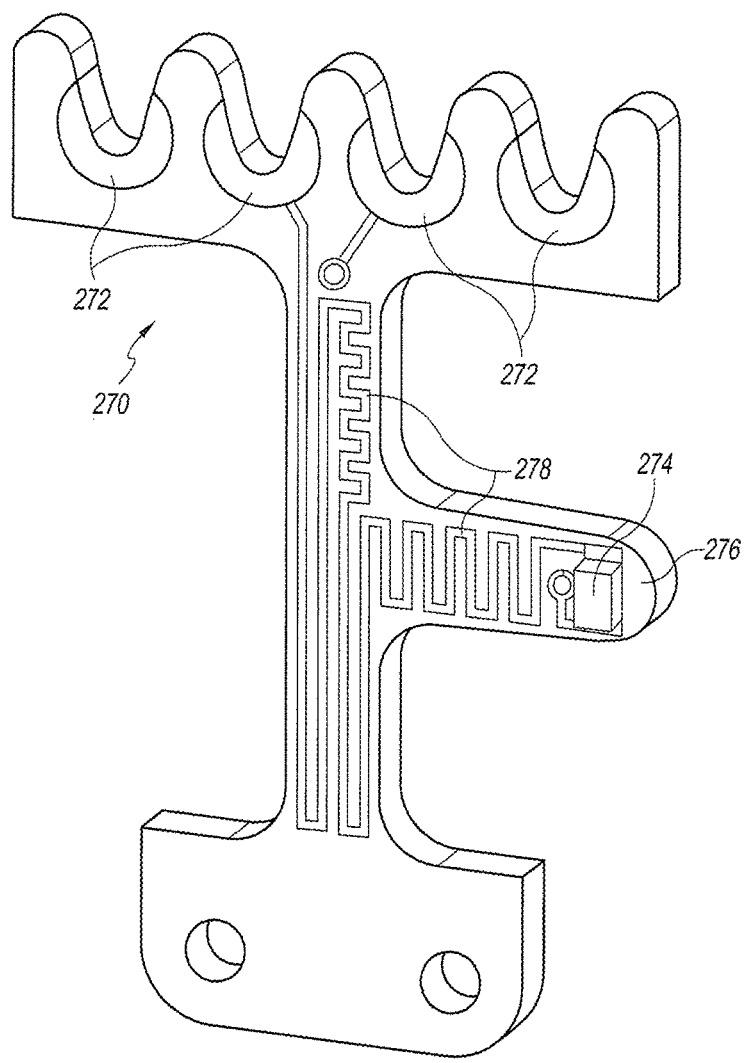
FIG. 15A illustrates an example PCB for a patient-end connector.

FIG. 15A illustrates an example patient-end PCB 270 of the patient-end connector 804. The patient-end PCB 270 includes connection pads 272 for the heater wires and sensor connections. The connection pads 272 are configured to be on only one side of the patient-end PCB 270 to connect to spirally wound heater and signal wires from the inspiratory limb. Two of the connection pads 272 can be directly electrically coupled to one another as an electrical passthrough. The heater wires can be coupled to the connection pads 272 which are directly electrically coupled. The remaining two connection pads 272 can be electrically coupled to the sensor connection pads 274. The electrical tracks 278 to and from the sensor connection pads 274 can be configured to reduce or minimize the width of the trace and increase or maximize the length of the track to thermally isolate the sensor connected to the sensor connection pads 274. The patient-end PCB 270 can include a similar protruding feature 276 as was described with reference to the PCB 250 illustrated in FIGS. 14A and 14B. The protruding feature 276 can be configured to further thermally isolate the sensor from the effects of the electrical current and components on the patient-end PCB 270.

Figure 15D:
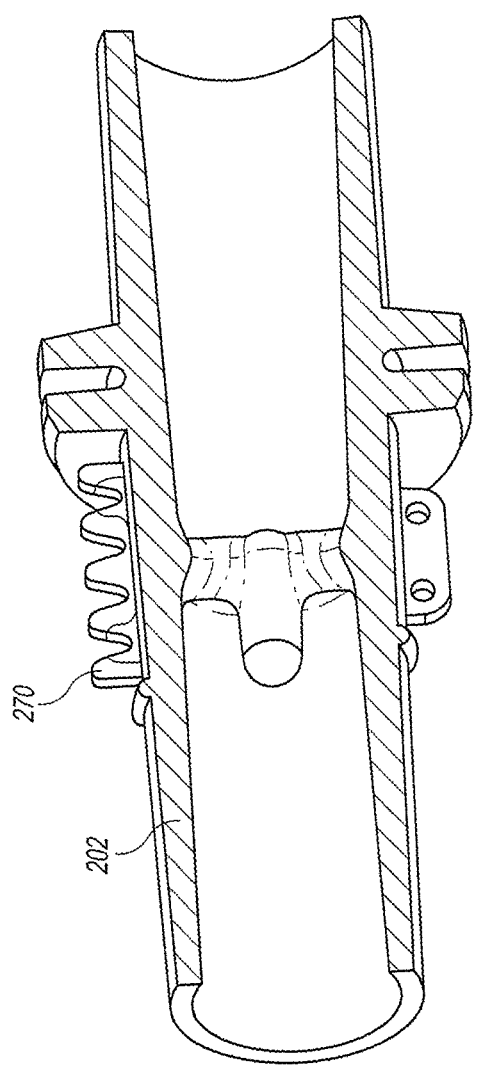
Figure 15E:
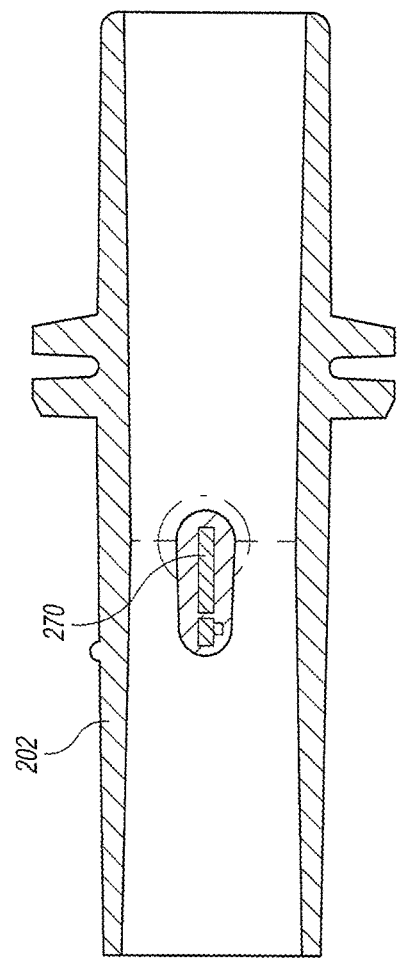

FIGS. 15B-15E illustrate example embodiments of the patient-end connectors 804. FIGS. 15B and 15D illustrate example embodiments of the patient-end PCB 270 overmolded as part of the inspiratory limb 202. The cross-section of the patient-end PCB 270, illustrated respectively in FIGS. 15C and 15E, can be configured to be aerodynamic to reduce or minimize turbulence in the gases being delivered to the patient.

Segmented Inspiratory Limb Placement Limiters

Figure 16A:
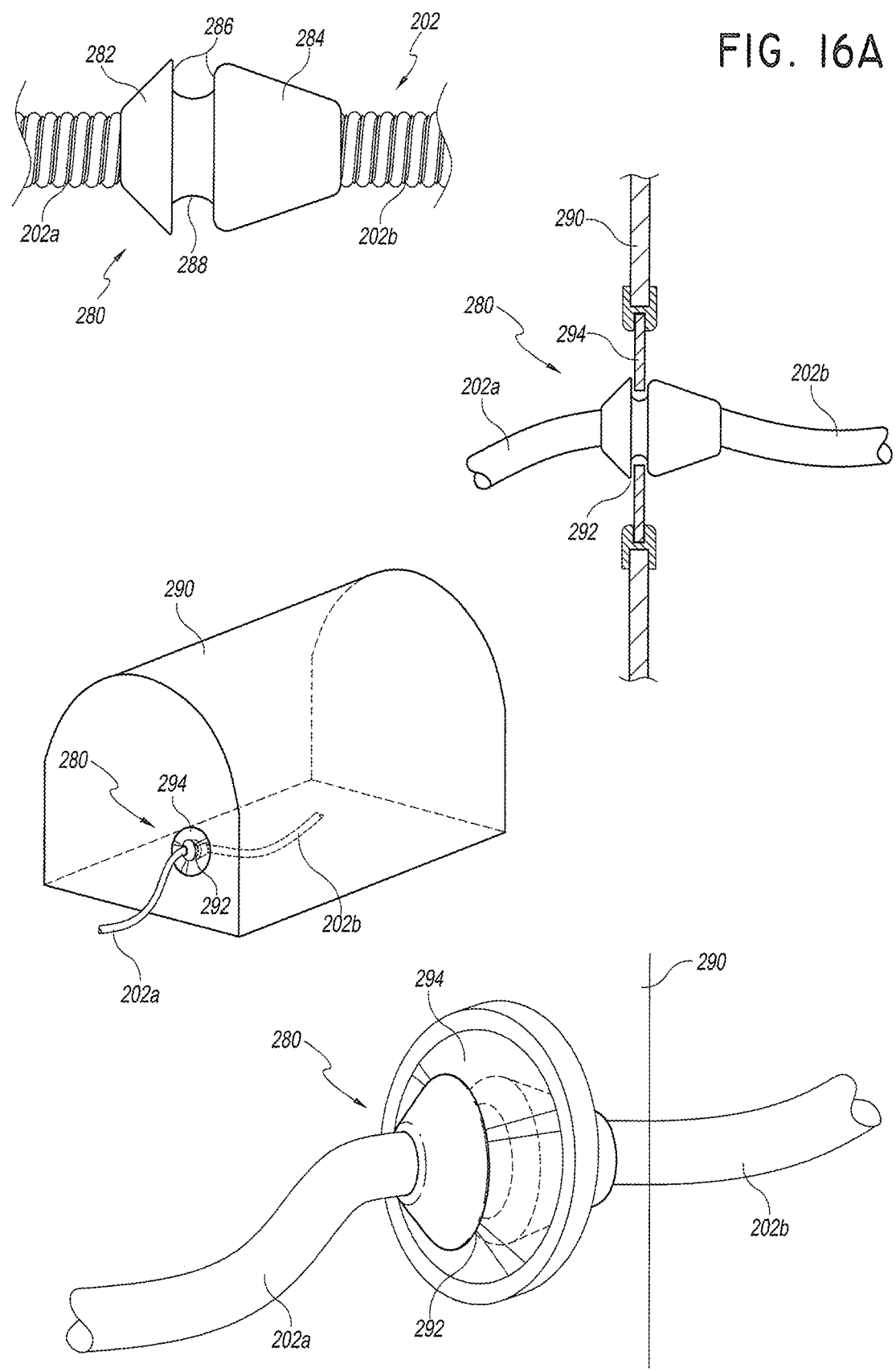
FIGS. 16A-16E illustrate example embodiments of placement limiters for a segmented inspiratory limb.
Figure 16B:
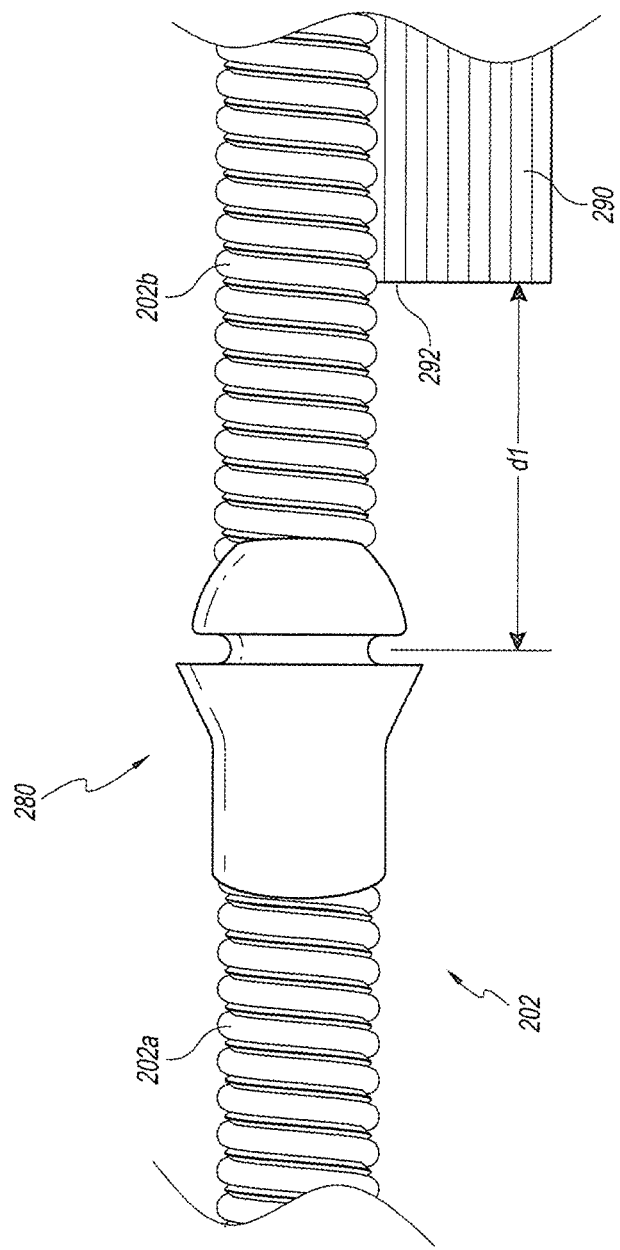

FIGS. 16A-16E illustrate example embodiments of placement limiters 280 for a segmented inspiratory limb 202. FIG. 16A illustrates an example placement limiter 280 configured with a larger chamber end 282 (e.g., an end nearer a gas supply), a smaller patient end 284, and sharp corners 286 with a groove 288 into which a grommet 294 can be placed. The placement limiter 280 can be configured to prevent or reduce the probability that the intermediate connector or the segment connection point of the inspiratory limb 202 (e.g., where the intermediate PCB 250 is located), enters the incubator 290 through the incubator opening 292. The smaller patient end 284 can be configured to enter the incubator 290 while the larger chamber end 282 can be configured to prevent or resist entry through the incubator opening 292 through contact with the grommet 294. In some embodiments, the placement limiter 280 is configured to substantially secure the location of the intermediate PCB 250 within a targeted or desired distance from the incubator or other such point defining a different temperature environment. The targeted or desired distance can be less than or equal to about 20 cm, less than or equal to about 10 cm, less than or equal to about 5 cm, or about 0 cm. FIG. 16B shows the example placement limiter 280 used with the inspiratory limb 202 where the placement limiter is located a distance dl from the incubator opening 292 to the incubator 290.

Figure 16C:
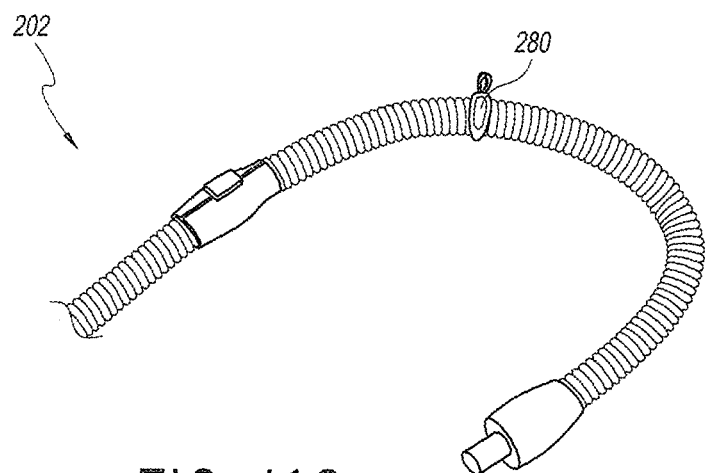
Figure 16D:
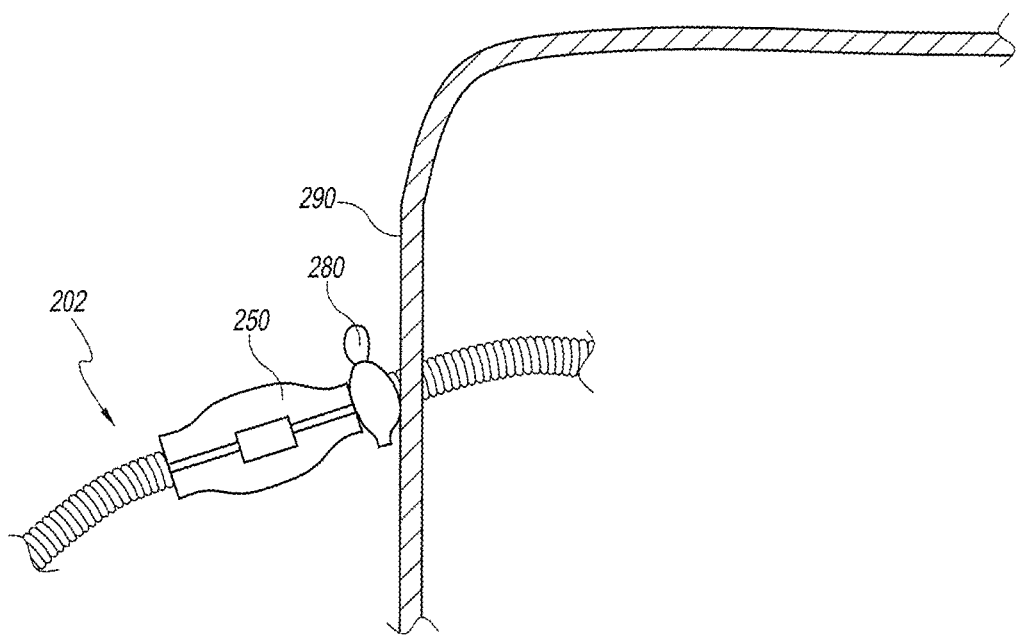
Figure 16E:
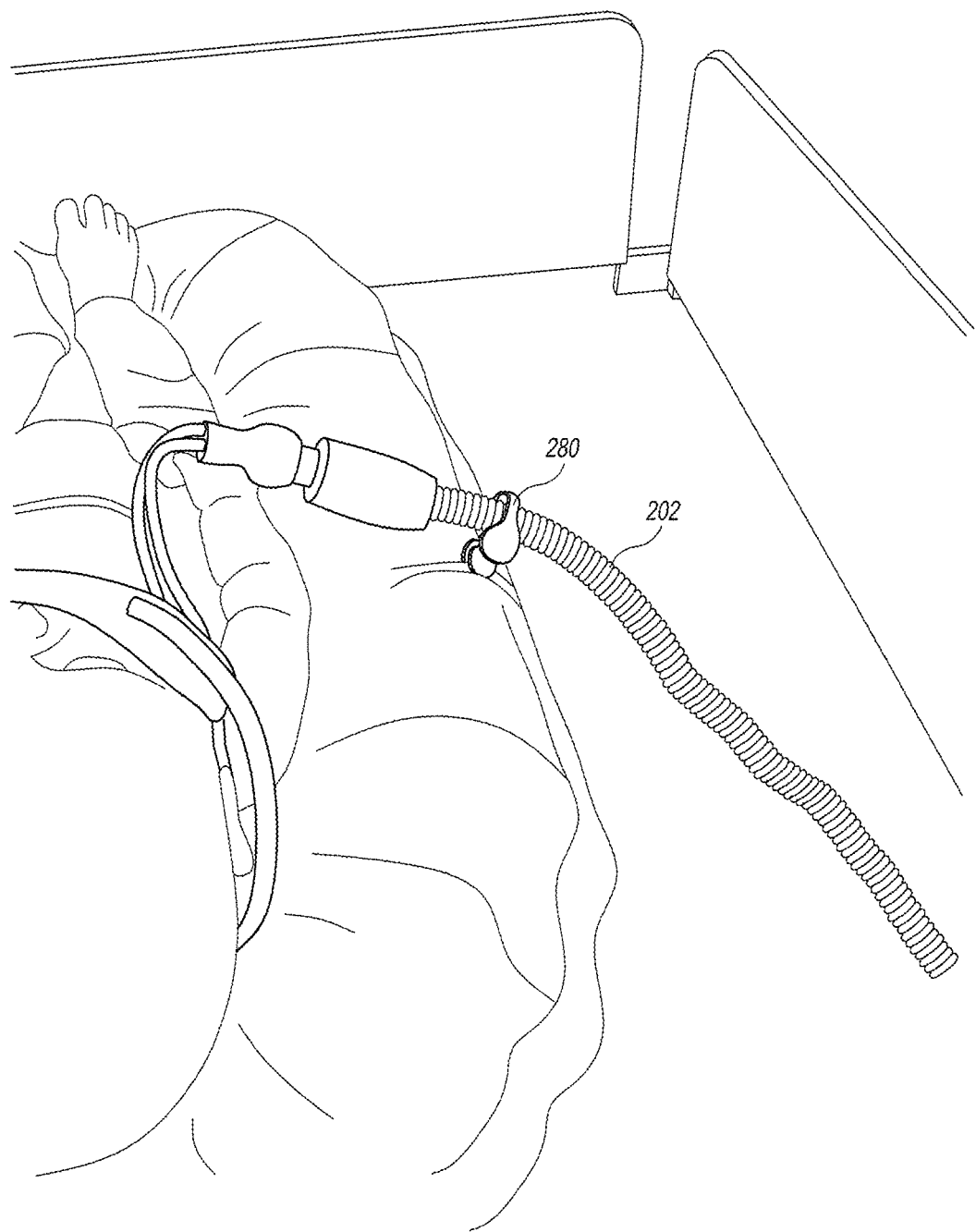

FIG. 16C illustrates an example embodiment of a placement limiter 280 configured to clip or be secured to an object, such as clothing, a blanket, or another object that is separate from the patient. The placement limiter 280 is secured to an inspiratory limb 202 and is configured to be able to be moved along the inspiratory limb 202 to adjust the placement of the inspiratory limb 202. FIG. 16D illustrates the inspiratory limb 202 with the placement limiter 280 in use with an incubator 290 to resist or prevent entry of the intermediate PCB connector 250 into the incubator 290. FIG. 16E illustrates the inspiratory limb 202 with the placement limiter 280 in use with a patient where the placement limiter 280 is secured to a blanket of the patient to resist or prevent movement inspiratory limb 202 relative to the patient and/or the blanket. The placement limiter 280 can also be used with an expiratory limb or other medical tube used in conjunction with gas delivery systems.

Segmented Medical Tubing for Use with Respiratory Humidification Systems

Figure 17A:
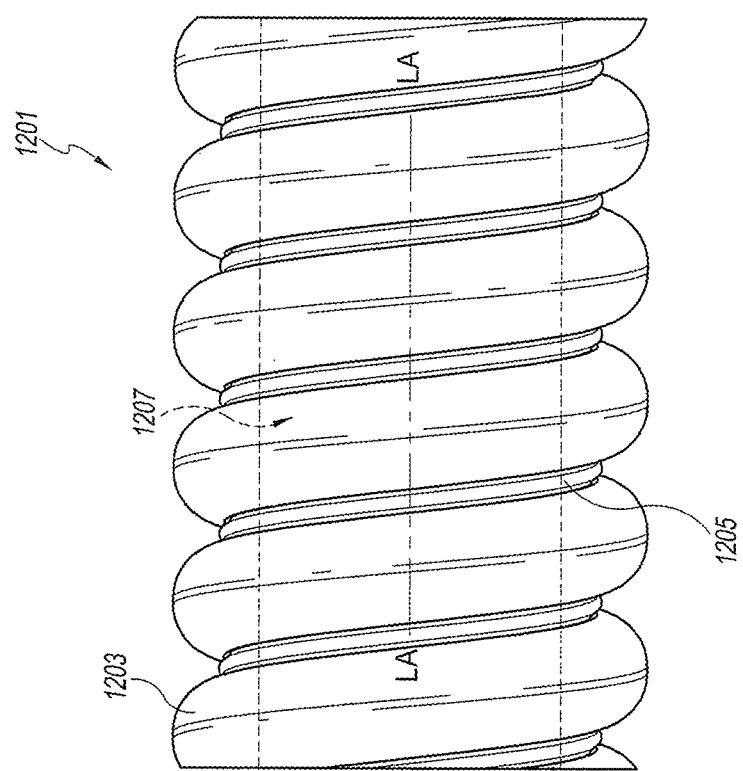
FIG. 17A illustrates a side-plan view of a section of an example composite tube.

FIG. 17A shows a side-plan view of a section of example composite tube 1201 which can be used in conjunction with the respiratory humidification system 100 described with reference to FIG. 1. The composite tube 1201 can be used as the inspiratory limb 202 and can be configured, as described herein, to provide thermally beneficial properties that assist in the prevention of condensation of gases along the tube. The composite tube 1201 includes a plurality of elongate members wrapped and joined to form a passageway, where the plurality of elongate members can include one or more of the heater wires described herein. Based at least in part on the heater wires being embedded in the walls of the composite tube 1201, the use of the composite tube 1201 as the inspiratory limb 202 can reduce condensation and rain out and maintain a more desirable or targeted temperature profile along the length of the inspiratory limb 202. The composite tube's walls can provide a greater thermal mass which resists temperature changes and increases the insulating effects of the walls in relation to the ambient temperature outside the limb 202. As a result, the temperature along the length of the limb 202, including through any number of differing temperature environments, can be more accurately controlled and less power or energy can be expended in controlling the temperature of the gases delivered to the patient. In some embodiments, the composite tube 1201 can be used as the expiratory limb 210.

In general, the composite tube 1201 comprises a first elongate member 1203 and a second elongate member 1205. Member is a broad term and is to be given its ordinary and customary meaning to a person of ordinary skill in the art (i.e., it is not to be limited to a special or customized meaning) and includes, without limitation, integral portions, integral components, and distinct components. Thus, although FIG. 17A illustrates an embodiment made of two distinct components, it will be appreciated that in other embodiments, the first elongate member 1203 and second elongate member 1205 can also represent regions in a tube formed from a single material. Thus, the first elongate member 1203 can represent a hollow portion of a tube, while the second elongate member 1205 represents a structural supporting or reinforcement portion of the tube which adds structural support to the hollow portion. The hollow portion and the structural supporting portion can have a spiral configuration, as described herein. The composite tube 1201 may be used to form the inspiratory limb 202 and/or the expiratory limb 210 as described herein, a coaxial tube as described below, or any other tubes as described elsewhere in this disclosure.

In this example, the first elongate member 1203 comprises a hollow body spirally wound to form, at least in part, an elongate tube having a longitudinal axis LA-LA and a lumen 1207 extending along the longitudinal axis LA-LA. In at least one embodiment, the first elongate member 1203 is a tube. Preferably, the first elongate member 1203 is flexible. Furthermore, the first elongate member 1203 is preferably transparent or, at least, semi-transparent or semi-opaque. A degree of optical transparency allows a caregiver or user to inspect the lumen 1207 for blockage or contaminants or to confirm the presence of moisture. A variety of plastics, including medical grade plastics, are suitable for the body of the first elongate member 1203. Examples of suitable materials include Polyolefin elastomers, Polyether block amides, Thermoplastic co-polyester elastomers, EPDM-Polypropylene mixtures, and Thermoplastic polyurethanes.

The hollow body structure of the first elongate member 1203 contributes to the insulating properties to the composite tube 1201. A composite tube 1201 is desirable because, as explained herein, it prevents or reduces heat loss. This can allow the tube 1201 to deliver gas from a heater/humidifier to a patient while substantially maintaining the gas's conditioned state with reduced or minimal energy consumption.

In at least one embodiment, the hollow portion of the first elongate member 1203 is filled with a gas. The gas can be air, which is desirable because of its low thermal conductivity ($2.62 \times 10^{-2}$ W/m·K at 300K) and very low cost. A gas that is more viscous than air may also advantageously be used, as higher viscosity reduces convective heat transfer. Thus, gases such as argon ($17.72 \times 10^{-3}$ W/m·K at 300K), krypton ($9.43 \times 10^{-3}$ W/m·K at 300K), and xenon ($5.65 \times 10^{-3}$ W/m·K at 300K) can increase insulating performance. Each of these gases is non-toxic, chemically inert, fire-inhibiting, and commercially available. The hollow portion of the first elongated member 1203 can be sealed at both ends of the tube, causing the gas within to be substantially stagnant. Alternatively, the hollow portion can be a secondary pneumatic connection, such as a pressure sample line for conveying pressure feedback from the patient end of the tube to a controller. The first elongate member 1203 can be optionally perforated. For instance, the surface of the first elongate member 1203 can be perforated on an outward-facing surface, opposite the lumen 1207. In another embodiment, the hollow portion of the first elongate member 1203 is filled with a liquid. Examples of liquids can include water or other biocompatible liquids with a high thermal capacity. For instance, nanofluids can be used. An example nanofluid with suitable thermal capacity comprises water and nanoparticles of substances such as aluminum.

The second elongate member 1205 is also spirally wound and joined to the first elongate member 1203 between adjacent turns of the first elongate member 1203. The second elongate member 1205 forms at least a portion of the lumen 1207 of the elongate tube. The second elongate member 1205 acts as structural support for the first elongate member 1203.

In at least one embodiment, the second elongate member 1205 is wider at the base (proximal the lumen 1207) and narrower at the top. For example, the second elongate member can be generally triangular in shape, generally T-shaped, or generally Y-shaped. However, any shape that meets the contours of the corresponding first elongate member 1203 is suitable.

Preferably, the second elongate member 1205 is flexible, to facilitate bending of the tube. Desirably; the second elongate member 1205 is less flexible than the first elongate member 1203. This improves the ability of the second elongate member 1205 to structurally support the first elongate member 1203. For example, the modulus of the second elongate member 1205 is preferably 30-50 MPa (or about 30-50 MPa). The modulus of the first elongate member 1203 is less than the modulus of the second elongate member 1205. The second elongate member 1205 can be solid or mostly solid. In addition, the second elongate member 1205 can encapsulate or house conductive material, such as filaments, and specifically heating filaments or sensors (not shown). Heating filaments can minimize the cold surfaces onto which condensate from moisture-laden air can form. Heating filaments can also be used to alter the temperature profile of gases in the lumen 1207 of composite tube 1201. A variety of polymers and plastics, including medical grade plastics, are suitable for the body of the second elongate member 1205. Examples of suitable materials include Polyolefin elastomers, Polyether block amides, Thermoplastic co-polyester elastomers, EPDM-Polypropylene mixtures and Thermoplastic polyurethanes. In certain embodiments, the first elongate member 1203 and the second elongate member 1205 may be made from the same material. The second elongate member 1205 may also be made of a different color material from the first elongate member 1203, and may be transparent, translucent or opaque. For example, in one embodiment the first elongate member 1203 may be made from a clear plastic, and the second elongate member 1205 may be made from an opaque blue (or other color) plastic.

This spirally-wound structure comprising a flexible, hollow body and an integral support can provide crush resistance, while leaving the tube wall flexible enough to permit short-radius bends without kinking, occluding or collapsing. Preferably, the tube can be bent around a 25 mm diameter metal cylinder without kinking, occluding, or collapsing, as defined in the test for increase in flow resistance with bending according to ISO 5367:2000(E). This structure also can provide a smooth lumen 1207 surface (tube bore), which helps keep the tube free from deposits and improves gas flow. The hollow body has been found to improve the insulating properties of a tube, while allowing the tube to remain light weight.

As explained above, the composite tube 1201 can be used as an expiratory tube and/or an inspiratory tube in a breathing circuit, or a portion of a breathing circuit. Preferably, the composite tube 1201 is used at least as an inspiratory tube.

Figure 17B:
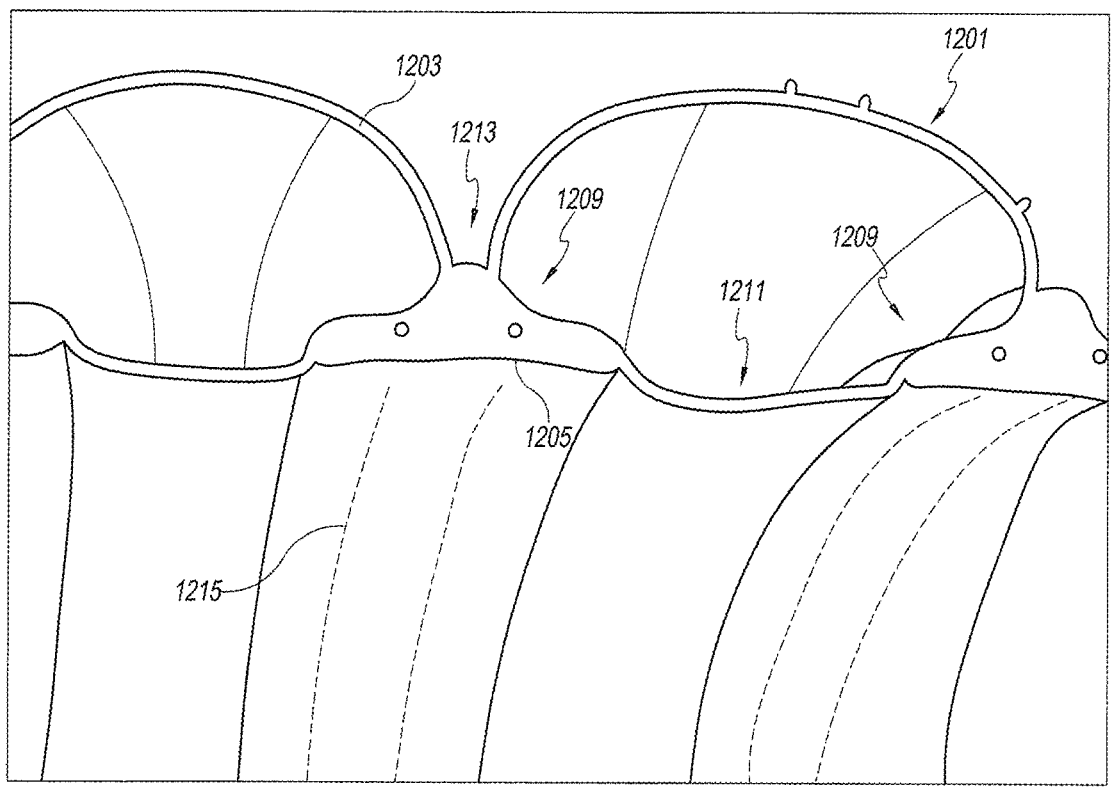
FIG. 17B illustrates a longitudinal cross-section of a top portion a tube similar to the example composite tube of FIG. 17A.

FIG. 17B shows a longitudinal cross-section of a top portion of the example composite tube 1201 of FIG. 17A. FIG. 17B has the same orientation as FIG. 17A. This example further illustrates the hollow-body shape of the first elongate member 1203. As seen in this example, the first elongate member 1203 forms in longitudinal cross-section a plurality of hollow bubbles. Portions 1209 of the first elongate member 1203 overlap adjacent wraps of the second elongate member 1205. A portion 1211 of the first elongate member 1203 forms the wall of the lumen (tube bore).

It was discovered that having a gap 1213 between adjacent turns of the first elongate member 1203, that is, between adjacent bubbles, unexpectedly improved the overall insulating properties of the composite tube 1201. Thus, in certain embodiments, adjacent bubbles are separated by a gap 1213. Furthermore, certain embodiments include the realization that providing a gap 1213 between adjacent bubbles increases the heat transfer resistivity (the R value) and, accordingly, decreases the heat transfer conductivity of the composite tube 1201. This gap configuration was also found to improve the flexibility of the composite tube 1201 by permitting shorter-radius bends. A T-shaped second elongate member 1205, as shown in FIG. 17B, can help maintain a gap 1213 between adjacent bubbles. Nevertheless, in certain embodiments, adjacent bubbles are touching. For example, adjacent bubbles can be bonded together.

One or more conductive materials can be disposed in the second elongate member 1205 for heating or sensing the gas flow. In this example, two heating filaments 1215 are encapsulated in the second elongate member 1205, one on either side of the vertical portion of the "T." The heating filaments 1215 comprise conductive material, such as alloys of Aluminum (Al) and/or Copper (Cu), or conductive polymer. Preferably, the material forming the second elongate member 1205 is selected to be non-reactive with the metal in the heating filaments 1215 when the heating filaments 1215 reach their operating temperature. The heating filaments 1215 may be spaced away from lumen 1207 so that the filaments are not exposed to the lumen 1207. At one end of the composite tube, pairs of filaments can be formed into a connecting loop.

In at least one embodiment, a plurality of filaments are disposed in the second elongate member 1205. The filaments can be electrically connected together to share a common rail. For example, a first filament, such as a heating filament, can be disposed on a first side of the second elongate member 1205. A second filament, such as a sensing filament, can be disposed on a second side of the second elongate member 1205. A third filament, such as a ground filament, can be disposed between the first and second filaments. The first, second, and/or third filaments can be connected together at one end of the second elongate member 1205.

Figure 17C:
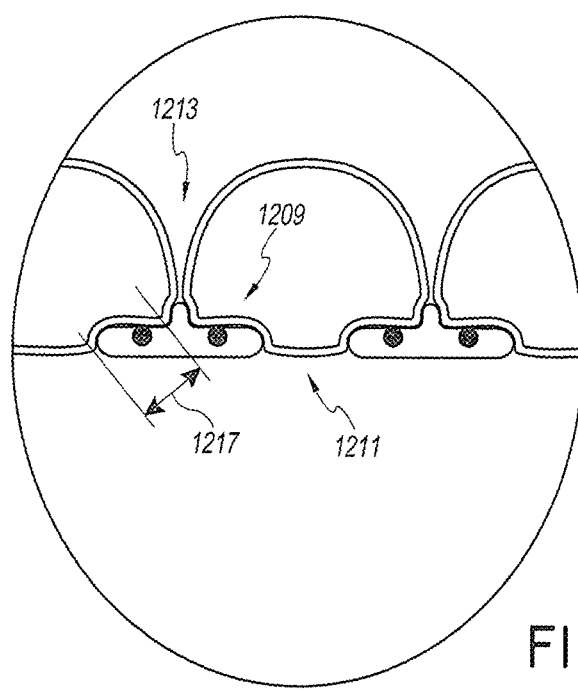
FIG. 17C illustrates another longitudinal cross-section illustrating a first elongate member in the composite tube.
Figure 17D:
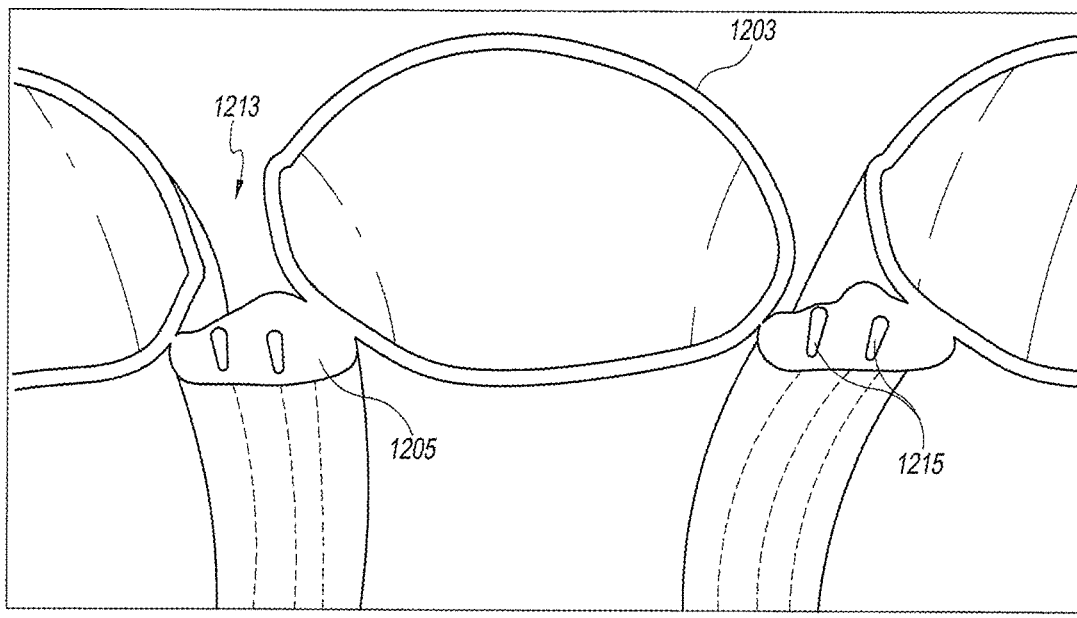
FIG. 17D illustrates another longitudinal cross-section of a top portion of a tube.
Figure 19A:
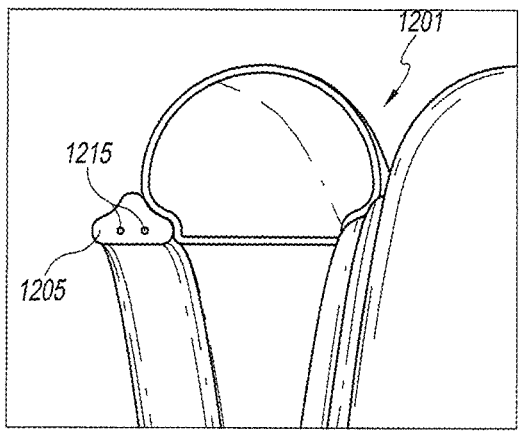
FIGS. 19A-C illustrate examples of first elongate member shapes configured to improve thermal efficiency.
Figure 19B:
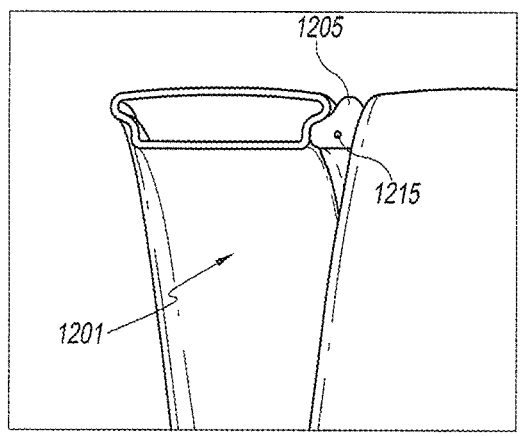
Figure 19C:
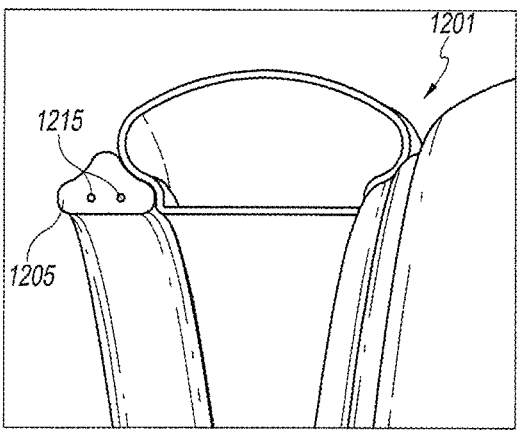

FIG. 17C shows a longitudinal cross-section of the bubbles in FIG. 17B. As shown, the portions 1209 of the first elongate member 1203 overlapping adjacent wraps of the second elongate member 1205 are characterized by a degree of bond region 1217. A larger bond region improves the tubes resistance to delamination at the interface of the first and second elongate members. Additionally or alternatively, the shape of the bead and/or the bubble can be adapted to increase the bond region 1217. For example, FIG. 17D shows a relatively small bonding area on the left-hand side. FIG. 19B also demonstrates a smaller bonding region. In contrast, FIG. 17E has a much larger bonding region than that shown in FIG. 17D, because of the size and shape of the bead. FIGS. 19A and 19C also illustrate a larger bonding region. Each of these figures is discussed in more detail below. It should be appreciated that although the configurations in FIGS. 17E, 19A, and 19C may be preferred in certain embodiments, other configurations, including those of FIGS. 17D, 19B, and other variations, may be utilized in other embodiments as may be desired.

FIG. 17D shows a longitudinal cross-section of a top portion of another composite tube. FIG. 17D has the same orientation as FIG. 17B. This example further illustrates the hollow-body shape of the first elongate member 1203 and demonstrates how the first elongate member 1203 forms in longitudinal cross-section a plurality of hollow bubbles. In this example, the bubbles are completely separated from each other by a gap 1213. A generally triangular second elongate member 1205 supports the first elongate member 1203.

Figure 17E:
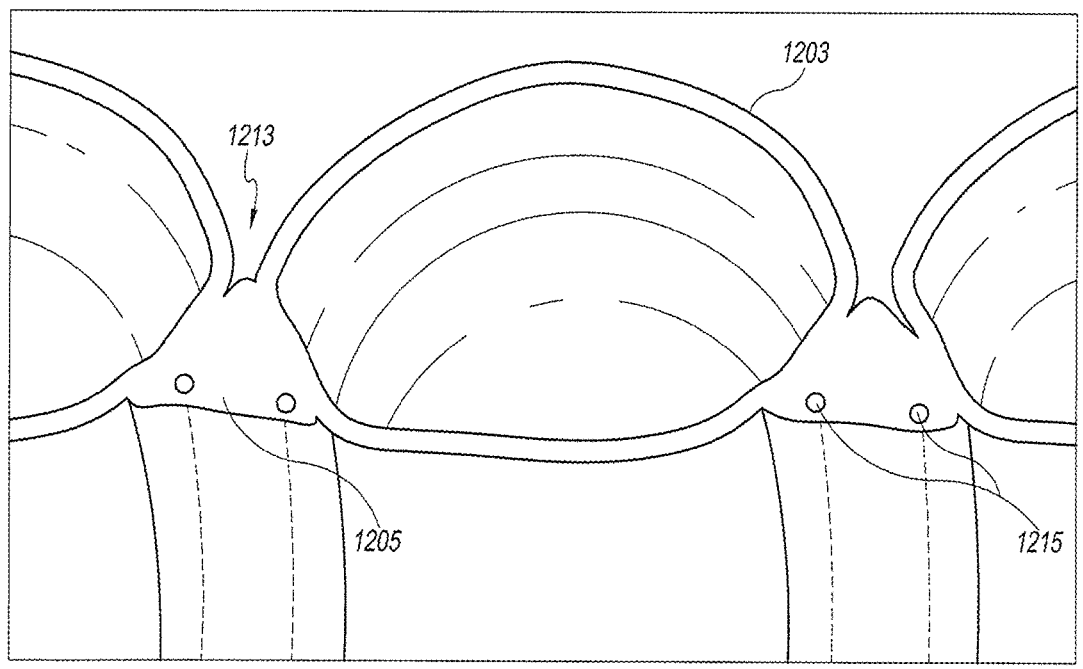
FIG. 17E illustrates another longitudinal cross-section of a top portion of a tube.

FIG. 17E shows a longitudinal cross-section of a top portion of another composite tube. FIG. 17E has the same orientation as FIG. 17B. In the example of FIG. 17E, the heating filaments 1215 are spaced farther apart from each other than the heating filaments 1215 in FIG. 17B. It was discovered that increasing the space between heating filaments can improve heating efficiency, and certain embodiments include this realization. Heating efficiency refers to the ratio of the amount of heat input to the tube to the amount of energy output or recoverable from the tube. Generally speaking, the greater the energy (or heat) that is dissipated from the tube, the lower the heating efficiency. For improved heating performance, the heating filaments 1215 can be equally (or about equally) spaced along the bore of the tube. Alternatively, the heating filaments 1215 can be positioned at extremities of the second elongate member 1205, which may provide simpler manufacturing.

Figure 18A:
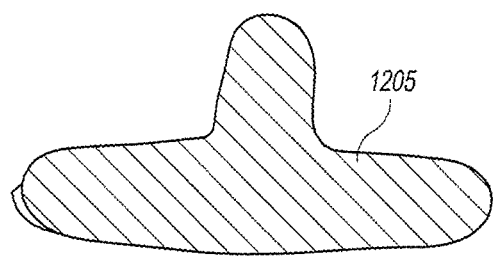
FIG. 18A illustrates a transverse cross-section of a second elongate member in the composite tube.

Reference is next made to FIGS. 18A through 18G which demonstrate example configurations for the second elongate member 1205. FIG. 18A shows a cross-section of a second elongate member 1205 having a shape similar to the T-shape shown in FIG. 17B. In this example embodiment, the second elongate member 1205 does not have heating filaments. Other shapes for the second elongate member 1205 may also be utilized, including variations of the T-shape as described below and triangular shapes.

Figure 18B:
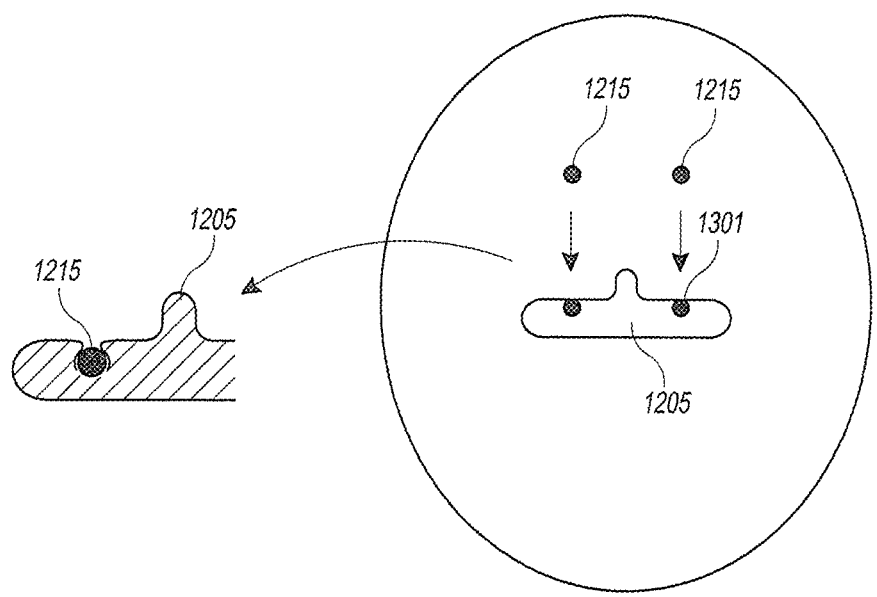
FIG. 18B illustrates another transverse cross-section of a second elongate member.

FIG. 18B shows another example second elongate member 1205 having a T-shape cross-section. In this example, heating filaments 1215 are embedded in cuts 1301 in the second elongate member 1205 on either side of the vertical portion of the "T." In some embodiments, the cuts 1301 can be formed in the second elongate member 1205 during extrusion. The cuts 1301 can alternatively be formed in the second elongate member 1205 after extrusion. For example, a cutting tool can form the cuts in the second elongate member 1205. Preferably, the cuts are formed by the heating filaments 1215 as they are pressed or pulled (mechanically fixed) into the second elongate member 1205 shortly after extrusion, while the second elongate member 1205 is relatively soft. Alternatively, one or more heating filaments can be mounted (e.g., adhered, bonded, or partially embedded) on the base of the elongate member, such that the filament(s) are exposed to the tube lumen. In such embodiments, it can be desirable to contain the filament(s) in insulation to reduce the risk of fire when a flammable gas such as oxygen is passed through the tube lumen.

Figure 18C:
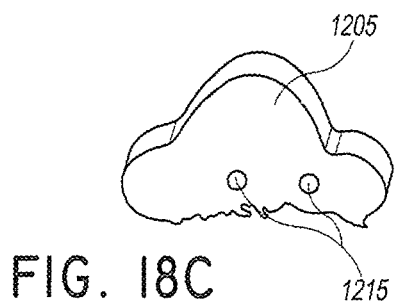
FIG. 18C illustrates another example second elongate member.

FIG. 18C shows yet another example second elongate member 1205 in cross-section. The second elongate member 1205 has a generally triangular shape. In this example, heating filaments 1215 are embedded on opposite sides of the triangle.

Figure 18D:
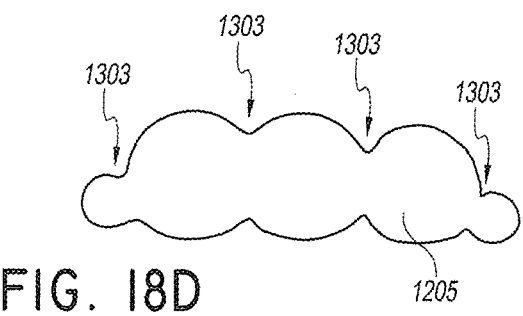
FIG. 18D illustrates another example second elongate member.

FIG. 18D shows yet another example second elongate member 1205 in cross-section. The second elongate member 1205 comprises four grooves 1303. The grooves 1303 are indentations or furrows in the cross-sectional profile. In some embodiments, the grooves 1303 can facilitate the formation of cuts (not shown) for embedding filaments (not shown). In some embodiments, the grooves 1303 facilitate the positioning of filaments (not shown), which are pressed or pulled into, and thereby embedded in, the second elongate member 1205. In this example, the four initiation grooves 1303 facilitate placement of up to four filaments, e.g., four heating filaments, four sensing filaments, two heating filaments and two sensing filaments, three heating filaments and one sensing filament, or one heating filament and three sensing filaments. In some embodiments, heating filaments can be located on the outside of the second elongate member 1205. Sensing filaments can be located on the inside.

Figure 18E:
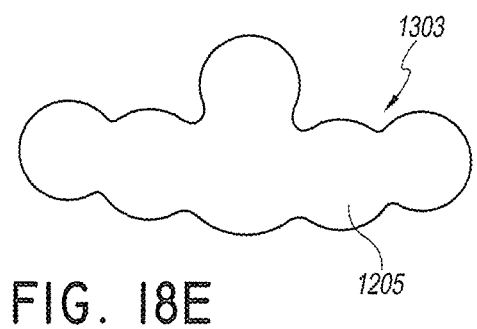
FIG. 18E illustrates another example second elongate member.

FIG. 18E shows still another example second elongate member 1205 in cross-section. The second elongate member 1205 has a T-shape profile and a plurality of grooves 1303 for placing heating filaments.

Figure 18F:
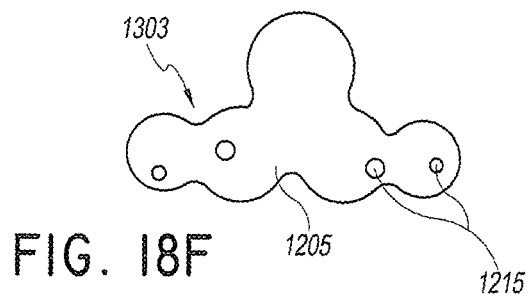
FIG. 18F illustrates another example second elongate member.

FIG. 18F shows yet another example second elongate member 1205 in cross-section. Four heating filaments 1215 are encapsulated in the second elongate member 1205, two on either side of the vertical portion of the "T." As explained in more detail below, the filaments are encapsulated in the second elongate member 1205 because the second elongate member 1205 was extruded around the filaments. No cuts were formed to embed the heating filaments 1215. In this example, the second elongate member 1205 also comprises a plurality of grooves 1303. Because the heating filaments 1215 are encapsulated in the second elongate member 1205, the grooves 1303 are not used to facilitate formation of cuts for embedding heating filaments. In this example, the grooves 1303 can facilitate separation of the embedded heating filaments, which makes stripping of individual cores easier when, for example, terminating the heating filaments.

FIG. 18G shows yet another example second elongate member 1205 in cross-section. The second elongate member 1205 has a generally triangular shape. In this example, the shape of the second elongate member 1205 is similar to that of FIG. 18C, but four heating filaments 1215 are encapsulated in the second elongate member 1205, all of which are central in the bottom third of the second elongate member 1205 and disposed along a generally horizontal axis.

As explained above, it can be desirable to increase the distance between filaments to improve heating efficiency. In some embodiments, however, when heating filaments 1215 are incorporated into the composite tube 1201, the heating filaments 1215 can be positioned relatively central in the second elongate member 1205. A centralized position promotes robustness of the composite tubing for reuse, due in part to the position reducing the likelihood of the filament breaking upon repeating flexing of the composite tube 1201. Centralizing the heating filaments 1215 can also reduce the risk of an ignition hazard because the heating filaments 1215 are coated in layers of insulation and removed from the gas path.

As explained above, some of the examples illustrate suitable placements of heating filaments 1215 in the second elongate member 1205. In the foregoing examples comprising more than one heating filament 1215, the heating filaments 1215 are generally aligned along a horizontal axis. Alternative configurations are also suitable. For example, two filaments can be aligned along a vertical axis or along a diagonal axis. Four filaments can be aligned along a vertical axis or a diagonal axis. Four filaments can be aligned in a cross-shaped configuration, with one filament disposed at the top of the second elongate member, one filament disposed at the bottom of the second elongate member (near the tube lumen), and two filaments disposed on opposite arms of a "T," "Y," or triangle base.

TABLES 1A and 1B show some preferred dimensions of medical tubes described herein, as well as some preferred ranges for these dimensions. The dimensions refer to a transverse cross-section of a tube. In these tables, lumen diameter represents the inner diameter of a tube. Pitch represents the distance between two repeating points measured axially along the tube, namely, the distance between the tips of the vertical portions of adjacent "T"s of the second elongate member. Bubble width represents the width (maximum outer diameter) of a bubble. Bubble height represents the height of a bubble from the tube lumen. Bead height represents the maximum height of the second elongate member from the tube lumen (e.g., the height of the vertical portion of the "T"). Bead width represents the maximum width of the second elongate member (e.g., the width of the horizontal portion of the "T"). Bubble thickness represents the thickness of the bubble wall.

TABLE 1A

| Feature | Infant | | Adult | |
| --- | --- | --- | --- | --- |
| | Dimension (mm) | Range (±) | Dimension (mm) | Range (±) |
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead height | 0.9 | 0.5 | 1.5 | 0.5 |
| Bubble thickness | 0.4 | 0.35 | 0.2 | 0.15 |

TABLE 1B

| Feature | Infant | | Adult | |
| --- | --- | --- | --- | --- |
| | Dimension (mm) | Range (±) | Dimension (mm) | Range (±) |
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 3.4 | 1 |
| Bubble height | 2.8 | 1 | 4.0 | 0.5 |
| Bead height | 0.9 | 0.5 | 1.7 | 0.5 |
| Bubble thickness | 0.4 | 0.35 | 0.2 | 0.15 |

TABLES 2A and 2B provide example ratios between the dimensions of tube features for the tubes described in TABLES 1A and 1B respectively.

TABLE 2A

| Ratios | Infant | Adult |
| --- | --- | --- |
| Lumen diameter:Pitch | 2.3:1 | 2.4:1 |
| Pitch:Bubble width | 1.1:1 | 1.1:1 |
| Pitch:Bead width | 2.2:1 | 3.1:1 |
| Bubble width:Bead width | 2.0:1 | 2.9:1 |
| Lumen diameter:Bubble height | 3.9:1 | 5.1:1 |
| Lumen diameter:Bead height | 12.2:1 | 12.0:1 |
| Bubble height:Bead height | 3.1:1 | 2.3:1 |
| Lumen diameter:Bubble thickness | 27.5:1 | 90.0:1 |

TABLE 2B

| Ratios | Infant | Adult |
| --- | --- | --- |
| Lumen diameter:Pitch | 2.3:1 | 2.4:1 |
| Pitch:Bubble width | 1.1:1 | 1.1:1 |
| Pitch:Bead width | 2.2:1 | 2.2:1 |
| Bubble width:Bead width | 2.0:1 | 2.1:1 |
| Lumen diameter:Bubble height | 3.9:1 | 4.5:1 |
| Lumen diameter:Bead height | 12.2:1 | 10.6:1 |
| Bubble height:Bead height | 3.1:1 | 2.4:1 |
| Lumen diameter:Bubble thickness | 27.5:1 | 90.0:1 |

The following tables show some example properties of a composite tube (labeled "A"), described herein, having a heating filament integrated inside the second elongate member. For comparison, properties of a Fisher & Paykel model RT100 disposable corrugated tube (labeled "B") having a heating filament helically wound inside the bore of the tube are also presented.

Measurement of resistance to flow (RTF) was carried out according to Annex A of ISO 5367:2000(E). The results are summarized in TABLE 3. As seen below, the RTF for the composite tube is lower than the RTF for the model RT100 tube.

TABLE 3

| | RTF (cm $H_2O$) | | | |
| --- | --- | --- | --- | --- |
| Flow rate (L/min) | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gas flow rate and room temperature of 18° C. Humidified air is flowed through the tube continuously from a chamber. The tube weights are recorded before and after each day of testing. Three consecutive tests are carried out with the tube being dried in between each test. The results are shown below in TABLE 4. The results showed that rainout is significantly lower in the composite tube than in the model RT100 tube.

TABLE 4

| | Tube | | | | | |
| --- | --- | --- | --- | --- | --- | --- |
| | A (Day 1) | A (Day 2) | A (Day 3) | B (Day 1) | B (Day 2) | B (day 3) |
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

The power requirement refers to the power consumed during the condensate test. In this test, the ambient air was held at 18° C. Humidification chambers (see, e.g., the humidification chamber 114 in FIG. 1) were powered by MR850 heater bases. The heating filaments in the tubes were powered independently from a DC power supply. Different flow rates were set and the chamber was left to settle to 37° C. at the chamber output. Then, the DC voltage to the circuits was altered to produce a temperature of 40° C. at the circuit output. The voltage required to maintain the output temperature was recorded and the resulting power calculated. The results are shown in TABLE 5. The results show that composite Tube A uses significantly more power than Tube B. This is because Tube B uses a helical heating filament in the tube bore to heat the gas from 37° C. to 40° C. The composite tube does not tend to heat gas quickly because the heating filament is in the wall of the tube (embedded in the second elongate member). Instead, the composite tube is designed to maintain the gas temperature and prevent rainout by maintaining the tube bore at a temperature above the dew point of the humidified gas.

TABLE 5

| Flow rate (L/min) | 40 | 30 | 20 |
|---|---|---|---|
| Tube A, power required (W) | 46.8 | 38.5 | 37.8 |
| Tube B, power required (W) | 28.0 | 27.5 | 26.8 |

Tube flexibility was tested by using a three-point bend test. Tubes were placed in a three point bend test jig and used along with an Instron 5560 Test System instrument, to measure load and extension. Each tube sample was tested three times; measuring the extension of the tube against the applied load, to obtain average respective stiffness constants. The average stiffness constants for Tube A and Tube B are reproduced in TABLE 6.

TABLE 6

| Tube | Stiffness (N/mm) |
|---|---|
| A | 0.028 |
| B | 0.088 |

As described above, inspiratory heating wires 206 can be placed within the inspiratory limb 202 and/or the expiratory limb 210 to reduce the risk of rain out in the tubes by maintaining the tube wall temperature above the dew point temperature.

Thermal Properties

In embodiments of a composite tube 1201 incorporating a heating filament 1215, heat can be lost through the walls of the first elongate member 1203, resulting in uneven heating. As explained above, one way to compensate for these heat losses is to apply an external heating source at the first elongate member 1203 walls, which helps to regulate the temperature and counter the heat loss. Other methods for optimizing thermal properties can also be used, however.

Reference is next made to FIGS. 19A through 19C, which demonstrate example configurations for bubble height (that is, the cross-sectional height of the first elongate member 1203 measured from the surface facing the inner lumen to the surface forming the maximum outer diameter) to improve thermal properties.

The dimensions of the bubble can be selected to reduce heat loss from the composite tube 1201. Generally, increasing the height of the bubble increases the effective thermal resistance of the tube 1201, because a larger bubble height permits the first elongate member 1203 to hold more insulating air. However, it was discovered that, at a certain bubble height, changes in air density cause convection inside the tube 1201, thereby increasing heat loss. Also, at a certain bubble height the surface area becomes so large that the heat lost through surface outweighs the benefits of the increased height of the bubble. Certain embodiments include these realizations.

The radius of curvature and the curvature of the bubble can be useful for determining a desirable bubble height. The curvature of an object is defined as the inverse of the radius of curvature of that object. Therefore, the larger a radius of curvature an object has, the less curved the object is. For example, a flat surface would have an infinite radius of curvature, and therefore a curvature of 0.

FIG. 19A shows a longitudinal cross-section of a top portion of a composite tube. FIG. 19A shows an embodiment of a composite tube 1201 where the bubble has a large height. In this example, the bubble has a relatively small radius of curvature and therefore a large curvature. Also, the bubble is approximately three to four times greater in height than the height of the second elongate member 1205.

FIG. 19B shows a longitudinal cross-section of a top portion of another composite tube. FIG. 19B shows an embodiment of a composite tube 1201 where the bubble is flattened on top. In this example, the bubble has a very large radius of curvature but a small curvature. Also, the bubble is approximately the same height as the second elongate member 1205.

FIG. 19C shows a longitudinal cross-section of a top portion of another composite tube. FIG. 19C shows an embodiment of a composite tube 1201 where the width of the bubble is greater than the height of the bubble. In this example, the bubble has radius of curvature and the curvature between that of FIG. 19A and FIG. 19B, and the center of the radius for the upper portion of the bubble is outside of the bubble (as compared to FIG. 19A). The inflection points on the left and right sides of the bubble are about at the middle (heightwise) of the bubble (as opposed to in the lower portion of the bubble, as in FIG. 19A). Also, the height of the bubble is approximately double that of the second elongate member 1205, resulting in a bubble height between that of FIG. 19A and FIG. 19B.

The configuration of FIG. 19A resulted in the lowest heat loss from the tube. The configuration of FIG. 19B resulted in the highest heat loss from the tube. The configuration of FIG. 19C had intermediate heat loss between the configurations of FIGS. 19A and 19B. However, the large external surface area and convective heat transfer in the configuration of FIG. 19A led to inefficient heating. Thus, of the three bubble arrangements of FIGS. 19A-19C, FIG. 19C was determined to have the best overall thermal properties. When the same thermal energy was input to the three tubes, the configuration of FIG. 19C allowed for the largest temperature rise along the length of the tube. The bubble of FIG. 19C is sufficiently large to increase the insulating air volume, but not large enough to cause a significant convective heat loss. The configuration of FIG. 19B was determined to have the poorest thermal properties, namely that the configuration of FIG. 19B allowed for the smallest temperature rise along the length of the tube. The configuration of FIG. 19A had intermediate thermal properties and allowed for a lower temperature rise than the configuration of FIG. 19C.

It should be appreciated that although the FIG. 19C configuration may be preferred in certain embodiments, other configurations, including those of FIGS. 19A, 19B and other variations, may be utilized in other embodiments as may be desired.

TABLE 7 shows the height of the bubble, the outer diameter of the tube, and the radius of curvature of the configurations shown in each of FIGS. 19A, 19B, and 19C.

TABLE 7

| Tube (FIG.) | 19A | 19B | 19C |
|---|---|---|---|
| Bubble height (mm) | 3.5 | 5.25 | 1.75 |
| Outer diameter (mm) | 21.5 | 23.25 | 19.75 |
| Radius of curvature (mm) | 5.4 | 3.3 | 24.3 |

Reference is next made to FIGS. 19C through 19F which demonstrate example positioning of heating element 1215 with similar bubble shapes to improve thermal properties. The location of the heating element 1215 can change the thermal properties within the composite tube 1201.

FIG. 19C shows a longitudinal cross-section of a top portion of another composite tube. FIG. 19C shows an embodiment of a composite tube 1201 where the heating elements 1215 are centrally located in the second elongate member 1205. This example shows the heating elements 1215 close to one another and not close to the bubble wall.

Figure 19D:
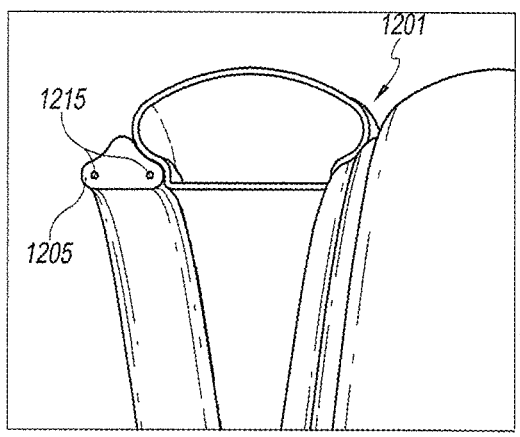
FIGS. 19D-F illustrate examples of filament arrangements configured to improve thermal efficiency.

FIG. 19D shows a longitudinal cross-section of a top portion of another composite tube. FIG. 19D shows an embodiment of a composite tube 1201 in which the heating elements 1215 are spaced farther apart, as compared to FIG. 19C, in the second elongate member 1205. These heating elements are closer to the bubble wall and provide for better regulation of heat within the composite tube 1201.

Figure 19E:
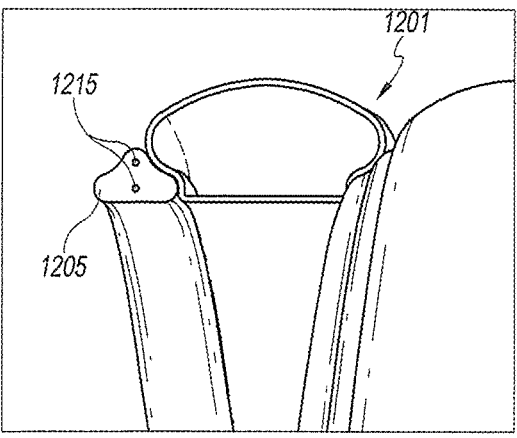

FIG. 19E shows a longitudinal cross-section of a top portion of another composite tube. FIG. 19E shows an embodiment of a composite tube 1201 wherein the heating elements 1215 are spaced on top of each other in the vertical axis of the second elongate member 1205. In this example, the heating elements 1215 are equally close to each bubble wall.

Figure 19F:
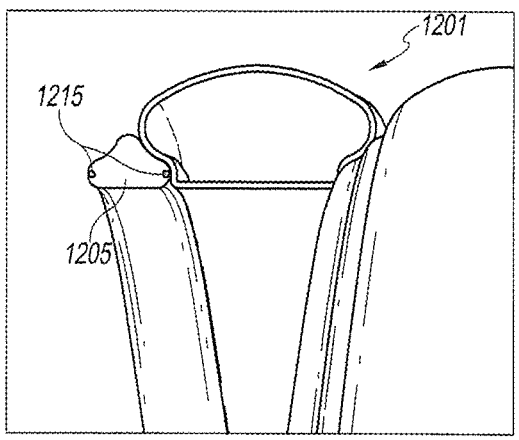

FIG. 19F shows a longitudinal cross-section of a top portion of another composite tube. FIG. 19F shows an embodiment of a composite tube 201 where the heating elements 1215 are spaced at opposite ends of the second elongate member 1205. The heating elements 1215 are close to the bubble wall, especially as compared to FIGS. 19C-19E.

Of the four filament arrangements of FIGS. 19C-19F, FIG. 19F was determined to have the best thermal properties. Because of their similar bubble shapes, all of the configurations experienced similar heat loss from the tube. However, when the same thermal energy was input to the tubes, the filament configuration of FIG. 19F allowed for the largest temperature rise along the length of the tube. The configuration of FIG. 19D was determined to have the next best thermal properties and allowed for the next largest temperature rise along the length of tube. The configuration of FIG. 19C performed next best. The configuration of FIG. 19E had the poorest performance and allowed for the smallest temperature rise along the length of the tube, when the same amount of heat was input.

It should be appreciated that although the FIG. 19F configuration may be preferred in certain embodiments, other configurations, including those of FIGS. 19C, 19D, 19E, and other variations, may be utilized in other embodiments as may be desired.

Figure 20A:
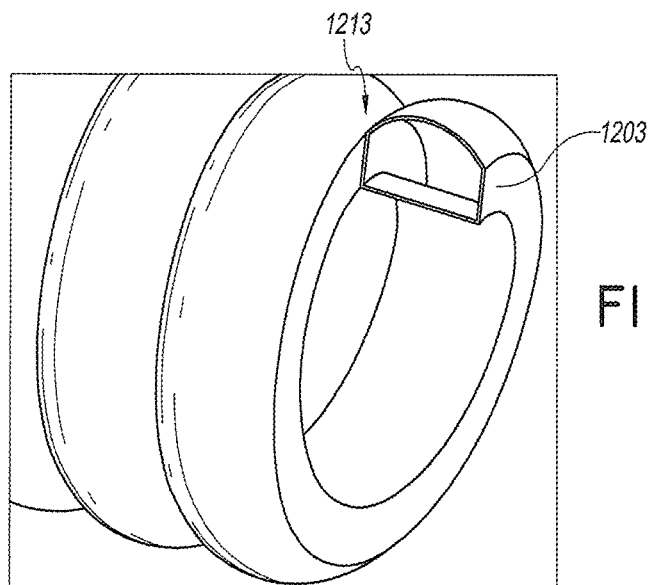
FIGS. 20A-C illustrate examples of first elongate member stacking.
Figure 20B:
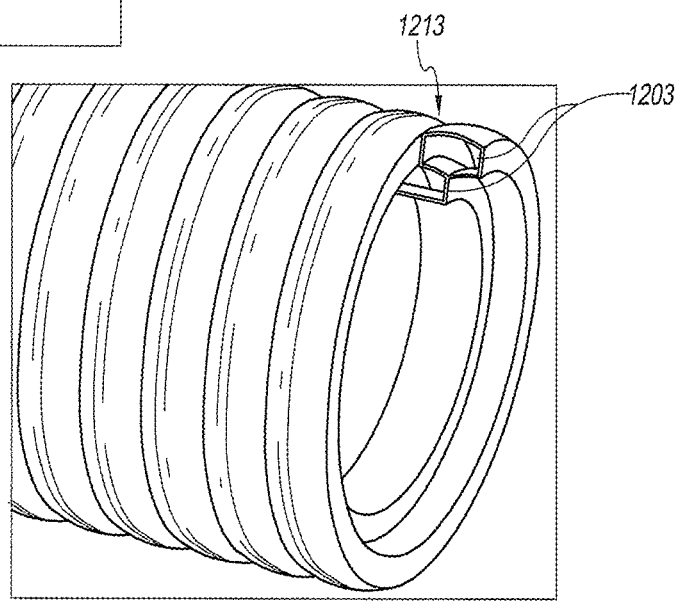
Figure 20C:
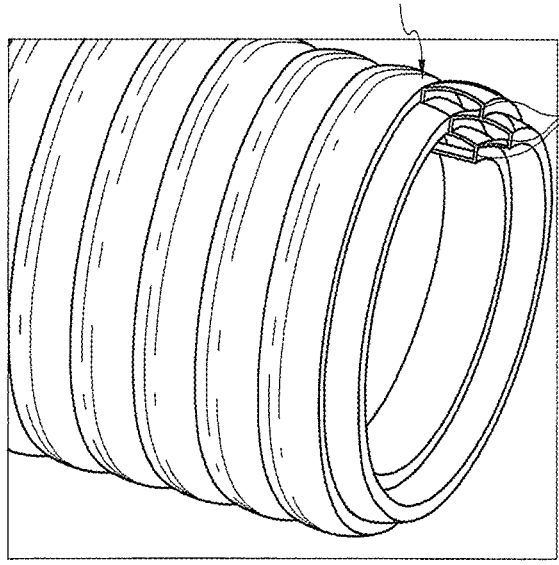

Reference is next made to FIGS. 20A through 20C, which demonstrate example configurations for stacking of the first elongate member 1203. It was discovered that heat distribution can be improved in certain embodiments by stacking multiple bubbles. These embodiments can be more beneficial when using an internal heating filament 1215. FIG. 20A shows a longitudinal cross-section of a top portion of another composite tube. FIG. 20A shows a cross section of a composite tube 1201 without any stacking.

FIG. 20B shows a longitudinal cross-section of a top portion of another composite tube. FIG. 20B shows another example composite tube 1201 with stacked bubbles. In this example, two bubbles are stacked on top of each other to form the first elongate member 1203. As compared to FIG. 20A, the total bubble height is maintained, but the bubble pitch is half of FIG. 20A. Also, the embodiment in FIG. 20B has only a slight reduction in air volume. The stacking of the bubbles reduces natural convection and heat transfer in the gap between bubbles and lowers the overall thermal resistance. The heat flow path increases in the stacked bubbles allowing heat to more easily distribute through the composite tube 1201.

FIG. 20C shows a longitudinal cross-section of a top portion of another composite tube. FIG. 20C shows another example of a composite tube 1201 with stacked bubbles. In this example, three bubbles are stacked on top of each other to form the first elongate member 1203. As compared to FIG. 20A, the total bubble height is maintained, but the bubble pitch is a third of FIG. 20A. Also, the embodiment in FIG. 20B has only a slight reduction in air volume. The stacking of the bubbles reduces natural convection and heat transfer in the gap between bubbles.

Additional Example Intermediate Connectors

Figure 32A:
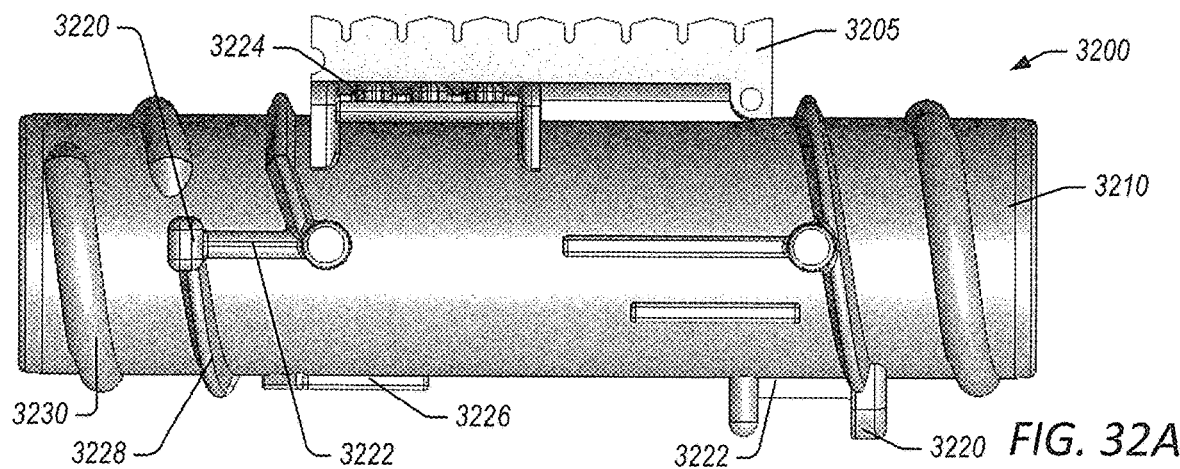
FIGS. 32A-C illustrate example intermediate connectors.
Figure 32B:
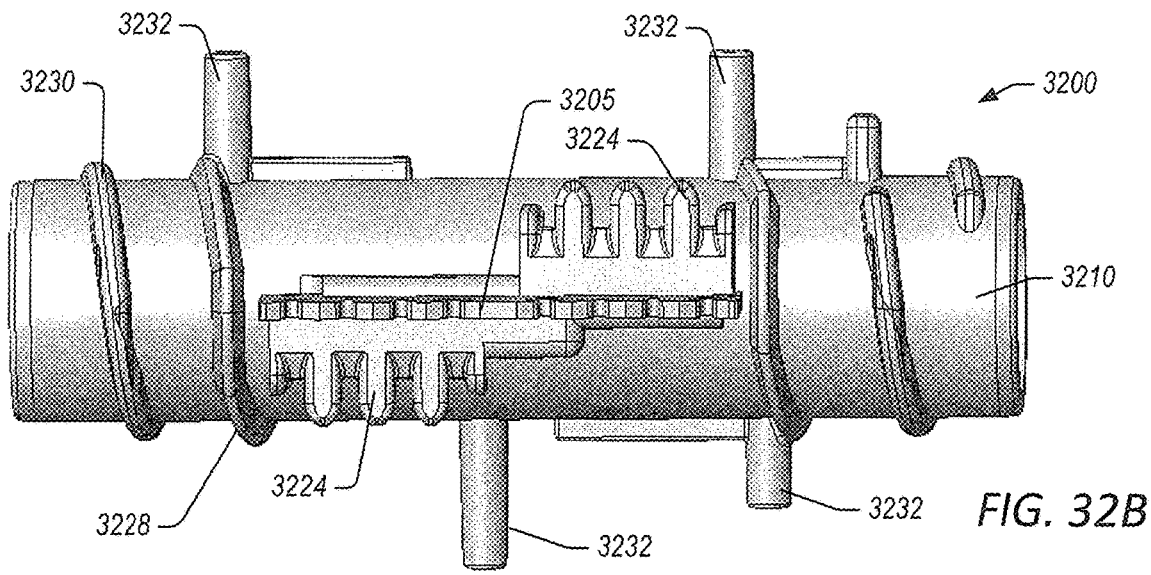
Figure 32C:
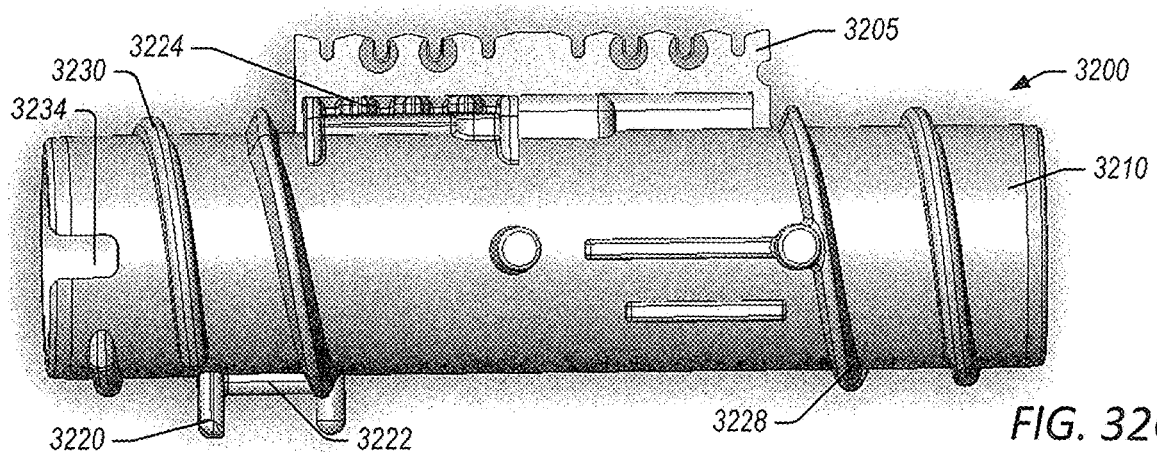

FIGS. 32A-C illustrate other examples of intermediate connectors 3200 comprising an intermediate PCB 3205 and an intermediate connection element 3210. The intermediate PCB 3205 can include a conformal coating configured to protect it from water ingress. For example, the water can follow the contour of the intermediate PCB 3205. The intermediate connector 3200 can include features configured to position the bead in a position suitable for attaching wires, such as for the heating or sensing elements of the circuits described herein. The intermediate PCB 3205 can extend partially through the intermediate connection element 3210. For example, a portion of the intermediate PCB 3205 can extend outside of a tube of the intermediate connection element 3210 and a portion can extend part-way through a lumen portion of the intermediate connection element 3210. In some implementations, the portion of the intermediate PCB 3205 that extends into the lumen is about one-third of the way through the lumen. This can provide relatively less resistance to flow relative to an intermediate PCB that extends the whole way through the lumen.

In some embodiments, the intermediate PCB 3205 generates heat during operation due at least in part to the diode on the intermediate PCB 3205. The heat generated by the intermediate PCB 3205 can help to evaporate excess condensation.

The intermediate connector 3200 can be overmolded to secure components in place and to seal the part. In some embodiments, a clam shell can be applied, which may provide increased insulation to the intermediate connector 3200.

The intermediate connector 3200 can include a pin 3220 configured to stop the tube from rotating too far as it can be configured to catch between the bubble and the bead. The pins 3220 can be configured to be positioned 180 degrees and/or 270 degrees from the PCB to correctly position correct alignment of the tube. The pins 3220 can be configured to provide attachment points for the tube. The intermediate connector 3200 can include one or more bridges 3222 configured to raise the bead to allow the polymer to flow beneath it to reduce water ingress. In some embodiments, the one or more bridges 3222 can be positioned on each side of the intermediate connector 3200. The intermediate connector 3200 can include a comb 3224 configured to hold wires (e.g., heater wires) in place in the slots. The intermediate connector 3200 can include an indicator such as an arrow 3226 configured to indicate orientation of the intermediate connector 3200 to ensure the diode faces the correct way. The arrow 3226 can also help to reduce or prevent water ingress. The intermediate connector 3200 can include a water ingress ring 3228 that forms a complete loop around the intermediate connector 3200. The water ingress ring 3228 can be configured to limit or eliminate the ingress of water to the exposed areas of the PCB 3205.

In some embodiments, the intermediate connection element 3210 can have a wall that is about 1-2 mm thick and can have a diameter that is between 4 and 15 mm. In some implementations, the inner diameter of the intermediate connection element 3210 can be about 8-9 mm and an outer diameter can be about 11.5 mm. The outer diameter of the intermediate connection element 3210 can be configured to be sufficiently large to reduce resistance to flow. A smaller passage in the intermediate connection element 3210 may mean gases pass through it faster which can reduce condensate.

The intermediate connector 3200 can include process aids 3230 configured to align the connected tube correctly so that the bubbles engage and hold the tube in place. The intermediate connector 3200 can include pins 3232 configured to locate the cover (e.g., the clam shell 3300 described herein with reference to FIG. 33) and retain it by a friction fit (e.g., it can engage with a matching recess in the cover). The intermediate connector 3200, in some implementations, includes 3 or 4 pins. The pins 3232 can be configured to have a sufficient length such that they protrude through the overmolding for alignment and/or locating purposes. The pins 3232 can be positioned on either side of the intermediate connector 3200 such that they are positioned at 90 degrees from the illustrated position, for example. In some embodiments, the intermediate connector 3200 includes slot 3234 that acts as a keying mechanism for processing to reduce the likelihood of incorrect orientation.

Figure 33A:
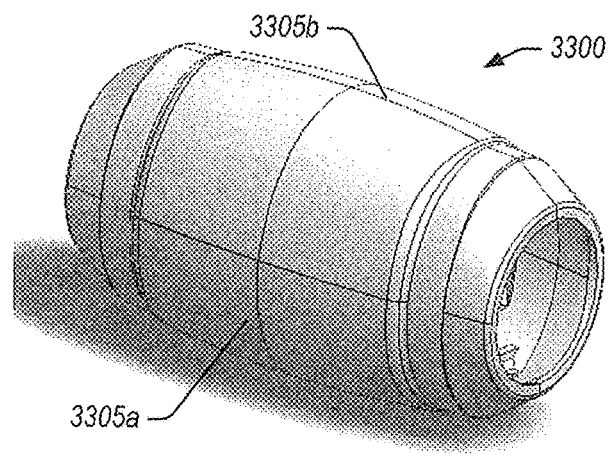
FIGS. 33A-C illustrate example covers for an intermediate connector.
Figure 33B:
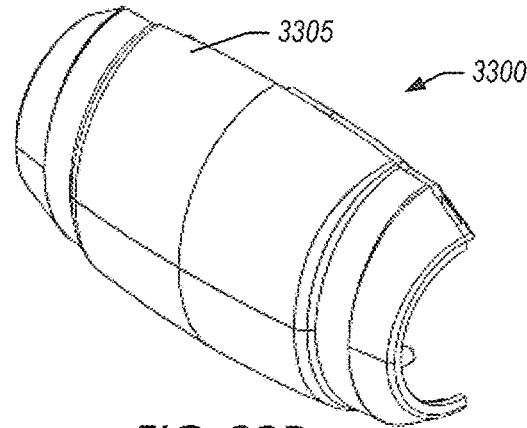
Figure 33C:
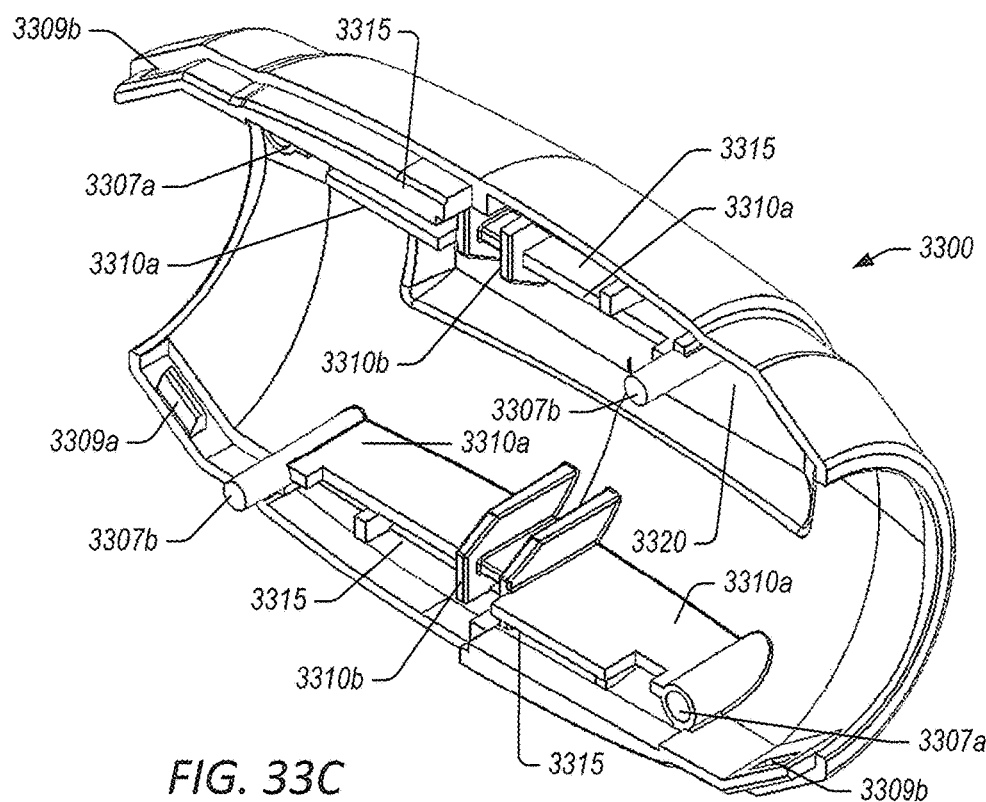

FIGS. 33A-C illustrate an example of a clam shell 3300 that can be applied to an intermediate connector, such as the intermediate connector 3200 described herein with reference to FIG. 32. The clam shell 3300 can be configured to provide an aesthetic cover for the overmolded intermediate connector, such as the intermediate connector 3200. The clam shell 3300 can also be configured to protect the PCB from damage.

The clam shell 3300 comprises two halves 3305*a*, 3305*b* that couple together. In some embodiments, the two halves 3305*a*, 3305*b* permanently couple together (e.g., decoupling the two halves involves at least partially damaging or breaking the clam shell 3300, or where it requires at least about 30 N of force to separate the two halves 3305*a*, 3305*b* of the clam shell 3300). Each half 3305*a*, 3305*b* can be formed from the same one-piece tool and can be symmetrical such that one half can be rotated and still fit with the other half. The clam shell 3300 can include snap-fit connections comprising clips 3309*a* and clip receiving mechanisms 3309*b*. The clips 3309*a* can be a pair of protruding clips that extend from two diagonally opposing covers of the clam shell 3300. The clips 3309*a* can be configured to interact with the complementary clip receiving mechanisms 3309*b* and form the primary coupling features of the clam shell 3300, to reduce gaps between the halves 3305*a*, 3305*b*, to keep the gap closed, and to hold the ends shut. The clam shell 3300 can include female locating slots 3307*a* configured to engage with male locating pins 3307*b*. In some implementations, the female locating slots 3307*a* can include a slight inward taper that requires a force to insert the male locating pins 3307*b*. The male locating pins 3307*b* can be configured to be press-fit into the corresponding female locating slots 3307*a* on another half of the claim shell 3300. This can act as a back-up connection if the snap-fit connections fail.

The clam shell 3300 includes features such as ribs 3310*a*, 3310*b* to make sure the clam shell is assembled correctly. This can occur due at least in part to the two halves 3305*a*, 3305*b* being configured so that they are not able to be fully engaged with one another when assembled incorrectly. The clam shell 3300 can include horizontal ribs 3310*a* to reduce vertical movement of the intermediate connector and vertical ribs 3310*b* to reduce horizontal movement of the intermediate connector. The vertical ribs 3310*b* can be configured such that a central rib is longer such that it is closer to the overmold and able to reduce rotation of the overmold. The ribs 3310*a*, 3310*b* can generally be configured to receive and locate pins from the overmolded intermediate connector. For example, the ribs 3310*a*, 3310*b* can be configured to prevent or impede incorrect positioning by pushing the pin of the overmolded intermediate connector off-center (e.g., pin 3232 of the intermediate connector 3200 described herein with reference to FIG. 32), which may also prevent or impede engagement of a second pin.

The clam shell 3300 can include coupling regions 3315 comprising a protruding section and a cut-out region. The coupling regions 3315 can be configured to interact with corresponding regions on the other half of the clam shell 3300. The coupling regions 3315 can be configured to prevent the formation of a rough edge between the two halves 3305*a*, 3305*b* leading to a better overall finish, and may aid in guiding correct alignment of the halves. The coupling regions 3315 can be configured to be symmetric to corresponding coupling regions on another half of the clam shell. The clam shell 3300 can include an internal cut-out region 3320 configured to allow space for the protruding overmolded PCB to fit within the cut-out region 3320.

In some embodiments, the overmolded intermediate connector 3200 can be configured to fit within the clam shell 3300 in at least four different positions. The intermediate connector 3200 can include three pins, for example, that are not centered with respect to the intermediate connector 3200. The central pin, in some embodiments, can be centered with respect to the other pins rather than the intermediate connector 3200.

In some embodiments, the overmolded intermediate connector 3200 includes three or more pins 3220 to securely fasten the overmolded intermediate connector 3200 to the clam shell 3300. The pins 3220 can be configured to reduce horizontal and/or vertical translation and/or rotation about the horizontal axis, as described herein with reference to FIGS. 32A-C. In some embodiments, four pins 3220 can be used to effectively position and locate the overmolded intermediate connector 3200 within the clam shell 3300. In such an embodiment, the two halves 3305*a*, 3305*b* of the clam shell 3300 may not be symmetric. In addition, the fourth pin may push the wires outwards potentially increasing the chance of exposing the wires due to a reduced amount of the overmold material covering the wires. The pins 3220 can be configured to be sufficiently long so that they engage with the ribs 3310a, 3310b to reduce or prevent rotation of the overmolded intermediate connector 3200. In some embodiments, the central pin can be longer than the other pins. In addition, the pins 3220 can be configured to be sufficiently thick for mechanical robustness.

The clam shell 3300 and the overmolded intermediate connector can include components that reduce or prevent misalignment of the overmolded intermediate connector within the clam shell 3300 during installation or fabrication. In some embodiments, when the overmolded intermediate connector is incorrectly positioned within the clam shell 3300, the overmolded intermediate connector may move within the clam shell 3300 thereby preventing the two halves 3305a, 3305b from coupling correctly. This may lead to the two halves 3305a, 3305b becoming disconnected and the clam shell 3300 disengaging from the overmolded intermediate connector.

The clam shell 3300 can be sized based on intended use. For example, the clam shell 3300 can be sized according to the size of the opening in the side of an incubator. The clam shell 3300 can be configured to fit within the opening of the incubator, allowing the tube to be positioned within the incubator. If the clam shell 3300 is too small, though, the material strength may be reduced below acceptable levels. This may be particularly true with respect to clipping mechanisms. In some embodiments, the clam shell 3300 is configured to sit snugly without touching the overmolded intermediate connector. As a result, it may be difficult to include additional structures or features in the clam shell 3300.

During fabrication, the tube can be wound onto either end of the intermediate connector prior to overmolding. The clam shell 3300 can be configured to sit close to the tube but with little or no contact as this may put pressure on the clam shell 3300. The clam shell 3300 can be made from materials including polypropylene, acetyl, or other materials with similar properties.

In some embodiments, a cover (e.g., the clam shell 3300) can include a live hinge that can be used to couple the two halves of the cover. This live hinge may provide a simple mechanism to assemble the cover. In some embodiments, an internal hinge can be integrated into the cover, the hinge being combined with the clips to provide an effective coupling mechanism.

In some embodiments, the cover can include pins that are used to replace the horizontal and vertical ribs of the clam shell 3300. These pins can be configured to provide the same locating function as the ribs 3310a, 3310b of the clam shell 3300. In certain implementations, the cover can use fewer or no pins. This may allow rotation of the intermediate connector, but may resist sliding of the intermediate connector. In some implementations, the ends of the locating pins may be fattened such that the insert forms the locating point.

In some embodiments, the overmold on the intermediate connector could form the outer cover. In some embodiments, a cover may be shaped such that it matches the shape of the overmolded intermediate connector. In such a configuration, the cover may be an asymmetrical part. The shape can be configured to reduce contact between the cover and the intermediate connector.

In some embodiments, the halves of the cover can be coupled using ultraviolet (UV) glue, adhesives, or using the male and female locating pins on the cover to form a press-fit coupling.

Control of a Segmented Heater

Figure 26:
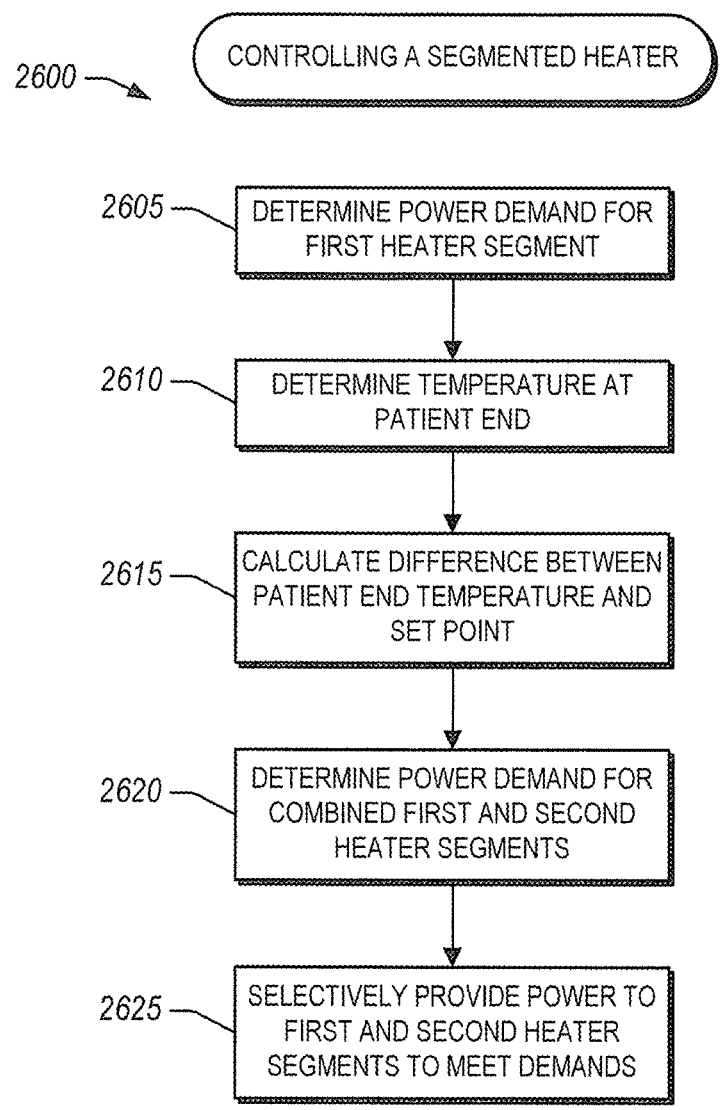
FIG. 26 illustrates a flow chart of an example method for controlling a segmented heater.

FIG. 26 illustrates a flow chart of an example method for controlling a segmented heater, such as in an inspiratory limb with a heater that is coupled to an extension limb also having a heater. The control method can be implemented by a humidification system, as described herein, or other control module. As such, and for ease of description, the following method is described as being performed by the control module, but one or more steps of the method, or portions of a single step of the method, can be performed by any combination of components in a humidification system. In some embodiments, the method 2600 can be run at least once every second to provide substantially continuous control and fine control of the humidification system.

In step 2605, the control module determines a power demand for a first heater segment (e.g., a heater in an inspiratory limb). This can be done, for example, using open loop control. A default duty cycle can be determined to be the power demand of the first heater segment determined at least in part by the flow of gases through the humidification system. In some embodiments, this default duty cycle can be used for control of the first heater segment and determined using a model configured to be applicable in a majority of situations. Advantageously, this can allow the control module to apply the same control parameters during most situations. For example, this can mean that the control module does not alter its control parameters for different ambient conditions.

Figure 27:
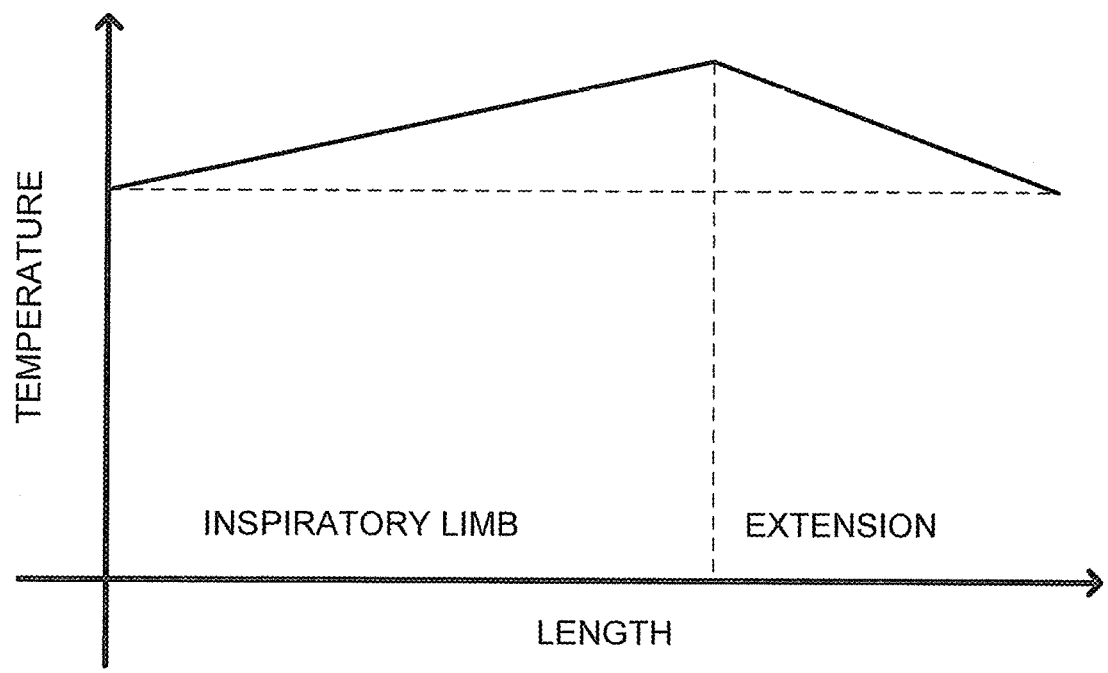
FIG. 27 illustrates an example targeted temperature profile.

The power demand can be configured so that the control module maintains a targeted temperature profile, an example of which is illustrated in FIG. 27. In some embodiments, the targeted temperature profile utilizes a greater amount of heating in the first heater segment to reduce condensate (e.g., relative to the second heater segment of the extension limb). For example, the first heater segment can be controlled to heat the inspiratory limb above a set point to give the gases a lower relative humidity. This can effectively control cooling of the gases by the time the gases reach the patient after flowing through the extension limb, allowing the gases to maintain a high absolute humidity.

In step 2610, the control module determines a temperature at the patient end of the combined inspiratory limb and extension limb, the temperature determined using a patient-end temperature sensor. The control module can be configured to monitor this temperature sensor frequently (e.g., once per second, twice per second, etc.). In response to the determined temperature, the control module can alter the duty cycle to achieve the targeted temperature profile, a targeted absolute or relative humidity of the gases at the patient end, and/or a targeted temperature of the gases at the patient end.

In step 2615, the control module determines a difference between the set point temperature and the measured temperature at the patient end. For ease of reference, the value of this difference is referred to as the error, but it is not to be inferred or understood that this value represents a mistake or other unintentional result.

In step 2620, the control module determines a power demand for a combination of the first heater segment and the second heater segment (e.g., the inspiratory limb and an extension limb coupled to the inspiratory limb). The power demand can be proportional to the length of the limb with respect to the flow rate. For example, the control module can determine a power demand as a power per unit length.

The power demand can be expressed as: $DC\_12 = Kp*e + Ki*\int e\, dt$, where DC_12 is the output of the control module (e.g., a power, a duty cycle, etc.) for the combination of the first and second heater segments, Kp is a proportional coefficient in a proportion-integral-derivative (PID) control scheme, Ki is an integral coefficient in the PID scheme, and e is the error (i.e., the current difference between the set point temperature and the measured temperature as determined in step 2615). The control module can be configured to reduce or eliminate the error. For example, the control module can be configured to control power to the heater segments to drive the current temperature to the set point considering short term and long term effects on temperature in response to power delivered to the respective heater segments.

In the PID control scheme, the value of Kp can be related to the rate of temperature change within the system. Changing Kp can be done to achieve a targeted or suitable rate of change of temperature within the system to achieve the set point temperature considering short term and long term effects. The product of Kp and e in the above equation can be referred to as the proportional term in the PID scheme.

In the PID control scheme, the value of Ki can be related to the speed with which the system achieves the targeted set point as the system nears steady-state operation. The value of Ki can also be related to how fast the system heats up. The value of the integral of the error (e.g., $\int e\, de$) represents the accumulated error over the time which the system has been running. The product of Ki and the accumulated error in the above equation can be referred to as the integral term in the PID scheme.

In some embodiments, there is no derivative term in the PID control scheme.

In step 2625, the control module selectively heats the first and second heater segments to meet the power demands of each. In some embodiments, the power demand for the first heater segment can be exceeded. In some implementations, the control module can implement an algorithm that allows the power demand for the first heater segment to be exceeded depending on other control parameters, as described herein with reference to FIG. 29.

The control module can be configured to consider the power demand for the first heater segment to be met where at least one of the following conditions applies: (1) the power demand of the first heater segment is met by heating of the first heater segment; (2) the power demand of the first heater segment is partially met by heating of the first heater segment and partially met by heating of the second heater segment, wherein the duty cycle of the combination of the first and second heater segments contributes to the overall demand and any deficit is met by heating of the first heater segment (an example of which is described with reference to FIG. 28; or (3) the demand of the first heater segment is met by heating of the combination of the first and second heater segments.

Figure 28:
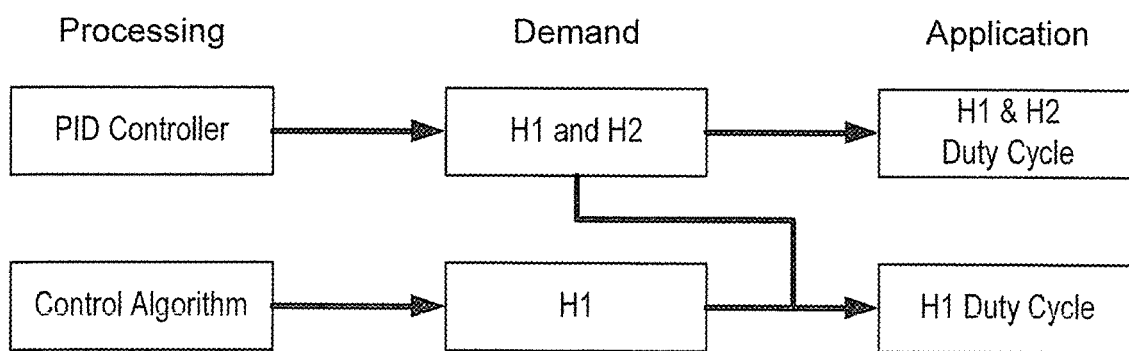
FIG. 28 illustrates a functional block diagram illustrating a relationship between processing components of a control module, demands related to heater segments, and application of determinations of the control module.

FIG. 28 illustrates a functional block diagram 2800 illustrating the relationship between processing components of the control module, the demands related to the heater segments, and the application of the resultant duty cycle determinations. For example, the control module can implement a PID controller 2802 as described herein with reference to FIGS. 26 and/or 30. The PID controller 2802 can be configured to control a combination of the first and second heater segments 2806 (e.g., an outer loop of an inspiratory limb coupled to an extension of the inspiratory limb) based at least in part on a demand determined by the control module, as described herein with reference to FIG. 26. The control module can implement a control algorithm 2804 as described herein with reference to FIGS. 26, 29 and/or 31. The control algorithm 2804 can be used to control the first heater segment 2808 based at least in part on a demand determined by the control module. The control module can apply power to the first and second heater segments based on a duty cycle 2810 determined to meet the demand for the first and second heater segments 2806 using the PID controller 2802. Similarly, the control module can apply power to the first heater segment based on a duty cycle 2812 determined to meet the demand for the first heater segment 2808 using the control algorithm 2804. In some embodiments, the control algorithm can determine the duty cycle 2812 for the first heater segment based at least in part on the demand for the combination of the first and second heater segments because power applied to the combination of heater segments affects the temperature and humidity of the gases in the first segment. For example, as described herein with reference to FIG. 26, the demand of the first heater segment can be met partially or wholly by the demand for the combination of the first and second heater segments. In certain implementations, the PID controller 2802 can be configured to be the principal means of controlling heating in the combined inspiratory limb and extension (e.g., the first and second heater segments) and the control algorithm 2804 for the inspiratory limb (e.g., the first heater segment) can act as a way to provide supplemental heating, which may be particularly appropriate during particular phases of operation (e.g., during start up, warm-up period, during periods of changing temperature, etc.).

Figure 29:
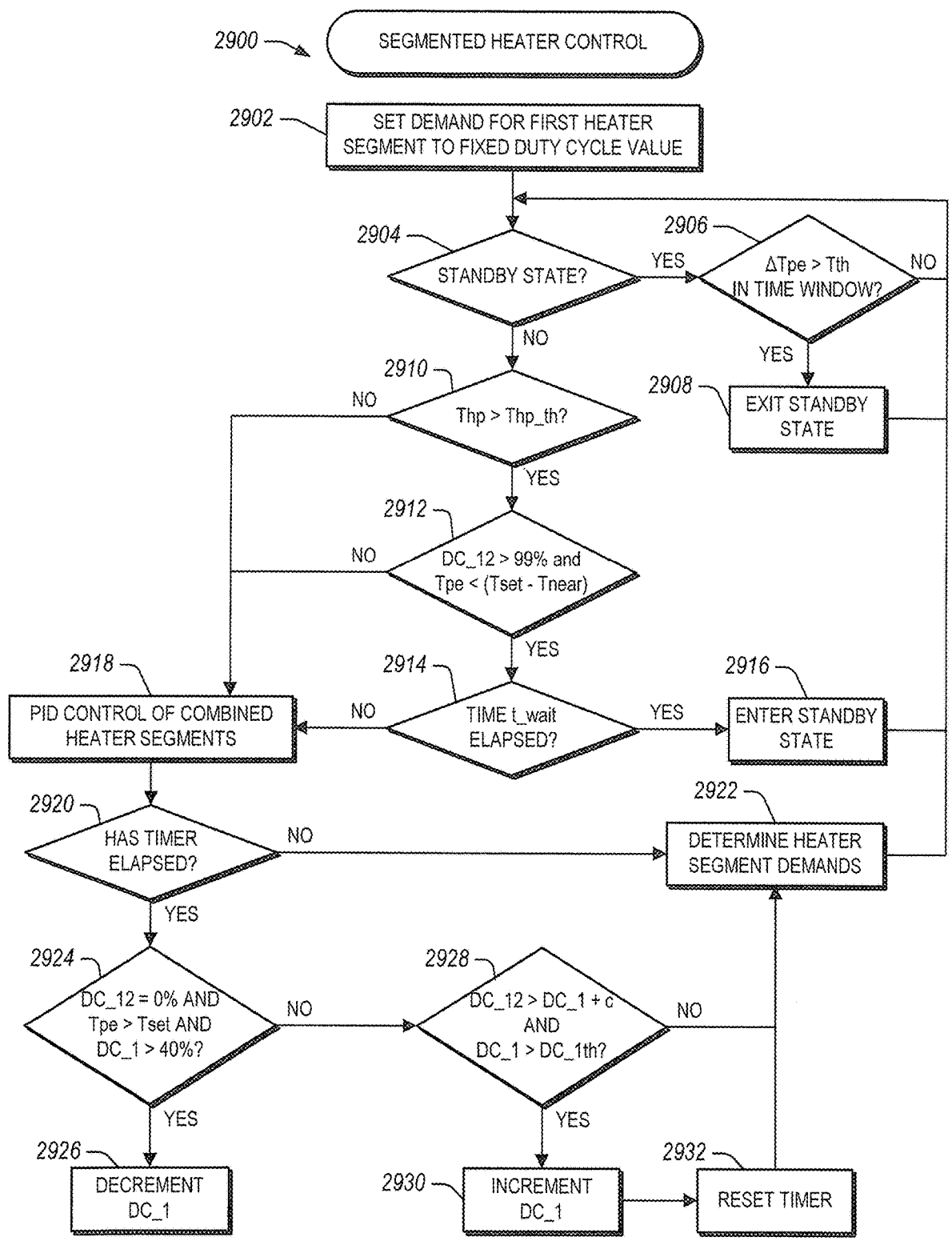
FIG. 29 illustrates a flow chart of an example control algorithm.

FIG. 29 illustrates a flow chart of an example control algorithm 2900 implemented by a control module to control a segmented heater. In step 2902, the control module operates in open loop control mode by setting the demand for the first heater segment to be a fixed duty cycle value. In some implementations, the fixed duty cycle value can be set initially at 80%. The duty cycle value can be incremented or decremented as determined by the steps in the control algorithm.

In step 2904, the control module determines whether the humidification system is in a standby state. In some embodiments, the control module can determine that the humidification system is in the standby state by examining a value stored in a local variable. If the humidification system is in the standby state, the control module proceeds to step 2906 to determine if the patient-end temperature (Tpe) has increased by more than a change threshold, Tth, (e.g., about 2° C.) in a time window (e.g., about 1 minute). This can effectively determine if flow has been added to the humidification system. If flow has been added as determined in step 2906, the control module exits the standby state in step 2908.

When the unit is not in the standby state as determined in step 2904 or after exiting step 2908, the control module determines whether the heater plate temperature exceeds a heater plate temperature threshold, Tth_hp, (e.g., about 50° C.) in step 2910. This can correspond to a warm-up period. If the control unit determines the heater plate temperature exceeds the heater plate temperature threshold, then the control module determines whether the duty cycle of the combination of the first and second heater segments, DC_12 (e.g., the outer section), is greater than about 99% and the patient-end temperature, Tpe, is less than the set point temperature minus a temperature value, Tnear, configured to determine when the patient-end temperature is near the set point temperature in step 2912. In some embodiments, the value of Tnear can be about 2° C. If the control module determines that the combination of the first and second heater segments is greater than about 99% and that the patient-end temperature is less than the set point temperature minus Tnear, then it is possible that there is a no flow condition in the humidification system. For example, a no flow condition may exist where the humidification system is applying about 100% duty cycle but the patient-end temperature is not near enough to the set point. The control module proceeds to step 2914 if this is true to account for potential disturbances in the system (e.g., putting something cold onto the system) and waits for tailored amount of time, t_wait (e.g., about 5 minutes). If it has been longer than the time t_wait, the control module proceeds to step 2916 and enters a standby state until flow is applied or re-applied to the humidification system. In the standby state, the control mode sets the duty cycle of the first heater segment to 0% and the combination of the first and second heater segments to about 40%.

If the result of the determinations in any of steps 2910, 2912, or 2914 is no, then the control module proceeds to step 2918 to control the combination of the first and second heater segments using a PID control scheme to achieve a targeted set point to the patient end. In some embodiments, the PID control scheme is the method described herein with reference to FIG. 30. For example, the control module can control the combined first and second heater segments to achieve the targeted set point based on a difference between the current, measured temperature at the patient end and the set point. In certain implementations, the control is proportional to the difference between the measured temperature and the temperature set point. The control module can monitor a timer to determine when a tailored time threshold has elapsed (e.g., 30 seconds) in step 2920. This tailored time threshold can be set to allow enough time to pass for the PID controller to take effect. The control module implements the PID control scheme to achieve a duty cycle that results in meeting the relevant demands, demands that are determined in step 2922. For example, the PID control scheme can be implemented to achieve a duty cycle of DC_12 for the combination of the first and second heater segments and/or a duty cycle of DC_1 for the first heater segment, wherein the duty cycle for the first heater segment accounts for the demands of the combination of the first and second heater segments.

After the tailored time threshold has elapsed, the control module can proceed to step 2924 to determine whether (a) the duty cycle for the combined first and second heater segments is equal to 0%, (b) the patient-end temperature exceeds the set point (e.g., about 39° C.), and (c) the duty cycle for the first heater segment is greater than a duty cycle threshold (e.g., about 40%). This test may be true where the combined first and second heater segments have stopped heating the gas, thus indicating that it is appropriate to reduce the temperature profile of the inspiratory limb. This can be achieved, for example, by decreasing the duty cycle of the first heater segment. Thus, if this is true, the computer module decrements the duty cycle for the heater cycle by a decrement value (e.g., 2%), in step 2926. If it is not true, then the control module proceeds to step 2928 to determine whether (a) the duty cycle for the combined first and second heater segments is greater than the duty cycle for the first heater segment plus a constant, c, (e.g., test whether DC_12>DC_1+c, where c can be about 20%) and (b) the duty cycle for the first heater segment is less than an inner section threshold, DC_1th (e.g., about 80%). The constant can be tailored so that the initial duty cycle value plus the constant is 100% (e.g., the initial duty cycle value can be 80% so the constant can be 20%). This test may be true where it may be suitable to increase the duty cycle of the first heater segment to maintain the temperature profile of the inspiratory limb. Thus, if this test is true, the control module proceeds to step 2930 to increment the duty cycle of the first heater segment by an increment value (e.g., about 2%). If it is not true, the control module returns to step 2922, described above. If the control module increments or decrements the duty cycle of the first heater segment, then the control module resets the timer in step 2932. Control can then return to step 2922.

Figure 30:
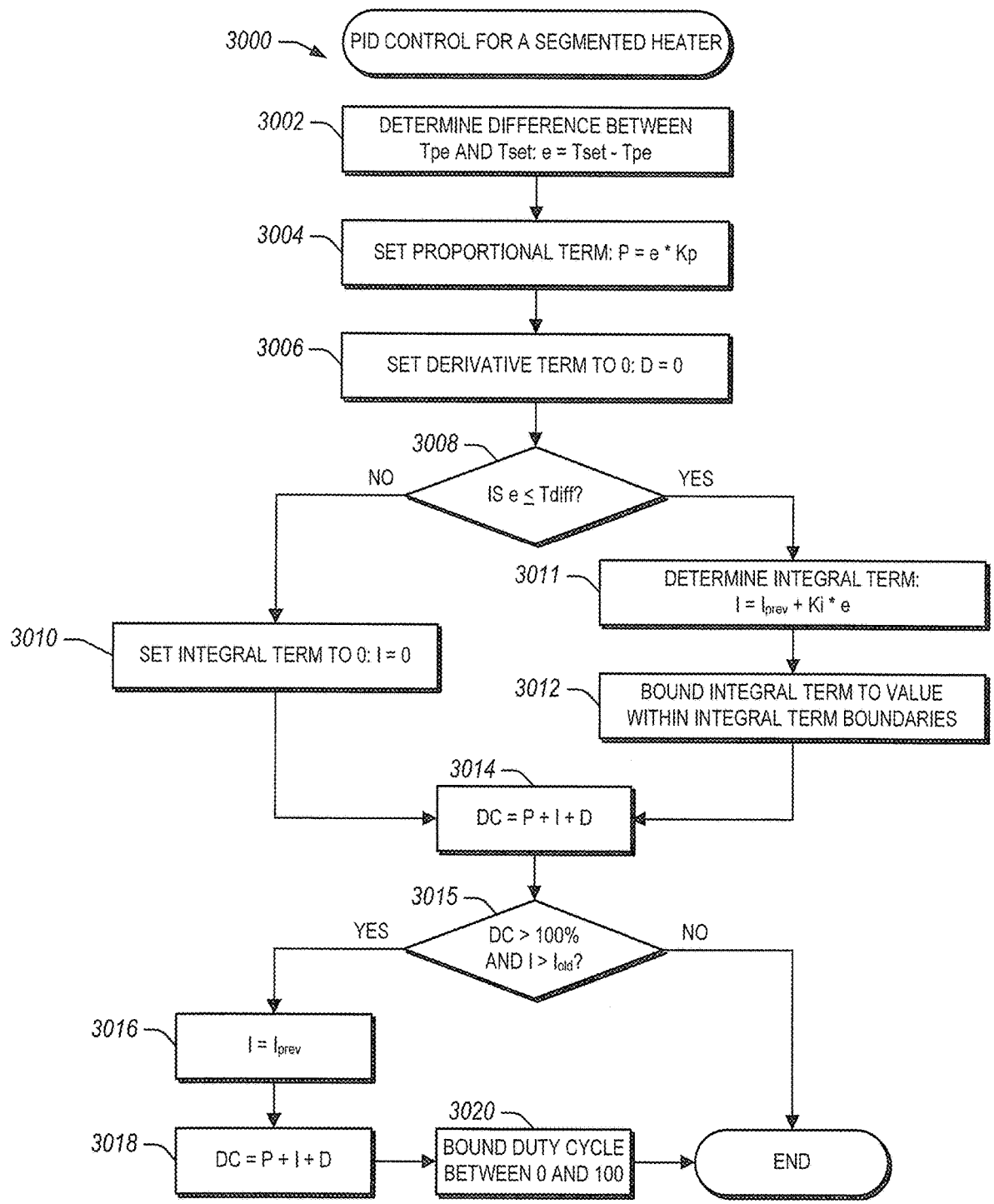
FIG. 30 illustrates a flow chart of an example PID control scheme.

FIG. 30 illustrates a flow chart of an example PID control scheme 3000 configured to provide closed-loop control to achieve a targeted temperature set point at the patient end using the combined first and second heater segments. The PID control scheme can be used to determine a duty cycle for the combined first and second heater segments.

In step 3002, the control module initializes the PID parameters by determining a difference between the measured temperature Tpe and the temperature set point, Tset, the difference referred to as the error, e: e=Tset−Tpe. In step 3004, the control module sets the proportional term of the PID control scheme to a product of the constant Kp and the error, e: P=Kp*e. In certain implementations, the constant Kp is set to about 10. In step 3006, the control module sets the derivative term, D, of the PID control scheme to 0. Other values may be used as well.

In step 3008, the control module determines whether the error is less than or equal to a temperature difference threshold, Tdiff, (e.g., about 100). This can be used to determine when it is appropriate to set the integral term, I, of the PID control scheme to 0, as shown in step 3010. If the current temperature is within the temperature difference threshold of the temperature set point, then the control module can proceed to step 3011 to assign the integral term, I, of the PID control scheme to be the old or previous integral term plus a fraction, Ki, of the error, e: I=$I_{prev}$+Ki*e. In certain implementations, the fraction, Ki, can be about 0.05. The control module can further check that the integral term, I, is within acceptable or suitable boundaries (e.g., −2<I<100), in step 3012, and the control module can set the integral term to the boundary values if it is outside the suitable range.

In step 3014, the control module determines the duty cycle as the sum of the proportional term, P, the integral term, I, and the derivative term, D: DC=P+I+D. If the duty cycle is greater than 100% and the integral term is greater than the previous integral term (e.g., I>$I_{prev}$), as determined by the control module in step 3015, then the control module resets the integral term to its previous value in step 3016 and recalculates the duty cycle in step 3018. In step 3020, the control module binds the value of the duty cycle to be between 0 and 100 (e.g., if it is less than 0 the control module sets the duty cycle to 0 and if the duty cycle is greater than 100 the control module sets the duty cycle to 100.

Figure 31:
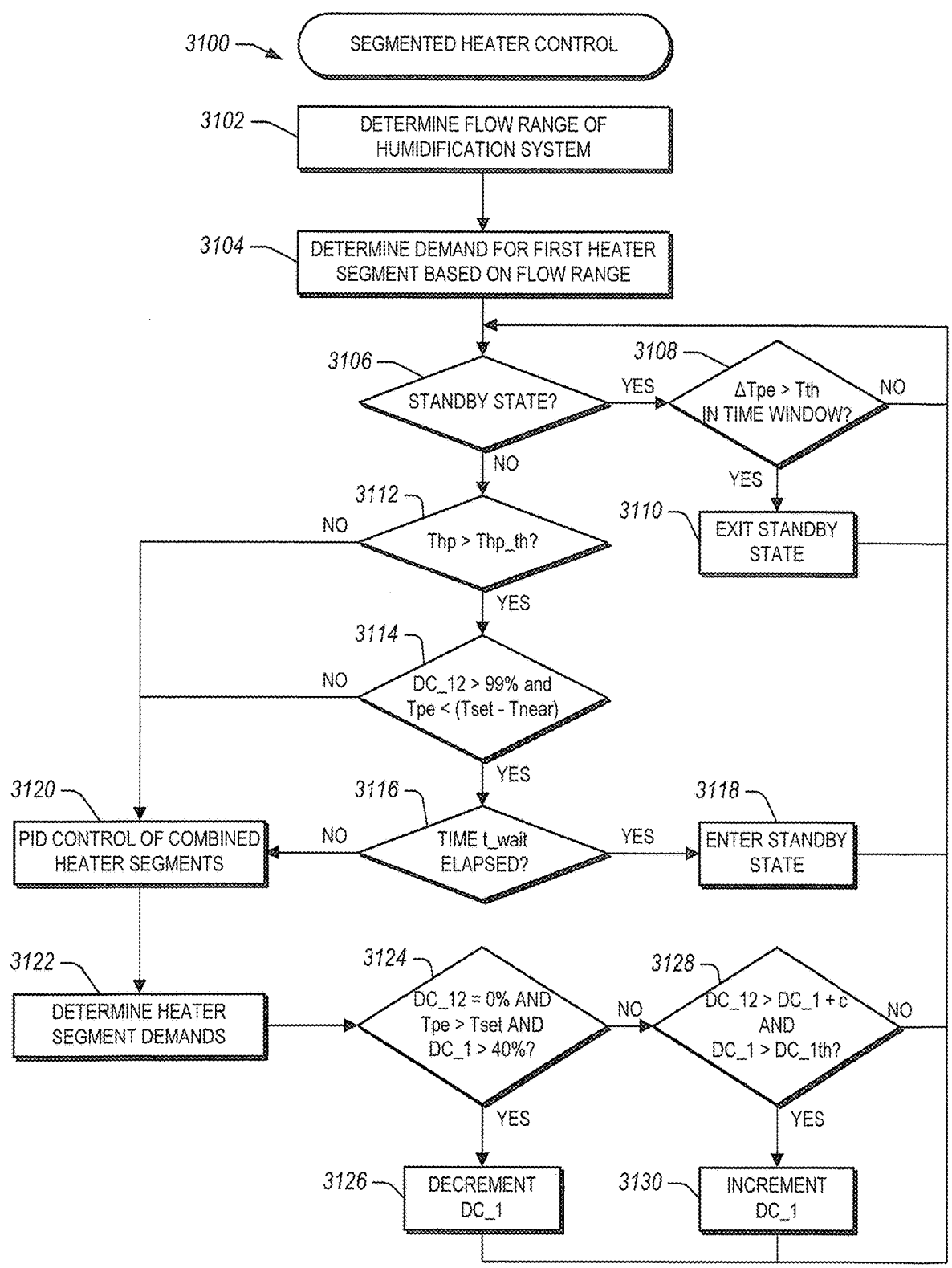
FIG. 31 illustrates a flow chart of another example control algorithm.

FIG. 31 illustrates a flow chart of another example control algorithm 3100 that can be implemented by the control module in a humidification system. In step 3102, the control module determines a flow range of the humidification system. In step 3104, the control module determines a demand of the first heater segment based on the determined flow range. In some embodiments, the flow ranges can be levels of flow with corresponding demands. For example, the flow range can be in a low flow range, a medium flow range, or a high flow range and a low flow demand can be determined for the low flow range, a medium flow demand can be determined for the medium flow range, and a high flow range can be determined for the high flow range. In some embodiments, the flow ranges can overlap. In certain implementations, the control module determines the flow range to determine an initial demand for the first heater segment only at start up. In such instances, the control module can use the demand for the combination of the first and second heater segments for the bulk of the control of the humidification system. After this initial setting, the rest of the control algorithm 3100 can adjust the demand of the first heater segment.

In step 3106, the control module determines whether the humidification system is in a standby state. For example, the control module can determine that the humidification system is in the standby state by examining a value stored in a local variable. If the humidification system is in the standby state, the control module proceeds to step 3108 to determine if the patient-end temperature (Tpe) has increased by more than 2° C. in about 1 minute. This can effectively determine if flow has been added to the humidification system. If flow has been added as determined in step 3108, the control module exits the standby state in step 3110.

When the unit is not in the standby state as determined in step 3106, the control module determines whether the heater plate temperature exceeds about 50° C. in step 3112. This can correspond to a warm-up period. If the control unit determines the heater plate temperature exceeds about 50° C., then the control module determines whether the duty cycle of the combination of the first and second heater segments (e.g., the outer section) is greater than about 99% and the patient-end temperature Tpe is less than the set point temperature minus a temperature value, Tnear (e.g., about 2° C.), in step 3114. If the control module determines this is true, then it is possible that there is a no flow condition in the humidification system. For example, a no flow condition may exist where the humidification system is applying about 100% duty cycle but the patient-end temperature is not near enough to the set point. The control module proceeds to step 3116 if this is true to account for potential disturbances in the system (e.g., putting something cold onto the system) and waits for about 5 minutes. If it has been greater than about 5 minutes, the control module proceeds to step 3118 and enters a standby state until flow is applied or re-applied to the humidification system. In the standby state, the control mode sets the duty cycle of the first heater segment to 0% and the combination of the first and second heater segments to about 40%.

If the result of the determinations in any of steps 3112, 3114, or 3116 is no, then the control module proceeds to step 3120 to control the combination of the first and second heater segments using a PID control scheme to achieve a targeted set point to the patient end. In some embodiments, the PID control scheme is the method described herein with reference to FIG. 30. For example, the control module can control the combined first and second heater segments to achieve the targeted set point based on a difference between the current, measured temperature at the patient end and the set point. In certain implementations, the control is proportional to the difference between the measured temperature and the temperature set point. The control module implements the PID control scheme to achieve a duty cycle that results in meeting the relevant demands, demands that are determined in step 3122. For example, the PID control scheme can be implemented to achieve a duty cycle of DC_12 for the combination of the first and second heater segments and/or a duty cycle of DC_1 for the first heater segment, wherein the duty cycle for the first heater segment accounts for the demands of the combination of the first and second heater segments.

The control module proceeds to step 3124 to determine whether (a) the duty cycle for the combined first and second heater segments is equal to 0%, (b) the patient-end temperature exceeds the set point (e.g., about 39° C.), and (c) the duty cycle for the first heater segment is greater than a duty cycle threshold (e.g., about 40%). This test may be true where the combined first and second heater segments have stopped heating the gas, thus indicating that it is appropriate to reduce the temperature profile of the inspiratory limb. This can be achieved, for example, by decreasing the duty cycle of the first heater segment. Thus, if this is true, the computer module decrements the duty cycle for the heater cycle by a decrement value (e.g., 2%) every 30 seconds while this is true, in step 3126. If it is not true, then the control module proceeds to step 3128 to determine whether (a) the duty cycle for the combined first and second heater segments is greater than the duty cycle for the first heater segment plus a constant (e.g., test whether DC_12>DC_1+c, where the constant can be about 20%) and (b) the duty cycle for the first heater segment is less than an inner section threshold (e.g., about 80%). The constant can be tailored so that the initial duty cycle value plus the constant is 100% (e.g., the initial duty cycle value can be 80% so the constant can be 20%). This test may be true where it may be suitable to increase the duty cycle of the first heater segment to maintain the temperature profile of the inspiratory limb. Thus, if this test is true, the control module proceeds to step 3130 to increment the duty cycle of the first heater segment by an increment value (e.g., about 2%). If it is not true, the control module can return to step 3122 or to step 3106, described above. If the control module increments or decrements the duty cycle of the first heater segment, then the control module can return to step 3122 or to step 3106.

Additional Control System

Another example control system for the circuit diagram 2500 of FIGS. 25A-C will be described next. As described above, the circuit diagram 2500 can be implemented in a system that does not include a temperature sensor on an intermediate connector connecting the first heater segment H1 in the inspiratory limb to the second heater segment H2 in the extension limb. The circuit diagram 2500 can be implemented using a control system configured to alter the switching of the MOSFET pairs to heat either in inner loop HW1 or an outer loop HW2. Loop HW1 (shown in FIG. 25C) can include the first heater segment H1 of an inspiratory segment. Loop HW2 (shown in FIG. 25B) can include the first and second heater segments H1, H2. Power can be supplied to Loop HW1 to heat H1 or to Loop HW2 to heat both H1 and H2 depending on the polarity of the voltage. In this application, power can include electrical power, voltage and/or current. Loop HW1 can be activated by switching on/off MOSFETS in the switching arrangement as shown in FIG. 25C. The diodes/switches could be MOSFETS. Polarity of the supplied power can be switched to activate only Loop HW2 as shown in FIG. 25B. The controller can be configured to operate the MOSFETS to switch polarity as required and provide an appropriate duty cycle to the heater wires.

Figure 35:
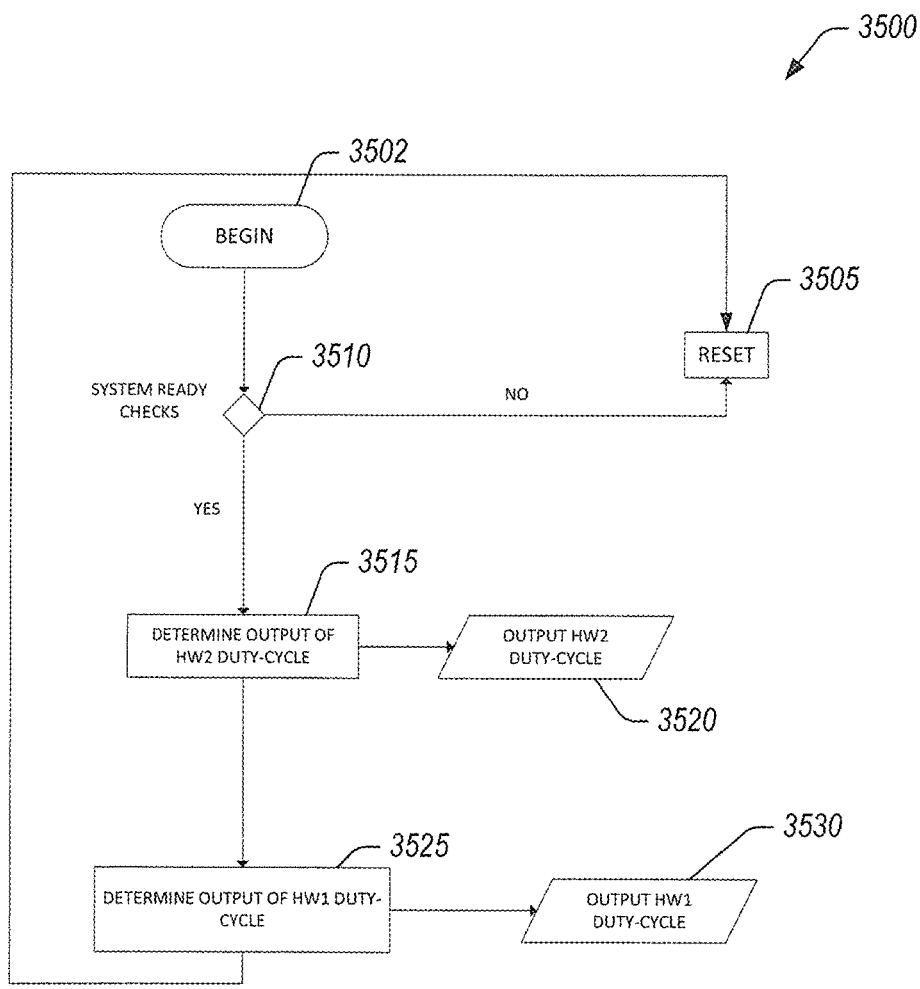
FIG. 35 illustrates a flow chart of another example control algorithm.
Figure 37:
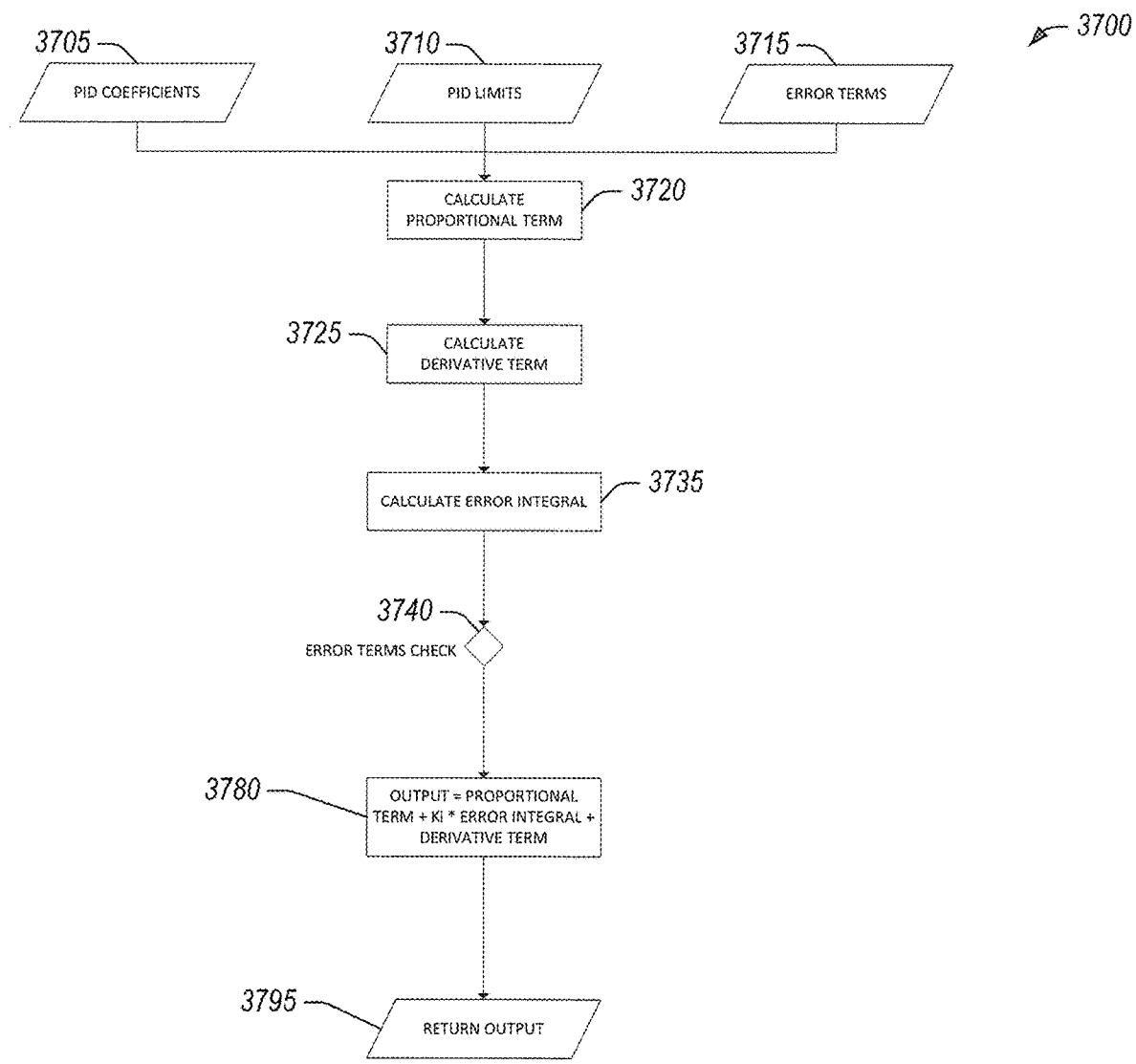
FIG. 37 illustrates a flow chart of another example PID control scheme.

FIG. 35 illustrates an example control algorithm 3500 for controlling Loops HW1 and HW2. In the illustrated embodiment, Loops HW1 and HW2 can be controlled sequentially, thereby allowing the algorithm 3500 to run smoothly. The controller can continue to repeat all the steps in order to determine if outputs of the HW1 or HW2 duty cycles need to be controlled and at what level. The controller can determine at step 3502 an error between a patient end temperature measured by the patient end sensor, such as the sensor 204b shown in FIG. 13, and a patient end set point. Outputs of the HW1 and HW2 duty cycles can each be controlled using a PID controller known in the art based on the error. The controller can optionally go through one or more initial system ready checks in step 3510. A system reset 3505 can be performed if the system is not ready. If the system is ready, the output of the HW1 duty cycle can be determined based on the error between the measured patient-end temperature and the patient-end temperature set point at step 3515. The output of the HW1 duty cycle can optionally be based on a standard PID controller with a set of constants. In some embodiments, the PID controllers can implement a PID control scheme 3700 as shown in FIG. 37, which will be described in more detail below. The controller can determine an output of each term (i.e. proportional, integral and derivative terms) based on the error and the set of constants. The constants can be predetermined for the system and stored in a memory or in a lookup table or any other suitable format. The constants may be modified depending on changes to the conditions, as the system can store a plurality of constants that can relate to multiple environments. One non-limiting example is if a portion of the conduit is inside an incubator or not.

In one embodiment, the entire inspiratory conduit including the inspiratory limb and the extension limb is exposed to the same ambient environment along its length. In this embodiment, the controller can function as a normal PID controller controlling the output of the HW2 duty cycle at step 3515. As the error between the measured patient-end temperature and the patient-end temperature set point can be large, Loop HW2 can be heated using a set of constants. The error can be large because the patient end of the inspiratory conduit is exposed to the ambient temperature, which can be much lower than the patient end temperature set point. In this embodiment, the algorithm 3500 can output a large HW2 duty cycle at step 3520. The algorithm 3500 can then determine the output of the HW1 duty cycle at step 3625. In this embodiment, the HW1 duty cycle can be set to 0% due to the fact that the output of the HW1 duty cycle can be inversely related to the output of the HW2 duty cycle. If the output of the HW2 duty cycle is high enough, the output of the HW1 duty cycle can be set to 0%. This can happen if there is a large error value between the patient end temperature and the patient end set point.

As the heater wires H1 and H2 heat up with power supplied to Loop HW2, the error can be reduced to within an appropriate error threshold. As described above, the controller can run the algorithm 3500 continuously so that the error is monitored continuously. When the error is within the appropriate error threshold, Loop HW1 may be activated to achieve temperature control in this embodiment. More details of the activated Loop HW1 will be described below with referenced to another embodiment.

In another embodiment, the inspiratory limb and the extension limb can be exposed to different ambient environments. For example, the extension segment can be placed inside a controlled environment, such as an incubator or other suitable device that is a closed system. The controlled environment can control at least the temperature and/or the humidity within the environment. When the extension limb is inserted into the incubator, the patient end sensor can read a higher temperature value that is closer to the set point value because of the elevated temperature in the incubator than the ambient temperature. Therefore, the error can be smaller than when the extension limb is exposed to the ambient temperature. When the error is within a predetermined threshold value, which would typically be the case when the extension limb is placed inside the incubator, Loop HW1 can be activated. In a non-limiting example, the threshold error value can be equal to or smaller than 2.5° C. The controller can determine the output of the HW1 duty cycle at the step 3525. In some embodiments, the controller can provide PID control 3700 of the output of the HW1 duty cycle as shown in FIG. 37. As the error is further reduced by the heating of H1, the output of the HW1 duty cycle can be further increased because the output of the HW2 duty-cycle determined in the step 3515 would be further reduced.

With continued reference to the incubator embodiment, the controller is configured to control the power supplied to Loop HW1 to energize H1 to a maximum capacity until H1 reaches a predetermined surface temperature threshold. The surface temperature threshold can prevent the inspiratory limb from getting too hot so that the humidification system becomes unsafe to handle or use. In some embodiment, the surface temperature threshold can be mandated by regulatory standards. The predetermined surface temperature threshold can be related to a maximum power/voltage supplied to Loop HW1. The maximum power/voltage can be set based on experimental data.

Further, as H2 is not energized and therefore does not heat up when the controller supplies the power to Loop HW1 at the step 3530, there can be a temperature drop across the extension limb from the intermediate connector to the patient end. This temperature drop can be at a known decay rate due to the well-known cooling characteristics in an incubator. The power supplied to Loop HW1 can be controlled to achieve a temperature at the start of the extension limb such that the temperature drop across the extension limb can result in a desired patient end temperature. FIG. 27 illustrates an example heating profile of the inspiratory conduit in this incubator embodiment. At the end where the inspiratory conduit couples the humidification chamber, the temperature can be above or below the patient end temperature depending on the chamber outlet temperature set point. The controller can determine a difference between the chamber outlet temperature and the measured patient end temperature and can accordingly adjust the output of the HW1 duty cycle. The temperature of the inspiratory limb can rise along the length of the inspiratory limb, which can end at the intermediate connector, and can taper downward from the intermediate connector to the patient end along the extension limb, which is not heated when Loop HW1 is activated.

In the control algorithm 3500, Loop HW1 can do the bulk of heating of the humidification system. Loop HW2 can take over if the error exceeds the threshold value. In addition, the controller can keep the output of the HW2 duty cycle at a low value. On the one hand, the low output of the HW2 duty cycle can advantageously reduce the possibility of overheating the extension limb inside the incubator, thereby improving safety of the humidification system. For example, the low output of the HW2 duty cycle can prevent infants in the incubator or the caregiver handling the inspiratory conduit from getting burnt. At the same time, H1 can be heated to the surface temperature threshold to advantageously prevent condensation in the inspiratory limb. On the other hand, the low output of the HW2 duty cycle can advantageously allow Loop HW2 to respond quickly to changes in an environment and to maintain the heating profile as shown in FIG. 27. Sudden changes in the environment can include, but are not limited to, temperature changes inside the incubator, draft, cold ambient temperature, and the like. Moreover, supplying power to Loop HW2 can further advantageously provide a more stable heating profile. The more stable heating profile can be achieved by reducing or removing oscillations when Loop HW2 is activated. Oscillations can occur when only Loop HW1 is activated because of the time taken for the heat to be transferred by the heated gases traveling from the inspiratory limb to the patient end and to be detected at the patient-end sensor. The oscillations can be reduced because when both of the heater segments H1 and H2 are activated, the patient-end sensor can detect a faster temperature change response at the patient end than when only Loop HW1 is activated.

As the PID control scheme is configured to reduce the error, in some embodiments, the output of the HW2 duty cycle can reach a steady state at 0% and Loop HW2 will be activated only to react to sudden changes in the environment as described above. The steady state can be due to the proportional and differential terms for Loop HW2 being reduced to substantially 0 when the error is within the threshold. In other embodiments, the output of the HW2 duty cycle may not achieve a steady state but has a low value. For example and not by way of limitation, when the inspiratory conduit is in a cold ambient condition, there can be increased cooling of the gases in the inspiratory limb that is outside the incubator. The rapid cooling can be due to lower ambient temperatures that can cause a greater rate of heat dissipation from the heated and humidified gases in the tube to the ambient environment. Power supplied to both H1 and H2 in the activated Loop HW2 at 3530 can compensate for the increased cooling of gases in the inspiratory limb and to achieve a desired patient-end temperature.

Figure 36:
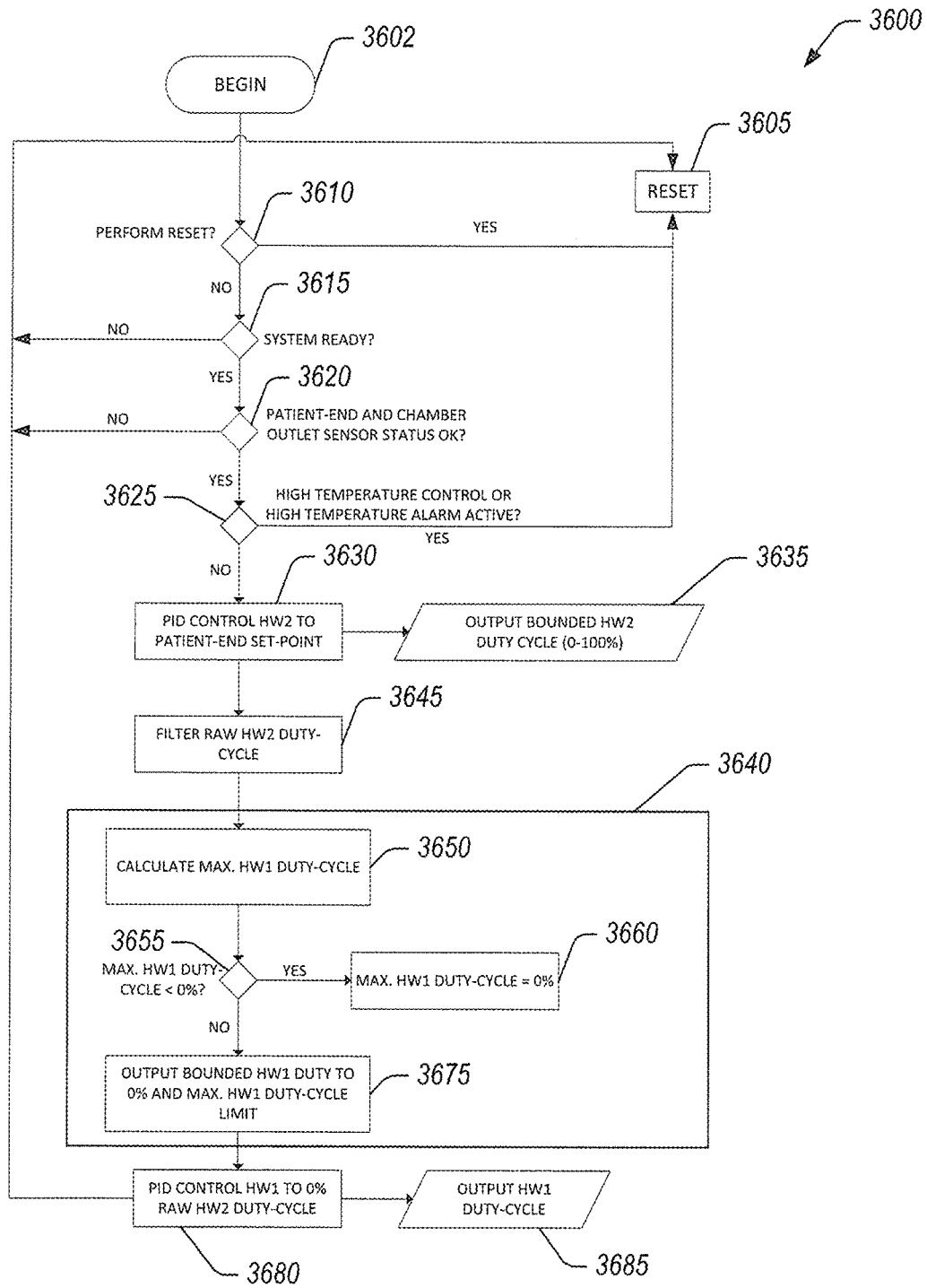
FIG. 36 illustrates a flow chart of another example control algorithm.

FIG. 36 illustrates another example control algorithm 3600 for controlling the outputs of the HW1 and HW2 duty cycles. The control algorithm 3600 can have the same features as the control algorithm 3500 except as described below. Accordingly, features of the control algorithm 3600 can be incorporated into features of the control algorithm 3500 and features of the control algorithm 3500 can be incorporated into features of the control algorithm 3600.

The controller can run the algorithm 3600 continuously. Continuous running of the algorithm 3600 can provide substantially continuous and fine control of the humidification system. The controller can begin 3602 with determining the error between the measured patient end temperature and the patient end set point. In some embodiments, the patient end set point can be independent of a gas flow rate in the inspiratory conduit. The set point can be a function of the chamber outlet temperature set point. For example, the patient end temperature set point can be set higher or lower than the chamber outlet temperature set point. The patient end set point can be changed if the humidification system is in very cold ambient environments. Further, continuous running of the algorithm 3600 can allow the system to be reset 3605 any time when there is massive overheating. In the illustrated embodiment, the reset 3605 can reset error terms used in the PID control algorithm to 0 and reset both the outputs of the HW1 and HW2 duty cycles to 0%.

As shown in FIG. 36, the controller can begin the algorithm 3600 with a series of checks 3610, 3615, 3620, 3625 to ensure that all sensors are working, all alarms are working and the system is in an operational condition. These checks can be optional. Specifically, the controller can check whether a reset needs to be performed 3610. In some embodiments, the controller can be programmed to determine whether reset needs to be performed based on predetermined algorithms. In other embodiments, the system may have a user interface to allow a user or caregiver to manually reset the system. For example, the reset can be done by turning the device off and on using an on/off button, by unplugging the device, or automatically in the software when required conditions are met. If no reset is needed at the step 3610, the controller can determine if the system is ready for running the algorithm 3600 at step 3615. If the system is not ready, the reset 3605 can be performed. If the system is ready, the controller can then determine statuses 3620 of the patient end sensor and a sensor at the outlet of the humidification chamber. The system can be reset 3605 if the sensors are not responsive or do not function as designed. If the statuses of the sensor are satisfactory, the controller can determine if a high temperature control or high temperature alarm is active in step 3625. The reset 3605 can be activated if the measured temperature is greater than an overheating temperature threshold to prevent overheating of the inspiratory conduit. In some embodiments, if the patient end temperature exceeds the overheating temperature threshold, a separate software module configured for controlling overheating can take over. This overheating module can set both the outputs of the HW1 and HW2 duty cycles to 0. The reset 3605 can be conducted to prevent accumulation of the integral error term of the PID control scheme 3630, 3680.

With continued reference to FIG. 36, after determining that the patient end temperature is below the set point and after the optional series of checks, the controller can determine the output of the HW2 duty cycle to bring the system to the desired set point temperature. The controller can implement a PID control scheme for the output of the HW2 duty cycle at step 3630. In the illustrated embodiment, the PID control step 3630 can be performed with a PID control scheme known in the art. Generally, an output of the controller for HW1 or HW2 in a PID control scheme can expressed with the equation $DC=K_p*e+K_i*\int e\,dt+K_d*de/dt$, where DC is the output of either the HW1 or HW2 duty cycle, $K_p$ is a proportional coefficient, $K_i$ is an integral coefficient, and $K_d$ is a derivative coefficient. Further, e is the error as determined in step 3602. In addition, $\int e\,de$ is an error integral, that is, an integration of past error from time 0 to the present time t. de/dt is the rate of change of the current error (that is, a differential term). The PID control scheme can be configured to reduce or eliminate the error.

FIG. 37 illustrates an example PID control scheme 3700. PID coefficients 3705, PID limits 3710, and error terms 3715 can be inputted into the PID control scheme 3700. As described above, the PID coefficients 3705 can include the proportional coefficient $K_p$, the integral coefficient $K_i$, the derivative coefficient $K_d$, and an error at which to introduce the integral term. In some embodiments, the proportional coefficient can be system-based terms determined by testing. In some embodiments, the derivative coefficient $K_d$ can be determined for a heater plate (not shown) of the system and/or Loops HW1 and HW2. For example, $K_d$ can be determined experimentally. The PID control scheme 3700 including the derivative coefficient $K_d$ can increase stability of the system and decrease overshoot when correcting the error. In some embodiments, a PI control scheme can be used instead of the PID control scheme 3700, excluding the derivative term. The output of the controller in the PI control scheme can be expressed as: $DC=K_p*e+K_i*\int e\,dt$. The PID limits 3710 can include minimum and maximum integral terms, and minimum and maximum output limits of the HW1 and HW2 duty cycles. Error terms 3715 can include a current error, the error integral, and a previous error.

From the inputs described above, the controller can calculate a proportional term 3720, which is the product of the proportional coefficient Kp and a current error of the system in the equation described above. The controller can also calculate a derivative term 3725, which is the product of the derivative coefficient Kd and the rate of change of the current error de/dt in the equation described above. The controller can calculate the error integral in step 3735. The controller can then perform error terms checks at step 3740. For example, the controller can check the error terms of any PID variables.

After the error terms check 3740, the output of the controller can then be calculated as DC=Proportional Term+Ki*Error Integral+Derivative Term at step 3780. The controller can bound the output value calculated from the step 3780 to the maximum and minimum output limits of the controller at step 3795. The controller can provide the resulting output 3795 of the controller to the step 3630 in FIG. 37, or to the step 3680, which will be described below.

Returning to FIG. 36, the controller can output the HW2 duty cycle bounded between 0% to 100% at the step 3635 based on the PID control in the step 3630. The algorithm 3600 can use the output of the HW2 duty cycle to control the patient end temperature to maintain the heating profile as shown in FIG. 27. As described above, the output of the HW2 can be low, allowing Loop HW2 to respond quickly to sudden changes while also improving patient and caregiver safety by preventing overheating of the extension limb.

The algorithm 3600 can also use the output of the HW2 duty cycle to control the output of the HW1 duty cycle. Before providing the output of the HW2 duty cycle to the step 3640 to calculate the PID limit of the output of the HW1 duty cycle, the controller can filter the raw output of the HW2 duty cycle at step 3645. The filtering can dampen the output of the HW1 duty cycle. The filter can allow smoothing out of noises from Loop HW2 being heated, which in turn can allow dampening of the output of the HW1 duty cycle. As shown in FIG. 36, the controller can control the output of the HW2 and HW1 duty cycles sequentially, which can advantageously provide a simple allocation of the electrical power, voltage or current available. The PID control of the output of the HW2 duty cycle at the step 3630 and the PID control of the output of the HW1 duty cycle at the step 3680 can then work together to provide more stable controlling of the system. If the output of the HW1 duty cycle causes the patient-end temperature to become too hot or cold, the output of the HW2 duty cycle can compensate for over- or under-heating. In some embodiments, the output of the HW2 duty cycle can be negative to cause a quick change to the integral term of the PID control algorithm. The controller can bound the output of the HW2 duty cycle to 0 at the step 3635 when the output of the HW2 duty cycle is negative at the step 3630. The controller can also quickly drive down the output of the HW1 duty cycle in overheating conditions.

With continued reference to FIG. 36, the controller can determine a PID limit for the output of the HW1 duty cycle in the step 3640. Specifically, the controller can calculate a maximum output of the HW1 duty cycle at step 3650. Also as described above, the maximum output of the HW1 duty cycle can be capped to prevent the inspiratory limb from exceeding the surface temperature threshold so that it is unsafe to handle or use. In some embodiments, the maximum output of the HW1 duty cycle can be calculated using a function including the maximum capped output of the HW1 duty cycle and the bounded output of the HW2 duty cycle. In one embodiment, the determination of the output of the HW1 duty cycle can also include a term to compensate for differences in resistances of the two heater segments H1 and H2.

The controller can then determine if the maximum output of the HW1 duty cycle calculated from the step 3650 is negative. If the calculated maximum output of the HW1 duty cycle is negative, the controller can set the maximum output of the HW1 duty cycle at 0% in step 3660. If the calculated maximum output of the HW1 duty cycle is not negative, the controller can bound the output of the HW1 duty cycle to between (and including) 0% and a maximum output limit of the HW1 duty-cycle at step 3675. In some embodiments, the maximum output limit of the HW1 duty-cycle can be calculated by subtracting the output of the HW2 duty cycle from 100%.

With the PID limit calculated from the step 3640, the controller can perform a PID control of the output of the HW1 duty cycle at step 3680. The controller can output the HW1 duty cycle at step 3685. In one embodiment, the controller can use the PID control scheme of FIG. 37 to perform PID control of the output of the HW1 duty cycle. The controller can also reset 3605 the system after the PID control of the output of the HW1 duty cycle at the step 3680.

Figure 38:
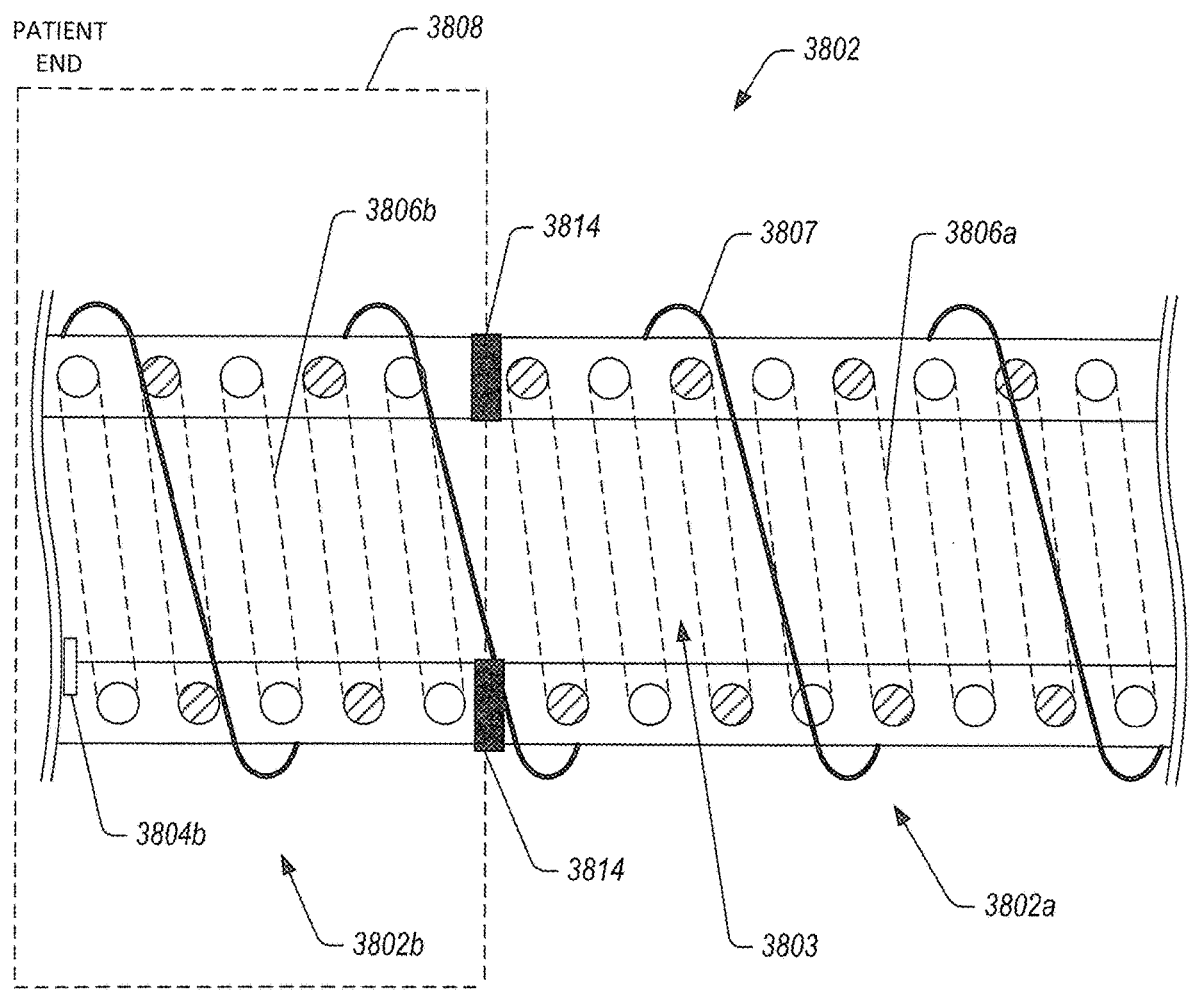
FIG. 38 illustrates another example embodiment of an inspiratory conduit for use with a humidification system.

FIG. 38 illustrates another example embodiment of an inspiratory conduit 3802 that can be controlled using the algorithms 3500, 3600. The inspiratory conduit 3802 of FIG. 35 can have the same features as the inspiratory limb 202 of FIG. 1 except as described below. Features of the inspiratory conduit 3802 can be incorporated into features of the inspiratory limb 202 and features of the inspiratory limb 202 can be incorporated into the inspiratory conduit 3802 of FIG. 38.

As shown in FIG. 38, the inspiratory conduit 3802 can be used in conjunction with an incubator 3808, as illustrated, or with another system where there are different temperatures along different segments of the inspiratory conduit 3802, such as in conjunction with a radiant warmer. The inspiratory conduit 3802 can comprise two segments. A first segment or inspiratory conduit 3802a can be outside the incubator 3808 and a second segment, or extension limb 3802b can be inside the incubator 3808. The first segment 3802a can include one or more first inner heater wires 3806a and the second segment 3802b can include one or more second inner heater wires 3806b. The first and second inner heater wires 3806a, 3806b can have the same features as the first and second heater wires 206a, 206b of FIG. 2. The inspiratory conduit 3802 can have a gas lumen 3803. The first and second inner heater wires 3806a, 3806b can be wrapped around the gas lumen 3803.

With continued reference to FIG. 38, the inspiratory conduit 3802 can include an intermediate connector 3814 having an intermediate circuit configured to couple elements of the first and second segments 3802a, 3802b of the inspiratory conduit 3802. In some embodiments, the intermediate connector 3814 can be configured to physically and electrically couple the first inner heater wire 3806a to the second inner heater wire 3806b. In addition, the inspiratory conduit 3802 can include one or more outer heater wires 3807. The outer heater wire 3807 can have the same or different features as the first and second inner heater wires 3806a, 3806b. In some embodiments, the outer heater wire 3807 can be wrapped around the inspiratory conduit 3802. In other embodiments, the outer heater wire 3807 can be located inside the gas lumen 3803. In the illustrated embodiment, the outer heater wire 3807 can be in a spiral configuration. However, a person of ordinary skill in the art will appreciate that the number or configuration of the outer heater wire 3807 is not limiting.

A controller (shown in FIG. 9) can be configured to control the first inner heater wire 3806a forming an inner control loop (Loop HW1). The controller can also be configured to control the outer heater wire 3807 forming an outer control loop (Loop HW2). FIGS. 25A-C illustrate the circuit diagram 2500 for the inspiratory conduit 3802, with H1 corresponding to the first inner heater wire 3806a and H2 corresponding to the outer heater wire 3807.

The inspiratory conduit 3802 can include one or more sensors and the controller can be configured to receive outputs of the one or more sensors. As shown in FIG. 38, a sensor 3804b can be positioned near a patient-end of the second segment 3802b so that a parameter derived from the sensor 3804b (a patient end temperature) can correspond to a parameter of the humidified gas delivered to the patient or user. In some embodiments, the sensor 3804b can function in the same manner as the sensors 204a, 204b described above. Outputs of the sensor 3804b can be sent to the controller as feedback for use in controlling power, voltage, and/or current delivered to the HW2 loop and the HW1 loop.

Additional Control System for Low Flow Conditions

Figure 39A:
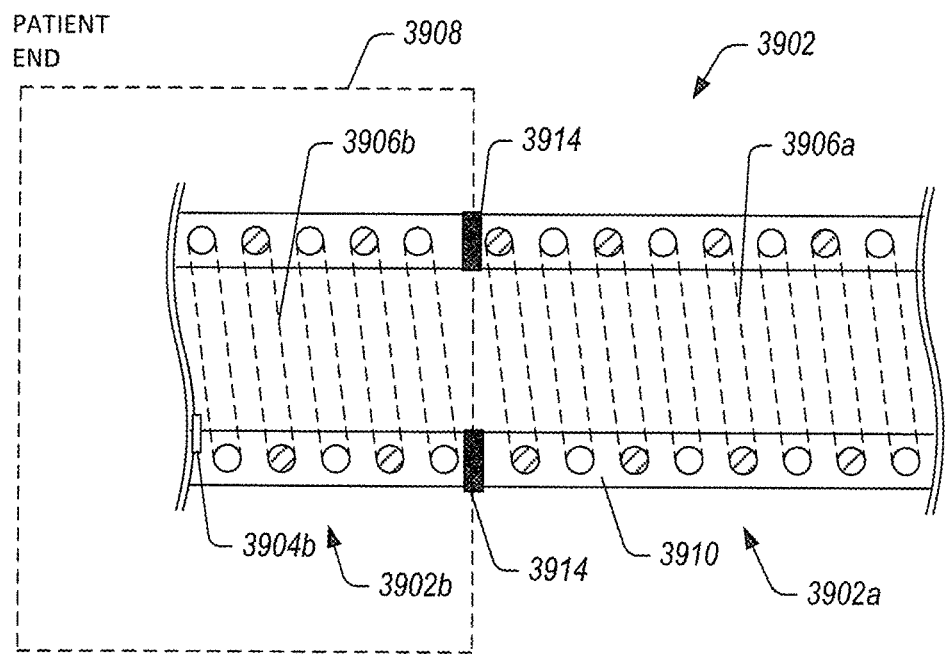
FIGS. 39A-B illustrate example configurations of an inspiratory limb and extension limb with respect to an incubator.

As described herein, the humidification system incorporating the circuit diagram 2500 of FIGS. 25A-C can be used with an incubator. A non-limiting example use with the incubator can be when the humidification system is operating in a neonatal therapy mode and connected to an infant patient inside the incubator. FIG. 39A illustrates an example intended configuration of the inspiratory conduit 3902 of the humidification system and the incubator 3908. The inspiratory limb 3902a with the heater wire segment H1 3906a can remain outside the incubator 3908 and be exposed to the ambient environment. The extension limb 3902b with the heater wire segment H2 3906b can be placed inside the incubator 3908 and be exposed typically to an elevated temperature compared to the ambient environment. In the intended configuration as shown in FIG. 39A, the intermediate connector 3914 can be at an interface between the incubator 3908 and the ambient environment.

However, the inspiratory conduit 3902 can be susceptible to movements. For example, the incubator 3908 may be moved when the inspiratory conduit 3902 is still connected to the patient inside the incubator 3908. In another example, the infant patient inside the incubator 3908 and connected to the humidification system can move around. As a result, a segment 3902c of the inspiratory limb 3902a can shift into the incubator 3908 by mistake, as indicated by the arrow in FIG. 39B. The segment 3902c can vary in length.

Figure 39B:
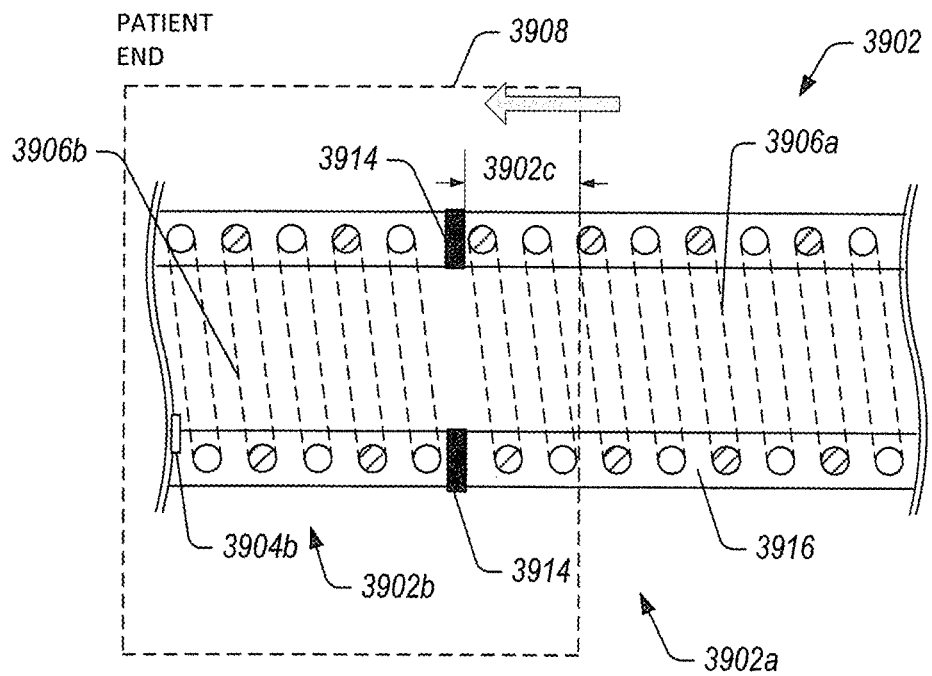

In both FIGS. 39A and 39B, the control algorithms 3500, 3600 of FIGS. 35-36 can cause Loop HW1 (including H1 3906a) to be heated up to the surface temperature threshold when the error is less than a predetermined threshold. The control algorithms 3500, 3600 can cause Loop HW2 (including H1 and H2 3906a, 3906b) to heat up to maintain the patient end set point when the error is greater than the predetermined threshold. The elevated temperature inside the incubator 3908 can reduce the need of driving up the HW2 duty cycle and can result in Loop HW1 having a high duty cycle to do the bulk of the heating. As the segment 3902c is part of a portion of Loop HW1, the segment 3902c can have a higher surface temperature than the extension limb 3902b, since in a primary control scheme HW1 is primarily heated.

However, when the humidification system is in low flow conditions and the segment 3902c is inside the incubator as shown in FIG. 39B, the surface temperature difference between the segment 3902c and the extension limb 3902b can be greater than when the segment 3902c is outside the incubator 3908 as shown in FIG. 39A. Low flow conditions can occur more often in the neonatal therapy mode because infants can be delivered gases at a lower flow rate than adults. One of ordinary skill in the art would appreciate that gases can be delivered at a low flow rate for other patients. In some embodiments, low flow can occur when the flow rate is below a predetermined value. In some embodiments, low flow can occur when the flow rate is below about 2.4 litres per minute (lpm) to about 5 lpm. In some embodiments, low flow can occur when the flow rate is below about 5 lpm. In some embodiments, low flow can occur when the flow rate is below about 3.5 lpm. In some embodiments, low flow can occur when the flow rate is below about 3 lpm. The definition of low flow conditions is not limiting. Low flow conditions can increase heat loss from the gases as it takes longer for the gases to travel through the inspiratory conduit 3902. It can also take longer for the patient end sensor 3904b to sense presence of the heated gases. The greater heat loss and/or the delay in detecting an increased patient end temperature can result in a large error between the measured patient end temperature and the patient end set point. The large error can in turn cause the controller to output a higher HW2 duty cycle than in normal or high flow conditions until the surface temperature threshold is reached on the inspiratory limb 3902a including the segment 3902c inside the incubator 3908.

One concern with the segment 3902c inside the incubator 3908 when the system is in low flow conditions can be overheating of the segment 3902c. Overheating can be due to a difficulty in heat dissipation inside the incubator 3908. Heat loss inside the incubator is proportional to a difference between the incubator temperature and the surface temperature of the segment 3902c. The elevated temperature inside the incubator results in a small difference between the incubator temperature and the surface temperature of the segment 3902c. Therefore, little amount of heat generated by the portion of Loop HW1 in the segment 3902c due to the higher HW1 duty cycle in low flow conditions can be transferred into an interior of the incubator. Instead, the heat can accumulate on the surface of the segment 3902c. Heat accumulation on the surface of the segment 3902c can be significant as the heater wires 3906a, 3906b are embedded in the wall 3916 of the inspiratory conduit 3902. The accumulated heat can cause the surface temperature of the segment 3902c inside the incubator to exceed the surface temperature threshold.

Overheating of the segment 3902c can be dangerous to the patient inside the incubator 3908 because the segment 3902c is now closer to the patient than when it is outside the incubator 3908. Overheating of the segment 3902c can also lead to noncompliance with regulations or temperature standards set by regulatory authorities, when the surface temperature threshold is mandated by those regulations or temperature standards. Accordingly, it is important in low flow conditions to prevent the segment 3902c from exceeding the surface temperature threshold when the segment 3902c shifts inside the incubator 3908.

Figure 40:
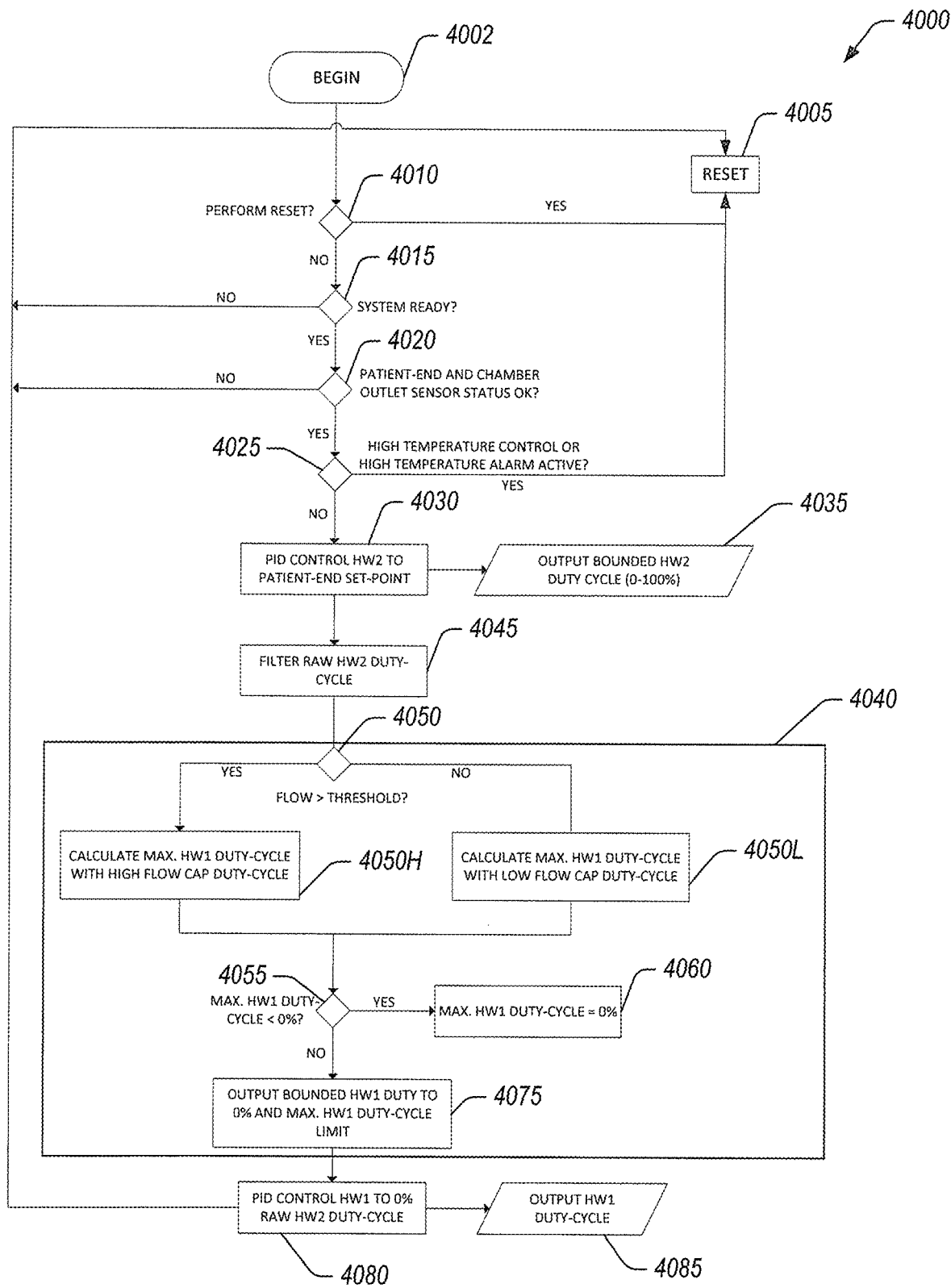
FIG. 40 illustrates a flow chart of another example control algorithm with a low flow control component.

FIG. 40 illustrates a control algorithm 4000 to address overheating of the segment 3902c in low flow conditions. The control algorithm 4000 can reduce the likelihood of the surface temperature of the segment 3902c exceeding the surface temperature threshold even if the segment 3902c is moved inside the incubator 3908. The control algorithm 4000 can have the same features as the control algorithm 3600 of FIG. 36 except as described below. Accordingly, features of the control algorithm 4000 of FIG. 40 can be incorporated into features of the control algorithm 3600 of FIG. 36 and features of the control algorithm 3600 of FIG. 36 can be incorporated into features of the control algorithm 4000 of FIG. 40. Based on the control algorithm 4000 the duty cycle or power supplied to either HW1 and/or HW2 is capped using a suitable cap or limit that prevents the surface temperature exceeding a predefined threshold. The duty cycle caps or limit are predefined within the control algorithm 4000. The duty cycle caps or limits may be defined as a percentage or a specific value. The limit or cap may be defined based on system parameters or based on a system model. In the example of FIG. 40, the cap or limit may be hardcoded or predefined. In an alternative configuration the system may include a temperature sensor located on a portion of the tube or on the intermediate connector. The system may include a first temperature sensor located on a portion of the first segment to determine the surface temperature of the first segment and a second temperature sensor located on the second segment to determine the surface temperature of the second segment. The control algorithm 4000 may be modified to determine a duty cycle cap or limit based on a measured surface temperature value.

As shown in FIG. 40, the controller of the humidification system, such as the controller 122 illustrated in FIG. 1, can determine the error between the measured patient end temperature and the patient end set point at step 4002 and perform a series of checks in steps 4010, 4015, 4020, 4025. The series of checks can ensure that all the sensors and alarms are working and the system is in an operational condition. These checks can be optional. A reset 4005 can be performed to clear the error integral and the outputs of both the HW1 and HW2 duty cycles if the controller detects any issues in any of the steps 4010, 4015, 4020, 4025.

With continued reference to FIG. 40, after determining that the patient end temperature is below the set point and after the series of optional checks, the controller can determine the output of the HW2 duty cycle needed to bring the system to the patient end set point temperature. The controller can implement a PID control scheme for the output of the HW2 duty cycle at step 4030. In the illustrated embodiment, the PID control step 4030 can be performed with a PID control scheme as described herein and illustrated in FIG. 37. Based on the PID control in the step 4030, the controller can output the HW2 duty cycle bounded between 0% and 100% at step 4035. In one non limiting example, the duty cycle of HW2 may be bounded at an upper limit of 70% i.e. 70% of the maximum power deliverable by the drive circuits. The 70% cap or limit is set to ensure that the surface temperature of the tube i.e. both sections of the tube does not exceed the surface temperature threshold.

The algorithm 4000 can also use the output of the HW2 duty cycle to control the output of the HW1 duty cycle after filtering the raw output of the HW2 duty cycle at step 4045 as describe above. The controller can determine a PID limit for the output of the HW1 duty cycle in the step 4040. In the illustrated embodiment, the control algorithm 4000 can have a flow rate control component including steps 4050, 4050H, 4050L. Specifically, the controller can first determine at the step 4050 if the flow rate of the system is higher than a predetermined threshold. In some embodiments, the flow rate can be measured using an integrated flow sensor that is disposed on the humidifier housing. In some embodiments, the flow sensor can be located at the outlet and/or at the inlet of the humidifier.

The controller can bifurcate the calculation of the maximum output of the HW1 duty cycle based on comparing the measured flow rate and the predetermined threshold. The maximum output of the HW1 duty cycle can be calculated using a function including either a high flow or low flow maximum capped output of the HW1 duty cycle, and the bounded output of the HW2 duty cycle. The low flow maximum capped output of the HW1 duty cycle ("low flow cap") can be less than the high flow maximum capped output of the HW1 duty cycle ("high flow cap"). If the measured flow rate is higher than the predetermined threshold, the controller can calculate the maximum output of the HW1 duty cycle from the high flow cap at the step 4050H. If the measured flow rate is at or below the predetermined threshold, the controller can calculate the maximum output of the HW1 duty cycle from the low flow cap at the step 4050L. In one embodiment, the determination of the output of the HW1 duty cycle can also include a term to compensate for differences in resistances of the two heater wire segments H1 and H2. In one non limiting example the low flow cap for the HW1 duty cycle is capped at 37% of the maximum available power output possible from the drive circuits.

In some embodiments, the low flow caps may not affect the output of the HW2 duty cycle. The output of the HW2 duty cycle can be as high as 100% despite the low flow cap. In one embodiment, if the output of the HW2 duty cycle is between 0% and the low flow cap, the output of the HW1 duty cycle can be a difference between the low flow cap and the output of the HW2 duty cycle; if the output of the HW2 duty cycle is at or higher than the low flow cap, the output of the HW1 duty cycle can be 0%. The low flow cap may not need to affect the output of the HW2 duty cycle because the output of the HW2 duty cycle can be controlled by the patient end temperature, which is much lower than the surface temperature threshold. Further, the elevated temperature inside the incubator 3908 can reduce the need for a very high HW2 duty cycle to maintain the patient end temperature.

In some embodiments, the amount of condensate generated within the inspiratory conduit can be kept low because a smaller amount of gases flow through the inspiratory conduit at the low flow rate, even though the low flow cap may result in less heat being available to minimize condensate. Further, better insulation can be provided for the inspiratory limb to compensate for less heat being generated because of the low flow cap.

The bifurcation at the steps 4050H and 4050L can ensure that Loop HW1 is still heated up to the surface temperature threshold in high flow conditions, but is heated to a lesser extent as determined by the low flow cap in low flow conditions. In a non limiting example the loop HW1 is heated up to a surface temperature threshold based on the duty cycle cap applied to the output provided to HW1. The bifurcation is advantageous because the shift of the segment 3902c inside the incubator 3908 may not lead to overheating of the segment 3902c in high flow conditions. However, the low flow cap is needed to reduce the maximum HW1 duty cycle in low flow conditions so that the surface temperature of the segment 3902c does not exceed the surface temperature threshold even if the segment 3902c moves inside the incubator 3908.

After calculating the maximum output of the HW1 duty cycle from either the steps 4050H or 4050L, the controller can determine if the calculated maximum output of the HW1 duty cycle is negative at step 4055. If the calculated maximum output of the HW1 duty cycle is negative, the controller can set the maximum output of the HW1 duty cycle at 0% in step 4060. If the calculated maximum output of the HW1 duty cycle is not negative, the controller can bound the output of the HW1 duty cycle to between (and including) 0% and a maximum output limit of the HW1 duty cycle at step 4075. In some embodiments, the maximum output limit of the HW1 duty cycle can be calculated by subtracting the output of the HW2 duty cycle from 100%.

With the PID limit calculated from the step 4040, the controller can perform a PID control of the output of the HW1 duty cycle at step 4080. The controller can then output the HW1 duty cycle at step 4085. In one embodiment, the controller can use the PID control scheme of FIG. 37 to perform the PID control of the output of the HW1 duty cycle. The controller can reset 4005 the system after the PID control of the output of the HW1 duty cycle at the step 4080.

Figure 41:
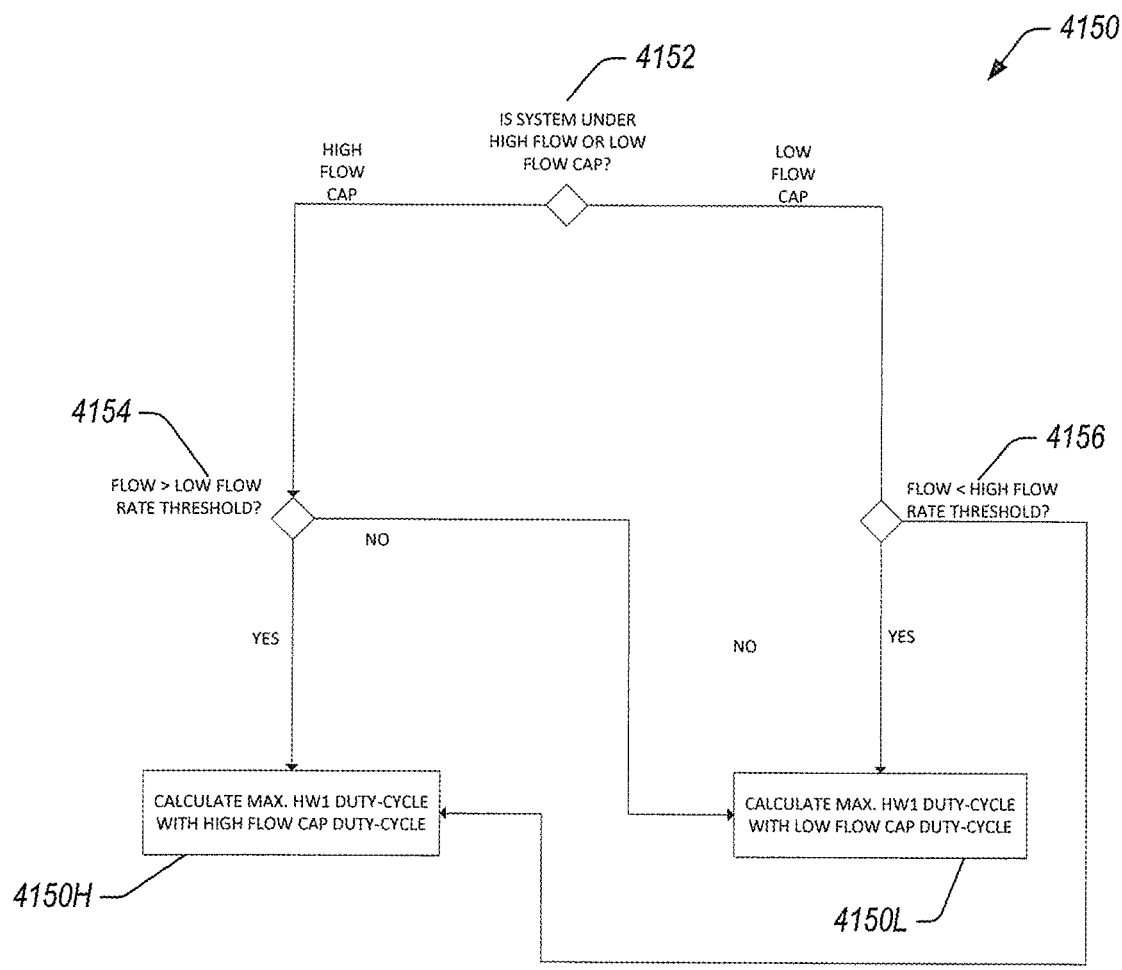
FIG. 41 illustrates a flow chart of another example low flow control component.

Turning to FIG. 41, another example flow rate control component 4150 can be implemented in a control algorithm described herein. The flow rate control component 4150 can be implemented in the control algorithm 3500 as part of the step 3525, or in the control algorithm 3600 as part of the step 3650. The flow rate control component 4150 can also replace the steps 4045, 4050H, 4050L of the control algorithm 4000.

In the flow rate control component 4150, the controller can utilize different threshold values to determine whether the maximum output of the HW1 duty cycle should be calculated using the high flow cap or the low flow cap. The controller can first determine if the system is currently under the high flow cap or the low flow cap for calculating the maximum output of the HW1 duty cycle at step 4152.

If the system is currently under the high flow cap, the controller can determine if the measured flow rate is higher than a predetermined low flow rate threshold at step 4154. If the measured flow rate is higher than the predetermined low flow rate threshold, the controller can continue using the high flow cap to calculate the maximum output of the HW1 duty cycle at step 4150H. If the measured flow rate falls to or below the predetermined low flow threshold, the controller can switch to step 4150L to calculate the maximum output of the HW1 duty cycle using the low flow cap.

If the system is currently under the low flow cap, the controller can determine if the measured flow rate is lower than a predetermined high flow rate threshold. If the measured flow rate is lower than the predetermined high flow rate threshold, the controller can continue using the low flow cap to calculate the maximum output of the HW1 duty cycle at the step 4150L. If the measured flow rate reaches or exceeds the predetermined high flow threshold, the controller can switch to the step 4150H to calculate the maximum output of the HW1 duty cycle using the high flow cap.

In some embodiments, the high flow rate threshold can be higher than the low flow rate threshold. The low flow and high flow rate thresholds can be determined experimentally. In some embodiments, the thresholds can be device or sensor specific. In some embodiments, the low flow rate threshold can be about 2.4 lpm to about 5 lpm. In some embodiments, the low flow rate threshold can be about 3.5 lpm. In some embodiments, the low flow rate threshold can be about 5 lpm. In some embodiments, the high flow rate threshold can be about 6.5 lpm. Switching the duty cycle cap at a different flow rate threshold when the system is moving from low flow conditions to high flow conditions can reduce oscillations at the low flow/high flow boundary.

Additional Embodiment of the Midpoint/Intermediate PCB Design

Figure 42:
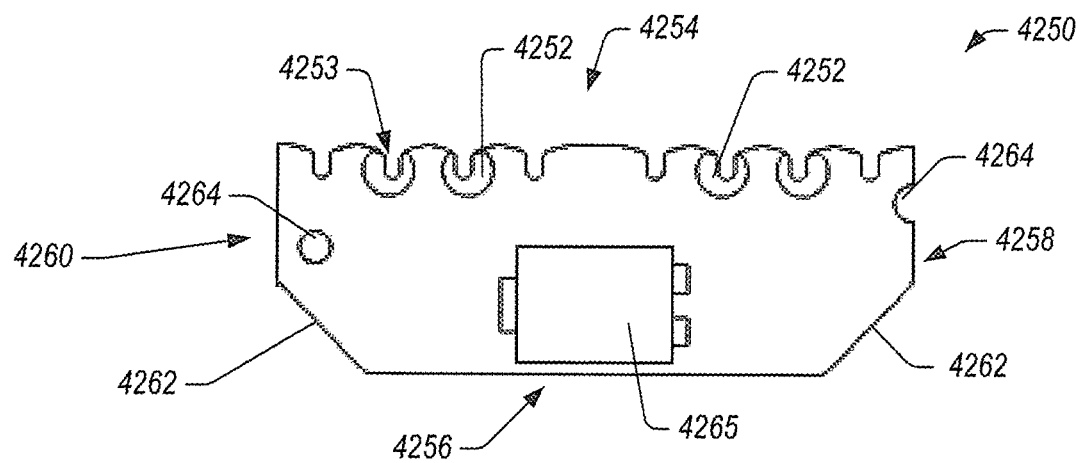
FIG. 42 illustrates another example PCB of an intermediate connector.

FIG. 42 illustrates another example intermediate PCB 4250 of the intermediate connector 214, 3514. Detailed descriptions of how the intermediate PCB can be assembled within an inspiratory limb are described above in connection with FIGS. 32A-C. The intermediate PCB 4250 can include a diode 4265. The diode 4265 can allow control of HW1 or HW2 as shown in FIGS. 25A-C depending on the polarity of the supplied voltage. Unlike the PCB 250 of FIGS. 14A-B, the intermediate PCB 4250 can have no thermistor. Having no thermistor can advantageously allow the controller to function more efficiently.

As shown in FIG. 42, the intermediate PCB 4250 can have a generally rectangular shape with two long sides 4254, 4256 and two short sides 4258, 4260. The diode 4265 can be located near one of the long sides 4256 and near a midpoint of the long side 4256. The intermediate PCB 4250 can include connection pads 4252 for the heater wires and/or sensor connections. The connection pads 4252 can be configured to be on a same side of the intermediate PCB 4250 and on both front (shown in FIG. 42) and back (not shown) sides of slots 4253. As shown in FIG. 42, a front side of the intermediate PCB 4250 can have two sets of four connection pads 4252 along the long side 4254, with two connection pads on each side of the diode 4265. The intermediate PCB 4250 can further have locating slots 4264 on each of the short sides 4258, 4260. The locating slots can aid in aligning the PCB during moulding. Having two locating slots can reduce swivel or movement of the PCB during moulding. The slots, the shape of the intermediate PCB 4250 and the arrangements of the connection pads 4252 can advantageously allow easier fabrication and assembly of the intermediate PCB 4250. The shape of the intermediate PCB 4250 and the arrangements of the connection pads 4252 can also reduce likelihood of short circuit and noise. The short sides 4258, 4260 of the intermediate PCB 4250 can each have a diagonal edge 4262 where the short sides 4258, 4260 meet the long side 4256. The diagonal edges 4262 can help to maintain a good flow profile of the gases. In addition, the intermediate PCB 4250 does not extend through the entire diameter of the inspiratory limb, but can extend approximately ⅓ of the diameter because of reduced lengths of the short sides. The short sides 4258, 4260 can advantageously reduce resistance to flow (described above) within the inspiratory limb.

Additional Embodiment of the Patient-End Connector PCB Design

Figure 43:
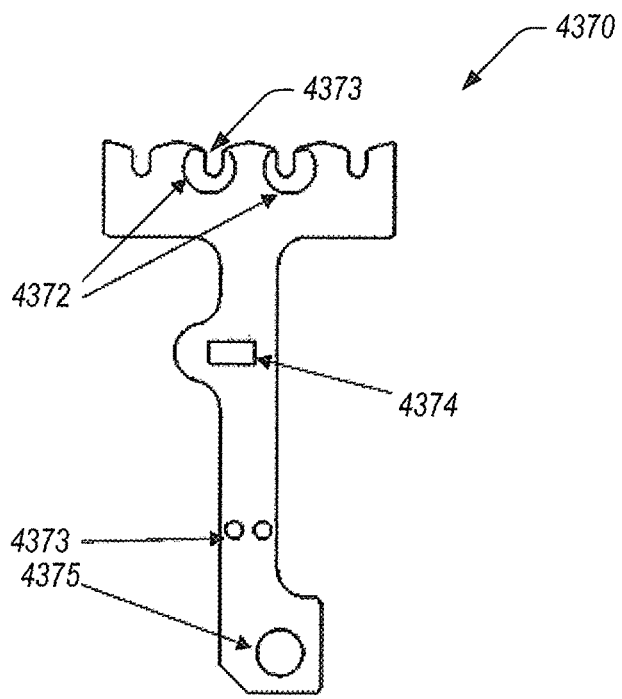
FIG. 43 illustrates another example PCB for a patient-end connector.

FIG. 43 illustrates another example patient-end PCB 4370 of the patient-end connector. The patient-end PCB 4370 can function in the same manner as the patient-end PCB 270 of FIG. 15A. However, the patient-end PCB 4370 can be longer than the patient-end PCB 270 of FIG. 15A for easier moulding. The patient-end PCB 4370 can also have locating slots so that the PCB 4370 can only be mounted onto an assembly tool in one orientation for easier assembly. As show in FIG. 43, the patient-end PCB 4370 can have a plurality of upper locating slots 4373 and a lower locating slot 4375. The locating slots can aid in aligning the PCB during moulding. A portion of the PCB 4370 below the upper locating slots 4373 or below the lower locating slot 4375 can be snapped off once the PCB 4370 is assembled.

The patient-end PCB 4370 can also include connection pads 4372 for the heater wires and/or sensor connections. The connection pads 4372 can be configured to be on either end of the patient-end PCB 4370. In the illustrated embodiment, the patient-end PCB 4370 can have two connection pads 4372 on a front side of slots 4373. Although not shown in FIG. 43, the patient-end PCB 4370 can also have two connection pads 4372 on a back side of the slots 4373. Having connection pads 4372 on either end of the PCB 4370 can advantageously prevent or reduce water ingress. The patient-end PCB 4370 can also have a thermistor 4374.

Unlike the patient-end PCB 270 of FIG. 15A, the thermistor 4374 on the patient-end PCB 4370 can be located near a center of the patient-end PCB 4370. In some embodiments, the patient-end PCB 4370 can have tracks that go from the connection pads 4372 to the thermistor 4374 in a substantially straight line. One of ordinary skill in the art would appreciate that any suitable arrangement of the tracks can be disposed on the patient-end PCB 4370. The position of the thermistor 4374 can also allow easier fabrication of the PCB 4370.

In some embodiments, the lower locating slots 4375 may not be present. In other embodiments, the patient-end PCB 4370 may not include portions below the upper locating slots 4373. In one embodiment, the patient-end PCB 4370 may not be moulded and may terminate below the upper locating slots 4373.

Embodiment of Chamber-End PCB Design

Figure 44A:
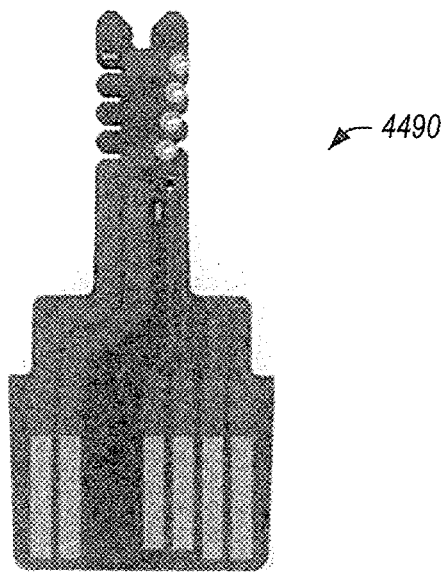
FIGS. 44A-B illustrate an example PCB of a chamber-end connector.
Figure 44B:
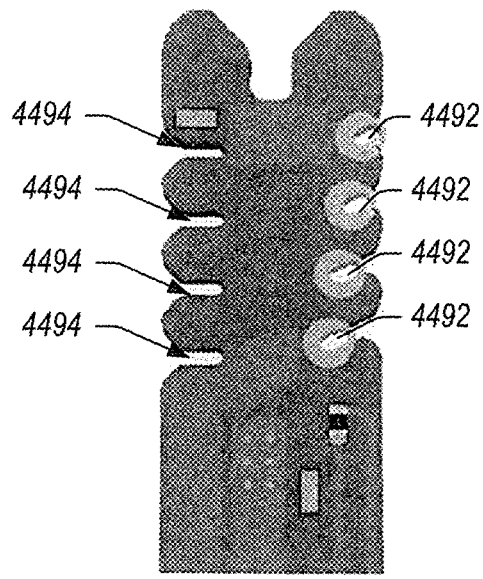

FIGS. 44A-B illustrates an example chamber-end PCB 4490 for connecting to a complementary connector on a cartridge (as shown in FIG. 8A) that can include electrical connection pads. Detailed descriptions of a shape and function of the chamber-end PCB are described in U.S. patent application Ser. No. 15/105,531, entitled "HUMIDIFICATION SYSTEM CONNECTIONS," filed Jun. 16, 2016, and U.S. patent application Ser. No. 15/021,673, entitled "CONNECTIONS FOR HUMIDIFICATION SYSTEM," filed Mar. 11, 2016, each of which is incorporated herein by reference in its entirety. As shown in FIG. 44B, which illustrates a detailed view of an upper portion of the chamber-end PCB 4490, the chamber-end PCB 4490 can have connection pads 4492 that are on a same side. In a non-limiting example as shown in FIGS. 44A-B, the chamber-end PCB 4490 can have four connection pads 4492 located on a right hand side of the PCB 4490. In other embodiments, the connection pads can be all located on the left hand side or any other suitable side of the PCB 4490. The PCB 4490 is plasma treated to reduce water ingress.

As more clearly shown in FIG. 44B, the connection pads 4492 can be angled. The chamber-end PCB 4490 can also have deep slots 4494 that are deeper than described in U.S. patent application Ser. Nos. 15/021,673 and 15/105,531, referenced above. The deep slots 4494 and angled connection pads 4492 can advantageously allow correct and even wire tension and to reduce risks of the wires moving about. The chamber-end PCB 4490 can also accommodate a flattened tag coming up at an angle and being positioned straight onto the chamber-end PCB 4490.

Example Embodiments

The following is a numbered list of example embodiments that are within the scope of this disclosure. The example embodiments that are listed should in no way be interpreted as limiting the scope of the embodiments. Various features of the example embodiments that are listed can be removed, added, or combined to form additional embodiments, which are part of this disclosure:

Embodiment 1. A medical tube comprising:
 a first segment of the medical tube comprising:
  a first structure forming a conduit configured to transport a humidified gas; and
  a first heater wire circuit;
 a second segment of the medical tube comprising:
  a second structure forming a conduit configured to transport the humidified gas; and
  a second heater wire circuit; and
 an intermediate connector comprising a connection circuit that electrically couples the first heater wire circuit to the second heater wire circuit, the intermediate connector coupled to a patient end of the first segment of the medical tube and a chamber end of the second segment of the medical tube to form a single conduit for the humidified gas,
 wherein at least a portion of the intermediate connector is covered by a portion of the first segment of the medical tube and/or a portion of the second segment of the medical tube such that the intermediate connector is internal to the medical tube,
 wherein, in a first mode, electrical power passes through the connection circuit to provide power to the first heater wire circuit without providing power to the second heater wire circuit, and in a second mode, electrical power passes through the connection circuit to provide power to both the first heater wire circuit and the second heater wire circuit.

Embodiment 2. The medical tube of embodiment 1, wherein the connection circuit comprises a diode.

Embodiment 3. The medical tube of any of embodiments 1 to 2, further comprising a first sensor positioned at the patient end of the first segment.

Embodiment 4. The medical tube of embodiment 3, wherein the first sensor is one of a temperature sensor or a humidity sensor.

Embodiment 5. The medical tube of any of embodiments 1 to 4, further comprising a second sensor positioned at a patient end of the second segment of the medical tube.

Embodiment 6. The medical tube of embodiment 5, wherein the second sensor is one of a temperature sensor or a humidity sensor.

Embodiment 7. The medical tube of any of embodiments 1 to 6, wherein the first structure comprises an elongate tube comprising:
 a first elongate member comprising a hollow body spirally wound to form at least in part the conduit having a longitudinal axis, a lumen extending along the longitudinal axis, and a hollow wall surrounding the lumen;
 a second elongate member spirally wound and joined between adjacent turns of the first elongate member, the second elongate member forming at least a portion of the lumen of the elongate tube.

Embodiment 8. The medical tube of embodiment 7, wherein the first elongate member forms in longitudinal cross-section a plurality of bubbles with a flattened surface at the lumen.

Embodiment 9. The medical tube of embodiment 8, wherein adjacent bubbles are separated by a gap above the second elongate member.

Embodiment 10. The medical tube of embodiment 8, wherein adjacent bubbles are not directly connected to each other.

Embodiment 11. The medical tube of embodiment 8, wherein the plurality of bubbles have perforations.

Embodiment 12. A respiratory humidification system comprising:
 an inspiratory limb comprising a first segment of the inspiratory limb having a first heater wire circuit, a second segment of the inspiratory limb having a second heater wire circuit, an intermediate connector having a connector circuit configured to electrically couple the first heater wire circuit to the second heater wire circuit, a first sensor positioned at a patient end of the first segment, and a second sensor positioned at a patient end of the second segment; and a controller;
wherein the controller is adapted to selectively switch between a first mode and a second mode wherein in the first mode the controller provides electrical power to the first heater wire circuit through the connector circuit and in a second mode the controller provides electrical power to the first and second heater wire circuits.

Embodiment 13. The system of embodiment 12, wherein the switching is done based on input from one or both sensors.

Embodiment 14. The system of embodiment 13, wherein the input from one or both sensors includes one or more of temperature, flow, humidity, and power.

Embodiment 15. The system of any of embodiments 12 to 14, wherein the first and second modes are defined by a direction of current provided by a power source.

Embodiment 16. The system of any of embodiments 12 to 15, wherein the controller is adapted to selectively switch between a first sensor reading mode and a second sensor reading mode wherein in the first sensor reading mode the controller reads a signal from the second sensor and in the second sensor reading mode the controller reads a signal from both the first sensor and the second sensor.

Embodiment 17. The system of any of embodiments 12 to 16, wherein the first sensor and the second sensor are temperature sensors.

Embodiment 18. A dual limb circuit comprising:
an inspiratory limb comprising a first segment of the inspiratory limb having a first heater wire circuit, a second segment of the inspiratory limb having a second heater wire circuit, an intermediate connector having a connector circuit configured to electrically couple the first heater wire circuit to the second heater wire circuit, a first sensor positioned at a patient end of the first segment, and a second sensor positioned at a patient end of the second segment;
an expiratory limb;
an interface connected to the inspiratory limb and the expiratory limb; and
a controller;
wherein the controller is adapted to selectively switch between a first mode and a second mode wherein in the first mode the controller provides electrical power to the first heater wire circuit through the connector circuit and in a second mode the controller provides electrical power to the first and second heater wire circuits.

Embodiment 19. The dual limb circuit of embodiment 18, wherein the expiratory limb comprises an expiratory heater wire circuit.

Embodiment 20. The dual limb circuit of embodiment 19, wherein the expiratory limb is heated using the expiratory heater wire circuit.

Embodiment 21. The dual limb circuit of embodiment 2, wherein the expiratory heater wire circuit is powered in parallel with the first heater wire circuit in the first segment of the inspiratory limb.

Embodiment 22. The dual limb circuit of embodiment 21, wherein the expiratory heater wire circuit can be configured to be powered in only the first mode, in only the second mode, or in both the first mode and in the second mode.

Embodiment 23. The dual limb circuit of any of embodiments 18 to 22, wherein the interface is connected via a wye-piece.

Embodiment 24. A segmented inspiratory limb configured to be heated along at least two segments, each segment of the inspiratory limb comprising:
a first elongate member comprising a hollow body spirally wound to form at least in part an elongate tube having a longitudinal axis, a lumen extending along the longitudinal axis, and a hollow wall surrounding the lumen;
a second elongate member spirally wound and joined between adjacent turns of the first elongate member, the second elongate member forming at least a portion of the lumen of the elongate tube.

Embodiment 25. A medical tube comprising:
two segments, each segment comprising:
an elongate hollow body spirally wound to form an elongate tube having a longitudinal axis, a lumen extending along the longitudinal axis, and a hollow wall surrounding the lumen, wherein the elongate hollow body has in transverse cross-section a wall defining at least a portion of the hollow body;
a reinforcement portion extending along a length of the elongate hollow body being spirally positioned between adjacent turns of the elongate hollow body, wherein the reinforcement portion forms a portion of the lumen of the elongate tube;
one or more conductive filaments embedded or encapsulated within the reinforcement portion;
wherein the reinforcement portion is relatively thicker or more rigid than the wall of the elongate hollow body;
a segment connector attached to the first segment, the segment connector comprising:
connection pads configured to electrically coupled the conductive filaments from the first segment to the conductive filaments from the second segment when the first segment is physically coupled to the second segment; and
a power diode electrically coupled to the conductive filaments of the first segment,
wherein the power diode allows electrical power to be delivered to the conductive filaments of the first segment and prevents electrical power from being delivered to the conductive filaments of the second segment when provided with an electrical signal of a first polarity, and
wherein the power diode allows the conductive filaments of the first segment and the conductive filaments of the second segment to be provided with electrical power when provided with an electrical signal of a second polarity.

Embodiment 26. A connector comprising:
a first heater wire incoming connection configured to be electrically coupled to a first incoming heater wire;
a second heater wire incoming connection configured to be electrically coupled to a second incoming heater wire;
a first heater wire outgoing connection configured to be electrically coupled to a first outgoing heater wire and electrically coupled to the first heater wire incoming connection;
a second heater wire outgoing connection configured to be electrically coupled to a second outgoing heater wire and electrically coupled to the second heater wire incoming connection;
a first signal wire incoming connection configured to be electrically coupled to a first incoming signal wire;
a second signal wire incoming connection configured to be electrically coupled to a second incoming signal wire;

a first signal wire outgoing connection configured to be electrically coupled to a first outgoing signal wire and electrically coupled to the first signal wire incoming connection;

a second signal wire outgoing connection configured to be electrically coupled to a second incoming signal wire and electrically coupled to the second signal wire incoming connection;

a power diode electrically coupled to the first heater wire incoming connection and the second heater wire incoming connection, the power diode configured to allow current to flow from the second incoming heater wire to the first incoming heater wire and to prevent current to flow from the first incoming heater wire to the second incoming heater wire;

a sensor electrically coupled to the first signal wire incoming connection; and a signal diode electrically coupled to the sensor and the second signal wire incoming connection, the signal diode configured to allow current to flow from the second incoming signal wire through the sensor to the first incoming signal wire and to prevent current to flow from the first incoming signal wire through the sensor to the second incoming signal wire.

Embodiment 27. A respiratory humidification system comprising:

an inspiratory limb including a first segment with a first heater wire, a second segment with a second heater wire, and a sensor positioned at a patient end of the second segment for measuring a patient end parameter, wherein the first and second heater wires are electrically coupled, the first heater wire forming a first heater circuit and the first and second wire forming a second heater circuit; and a hardware controller, wherein the hardware controller is configured to receive an output of the sensor, the hardware controller further configured to provide electrical power to the first heater circuit when a difference between the output of the sensor and a patient end parameter set point is below a predetermined threshold and to provide electrical power to the second heater circuit when the difference between the output of the sensor and the patient end parameter set point is at or above the predetermined threshold, wherein when the hardware controller provides electrical power to the first heater circuit, the hardware controller is configured to provide a maximum power to the first heater circuit.

Embodiment 28. A respiratory humidification system comprising:

an inspiratory limb including a first segment with a first heater wire, a second segment with a second heater wire, and a sensor positioned at a patient end of the second segment for measuring a patient end parameter, wherein the first and second heater wires are electrically coupled, the first heater wire forming a first heater circuit and the first and second wire forming a second heater circuit, the first and second heater wires configured to heat respiratory gases passing through the inspiratory limb;

wherein the first and second heater wires are configured to be in communication with a hardware processor configured to execute software instructions which cause the processor to control the first and second heater circuits, wherein, when a difference between an output of the sensor and a patient end parameter set point is below a predetermined threshold, the processor is configured to heat the respiratory gases using the first heater circuit until a maximum temperature is reached in the first heater wire, and when the difference between the output of the sensor and the patient end parameter set point is at or above the predetermined threshold, the processor is configured to heat the respiratory gases using the second heater circuit.

Embodiment 29. A respiratory humidification system comprising:

a hardware processor configured to be in communication with a first heater wire circuit in a first segment of an inspiratory limb and a second heater wire circuit in a second segment of the inspiratory limb, the hardware processor also configured to be in communication with a connector circuit in an intermediate connector configured to electrically couple the first heater wire circuit to the second heater wire circuit, the hardware processor further configured to be in communication with a first sensor positioned at a patient end of the first segment and a second sensor positioned at a patient end of the second segment, wherein the hardware processor is configured to execute software instructions which cause the processor to selectively switch between a first mode and a second mode wherein in the first mode the processor provides electrical power to the first heater wire circuit through the connector circuit and in a second mode the processor provides electrical power to the first and second heater wire circuits.

Embodiment 30. A respiratory humidification system comprising:

an inspiratory limb comprising a first segment of the inspiratory limb having a first heater wire circuit, a second segment of the inspiratory limb having a second heater wire circuit, an intermediate connector having a connector circuit configured to electrically couple the first heater wire circuit to the second heater wire circuit, a first sensor positioned at a patient end of the first segment, and a second sensor positioned at a patient end of the second segment, wherein the first and second heater wires circuits, the connector circuit, and the first and second sensors are each configured to be in communication with a hardware controller, the hardware controller adapted to selectively switch between a first mode and a second mode wherein in the first mode the hardware controller provides electrical power to the first heater wire circuit through the connector circuit and in a second mode the hardware controller provides electrical power to the first and second heater wire circuits.

Embodiment 31. A dual limb circuit comprising:

an inspiratory limb comprising a first segment of the inspiratory limb having a first heater wire circuit, a second segment of the inspiratory limb having a second heater wire circuit, an intermediate connector having a connector circuit configured to electrically couple the first heater wire circuit to the second heater wire circuit, a first sensor positioned at a patient end of the first segment, and a second sensor positioned at a patient end of the second segment;

an expiratory limb; and an interface connected to the inspiratory limb and the expiratory limb, wherein the first and second heater wires circuits, the connector circuit, and the first and second sensors are each configured to be in communication with a hardware controller, the hardware controller adapted to selectively switch between a first mode and a second mode wherein in the first mode the hardware controller provides electrical power to the first heater wire circuit through the connector circuit and in a second mode the hardware controller provides electrical power to the first and second heater wire circuits.

Embodiment 32. A respiratory humidification system comprising:
- a heater circuit comprising a first heater, a second heater, a first pair of switches, and a second pair of switches, and a power source,
- wherein the heater circuit is configured to be in communication with a hardware control module, the hardware control module adapted to control flow of electrical current from the power source to the first heater by selectively opening and closing the first pair of switches and to control flow of electrical current from the power source to the second heater by selectively opening and closing the second pair of switches,
- wherein the first pair of switches and the second pair of switches can be selectively opened and closed independent of one another, thereby providing independent control of the first and second heaters.

Embodiment 33. A respiratory humidification system comprising:
- a hardware processor configured to be in communication with a heater circuit comprising a first heater, a second heater, a first pair of switches, and a second pair of switches, and a power source,
- wherein the hardware processor is configured to execute software instructions which cause the processor to control flow of electrical current from the power source to the first heater by selectively opening and closing the first pair of switches and to control flow of electrical current from the power source to the second heater by selectively opening and closing the second pair of switches,
- wherein the first pair of switches and the second pair of switches can be selectively opened and closed independent of one another, thereby providing independent control of the first and second heaters.

Embodiment 34. A respiratory humidification system comprising:
- a heater circuit comprising a first pair of switches, a second pair of switches, a power source, a main relay, and a mode relay,
- wherein the heater circuit is configured to be in communication with a logic module and a control module,
- wherein the control module is adapted to provide control signals to the logic module to control flow of electrical current from the power source to the mode relay by selectively opening and closing the first and second pair of switches,
- wherein the control module is adapted to provide a mode signal to the logic module, the mode signal comprising a first mode signal and a second mode signal,
- wherein the first pair of switches and the second pair of switches can be selectively opened and closed independent of one another.

Embodiment 35. A respiratory humidification system comprising:
- a heater circuit comprising a first pair of switches, a second pair of switches, a power source, a main relay, and a heater module,
- wherein the heater circuit is configured to be in communication with a logic module and a control module,
- wherein the control module is adapted to provide control signals to the logic module to control flow of electrical current from the power source to the heater module by selectively opening and closing the first and second pair of switches,
- wherein the control module is adapted to provide a mode signal to the logic module, the mode signal comprising a first mode signal and a second mode signal,
- wherein the first pair of switches and the second pair of switches can be selectively opened and closed independent of one another.

Embodiment 36. The respiratory humidification system as per any one of embodiments 32 to 36 further comprising a flow sensor in a flow path of the system and configured to measure a flow rate of the gases, wherein the maximum power provided to the first heater circuit has first and second maximum values, the first maximum value higher than the second maximum value, and wherein the maximum power is the first maximum value when the measured flow rate is higher than a flow rate threshold and a second maximum value when the measured flow rate is below the flow rate threshold.

Embodiment 37. The respiratory humidification system as per any one of embodiments 32 to 36, further comprising a flow sensor in a flow path of the system and configured to measure a flow rate of the gases, wherein the maximum power provided to the first heater circuit has first and second maximum values, the first maximum value higher than the second maximum value, wherein when the first maximum power is being provided to the first heater circuit and the measured flow rate decreases to a high flow to low flow threshold, the maximum power provided to the first heater circuit switches to the second maximum power, and when the second maximum power is being provided to the first heater circuit and the flow rate increases to a low flow to high flow threshold, the maximum power provided to the first heater circuit switches to the first maximum power, the high flow to low flow threshold being lower than the low flow to high flow threshold.

Examples of respiratory humidification systems with dual zone heating control and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate principles related to providing dual zone heating control, and details regarding divisions of modules or systems have been provided for ease of description rather than attempting to delineate separate physical embodiments. The examples and figures are intended to illustrate and not to limit the scope of the present disclosure. For example, the principles herein may be applied to a respiratory humidifier as well as other types of humidification systems, including surgical humidifiers. The principles herein may be applied in respiratory applications as well as in other scenarios where a temperature of gases is to be controlled along multiple segments subject to varying ambient temperatures.

As used herein, the term "processor" refers broadly to any suitable device, logical block, module, circuit, or combination of elements for executing instructions. For example, the controller 122 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module 504 can be a software-implemented function block which does not utilize any additional and/or specialized hardware elements. Controller 122 can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller 122. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within 10%, within 5%, or within +1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A respiratory humidification system comprising:
an inspiratory limb including a first segment with a first heater wire, a second segment with a second heater wire, and a temperature sensor positioned at a patient end of the second segment for measuring a patient end parameter, wherein the first and second heater wires are electrically coupled, the first heater wire forming a first heater circuit and the first and second heater wires forming a second heater circuit, the first and second heater wires configured to heat respiratory gases passing through the inspiratory limb; and
a flow sensor in a flow path of the system and configured to measure a flow rate of the respiratory gases;
wherein the first and second heater wires and the temperature and flow sensors are configured to be in electrical communication with a hardware processor configured to execute software instructions which cause the processor to control the first and second heater circuits, wherein, when a difference between an output of the temperature sensor and a patient end parameter set point is below a predetermined error threshold, the processor is configured to heat the respiratory gases using the first heater circuit until a maximum temperature is reached in the first heater wire, and when the difference between the output of the temperature sensor and the patient end parameter set point is at or above the predetermined error threshold, the processor is configured to heat the respiratory gases using the second heater circuit, and
wherein a maximum power provided to the first heater circuit is a first maximum value or a second maximum value based on the flow rate, the first maximum value higher than the second maximum value.

2. The respiratory humidification system of claim 1, wherein the maximum power is the first maximum value when the measured flow rate is higher than a flow rate threshold, and the maximum power is the second maximum value when the measured flow rate is below the flow rate threshold.

3. The respiratory humidification system of claim 2, wherein the flow rate threshold is between about 2.4 lpm and about 5 lpm.

4. The respiratory humidification system of claim 2, wherein the flow rate threshold is about 3.5 lpm.

5. The respiratory humidification system of claim 1, wherein when the first maximum power is being provided to the first heater circuit and the measured flow rate decreases to a high flow to low flow threshold, the maximum power provided to the first heater circuit switches to the second maximum power, and when the second maximum power is being provided to the first heater circuit and the flow rate increases to a low flow to high flow threshold, the maximum power provided to the first heater circuit switches to the first maximum power, the high flow to low flow threshold being lower than the low flow to high flow threshold.

6. The respiratory humidification system of claim 5, wherein the high flow to low flow threshold is between about 2.4 lpm and about 5 lpm.

7. The respiratory humidification system of claim 5, wherein the low flow to high flow threshold is about 6.5 lpm.

8. The respiratory humidification system of claim 5, wherein a portion of the first segment of the inspiratory limb that is adjacent to the second segment is exposed to the same ambient environment as the second segment.

9. The respiratory humidification system of claim 8, wherein the portion of the first segment and the second segment are inside an incubator and a remaining portion of the first segment is outside the incubator.

10. A respiratory humidification system comprising:
an inspiratory limb including a first segment with a first heater wire, a second segment with a second heater wire, and a temperature sensor positioned at a patient end of the second segment for measuring a patient end parameter, wherein the first and second heater wires are electrically coupled, the first heater wire forming a first heater circuit and the first and second heater wires forming a second heater circuit, the first and second heater wires configured to heat respiratory gases passing through the inspiratory limb; and
a flow sensor in a flow path of the system and configured to measure a flow rate of the respiratory gases;
a controller in electrical communication with the first and second heater wires and the temperature and flow sensors and configured to control the first and second heater circuits, wherein, when a difference between an output of the temperature sensor and a patient end parameter set point is below a predetermined error threshold, the controller is configured to heat the respiratory gases using the first heater circuit until a maximum temperature is reached in the first heater wire, and when the difference between the output of the temperature sensor and the patient end parameter set point is at or above the predetermined error threshold, the controller is configured to heat the respiratory gases using the second heater circuit, and
wherein when a measured flow rate is at or below a predetermined flow rate threshold, the controller is configured to control a duty cycle or power supplied to one or both of the first heater circuit or the second heater circuit using a first heater circuit low flow cap or limit and/or a second heater circuit low flow cap or limit to prevent a surface temperature of a portion of the first segment of the inspiratory limb adjacent the second segment of the inspiratory limb from exceeding a surface temperature threshold.

11. The respiratory humidification system of claim 10, wherein the second heater circuit low flow cap or limit for the duty cycle or power supplied to the second heater circuit is 70% of a maximum available power deliverable by drive circuits.

12. The respiratory humidification system of claim 10, wherein the first heater circuit low flow cap or limit for the duty cycle or power suppled to the first heater circuit is 37% of a maximum available power deliverable by drive circuits.

13. The respiratory humidification system of claim 10, wherein the controller is configured to determine:
a duty cycle or power supplied to the second heater circuit needed to bring the system to the patient end parameter set point; and
a maximum duty cycle or power supplied to the first heater circuit using the determined duty cycle or power supplied to the second heater circuit and the low flow cap or limit for the duty cycle or power supplied to the first heater circuit.

14. The respiratory humidification system of claim 13, wherein the controller is further configured to determine a duty cycle or power supplied to the first heater circuit needed to bring the system to the patient end parameter set point, wherein the determined duty cycle or power supplied to the first heater circuit is inversely related to the determined duty cycle or power supplied to the second heater circuit.

15. The respiratory humidification system of claim 13, wherein the controller is further configured to determine a duty cycle or power supplied to the first heater circuit needed to bring the system to the patient end parameter set point, wherein when the determined duty cycle or power supplied to the second heater circuit is less than the second heater circuit low flow cap or limit, the determined duty cycle or power supplied to the first heater circuit corresponds to a difference between the second heater circuit low flow cap or limit and the determined duty cycle or power supplied to the second heater circuit.

16. The respiratory humidification system of claim 10, wherein when the first heater circuit is heated and the measured flow rate decreases to a first heater circuit high flow to low flow threshold, the controller determines the duty cycle or power supplied to the first heater circuit using at least the first heater circuit low flow cap or limit, and when the first heater circuit is heated and the measured flow rate increases to a first heater circuit low flow to high flow threshold, the controller determines the duty cycle or power supplied to the first heater circuit using at least a first heater circuit high flow cap or limit, the first heater circuit high flow to low flow threshold being lower than the first heater circuit low flow to high flow threshold.

17. The respiratory humidification system of claim 16, wherein the first heater circuit high flow to low flow threshold is between about 2.4 lpm and about 5 lpm and/or the first heater circuit low flow to high flow threshold is about 6.5 lpm.

18. The respiratory humidification system of claim 10, comprising at least one additional temperature sensor configured to measure a surface temperature of the inspiratory limb and positioned on a portion of the inspiratory limb or on an intermediate connector disposed between the first and second segments.

19. The respiratory humidification system of claim 18, wherein the at least one additional temperature sensor comprises a first temperature sensor located on a portion of the first segment to determine a surface temperature of the first segment, and a second temperature sensor located on a portion of the second segment to determine a surface temperature of the second segment.

20. The respiratory humidification system of claim 18, wherein the first and/or second heater circuit low flow caps or limits are determined based on the surface temperature measured by the at least one additional temperature sensor.

* * * * *

UNITED STATES PATENT AND TRADEMARK OFFICE
CERTIFICATE OF CORRECTION

PATENT NO. : 10,960,167 B2  Page 1 of 2
APPLICATION NO. : 15/758714
DATED : March 30, 2021
INVENTOR(S) : Liu et al.

It is certified that error appears in the above-identified patent and that said Letters Patent is hereby corrected as shown below:

In the Specification

Column 12, Line 22, delete "abase" and insert -- a base --.

Column 17, Line 17, delete "overmoulded" and insert -- overmolded --.

Column 26, Line 52, delete "S," and insert -- S1, --.

Column 29, Line 24, delete "S," and insert -- S1, --.

Column 30, Line 20, delete "S," and insert -- S1, --.

Column 33, Line 14, delete "S," and insert -- S1, --.

Column 47, Line 27, delete ""T"s" and insert -- "T's" --.

Column 57, Line 54, delete "(an" and insert -- an --.

Column 60, Line 54, delete "(e.g.," and insert -- e.g., --.

Column 66, Line 35, delete "DC=Kp*e+Ki*e dt" and insert -- DC = Kp*e + Ki*∫e dt --.

Column 66, Line 61, delete "Ki*e dt." and insert -- Ki*∫e dt. --.

Column 77, Line 54, delete "2" and insert -- 20 --.

Column 84, Line 19, delete "10%" and insert -- ±10% --.

Column 84, Line 19, delete "5%" and insert -- ±5% --.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*

Column 84, Line 20, delete "1%" and insert -- ±1% --.

In the Claims

Column 86, Line 47, Claim 12, delete "suppled" and insert -- supplied --.